(12) United States Patent
Swager et al.

(10) Patent No.: US 11,656,226 B2
(45) Date of Patent: May 23, 2023

(54) IMAGE GENERATION FOR DETECTION AND RELATED METHODS

(71) Applicant: C2Sense, Inc., Watertown, MA (US)

(72) Inventors: Timothy Manning Swager, Newton, MA (US); Jason R. Cox, Worcester, MA (US); Robert Deans, Grafton, MA (US); Zhengguo Zhu, Chelmsford, MA (US); Brian E. Fratto, Holden, MA (US); Gabriel Davis, Aliquippa, PA (US)

(73) Assignee: C2Sense, Inc., Watertown, MA (US)

( * ) Notice: Subject to any disclaimer, the term of this patent is extended or adjusted under 35 U.S.C. 154(b) by 245 days.

(21) Appl. No.: 17/072,999

(22) Filed: Oct. 16, 2020

(65) Prior Publication Data

US 2021/0120193 A1  Apr. 22, 2021

Related U.S. Application Data

(60) Provisional application No. 63/085,929, filed on Sep. 30, 2020, provisional application No. 63/069,544, (Continued)

(51) Int. Cl.
*C09K 11/06* (2006.01)
*G01N 33/543* (2006.01)
(Continued)

(52) U.S. Cl.
CPC .............. *C09K 11/06* (2013.01); *G01J 5/02* (2013.01); *G01N 21/00* (2013.01); *G01N 21/251* (2013.01);
(Continued)

(58) Field of Classification Search
CPC ............. G01N 33/54386; G01N 21/00; G01N 21/251; G01N 21/6408; G01N 21/6428;
(Continued)

(56) References Cited

U.S. PATENT DOCUMENTS

| 4,822,733 A | 4/1989 | Morrison |
| 5,874,046 A | 2/1999 | Megerle et al. |
| 6,406,914 B1 | 6/2002 | Kaburaki et al. |
| 7,173,702 B2 | 2/2007 | Maurer et al. |

(Continued)

FOREIGN PATENT DOCUMENTS

| WO | WO 2009/136978 A2 | 11/2009 |
| WO | WO 2010/123482 A2 | 10/2010 |

(Continued)

OTHER PUBLICATIONS

International Search Report and Written Opinion dated Jan. 7, 2021 for Application No. PCT/US2020/056024.
(Continued)

*Primary Examiner* — David P Porta
*Assistant Examiner* — Fani Polyzos Boosalis
(74) *Attorney, Agent, or Firm* — Wolf, Greenfield & Sacks, P.C.

(57) ABSTRACT

Embodiments described herein generally relate to: sensing and/or authentication using luminescence imaging; diagnostic assays, systems, and related methods; temporal thermal sensing and related methods; and/or to emissive species, such as those excitable by white light, and related systems and methods.

37 Claims, 46 Drawing Sheets

Related U.S. Application Data filed on Aug. 24, 2020, provisional application No. 63/054,176, filed on Jul. 20, 2020, provisional application No. 62/916,331, filed on Oct. 17, 2019.

(51) Int. Cl.

| | |
|---|---|
| *G01N 21/76* | (2006.01) |
| *G01N 33/569* | (2006.01) |
| *G01N 21/64* | (2006.01) |
| *G06K 19/14* | (2006.01) |
| *H01L 51/50* | (2006.01) |
| *G01J 5/02* | (2022.01) |
| *H04N 5/33* | (2023.01) |
| *G01N 21/25* | (2006.01) |
| *G01N 33/58* | (2006.01) |
| *G06V 20/80* | (2022.01) |
| *G06V 40/13* | (2022.01) |
| *G01N 21/00* | (2006.01) |
| *H04N 25/53* | (2023.01) |
| *H04N 25/76* | (2023.01) |
| *G06V 10/141* | (2022.01) |
| *G06V 10/143* | (2022.01) |
| *A61B 5/00* | (2006.01) |
| *A61B 5/117* | (2016.01) |
| *G01N 21/75* | (2006.01) |
| *G01J 5/00* | (2022.01) |
| *G01N 21/21* | (2006.01) |

(52) U.S. Cl.
CPC ........ *G01N 21/645* (2013.01); *G01N 21/6408* (2013.01); *G01N 21/6428* (2013.01); *G01N 21/76* (2013.01); *G01N 33/54386* (2013.01); *G01N 33/56983* (2013.01); *G01N 33/582* (2013.01); *G06K 19/14* (2013.01); *G06V 10/141* (2022.01); *G06V 10/143* (2022.01); *G06V 20/80* (2022.01); *G06V 40/1318* (2022.01); *H01L 51/5012* (2013.01); *H01L 51/5016* (2013.01); *H04N 5/33* (2013.01); *H04N 25/53* (2023.01); *H04N 25/76* (2023.01); *A61B 5/0077* (2013.01); *A61B 5/117* (2013.01); *C09K 2211/1007* (2013.01); *C09K 2211/1029* (2013.01); *C09K 2211/1044* (2013.01); *C09K 2211/1059* (2013.01); *C09K 2211/1092* (2013.01); *C09K 2211/182* (2013.01); *G01J 2005/0077* (2013.01); *G01N 21/21* (2013.01); *G01N 2021/6432* (2013.01); *G01N 2021/6439* (2013.01); *G01N 2021/6441* (2013.01); *G01N 2021/6471* (2013.01); *G01N 2021/757* (2013.01); *G01N 2201/062* (2013.01); *G01N 2333/165* (2013.01)

(58) Field of Classification Search
CPC .............. G01N 21/645; G01N 21/76; G01N 33/56983; G01N 33/582; G01N 21/21; G01N 2021/6432; G01N 2021/6439; G01N 2021/6441; G01N 2021/6471; G01N 2021/757; G01N 2201/062; G01N 2333/165; G06V 40/1318; G06V 20/80; C09K 11/06; C09K 2211/1007; C09K 2211/1029; C09K 2211/1044; C09K 2211/1059; C09K 2211/1092; C09K 2211/182; G01J 5/02; G01J 2005/0077; G06K 19/14; H01L 51/5012; H01L 51/5016; H04N 5/33; H04N 5/353; H04N 5/374; A61B 5/0077; A61B 5/117
See application file for complete search history.

(56) References Cited

U.S. PATENT DOCUMENTS

| | | | |
|---|---|---|---|
| 7,611,907 B2 | 11/2009 | Dickson et al. | |
| 7,777,233 B2 | 8/2010 | Kahen et al. | |
| 7,812,324 B2 | 10/2010 | Connally et al. | |
| 8,007,999 B2 | 8/2011 | Holmes et al. | |
| 8,323,221 B2 | 12/2012 | Hall et al. | |
| 8,435,735 B2 | 5/2013 | Lohse et al. | |
| 8,456,073 B2 | 6/2013 | Swager et al. | |
| 8,802,447 B2 | 8/2014 | Swager et al. | |
| 9,404,870 B2 | 8/2016 | Butte et al. | |
| 9,968,258 B2 | 5/2018 | Guo et al. | |
| 10,021,747 B2 | 7/2018 | Powers et al. | |
| 10,041,883 B2 | 8/2018 | Grundfest et al. | |
| 10,191,267 B2 | 1/2019 | Endo et al. | |
| 10,288,567 B2 | 5/2019 | Butte et al. | |
| 10,596,387 B2 | 3/2020 | Walder et al. | |
| 10,670,526 B2 | 6/2020 | Xu et al. | |
| 10,761,039 B2 | 9/2020 | Heissenstein et al. | |
| 2004/0233465 A1 | 11/2004 | Coyle et al. | |
| 2005/0089890 A1 | 4/2005 | Cubicciotti et al. | |
| 2006/0014237 A1 | 1/2006 | Maurer et al. | |
| 2006/0051878 A1 | 3/2006 | Dickson et al. | |
| 2007/0117208 A1 | 5/2007 | Niwa | |
| 2007/0264629 A1 | 11/2007 | Holmes et al. | |
| 2008/0085566 A1 | 4/2008 | Swager et al. | |
| 2008/0118934 A1 | 5/2008 | Gerdes et al. | |
| 2008/0265177 A1* | 10/2008 | Connally ........... | G01N 21/6458 250/461.2 |
| 2009/0109435 A1 | 4/2009 | Kahen et al. | |
| 2010/0240047 A1 | 9/2010 | Lohse | |
| 2010/0240085 A1 | 9/2010 | Lohse | |
| 2011/0097723 A1 | 4/2011 | Liu et al. | |
| 2011/0098609 A1 | 4/2011 | Hall et al. | |
| 2011/0262897 A1 | 10/2011 | Williams et al. | |
| 2012/0252685 A1 | 10/2012 | Treynor et al. | |
| 2014/0024024 A1 | 1/2014 | Sood et al. | |
| 2014/0038222 A1 | 2/2014 | Alt et al. | |
| 2014/0193839 A1 | 7/2014 | Cunningham et al. | |
| 2014/0308661 A1 | 10/2014 | Holmes et al. | |
| 2014/0312247 A1 | 10/2014 | McKee et al. | |
| 2015/0031138 A1 | 1/2015 | Swager et al. | |
| 2015/0053871 A1 | 2/2015 | Grundfest et al. | |
| 2015/0099650 A1 | 4/2015 | Sood et al. | |
| 2015/0105284 A1 | 4/2015 | Willson et al. | |
| 2015/0173621 A1 | 6/2015 | Guo et al. | |
| 2015/0182166 A1 | 7/2015 | Evans et al. | |
| 2015/0226743 A1 | 8/2015 | Weiss et al. | |
| 2015/0355118 A1* | 12/2015 | Heissenstein ......... | G01N 25/72 250/340 |
| 2016/0067357 A1 | 3/2016 | Francois et al. | |
| 2017/0050046 A1 | 2/2017 | Walder et al. | |
| 2018/0092177 A1 | 3/2018 | Powers et al. | |
| 2018/0172580 A1 | 6/2018 | Bjoroy et al. | |
| 2019/0008973 A1 | 1/2019 | Eldor et al. | |
| 2019/0226990 A1 | 7/2019 | Reinhardt et al. | |
| 2019/0236886 A1 | 8/2019 | Dorier et al. | |
| 2019/0249240 A1 | 8/2019 | Rothberg et al. | |
| 2019/0271645 A1 | 9/2019 | Xu et al. | |
| 2020/0033579 A1 | 1/2020 | Chou et al. | |
| 2020/0106932 A1 | 4/2020 | Chou et al. | |
| 2020/0249237 A1 | 8/2020 | Deans et al. | |
| 2020/0384126 A1 | 12/2020 | Francois et al. | |
| 2021/0116371 A1 | 4/2021 | Swager et al. | |
| 2021/0116376 A1 | 4/2021 | Swager et al. | |
| 2021/0116377 A1 | 4/2021 | Swager et al. | |
| 2021/0116378 A1 | 4/2021 | Swager et al. | |
| 2021/0116384 A1 | 4/2021 | Swager et al. | |
| 2021/0116449 A1 | 4/2021 | Swager et al. | |
| 2021/0123921 A1 | 4/2021 | Swager et al. | |
| 2021/0269711 A1 | 9/2021 | Naumov et al. | |

FOREIGN PATENT DOCUMENTS

| | | |
|---|---|---|
| WO | WO 2011/044221 A2 | 4/2011 |
| WO | WO 2011/056936 A2 | 5/2011 |

(56) References Cited

FOREIGN PATENT DOCUMENTS

| WO | WO 2012/044778 A1 | 4/2012 |
| WO | WO 2012/051610 A1 | 4/2012 |
| WO | WO 2012/067665 A1 | 5/2012 |
| WO | WO 2013/131062 A1 | 9/2013 |
| WO | WO 2016/001018 A1 | 1/2016 |
| WO | WO 2016/010855 A1 | 1/2016 |
| WO | WO 2018/080993 A1 | 5/2018 |

OTHER PUBLICATIONS

International Preliminary Report on Patentability dated Apr. 28, 2022 for Application No. PCT/US2020/056024.
Invitation to Pay Additional Fees dated Dec. 21, 2020 for Application No. PCT/US2020/056091.
International Search Report and Written Opinion dated Mar. 8, 2021 for Application No. PCT/US2020/056091.
International Preliminary Report on Patentability dated Apr. 28, 2022 for Application No. PCT/US2020/056091.
Bueno et al., Fluorescence analyzer based on smartphone camera and wireless for detection of Ochratoxin A. Sensors and Actuators B: Chemical. Sep. 2016;232:462-8.
Tsujimoto et al., Thermally Activated Delayed Fluorescence and Aggregation Induced Emission with Through-Space Charge Transfer. J Am Chem Soc. Apr. 5, 2017;139(13):4894-4900. doi: 10.1021/jacs.7b00873. Epub Mar. 27, 2017.
Wang et al., Luminescent probes and sensors for temperature. Chem Soc Rev. Jun. 24, 2013;42:7834-69.
Yu et al., Smartphone Fluorescence Spectroscopy. Aug. 6, 2014;86(17):8805-13.

\* cited by examiner

1:300 dilution (10uL per strip) (shutter speed 800) - Wet

1:300 dilution (5uL per strip) (shutter speed 500) - Wet

1:300 dilution (3uL per strip) (shutter speed 500) - Wet

1:200 dilution (5uL per strip) (shutter speed 500) - DRY

1:200 dilution (5uL per strip) (shutter speed 800) - DRY

1:200 dilution (5uL per strip) (shutter speed 1600) - DRY

1:200 dilution (5uL per strip) (shutter speed 3200) - DRY

Figure 2 – Holder

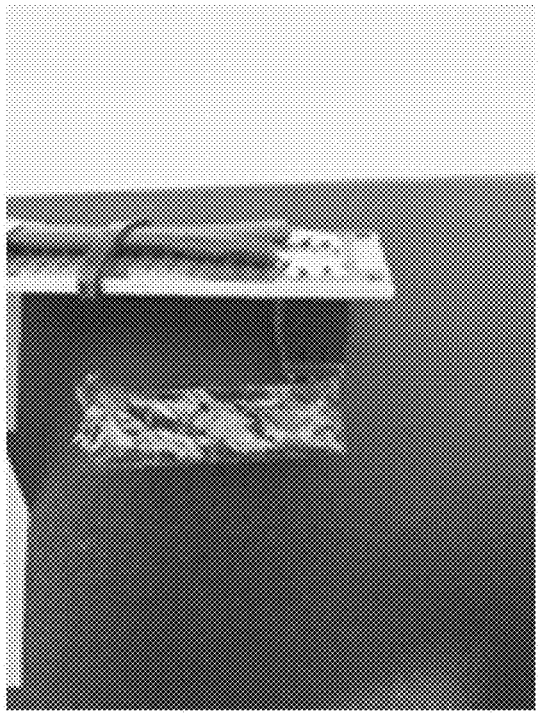 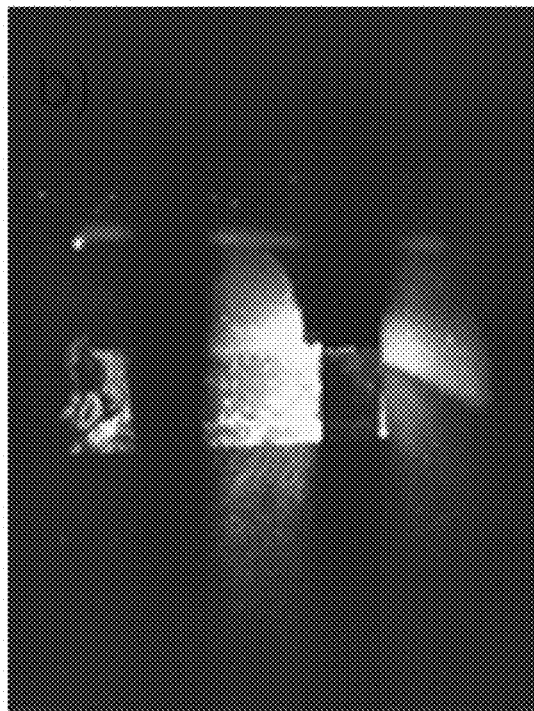
Room Lights On Ambient Image
FIG. 24A
Room Lights Off with External (Pulsed) White Light LED Excitation
FIG. 24B

IMAGE GENERATION FOR DETECTION AND RELATED METHODS

RELATED APPLICATIONS

This Application claims priority under 35 U.S.C. § 119(e) to U.S. Provisional Patent Application No. 63/085,929, filed Sep. 30, 2020, entitled "WHITE LIGHT EMISSIVE SPECIES AND RELATED METHODS," to U.S. Provisional Patent Application No. 63/069,544, filed Aug. 24, 2020, entitled "DIAGNOSTIC ASSAYS AND RELATED METHODS," to U.S. Provisional Patent Application No. 63/054,176, filed Jul. 20, 2020, entitled "TEMPORAL THERMAL SENSING AND RELATED METHODS," and to U.S. Provisional Patent Application No. 62/916,331, filed Oct. 17, 2019, entitled "LUMINESCENCE IMAGING FOR SENSING AND/OR AUTHENTICATION," the contents of each of which are hereby incorporated by reference in their entirety for all purposes.

FIELD

Embodiments described herein generally relate to: sensing and/or authentication using luminescence imaging; diagnostic assays, systems, and related methods; temporal thermal sensing and related methods; and/or to emissive species, such as those excitable by white light, and related systems and methods.

BACKGROUND

Sensing technology is being used in a wide variety of applications such as safety, security, process monitoring, and air quality control. However, many sensors are limited by complex manufacturing processes, low sensitivity, and/or false indications of detection. As such, the applications of such sensors are often limited.

Many products can be damaged when exposed to temperatures above or below a threshold level for a period of time. Products at risk of degradation include biological materials, tissue, medicines, food, beverages, electronics, live cells, organs, livestock, and the like. It is often the case that it is not simply the peak temperature that is most important, but may also include the time spent at a given temperature. For example, a short time at a higher temperature can cause similar degradation to a product as a longer time at a lower temperature exceeding a threshold value. In simple terms the product of the temperature and time is an important metric. Materials and methods capable of providing this information may include time temperature indicators (TTI) and/or dosimetric labels when applied to packaging. For example, thermally activated color changes in a dosimeter label are one way to monitor such changes. However, these methods have limited utility and new methods that provide more information which can be readily captured by readers and greater precision are needed.

Molecular and biological diagnostic tests generally leveraging the low-cost nature and ubiquity of lateral flow assays as well as vertical flow assays and genetic assays based on biological components such as antigens, antibodies, and nucleotides are critical to ensuring public health and safety. Although these assays are easy to use, they are typically analyzed visually using the human eye which injects a high degree of variability and/or subjectivity into the data interpretation. To address this shortcoming, new approaches employing automation and machine vision are necessary to improve the sensitivity and accuracy of lateral flow assays. Although smartphones have recently been used to provide high-resolution image acquisition and analysis, these methods are still limited.

Accordingly, improved methods and systems are needed.

SUMMARY

Articles, systems, and methods for luminescence imaging for sensing and/or authentication are generally disclosed.

In some aspects, an imaging device is provided. In some embodiments, the imaging device comprises a source of electromagnetic radiation configured to emit radiation to excite non-steady-state emission in emissive species during emission time periods (e.g., emission lifetime) of the emissive species. In some embodiments, the emission time period is at least 10 nanoseconds. In some embodiments, an electromagnetic radiation sensor comprising a plurality of photodetectors is arranged in an array of rows and columns, wherein the electromagnetic radiation sensor is configured to sense the non-steady-state emission from the emissive species during the emission time period and processing circuitry configured to sequentially read out rows or columns of the array to provide a plurality of time-encoded signals and identify a characteristic of the emissive species based on a comparison of at least two of the plurality of time-encoded signals.

In some embodiments, the imaging device comprises a source of electromagnetic radiation configured to emit radiation to excite non-steady-state emission in emissive species during emission time periods of the emissive species, the emission time periods being at least 10 nanoseconds, an electromagnetic radiation sensor comprising a plurality of photodetectors arranged in an array of rows and columns, wherein the electromagnetic radiation sensor is configured to sense the non-steady-state emission from the emissive species during the emission time period and processing circuitry configured to globally expose and/or read data from the electromagnetic radiation sensor to provide a plurality of time-encoded signals and identify a characteristic of the emissive species based on a comparison of two or more of the plurality of time-encoded signals.

In some embodiments, the processing circuitry is further configured to generate one or more images based on the plurality of time-encoded signals, and wherein identifying the characteristic of the emissive species is based on the one or more images.

In some aspects, a system is provided. In some embodiments, the system comprises an excitation component configured to excite an emissive species such that the emissive species produces a detectable non-steady-state emission during an emission time period. In some embodiments, the emission time period is at least 10 nanoseconds. In some embodiments, the system comprises an image sensor configured to detect at least a portion of the detectable non-steady-state emission. In some embodiments, the system comprises an electronic hardware component configured to produce a single image comprising a first portion corresponding to a first portion of the emission time period and a second portion corresponding to a second portion of the emission time period.

In some embodiments, the system comprises an excitation component configured to expose an emissive species to non-steady-state electromagnetic radiation. In some embodiments, the system comprises an image sensor configured to detect at least a portion of electromagnetic radiation emitted by the emissive species. In some embodiments, the system comprises an electronic hardware component configured to produce a single image comprising at least a first image portion corresponding to emission of electromagnetic radiation by the emissive species at least at a first point in time, and a second image portion corresponding to emission of electromagnetic radiation by the emissive species at least at a second point in time.

In some embodiments, a system configured for identification of a characteristic of an article is provided. In some embodiments, the system comprises a chemical tag associated with the article. In some embodiments, the chemical tag comprises an emissive species. In some embodiments, the emissive species produces a detectable non-steady-state emission during an emission time period under a set of conditions. In some embodiments, the emission time period is at least 10 nanoseconds. In some embodiments, the system comprises an excitation component configured to excite the emissive species under the set of conditions such that the detectable non-steady-state emission, which varies over the image capture time period, is produced. In some embodiments, the system comprises an image sensor configured to detect the detectable emission. In some embodiments, the system comprises an electronic hardware component configured to convert the detectable emission into a single image. In some embodiments, the single image comprises a first portion corresponding to a first portion of the emission time period and a second portion corresponding to a second portion of the emission time period. In some embodiments, a difference between a property of the first portion and the second portion is associated with a characteristic of the article.

In some embodiments, a system configured for identification of a characteristic of an article is provided. In some embodiments, the system comprises a chemical tag associated with the article. In some embodiments, the chemical tag comprises an emissive species. In some embodiments, the chemical tag produces a detectable non-steady-state emission during an emission time period under a set of conditions. In some embodiments, the emission time period is at least 10 nanoseconds. In some embodiments, the system comprises an excitation component configured to excite the emissive species under the set of conditions such that the detectable non-steady-state emission, which varies over the data/image capture time-period, is produced. In some embodiments, the system comprises an image sensor configured to detect the detectable non-steady-state emission. In some embodiments, the system comprises an electronic hardware component configured to convert the detected emission into a single image. In some embodiments, the single image comprises a first portion corresponding to a first portion of the emission time period and a second portion corresponding to a second portion of the emission time period. In some embodiments, a difference between a property of the first portion and the second portion is associated with a characteristic of the article.

In some embodiments, a system configured for identification of a characteristic of a chemical tag is provided. In some embodiments, the system comprises a chemical tag. In some embodiments, the chemical tag produces a detectable emission during an emission time period under a set of conditions. In some embodiments, the emission time period is at least 10 nanoseconds. In some embodiments, the system comprises an excitation component configured to excite the chemical tag under the set of conditions such that the detectable emission is produced. In some embodiments, the system comprises an image sensor configured to detect the detectable photon emission. In some embodiments, the system comprises an electronic hardware component configured to convert the detected emission into a single image. In some embodiments, the single image comprises a first portion corresponding to a first portion of the emission time period and a second portion corresponding to a second portion of the emission time period. In some embodiments, a difference between a property of the first portion and the second portion is associated with a characteristic of the chemical tag.

In some embodiments, a system comprises a radiation source configured to generate electromagnetic radiation for exciting an emissive species such that the emissive species produces a detectable non-steady-state emission during an emission time period, the emission time period being at least 10 nanoseconds, a sensor configured to detect, during a first portion of the emission time period, a first emission from the emissive species, and detect, during a second portion of the emission time period, a second emission from the emissive species, and processing circuitry configured to identify a characteristic of the emissive species based on a difference between a property of the first emission detected during the first portion of the emission time period and a property of the second emission detected during the second portion of the emission time period.

In some embodiments, the system comprises a radiation source configured to generate electromagnetic radiation for exciting an emissive species such that the emissive species produces a detectable non-steady-state emission during an emission time period, an electromagnetic radiation sensor configured to sense during a single exposure: first emission from the emissive species during a first portion of the emission time period, and second emission from the emissive species during a second portion of the emission time period, wherein the emission time period is at least 10 nanoseconds and is less than a duration of the single exposure and processing circuitry configured to identify a characteristic of the emissive species based on a difference between a property of the first emissions detected during the first portion of the emission time period and a property of the second emissions detected during the second portion of the emission time period.

In some aspects, a method for identifying a change in an emissive species over a period of time is provided. In some embodiments, the method comprises exciting the species such that it produces a detectable non-steady-state emission during an emission time period. In some embodiments, the excited state emission lifetime (e.g., the emission time period) of one or more of the emissive species is at least 10 ns. In some embodiments, the method comprises obtaining, using an image sensor, capable of collecting photon emission data, a single image of which has at least a portion of the detectable non-steady-state photon emission. In some embodiments, a first portion of the single image corresponds to a first portion of the emission time period. In some embodiments, a second portion of the single image corresponds to a second portion of the emission time period. In some embodiments, the method comprises determining, based upon a difference between the first portion and the second portion of the single image, the change in the species.

In some embodiments, a first portion of the single image corresponds to a steady-state emission. In some embodiments, a second portion of the single image corresponds to a non-steady-state emission. In some embodiments, the method comprises determining, based upon a difference between the steady-state and non-steady-state emission, a characteristic and/or change in the species. In some embodiments, the method comprises determining the difference between multiple non-steady-state emissions. In some embodiments, the method comprises determining the difference between multiple steady-state and non-steady-state emissions.

In some embodiments, a method for identifying a change in an emissive species over a period of time is provided. In some embodiments, the method comprises causing the species to emit such that a non-steady-state photon emission is detectable during an emission time period. In some embodiments, the method comprises obtaining, using an image sensor, a single image of at least a portion of the electromagnetic radiation emitted by the emissive species. In some embodiments, the method comprises identifying information from a first image portion corresponding to emission of electromagnetic radiation by the emissive species at least at a first point in time. In some embodiments, the method comprises identifying information from a second image portion corresponding to emission of electromagnetic radiation by the emissive species at least at a second point in time. In some embodiments, the method comprises determining, from at least the information from the first image portion and the information from the second image portion, the change in the emissive species.

In some embodiments, a method for identifying a characteristic of an emissive species is provided. In some embodiments, the method comprises exciting the species such that the species produces a detectable non-steady-state emission during an emission time period. In some embodiments, the emission time period is at least 10 nanoseconds. In some embodiments, the method comprises obtaining, using an image sensor, a first image of the detectable non-steady-state emission. In some embodiments, a first portion of the first image corresponds to a first portion of the emission time period. In some embodiments, a second portion of the first image corresponds to a second portion of the emission time period. In some embodiments, the method comprises determining, based upon a difference between the first portion and the second portion of the first image, the characteristic of the species.

In some embodiments, a method for identifying a characteristic of an article is provided. In some embodiments, the method comprises positioning an image sensor proximate an article suspected of containing an emissive tag. In some embodiments, the method comprises stimulating the article such that the emissive tag, if present, produces a detectable non-steady-state emission. In some embodiments, the method comprises obtaining, using the image sensor, a single image of the detectable non-steady-state emission. In some embodiments, the method comprises adding a sample of the article to be analyzed to a second article, and then analyzing the second article with an image sensor. In some embodiments, a first portion of the single image corresponds to a first time period after stimulating the analyte. In some embodiments, a second portion of the single image corresponds to a second time period after stimulating the analyte, different than the first time period. In some embodiments, the method comprises determining, based upon a difference between the first portion and the second portion of the single image, the characteristic of the article.

In some embodiments, the method comprises generating electromagnetic radiation, exciting, using the electromagnetic radiation, an emissive species such that the emissive species produces a detectable non-steady-state emission during an emission time period, the emission time period being at least 10 nanoseconds, detecting, during a first portion of the emission time period, a first emission from the emissive species, and detecting, during a second portion of the emission time period, a second emission from the emissive species, and identifying the characteristic of the emissive species based on a difference between a property of the first emission detected during the first portion of the emission time period and a property of the second emission detected during the second portion of the emission time period.

In some embodiments, a method for detecting the presence of a stimulus is provided. In some embodiments, the method comprises exposing an article comprising a chemical tag to a set of conditions comprising the stimulus. In some embodiments, the chemical tag undergoes a chemical and/or biological reaction and/or association in the presence of the stimulus that changes the lifetime, wavelength, and/or intensity of one or more emissive species in the tag. In some embodiments, the method comprises positioning an image sensor proximate the article. In some embodiments, the method comprises obtaining, using the image sensor, a single image of a portion of the article comprising the chemical tag. In some embodiments, a first portion of the single image corresponds to a first time period after exposing the article. In some embodiments, a second portion of the single image corresponds to a second time period after exposing the article, different than the first time period. In some embodiments, the method comprises determining, based upon a difference between the first portion and the second portion of the single image, the characteristic of the article. In some embodiments, the method comprises determining, based upon a difference between a steady-state and non-steady-state photon emission, the characteristic of the article. In some embodiments, the method comprises determining, based upon a difference between different non-steady-state photon emissions, the characteristic of the article. In some embodiments a single image can be composed of emitted light from both steady-state and non-steady-state photon emission. In some embodiments, the method may be extended to obtain and use information from additional portions of the images at multiple points in time. In some embodiments, the portions are analyzed with plane or circularly polarized light, different wavelengths of light, or other non-steady-state electromagnetic radiation.

Components, systems, and methods for temporal thermal sensing are also generally disclosed.

In one aspect, compositions are provided. In some embodiments, the composition comprises an emissive species configured to be associated with an article, wherein excitation of the emissive species produces a detectable signal having one or more delayed emissions of greater than or equal to 10 nanoseconds, and wherein the detectable signal corresponds to a temporal thermal history of the article.

In another aspect, labels are provided. In some embodiments, the label comprises a first emissive species optionally having one or more first detectable delayed emission(s) from emissive species having excited state lifetimes greater than or equal to 10 nanoseconds corresponding to a first temporal thermal history of the first emissive species and optionally a second emissive species having one or more second detectable delayed emission(s) from emissive species having excited state lifetimes greater than or equal to 10 nanoseconds corresponding to a second temporal thermal history of the second emissive species, different than the first temporal thermal history. The first detectable delayed emission, if present upon excitation of the first emissive species, corresponds to identification of the first emissive species being exposed to the first temporal thermal history and the second detectable delayed emission, if detectable, corresponds to identification of the second emissive species being exposed to the second temporal thermal history. The first emissive species in some embodiments, transforms into the second emissive species as a result of a particular temporal thermal history. In some embodiments, multiple emissive species may change to provide additional information about an article's temporal thermal history. In some embodiments, one or more emissive species may provide information about a temporal thermal history (e.g., of an article, of the emissive species).

In another aspect, methods are provided. In some embodiments, the method comprises exciting one or more emissive species associated with an article and detecting, using a detector, a detectable delayed emission of the emissive species, wherein the detectable delayed emission, if present, has a delayed emission with an excited state lifetime greater than or equal to 10 nanoseconds, and wherein the detectable delayed emission, if present, corresponds to an exposure of the article to a temporal thermal history.

In some embodiments, the method comprises exciting one or more first emissive species, optionally, exciting one or more second emissive species, detecting, using a detector, a first detectable delayed emission(s) produced by the first emissive species and/or a second detectable delayed emission(s) produced by the second emissive species, wherein, the first detectable delayed emission, if present, corresponds to exposure of the first emissive species to a first temperature, and wherein, the second detectable delayed emission, if present, corresponds to exposure of the second emissive species to a second temperature, different than the first temperature, wherein, at least one detectable delayed emission is present.

In some embodiments, the system comprises an excitation component configured to excite, using electromagnetic radiation, an emissive species such that, if single or multiple emissive species, or their precursors, were exposed to a temporal thermal history, produces a detectable delayed emission with an excited state lifetime greater than or equal to 10 nanoseconds and a detector configured to detect at least a portion of the detectable delayed emission.

In some embodiments, the system comprises a radiation source configured to generate electromagnetic radiation for exciting an emissive species such that the emissive species produces a detectable non-steady-state emission during an emission time period, an electromagnetic radiation sensor including a plurality of photodetectors configured to detect the non-steady state emission during the emission time period; a controller configured to control a timing of generation of the electromagnetic radiation by the radiation source such that pulsed or frequency modulated intensity electromagnetic radiation is generated during the capture of the one or more images, and processing circuitry configured to generate, based on output of the plurality of photodetectors, one or more images, the emission time period being less than a time to capture a single image of the one or more images and for each of the one or more images, determine a first property of a first portion of the image and a second property of a second portion of the image, and identify a characteristic of the emissive species based, at least in part, on the first property and the second property.

Diagnostic assays and related methods are also generally disclosed.

In one aspect, methods are provided. In some embodiments, the method comprises determining an identity or characteristic of a chemical/biological species by combining a first electromagnetic radiation signal comprising at least a steady-state photon emission event, and a second electromagnetic radiation signal comprising at least a non-steady-state photon emission event. In some embodiments, the method comprises determining an identity or characteristic of a chemical/biological species by combining a first electromagnetic radiation signal and a second electromagnetic radiation signal, wherein the first electromagnetic signal comprises at least a first photon emission event from an emissive species with an excited state lifetime less than 10 nanoseconds. In some embodiments, the first photon emission event is detected under steady-steady state conditions. A second electromagnetic signal comprising at least a second photon emission event from an emissive species with an excited state lifetime of at least 10 nanoseconds is detected, in some embodiments, under non-steady-state conditions. In some embodiments, data (e.g., data useful for generating an image) and/or an image is collected after a non-steady-state pulsed emission and only a non-steady-state photon emission is detected. In some embodiments, an image is generated over the time period wherein one or more portions of the image are obtained with a steady-state excitation to detect a steady-state photon emission and one or more portions of the image are obtained after the excitation is removed to enable the detection of a non-steady-state photon emission.

In some embodiments, the first photon emission event comprises an emission produced by an emissive species having an excited state lifetime of less than or equal to 10 nanoseconds.

In some embodiments, the second photon emission event comprises an emission produced by an emissive species having an excited state lifetime of at least 10 nanoseconds.

In some embodiments, the method comprises detecting two or more signals emanating from the assay, wherein each of the two or more signals are selected from a subtractive color, reflected color, scattering, chemiluminescence, prompt-fluorescence, delayed-fluorescence, prompt-phosphorescence, and delayed-phosphorescence emission. In some embodiments, each signal is read using a smartphone or digital camera.

In another aspect, systems are provided. In some embodiments, the system comprises an excitation component configured to excite a first emissive species such that the first emissive species produces a detectable steady-state photon emission, the excitation component is configured to excite a second emissive species such that the second emissive species produces a detectable non-steady-state photon emission, and a sensor configured to detect at least a portion of the detectable steady-state photon emission and at least a portion of the detectable non-steady-state emission.

In some embodiments, the system comprises an electronic hardware component configured to combine the detectable steady-state emission and the detectable non-steady-state emission into a determinable signal.

In some embodiments, the detectable steady-state emission and/or the detectable non-steady-state emission correspond to a characteristic of the first emissive species and/or the second emissive species, respectively.

Emissive species, such as those excitable by white light, and related systems and methods are also generally disclosed.

In one aspect, systems are provided. In some embodiments, the system comprises a source of an electromagnetic radiation spectrum and an emissive species, wherein a first portion of the electromagnetic radiation spectrum comprises a wavelength of between 425 nm and 475 nm, wherein a second portion of the electromagnetic radiation spectrum comprises a wavelength of between 525 nm and 725 nm, and wherein the source produces a wavelength of electromagnetic radiation that interacts with the emissive species such that the emissive species produces a detectable signal having one or more delayed emissions from emissive species having excited state lifetimes greater than or equal to 10 nanoseconds.

In some embodiments, the system comprises a source of a plurality of wavelengths of electromagnetic radiation and an emissive species, wherein the emissive species produces a detectable signal having one or more delayed emissions of greater than or equal to 10 nanoseconds, and wherein the plurality of wavelengths of electromagnetic radiation generated by the source spans greater than or equal to 50 nm. In some embodiments, the system comprises a source of electromagnetic radiation associated with a consumer electronic device, a sensor associated with the consumer electronic device, and an emissive species capable of producing a detectable signal by the sensor, the detectable signal having one or more delayed emissions from an emissive species having an excited state lifetime greater than or equal to 10 nanoseconds.

In some embodiments, the electromagnetic radiation produced by the source is unadulterated prior to exposure to the emissive species. In some embodiments, the system does not comprise a light filter positioned between the source and the emissive species.

In some embodiments, the source is a component of a consumer electronic device. In some embodiments, the consumer electronic device is a smartphone, tablet, computer, digital camera, or the like.

In some embodiments, the system comprises an excitation component configured to produce a plurality of wavelengths of electromagnetic radiation, wherein the excitation component is configured to excite a first emissive species such that the first emissive species produces a detectable stead-state photon emission signal, the excitation component is configured to excite a second emissive species such that the second emissive species produces a detectable non-steady-state photon emission signal, and a sensor configured to detect at least a portion of the detectable steady-state photon emission signal and at least a portion of the detectable non-steady-state emission signal.

In some embodiments, the system comprises a radiation source configured to generate a plurality of wavelengths of electromagnetic radiation for exciting an emissive species such that the emissive species produces a detectable non-steady-state emission during an emission time period, the excited state lifetime of the emissive species being least 10 nanoseconds, a sensor configured to detect, during a first portion of the emission time period, a first emission from the emissive species, and detect, during a second portion of the emission time period, a second emission from the emissive species, and processing circuitry capable of identifying a characteristic of the emissive species based on a difference between a property of the first emission detected during the first portion of the emission time period and a property of the second emission detected during the second portion of the emission time period.

In another aspect, methods are provided. In some embodiments, the method comprises using a consumer electronic device to determine an identity or characteristic of a chemical/biological species, wherein the consumer electronic device comprises a source of a spectrum of electromagnetic radiation and exposing an emissive species to the spectrum of electromagnetic radiation such that the emissive species produces a detectable emission which corresponds to the identity or characteristic of the chemical/biological species and which is detectable by the consumer electronic device.

In some embodiments, the method comprises determining an identity or characteristic of a chemical/biological species by exposing an emissive species to an electromagnetic radiation spectrum generated by a source of electromagnetic radiation and having a range that spans greater than or equal to 50 nm, the emissive species associated with the chemical/biological species and detecting a detectable emission produced by the emissive species, wherein the detectable emission, if present, corresponds to the identity or characteristic of the chemical/biological species.

In some embodiments, the method comprises determining an identity or characteristic of a chemical/biological species by combining a first electromagnetic radiation signal and a second electromagnetic radiation signal, wherein the first electromagnetic signal comprises at least a first photon emission event occurring within 10 nanoseconds of an excitation event that caused the first photon emission event, and a second electromagnetic signal comprising at least a second photon emission event occurring after 10 nanoseconds of the excitation event that caused the second photon emission event, wherein the excitation event comprises an electromagnetic radiation spectrum, wherein a first portion of the electromagnetic radiation spectrum comprises a wavelength of between 425 nm and 475 nm, and wherein a second portion of the electromagnetic radiation spectrum comprises a wavelength of between 525 nm and 725 nm.

In another aspect, kits are provided. In some embodiments, the kit comprises an enclosure configured to receive a consumer electronic device, the consumer electronic device comprising a sensor and a source of electromagnetic radiation associated with the enclosure and/or consumer electronic device, wherein the enclosure is configured to position the consumer electronic device relative to an emissive species, if present, such that the sensor can detect a detectable emission from the emissive species, and the enclosure is configured to prevent external light from interacting with the sensor.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

FIGS. 18A-18D shows images collected using collected using an iPhone 11 and external (pulsed) white light LED of drop-cast samples of: FIG. 18A) Eu(fod)$_3$-MK;

FIG. 18B) Eu(tta)$_3$(dpbt); FIG. 18C) Eu(tta)$_3$(bpt); and FIG. 18D) Eu(pfppd)$_3$(tpy), according to some embodiments;

FIGS. 20A-20B show samples of Eu(tta)$_3$(dpbt) in PMMA analyzed using a: FIG. 20A) a fluorimeter; FIG. 20B) an iPhone 11 with external (pulsed) white light LED, with or without the presence of room lighting, according to one set of embodiments;

FIGS. 22A-22B show images of drop-cast samples of Eu(tta)$_3$(bpt) in a F8BT/PMMA mixture at: FIG. 22A) 0.6 mg/mL; and FIG. 22B) 1 mg/mL. Images were obtained using a commercially available flashlight app to strobe the white light LED of an iPhone 11, according to some embodiments.

FIGS. 24A-24B show images of a sample of Erythrosin B, a commercially available food coloring, incorporated into a Poly Vinyl Alcohol (PVA) matrix. The sample was imaged using an iPhone 11 under ambient (room) lighting (FIG. 24A) and in the dark using an external (pulsed) white light LED (FIG. 24B).

Figure 1A:
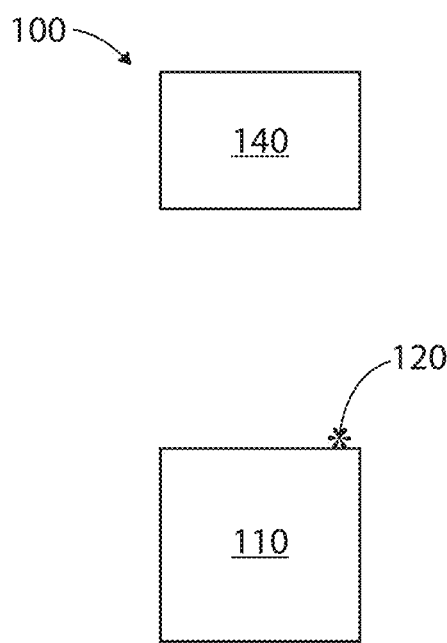
FIG. 1A is a schematic diagram of an article and a chemical tag associated with the article, according to one set of embodiments.

Other aspects, embodiments and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION

In one aspect, compositions, articles, systems, and methods for sensing and/or authentication using imaging are generally provided, in some embodiments. In connection with these, an image (or series of images) of one or more emissive species may be obtained, and time-dependence of image formation or manipulation may be leveraged to determine and identify information about the species, on the timeframe of image formation/obtaining.

In another aspect, some embodiments described herein generally relate to diagnostic assays and related methods. In connection with these, a first photon emission event (e.g., a steady state emission) and a second photo emission event (e.g., a non-steady state emission) may be detected and leveraged to determine and identify information about a chemical and/or biological species (e.g., a reaction, the presence of, etc.).

In another aspect, some embodiments described herein generally relate to temporal thermal sensing and related methods.

In another aspect, some embodiments described herein generally relate to systems and methods for identifying a characteristic and/or an identity of a chemical/biological species.

In yet another aspect, some embodiments are described herein generally relate to the ability to determine if an article is authentic or if an article has been modified.

In some cases, systems and methods described herein advantageously allow consumers to use consumer-level electronics with imaging capabilities (e.g., a smartphone, a digital camera, a tablet, a laptop, a home automation device, a smartwatch, a desktop computer) to evaluate a characteristic of an article (e.g., determine whether a product is authentic, whether food is fresh, whether a contaminant or other dangerous material is present). One factor that has limited the use of consumer-level electronics in conventional optical sensing applications has been the need to use optical filters (e.g., bandpass filters) to selectively emit electromagnetic radiation having a peak wavelength in a relatively narrow range (e.g., electromagnetic radiation configured to excite one or more fluorophores) and to detect electromagnetic radiation having a peak wavelength in a relatively narrow range (e.g., electromagnetic radiation emitted by the one or more fluorophores). For example, if a standard fluorophore (e.g., producing a detectable steady-state photon emission event) were excited using substantially white light emitted by the flash of a camera and/or smartphone, an emission from the fluorophore could be washed out by the overlapping reflected/scattered wavelengths present in white light. One solution to this problem may involve placing a bandpass filter over a lens of a camera and/or smartphone to selectively permit wavelengths originating from the fluorophore to enter the lens. Another solution may involve incorporating a source of electromagnetic radiation that selectively emits wavelengths that excite the fluorophore. However, these solutions may become prohibitively expensive and/or inconvenient if more than one fluorophore is used, as each fluorophore may require an additional filter and/or source of electromagnetic radiation. Advantageously, systems and methods described herein may not require an excitation component or image sensor to be associated with different optical filters (e.g., bandpass filters) for different types of emissive species.

Advantageously, the systems and methods described herein may be implemented on consumer-level electronics such as cellular phones (e.g., smartphones, iPhones, Android phones), digital cameras, tablets (e.g., iPads), laptop computers, home automation devices, watches (e.g., smartwatches), and/or desktop computers. These consumer electronics may be used with filters or other accessories, but in some cases for the methods described herein, such filters will not be required. However, the systems and methods are not limited to consumer-level electronics and may be implemented on other systems and devices as well.

In some embodiments, a system comprises an image sensor. An image sensor is generally configured to detect electromagnetic radiation (e.g., detectable emissions from emissive species) and to output signals (e.g., electrical signals) that may be used to generate an image. Any suitable type of image sensor may be used to detect an emission (or absence of an emission) from an emissive species under a particular set of conditions. Non-limiting examples of suitable image sensors include complementary metal oxide semiconductor (CMOS) sensors, charge-coupled device (CCD) sensors, and photodiodes. Those of ordinary skill in the art would be capable of selecting suitable image sensors based upon the teachings of this specification. The image sensor may be configured, in some embodiments, with an accompanying excitation source component to detect light emitted from steady-state photon emission events and/or non-steady-state photon emission events.

Turning now to the figures, as illustrated in FIG. 1A, in some embodiments, system 100 comprises an article 110 and a chemical tag 120 associated with article 110. In some embodiments, chemical tag 120 comprises one or more emissive species. In some embodiments, as described herein, the one or more emissive species may identify characteristic of article 110. In some embodiments, sensor 140 may be used to detect the presence (or absence) of chemical tag 120 and/or the one or more emissive species chemical tag 120 comprises. In some embodiments, chemical tag 120 may be positioned proximate, adjacent, or directly adjacent article 110.

Figure 1B:
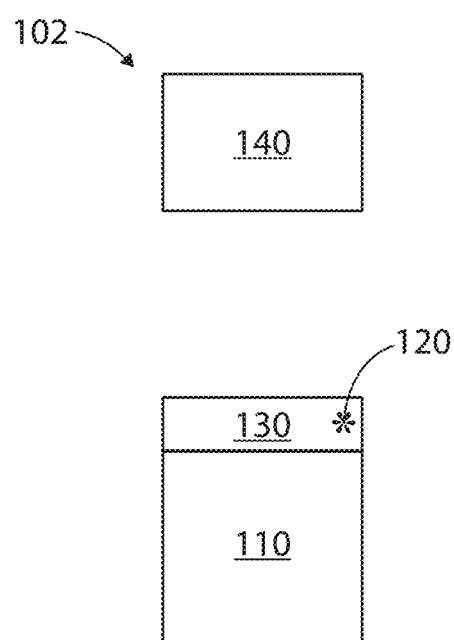
FIG. 1B is a schematic diagram of an article, a label, and a chemical tag associated with the label, according to one set of embodiments.

In some embodiments, the chemical tag is associated with the article and adjacent (e.g., directly adjacent) a label, the label associated with the article. For example, as illustrated in FIG. 1B, system 102 comprises article 110 and chemical tag 120 associated with article 110. In some embodiments, a label 130 is associated with article 110. In some embodiments, chemical tag 120 is associated with label 130. In some embodiments, label 130 comprises one or more compounds forming chemical tag 120. In some embodiments, the label is adjacent the article. In some embodiments, the label is directly adjacent (e.g., affixed to) the article. In some embodiments, the label is proximate the article but not necessarily adjacent the article. For example, in some embodiments, the label may be present in a container containing at least a portion of the article.

Figure 2:
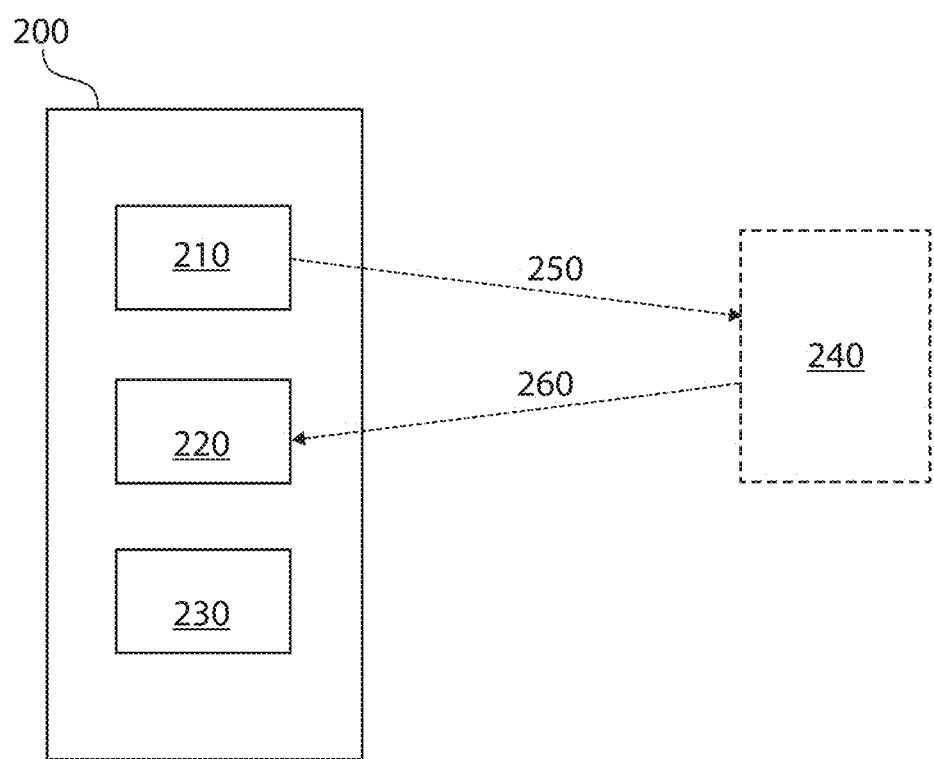
FIG. 2 shows, according to some embodiments, an exemplary system comprising an excitation component, an image sensor, and an electronic hardware component.

FIG. 2 illustrates an exemplary system. In FIG. 2, system 200 comprises excitation component 210. In some cases, excitation component 210 comprises a source of electromagnetic radiation. As one non-limiting example, excitation component 210 may comprise a source of substantially white light. In some instances, excitation component 210 is a source of one or more narrow bands of different wavelengths of electromagnetic radiation, and/or polarized electromagnetic radiation. In some instances, excitation component 210 is associated with an electronic and/or mechanical shutter. The electronic and/or mechanical shutter may be configured to modulate electromagnetic radiation emitted by excitation component 210. In other cases, the excitation component 210 is driven by periodic or pulsed electrical energy that causes flashes and/or modulation in the output intensity. In some cases, the excitation component 210 could be "room light," such as a fluorescent or LED light source. In some embodiments, system 200 further comprises image sensor 220 (e.g., a CMOS sensor, a CCD sensor, photodiode array, or other detector capable of detecting electromagnetic radiation). In some cases, system 200 further comprises electronic hardware component 230 (e.g., circuitry, one or more processors). In certain instances, electronic hardware component 230 is integrated with image sensor 220. In certain other instances, electronic hardware component 230 is separate from image sensor 220. In some embodiments, system 200 is a consumer-level electronic device, such as a cellular phone (e.g., a smartphone), a digital camera, a tablet, a laptop, a home automation device, a watch (e.g., a smartwatch), or a desktop computer.

In operation, system 200 may be positioned in proximity to article 240, which may be associated with one or more emissive species. Proximity can range from centimeters to multiple meters and may be determined by the size of article 240, the resolution of image sensor 220, and the information that is required. The orientation of article 240 and image sensor 220 may also be varied, with different orientations (e.g. angles, front/back, tilts) allowing for different information to be extracted. In some cases, other information gleamed by a device from article 240, or given by an external source, will inform the orientation and proximity required. Excitation component 210 may emit pulsed and/or modulated electromagnetic radiation 250, which may be absorbed by the one or more emissive species of article 240. This radiation may be in discrete narrow bands of wavelength or be in broad bands (such as white light). Excitation component 210 can simultaneously produce multiple different patterns of electromagnetic radiation at different wavelengths that vary in their time modulation, intensity, polarization, and the physical location upon which they impinge on article 240. In some cases, the electromagnetic radiation is absorbed by a first species that transfers energy to a second emissive species of article 240. In some cases, at least a portion of electromagnetic radiation 250 may excite or be reflected or scattered by the one or more emissive species of article 240. Reflected or scattered radiation may be generated by excitation component 210 or be the result of ambient light. The one or more emissive species may subsequently produce detectable emission 260 over an emission time period (e.g., emission lifetime). Image sensor 220 may detect at least a portion of detectable emission 260. Image sensor 220 may also detect at least a portion of reflected or scattered electromagnetic radiation. In some cases, detection of detectable emission 260 may begin after excitation component 210 has stopped emitting electromagnetic radiation 250. In certain instances, this may permit the use of a substantially white light source (e.g., a camera flash) as excitation component 210. In certain instances, electromagnetic radiation 260 is constantly varying in time as a result of the lifetime of emissive species of article 240 and a modulated excitation by excitation component 210. In some cases, electronic hardware component 230 generates a single image (or a series of images) comprising a first portion corresponding steady-state and non-steady-state photon emission. In some cases, the image is generated by measuring many different emission time periods, and/or with many different excitation methods, and/or at different distances, and/or with different orientations, and/or with different filters or polarizers. In some cases, electronic hardware component 230 receives instructions from article 240 and/or another source that changes the overall method of excitation and image capture. In some instances, a characteristic of an emissive species and/or a change in an emissive species is determined based upon a difference between the first portion of the single image (or series of images) and the second portion of the single image (or series of images). Many different time periods may be captured using this method. In certain non-limiting instances, an emission lifetime, or relative change in an emission lifetime, of an emissive species is determined from the single image or series of images (e.g., based upon a difference between the first portion of the single image or series of images and the second portion of the single image or series of images). In some cases, a characteristic of the article is determined from the single image or series of images (e.g., based upon a difference between the first portion of the single image or series of images and the second portion of the single image or series of images). In certain instances, a series of single images may be used to generate different sets of data (e.g., characteristics) from each single image by comparing, for example, different portions of each image over time.

Figure 3A:
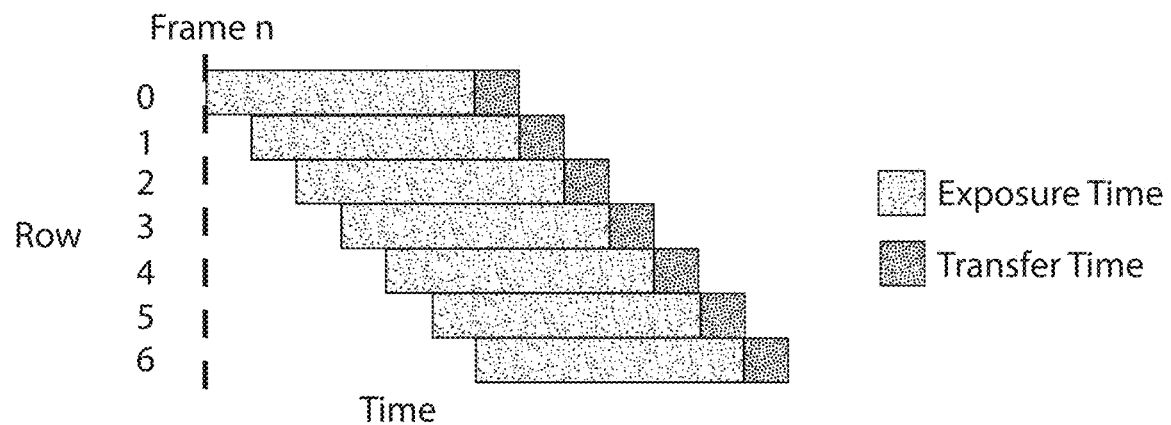
FIG. 3A shows a schematic plot of an exemplary rolling shutter mechanism, according to some embodiments.

In some embodiments, an image sensor uses a rolling shutter method of image capture, as described in more detail below. An image sensor often comprises an array of photodetectors (e.g., corresponding to one or more pixels), and in a rolling shutter method, individual rows or columns are sequentially read. Thus, in a single frame captured using a rolling shutter method, each row or column (depending on the particular rolling shutter method) represents a slice of time. To illustrate, FIG. 3A shows a plot of an exemplary rolling shutter mechanism in which individual rows are sequentially read. Rolling shutter methods may be implemented mechanically or electronically.

Figure 3B:
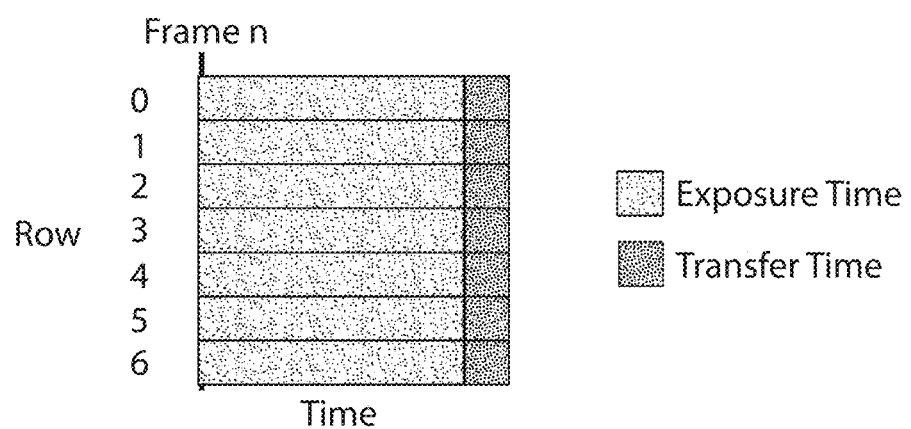
FIG. 3B shows a schematic plot of an exemplary global shutter mechanism, according to some embodiments.

In contrast, in a global shutter method, all pixels of an image sensor are simultaneously exposed to the photon emission and then read. To illustrate, FIG. 3B shows a plot of an exemplary global shutter mechanism in which all rows are simultaneously excited. This is the case, for example, with photographic film wherein a global shutter is used and all points on the film are exposed at the same time. In some embodiments, the image sensor uses a global shutter method of image capture, as described in more detail below.

In some embodiments, the system comprises an excitation component configured to excite an emissive species. Without wishing to be bound by theory, some optical emissions are generally effectively instantaneous and may include the reflection or scattering of electromagnetic radiation. In some embodiments, such emissions may be wavelength dependent and/or may be affected by the absorption of certain wavelengths (e.g., subtractive color). In the case of reflected or scattered light, without wishing to be bound by theory, photons may not be able to promote electrons to higher energy states in the material. Such processes are generally very fast. In some cases, for scattering and reflection by way of example, the photons interact with the material at very short time scales that may have excited state lifetimes shorter than picoseconds. Other emission events such as fluorescence and phosphorescence generally involve the promotion of electrons to higher energy states with the absorption of a photon. For example, relatively fast emissions may occur from materials displaying prompt fluorescence, wherein the emitter has an excited state lifetime less than 10 nanoseconds (ns). In some embodiments, these relatively fast emissions (and, in some embodiments all emissions) are detected/imaged under steady-state conditions wherein emission is detected while a constant excitation source is applied to an article of interest. In some such embodiments, the detectable signal is produced from a steady-state photon emission. In some embodiments, the excited state lifetime of an emissive material is long-lived (e.g., with an excited state lifetime 10 ns or more), such that additional information may be captured under non-steady state conditions wherein the emission varies over the course of a measurement. In some embodiments, capture of such additional information may involve data capable of generating one or more images. The non-steady state measurement is performed, in some embodiments, by using a non-steady-state excitation source that is pulsing, flashing, and/or modulated. By way of example, a long-lived emitter with an excited state lifetime more than 10 ns may continue, in some embodiments, to emit light after the excitation is removed or after the excitation intensity is changed. This may result, in some cases, in the long-lived emission to be selectively detected in the presence of emissive species with lifetimes less than 10 ns. The modulation may be performed, in some embodiments, by changes in intensity some or all of the wavelengths of light in time, or by changes in the polarization of light as a function of time. The modulation may, in some cases, be continuous in the form of a sine wave form, or can be a triangular wave form, or a square waveform. The modulation comprises, in some embodiments, a switch between entirely off (no excitation) to fully on (maximum intensity excitation) and/or comprises involving a modulation on a particular base intensity. In some embodiments, modulation comprises the modulation of a particular wavelength on a base intensity. By way of example and without wishing to be limited as such, a broad band of light that emulates natural light, e.g., white light, may be the base constant signal and an ultraviolet light signal may be used as the modulated signal. In this way, a scattering/reflection/prompt-fluorescence photon emission detection may be collected at the same time as a non-steady-state photon emission detection. Modulation of the excitation may result, in some embodiments, in a modulated emission intensity and in the case that the emissive materials have lifetimes less than 10 ns then the emission under certain conditions will have a modulated intensity that is in phase with the excitation light. However, if long-lived emitters with lifetimes more than 10 ns are present then under some conditions a phase shift may result, in some embodiments, in the emission intensity.

In some embodiments, the system comprises an excitation component configured to excite an emissive species. Without wishing to be bound by theory, some optical emissions are generally effectively instantaneous and may include the reflection or scattering of electromagnetic radiation. In some embodiments, such emissions may be wavelength dependent and/or may be affected by the absorption of certain wavelengths (e.g., subtractive color). In the case of reflected or scattered light, without wishing to be bound by theory, photons may not be able to promote electrons to higher energy states in the material. Such processes are generally very fast. In some cases, for scattering and reflection by way of example, the photons interact with the material at very short time scales that may have excited state lifetimes shorter than picoseconds. Other emission events such as fluorescence and phosphorescence generally involve the promotion of electrons to higher energy states with the absorption of a photon. For example, relatively fast emissions may occur from materials displaying prompt fluorescence, wherein the emitter has an excited state lifetime less than 10 nanoseconds (ns). In some embodiments, these relatively fast emissions (and, in some embodiments all emissions) are detected/imaged under steady-state conditions wherein emission is detected while a constant excitation source is applied to an article of interest. In some such embodiments, the detectable signal is produced from a steady-state photon emission. In some embodiments, the excited state lifetime of an emissive material is long-lived (e.g., with an excited state lifetime 10 ns or more), such that additional information may be captured under non-steady state conditions wherein the emission varies over the course of a measurement. In some embodiments, capture of such additional information may involve data capable of generating one or more images. The non-steady state measurement is performed, in some embodiments, by using a non-steady-state excitation source that is pulsing, flashing, and/or modulated. By way of example, a long-lived emitter with an excited state lifetime more than 10 ns may continue, in some embodiments, to emit light after the excitation is removed or after the excitation intensity is changed. This may result, in some cases, in the long-lived emission to be selectively detected in the presence of emissive species with lifetimes less than 10 ns. The modulation may be performed, in some embodiments, by changes in intensity some or all of the wavelengths of light in time, or by changes in the polarization of light as a function of time. The modulation may, in some cases, be continuous in the form of a sine wave form, or can be a triangular wave form, or a square waveform. The modulation comprises, in some embodiments, a switch between entirely off (no excitation) to fully on (maximum intensity excitation) and/or comprises involving a modulation on a particular base intensity. In some embodiments, modulation comprises the modulation of a particular wavelength on a base intensity. By way of example and without wishing to be limited as such, a broad band of light that emulates natural light, e.g., white light, may be used as the base constant signal and/or an ultraviolet light signal may be used as the modulated signal. In this way, in some embodiments, a scattering/reflection/prompt-fluorescence photon emission detection may be collected at the same time as a non-steady-state photon emission detection. Modulation of the excitation may result, in some embodiments, in a modulated emission intensity, and in the case that the emissive materials have lifetimes less than 10 ns, then the emission under certain conditions may have a modulated intensity that is in phase with the excitation light. However, in some embodiments, long-lived emitters with lifetimes more than 10 ns are present and, under some conditions, a phase shift may result in the emission intensity.

In some embodiments, the system comprises an excitation component configured to excite the emissive species e.g., in a way that allows for the detection of non-steady-state photon emission. In embodiments comprising a pulsed excitation, a steady-state emission may be detected while the steady-state excitation is applied and after the pulsed excitation, when there is no excitation, then the non-steady-state emission may be detected. In some embodiments, a non-steady-state (e.g., time varying) excitation enables the detection of both a steady-state photon emission and a non-steady-state photon emission. Similarly, in embodiments in which a modulated non-steady-state excitation is used, e.g., wherein the steady-state emission has a modulated intensity that is in phase with the modulated excitation, the non-steady-state emission has a phase lag with an appropriate paring of the emissive species and the cycle time (frequency) of the modulation. In some embodiments, the system comprises an image sensor configured to detect at least a portion of electromagnetic radiation emitted by the emissive species. In some embodiments, the system comprises an electronic hardware component configured to collect data and/or produce a single image comprising at least a first image portion corresponding to emission of electromagnetic radiation by the emissive species at least at a first point in time, and a second image portion corresponding to emission of electromagnetic radiation by the emissive species at least at a second point in time. In some embodiments, the electronic hardware component is configured to collect data and/or produce a single image comprising a steady-state photon emission and a non-steady-state photon emission. In some embodiments, the system separately detects a steady-state photon emission and a non-steady-state photon emission.

In some embodiments, the system comprises a chemical tag associated with the article. In some embodiments, the chemical tag comprises an emissive species. In some embodiments, the emissive species produces a detectable non-steady-state emission during emission time periods under a set of conditions. In some embodiments, the emission time period is at least 10 nanoseconds. In some embodiments, the emissive species produces a detectable steady-state and non-steady-state emission during emission time periods under a set of conditions. In some embodiments, the system comprises an excitation component configured to excite the emissive species under the set of conditions such that the detectable non-steady-state emission, which varies over the image capture time period, is produced. In some embodiments, the system comprises an image sensor configured to detect the detectable emission. In some embodiments, the system comprises an electronic hardware component configured to convert the detectable emission into a single image. For example, data created from photon emission events or different wavelengths and intensity (steady-state and non-steady state) may be used to create an image. In some embodiments, devices (e.g., smartphones, consumer electronic devices) that capture images are used generate photon emission data including intensity spatial relationships and information about the excited state lifetimes. In some embodiments, photon emission data comprises a signal and/or a detection. In some embodiments, data collected from a photo emission is used to generate one or more images. Some embodiments comprises a combination of one or more of images, data, signals, measurements, and detection pertaining to photon emission(s).

In some embodiments, an image (or associated data) is used to determine the most relevant photon emission signal(s) for detection to identify a characteristic of an article. In some embodiments, the system comprises an excitation component configured to excite the photon emissive species under the set of conditions to produce a detectable non-steady-state photon emission, which varies over the photon emission and/or image capture time period. In some embodiments, the system comprises an image sensor configured to detect the detectable photon emission. In some embodiments, the system comprises an electronic hardware component configured to convert the detectable photon emission data into one or more images. In some embodiments multiple images are used to identify a characteristic of an article that may be determined from one or more steady-state or non-steady-state photon emission measurements. In some embodiments, only a non-steady-state photo emission signal and/or image collected under non-steady-state conditions is used for identification of a characteristic of an article. In some embodiments, multiple (different) non-steady-state photon emission signals are used for identification of a characteristic of an article. In some embodiments, photon emission data or images from multiple locations of an article are used for identification of a characteristic of an article. In some embodiments, a single image is created by both steady-state and non-steady-state photon emission events for identification of a characteristic of an article. In some embodiments, a steady-state emission is used in conjunction with a non-steady state emission for identification of a characteristic of an article. In some embodiments a steady-state emission is used to determine the conditions upon which one or more non-steady-state photon emission measurements are performed. In some embodiments, multiple images are taken under different excitation conditions. In some embodiments, the excitation conditions involve one or more of the following excitation conditions: pulses, flashes, continuous intensity, modulation at a single frequency, and modulation at multiple frequencies. In some embodiments, the excitation is provided by a white light source. In some embodiments, narrow bands of light are used to excite an emissive species. In some embodiments, only one band of light is used for each image. In some embodiments, multiple bands of wavelength of electromagnetic radiation are used to excite an emissive species. In some embodiments, multiple excitations are used to create multiple steady-state and/or non-steady photon emission events for identification of a characteristic of an article.

In some embodiments, a single image comprises a first portion corresponding to a first portion of the emission time period and a second portion corresponding to a second portion of the emission time period. In some embodiments, a difference between a property of the first portion and the second portion is associated with a characteristic of the article.

In some embodiments, the system comprises a chemical tag associated with the article. In some embodiments, the chemical tag comprises an emissive species. In some embodiments, the chemical tag produces a detectable non-steady-state emission during an emission time period under a set of conditions. In some embodiments, the emission time period is at least 10 nanoseconds. In some embodiments, the system comprises an excitation component configured to excite the emissive species under the set of conditions such that the detectable non-steady-state emission, which varies over the data/image capture time-period, is produced. In some embodiments, the system comprises an image sensor configured to detect the detectable non-steady-state emission. In some embodiments, the system comprises an electronic hardware component configured to convert the detected emission into a single image. In some embodiments, the system comprises an image sensor configured to detect the detectable non-steady-state photon emission. In some embodiments, the system comprises an image sensor configured to detect both a detectable steady-state emission and a detectable non-steady-state photon emission. In some embodiments, the system comprises an electronic hardware component configured to convert the detected emission data into a single image. In some embodiments, the image created from the non-steady state photon emission is recognizable by visual inspection by a user and may provide information about the characteristic of an article. In some embodiments, the image is created by both steady-state emission and non-steady-state photon emission processes. In some embodiments, a series of images are generated from data collected under one or more different steady-state and non-steady-state conditions as described herein, and under one or more image sensor conditions, to provide information about the characteristic of an article. In some embodiments, images are generated by data from the detection of multiple non-steady-state photon emission events to provide information about the characteristic of an article. In some embodiments, images are created by the detection of one or more different steady-state photon emission and non-steady-state photon emission events that provide information about the characteristic of an article. In some embodiments, a plurality of non-steady-state photon emission events provide information about the characteristic of an article.

In some embodiments, a system configured for identification of a characteristic of a chemical tag is provided. In some embodiments, the system comprises a chemical tag. In some embodiments, the chemical tag produces a detectable photon emission under non-steady-state conditions. In some embodiments, one of more emissive species contribute to the non-steady-state emission that have excited state lifetimes of least 10 nanoseconds. In some embodiments, the system comprises an excitation component configured to excite the chemical tag under the set of conditions such that the detectable emission is produced. In some embodiments, the system comprises an image sensor configured to detect the detectable photon emission. In some embodiments, the system comprises an electronic hardware component configured to convert the detected emission into a single image. In some embodiments, the single image comprises steady-state and non-steady-state photon emission events. In some embodiments, a difference between a property of the steady-state and non-steady-state is associated with a characteristic of the chemical tag.

In some embodiments, the single image comprises a first portion corresponding to a first portion of the emission time period and a second portion corresponding to a second portion of the emission time period. In some embodiments, a difference between a property of the first portion and the second portion is associated with a characteristic of the chemical tag.

In some embodiments, methods described herein comprise exciting the species such that it produces a detectable non-steady-state emission during an emission time period. In some embodiments, the excited state emission lifetime of one or more of the emissive species is at least 10 ns. In some embodiments, the method comprises obtaining, using an image sensor, capable of collecting photon emission data, a single image of which has at least a portion of the detectable non-steady-state photon emission.

In some embodiments, a first portion of the single image corresponds to a steady-state emission. In some embodiments, a second portion of the single image corresponds to a non-steady-state emission. In some embodiments, the method comprises determining, based upon a difference between the steady-state and non-steady-state emission. In some embodiments, the method comprises determining the difference between multiple non-steady-state emissions. In some embodiments, the method comprises determining the difference between multiple steady-state and non-steady-state emissions.

In some embodiments, a method for identifying a change in an emissive species over a period of time is provided. In some embodiments, the method comprises causing the species to emit such that a non-steady-state photon emission is detectable during an emission time period. In some embodiments, the method comprises obtaining, using an image sensor, a single image of at least a portion of the electromagnetic radiation emitted is a non-steady-state emission. In some embodiments, the method comprises identifying information from a first image portion corresponding to emission of electromagnetic radiation by the emissive species at least at a first point in time. In some embodiments, the method comprises identifying information from a second image portion corresponding to emission of electromagnetic radiation by the emissive species at least at a second point in time. In some embodiments, the method comprises determining, from at least the information from the first image portion and the information from the second image portion, the change in the emissive species.

In some embodiments, a method for identifying a characteristic of an emissive species is provided. In some embodiments, the method comprises exciting the species such that the species produces a detectable non-steady-state emission during an emission time period. In some embodiments, the emission is produced by an emissive species having an excited state lifetime of at least 10 nanoseconds. In some embodiments, the method comprises obtaining, using an image sensor, a first image of the detectable non-steady-state emission. In some embodiments, a first portion of the first image corresponds to a first portion of the emission time period. In some embodiments, a second portion of the first image corresponds to a second portion of the emission time period. In some embodiments, the method comprises determining, based upon a difference between the first portion and the second portion of the first image, the characteristic of the species.

In some embodiments, a method for identifying a characteristic of an article is provided. In some embodiments, the method comprises positioning an image sensor proximate an article suspected of containing an emissive tag. In some embodiments, the method comprises stimulating the article such that the emissive tag, if present, produces a detectable non-steady-state emission. In some embodiments, the method comprises obtaining, using the image sensor, a single image of which at least a portion is a detectable non-steady-state photon emission. In some embodiments, the conditions for the detection of the non-steady-state photon emission are informed by a steady-state image. In some embodiments, the method comprises adding a sample of the article to be analyzed to a second article, and then analyzing the second article with an image sensor. In some embodiments, a first portion of the single image corresponds to a first time period after stimulating the analyte. In some embodiments, a second portion of the single image corresponds to a second time period after stimulating the analyte, different than the first time period. In some embodiments, the method comprises determining, based upon a difference between the first portion and the second portion of the single image, the characteristic of the article.

In some embodiments, a method for detecting the presence of a stimulus is provided. In some embodiments, the method comprises exposing an article comprising a chemical tag to a set of conditions comprising the stimulus. In some embodiments, the chemical tag undergoes a chemical and/or biological reaction or association in the presence of the stimulus that changes the lifetime, wavelength, and/or intensity of one or more emissive species in the tag. In some embodiments, the method comprises positioning an image sensor proximate the article. In some embodiments, the method comprises obtaining, using the image sensor, a single image of a portion of the article comprising the chemical tag. In some embodiments, a first portion of the single image corresponds to a first time period after exposing the article (e.g., to electromagnetic radiation, to a stimulus). In some embodiments, a second portion of the single image corresponds to a second time period after exposing the article (e.g., to electromagnetic radiation, to a stimulus), different than the first time period. In some embodiments, the method comprises determining, based upon a difference between the first portion and the second portion of the single image, the characteristic of the article. In some embodiments, the method may be extended to obtain and use information from additional portions of the images at multiple points in time. In some embodiments, the portions are analyzed with plane or circularly polarized light, different wavelengths of light, or other non-steady-state electromagnetic radiation. In some embodiments, the method comprises exciting one or more emissive species associated with an article and detecting, using a detector, a detectable delayed emission of the emissive species, wherein the detectable delayed emission, if present, has a delayed emission with an excited state lifetime greater than or equal to 10 nanoseconds, and wherein the detectable delayed emission, if present, corresponds to an exposure of the article to a temporal thermal history.

In some embodiments, the method comprises exciting one or more first emissive species, optionally, exciting one or more second emissive species, detecting, using a detector, a first detectable delayed emission(s) produced by the first emissive species and/or a second detectable delayed emission(s) produced by the second emissive species, wherein, the first detectable delayed emission, if present, corresponds to exposure of the first emissive species to a first temperature, and wherein, the second detectable delayed emission, if present, corresponds to exposure of the second emissive species to a second temperature, different than the first temperature, wherein, at least one detectable delayed emission is present.

In some embodiments, a composition comprising an emissive species is configured to be associated with an article, wherein excitation of the emissive species produces a detectable signal having one or more emissive species with excited state lifetimes than or equal to 10 nanoseconds, and wherein the detectable signal corresponds to a temporal thermal history of the article.

In some embodiments, the system comprises an excitation component configured to excite, using electromagnetic radiation, an emissive species such that, if single or multiple emissive species, or their precursors, were exposed to a temporal thermal history, produces a detectable delayed emission with an excited state lifetime greater than or equal to 10 nanoseconds and a detector configured to detect at least a portion of the detectable delayed emission.

In some embodiments, the system comprises one or more components of a diagnostic assay. In some embodiments, the method comprises determining an identity or characteristic of a chemical/biological species by combining a first electromagnetic radiation signal comprising at least a steady-state photon emission event, and a second electromagnetic radiation signal comprising at least a non-steady-state photon emission event. In some embodiments, the method comprises determining an identity or characteristic of a chemical/biological species by combining a first electromagnetic radiation signal and a second electromagnetic radiation signal, wherein the first electromagnetic signal comprises at least a first photon emission event from an emissive species with an excited state lifetime less than 10 nanoseconds. This emission is detected under steady-steady state conditions. A second electromagnetic signal comprising at least a second photon emission event from an emissive species with an excited state lifetime of at least 10 nanoseconds detected under non-steady-state conditions. In some embodiments, an image is collected after a non-steady-state pulsed emission and only a non-steady-state photon emission is detected. In some embodiments, an image is collected over the time period wherein one or more parts of the image are obtained with a steady-state excitation to detect steady-state photon emission and one or more parts of the image are obtained after the excitation is removed to enable the detection of a non-steady-state photon emission.

In some embodiments, a first photon emission event comprises an emission produced by an emissive species having an excited state lifetime of less than or equal to 10 nanoseconds. In some embodiments, a second photon emission event comprises an emission produced by an emissive species having an excited state lifetime of at least 10 nanoseconds.

In some embodiments, the method comprises detecting two or more signals emanating from an assay, wherein each of the two or more signals are selected from a subtractive color, reflected color, scattering, chemiluminescence, prompt-fluorescence, delayed-fluorescence, prompt-phosphorescence, and delayed-phosphorescence emission.

In some embodiments, the system comprises an excitation component configured to excite a first emissive species such that the first emissive species produces a detectable steady-state photon emission, the excitation component is configured to excite a second emissive species such that the second emissive species produces a detectable non-steady-state photon emission, and a sensor configured to detect at least a portion of the detectable steady-state photon emission and at least a portion of the detectable non-steady-state emission.

In some embodiments, the system comprises an electronic hardware component configured to combine the detectable steady-state emission and the detectable non-steady-state emission into a determinable signal. In some embodiments, the detectable steady-state emission and/or the detectable non-steady-state emission correspond to a characteristic of the first emissive species and/or the second emissive species, respectively, as described herein.

In an exemplary set of embodiments, the system comprises a source of an electromagnetic radiation spectrum and an emissive species, wherein a first portion of the electromagnetic radiation spectrum comprises a wavelength of between 425 nm and 475 nm, wherein a second portion of the electromagnetic radiation spectrum comprises a wavelength of between 525 nm and 725 nm, and wherein the source produces a wavelength of electromagnetic radiation that interacts with the emissive species such that the emissive species produces a detectable signal having one or more delayed emissions from emissive species having excited state lifetimes greater than or equal to 10 nanoseconds.

In some embodiments, the system comprises a source of a plurality of wavelengths of electromagnetic radiation and an emissive species, wherein the emissive species produces a detectable signal having one or more delayed emissions of greater than or equal to 10 nanoseconds, and wherein the plurality of wavelengths of electromagnetic radiation generated by the source spans greater than or equal to 50 nm. In some embodiments, a detectable signal is read using a smartphone or digital camera.

In some embodiments, the system comprises a source of electromagnetic radiation associated with a consumer electronic device, a sensor associated with the consumer electronic device, and an emissive species capable of producing a detectable signal by the sensor, the detectable signal having one or more delayed emissions from an emissive species having an excited state lifetime greater than or equal to 10 nanoseconds. In some embodiments, the source is a component of a consumer electronic device. In some embodiments, the consumer electronic device is a smartphone, tablet, computer, digital camera, or the like.

In some embodiments, the electromagnetic radiation produced by the source is unadulterated prior to exposure to the emissive species. In some embodiments, the system does not comprise a light filter positioned between the source and the emissive species.

In some embodiments, the system comprises an excitation component configured to produce a plurality of wavelengths of electromagnetic radiation, wherein the excitation component is configured to excite a first emissive species such that the first emissive species produces a detectable stead-state photon emission signal, the excitation component is configured to excite a second emissive species such that the second emissive species produces a detectable non-steady-state photon emission signal, and a sensor configured to detect at least a portion of the detectable steady-state photon emission signal and at least a portion of the detectable non-steady-state emission signal.

In some embodiments, the system comprises a radiation source configured to generate a plurality of wavelengths of electromagnetic radiation for exciting an emissive species such that the emissive species produces a detectable non-steady-state emission during an emission time period, the excited state lifetime of the emissive species being least 10 nanoseconds.

In some embodiments, the system comprises a sensor and processing circuitry configured to detect both steady-state and non-steady-state photon emissions in a given image, wherein the steady-state photon emission is detected while the emissive species is undergoing excitation and the non-steady-state photon emission is collected after the excitation is turned off. In some such embodiments, a pulsed excitation is used and the pulsing rate is selected to be about the same or faster than the image capture rate. Advantageously, in some such embodiments, multiple images may be combined containing information from both steady-state and non-steady state photon emissions. Advantageously, in some embodiments, excitation and emission capture need not necessarily be synchronized and computational methods may be used to extract data from the images.

In some embodiments, the method comprises using a consumer electronic device to determine an identity or characteristic of a chemical/biological species, wherein the consumer electronic device comprises a source of a spectrum of electromagnetic radiation and exposing an emissive species to the spectrum of electromagnetic radiation such that the emissive species produces a detectable emission which corresponds to the identity or characteristic of the chemical/biological species and which is detectable by the consumer electronic device. In some embodiments, the method comprises determining an identity or characteristic of a chemical/biological species by exposing an emissive species to an electromagnetic radiation spectrum generated by a source of electromagnetic radiation and having a range that spans greater than or equal to 50 nm, the emissive species associated with the chemical/biological species and detecting a detectable emission produced by the emissive species, wherein the detectable emission, if present, corresponds to the identity or characteristic of the chemical/biological species. In some embodiments, the method comprises determining an identity or characteristic of a chemical/biological species by combining a first electromagnetic radiation signal and a second electromagnetic radiation signal, wherein the first electromagnetic signal comprises at least a first photon emission coming from an emissive species with an excited state lifetime less than 10 ns, and a second electromagnetic signal comprising at least a second photon emission event coming from an emissive species with an excited state lifetime 10 ns or longer, wherein the excitation event comprises an electromagnetic radiation spectrum, wherein a first portion of the electromagnetic radiation spectrum comprises a wavelength of between 425 nm and 475 nm, and wherein a second portion of the electromagnetic radiation spectrum comprises a wavelength of between 525 nm and 725 nm.

In many instances in which images are obtained (one example is taking a photo with a cellphone), a single image is not simply obtained at one moment in time, but portions of the single image are taken at different times (although over a very short time span) to construct the single image. For example, one portion of the image (for example, the top portion) is obtained at a very slightly different time than another portion of the image (for example, the bottom portion). With a cellphone camera, a "shutter" (e.g., an electronic shutter) may block portions of the image from forming at different times depending on location in the image, so that the entire image is not over-exposed, and at any particular time, some portion but not the entire image is being recorded, but over time (very short) the entire image is constructed. With knowledge of when specific portions of the image were obtained, one can identify information about what happened with a subject of that image at those two (or more) different times and/or over the entire time period of image formation (or a portion of that time period). For example, if a feature of an emissive species (chemical or biological species, emissive tag, or the like) changes on the timescale of image formation, then the single image formed may be used to determine something about that change(s).

In some embodiments, the shutter is configured to determine the time over which light is captured by specific light sensors. In some embodiments, the shutter is a mechanical shutters, an electronic (e.g., digital) shutter, or combinations thereof. In some embodiments, a shutter may affect (e.g., inhibit the passing of light) for all wavelengths of light, or only certain wavelengths of light, or only specific polarizations of light.

In some instances, the electronic hardware component configured to produce a single image may not necessarily produce an image and may instead provide a different output (e.g., electronic signals). For example, in some embodiments, embodiments described herein may comprise an electronic hardware component which collects data capable of generating an image (e.g., and which may or may not be used to form an image).

As will be apparent from the description throughout this disclosure, the invention(s) includes many variations of the above description, not limited to any particular type of data and/or signal, particular type of image, number of images, type of equipment used to obtain an image, etc.

In some embodiments, an article (or packaging material of an article) is associated with an emissive material comprising an emissive species (e.g., a luminescent species). In some cases, the emissive species has an emission lifetime of at least 10 nanoseconds (ns). A person of ordinary skill in the art would understand that suitable emission timelines may be selected based on the time resolution of the image sensor. For some image sensors, a suitable lifetime may be on the order of milliseconds, while for other image sensors, a suitable lifetime may be on the order of microseconds. Image sensors with faster time responses will generally allow for lifetime-based images to be obtained using emissive species with shorter lifetimes. In some cases, a characteristic of an article (e.g., identity, authenticity, age, quality, purity) may be determined by obtaining an image (or series of images) comprising time-dependent information related to an emissive species. In certain instances, for example, the emission lifetime of an emissive species may be determined from an image (or series of images). Since the emission lifetime of an emissive species may be modified by a number of factors, including but not limited to binding or proximity to other molecules (e.g., water, oxygen, carbon dioxide, carbon monoxide, carbon dioxide), thermal history, mechanical manipulations, temperature, pH, and radiation exposure, the measured length of the emission lifetime (e.g., the observed emission lifetime, the emission time period) may provide information regarding a characteristic of an associated article. In some instances, an emissive material comprising one or more emissive species may be used to identify and/or authenticate an associated article.

According to some embodiments, an article (or packaging material of an article) is associated with an emissive material comprising an emissive species. In some embodiments, the emissive species is a chemical and/or biological species. In some instances, an excitation component emits non-steady-state pulsed and/or modulated electromagnetic radiation, at least a portion of which is absorbed by the emissive species. In some cases, a pulsed and/or modulated excitation component can have polarization, or one or more bands of wavelengths. In some cases, multiple excitation components may be used in sequence and/or may be overlapping in the time they are applied to an article. In certain cases, the absorbed electromagnetic radiation excites one or more electrons of the emissive species to a higher energy state. The one or more excited electrons are generally metastable and may, in some cases, relax to a lower energy state (e.g., the ground state) through emission of electromagnetic radiation, thermal dissipation (e.g., through vibrational energy transfer), and/or a chemical reaction. When an excited electron relaxes by emitting electromagnetic radiation, it may produce a detectable emission over a period of time (also referred to as an "emission time period" under the measurement conditions or "emission lifetime" when referring to the emissive species). In some cases, an image sensor may detect at least a portion of the detectable emission.

In certain cases, an electronic hardware component (e.g., circuitry, one or more processors) may subsequently generate an image (or series of images) comprising a first portion corresponding to a first portion of the emission time period and a second portion corresponding to a second portion of the emission time period. In some embodiments, the image comprises a first portion corresponding to a photon emission detected under steady-state conditions and a second portion corresponding to a photon emission detected under non-steady state conditions.

In certain cases, an electronic hardware component may generate an image by capturing electromagnetic radiation (e.g., visible light or other light) from different portions of emissions at a number of different lifetimes. The sequence and time periods over which the image is captured may be variable and in principle may be varied by programming or modification of the electronic hardware. In this manner, an image (or series of images) may be used to obtain time-dependent information regarding the emissive species and/or a characteristic of the article. For example, within the non-steady state component, the photon emission signal may vary. The amount to which the non-steady-state photon emission varies may depend, in some embodiments, on the excited state lifetime of the emissive species and the time period over which the image is collected. Without wishing to be bound by theory and by way of example, if the excited state lifetime is equal to or shorter than the time period over which the image is collected under rolling shutter conditions, then the signal intensity may vary. By collecting different parts of an image at different time periods in relation to the excitation component, unique images may be produced. These images may be used to convey information about the article and serve as an authentication code. As one non-limiting example, an image (or series of images) may be used to determine the emission lifetime of the emissive species. In some cases, the emission lifetime of an emissive species may be modified by binding and/or proximity to other molecules (e.g., water, oxygen, carbon dioxide, carbon monoxide), thermal history, mechanical manipulation, temperature, pH, radiation exposure, and/or other environmental factors. In some instances, therefore, the particular emission lifetime value may provide information about a characteristic of the associated article (e.g., the presence or absence of a label, a characteristic of the environment, information about prior chemical, physical, or other exposures). As another non-limiting example, a difference between a property of the first portion of an image and a property of the second portion of the image may provide information about a characteristic of the article (e.g., the presence or absence of a label, a characteristic of the environment, information about prior chemical, physical, or other exposures).

A person of ordinary skill in the art would understand that rolling shutter methods are often criticized as producing undesired artifacts, such as wobble, skew, spatial aliasing, and/or temporal aliasing. As a result, there is interest in having devices that have a more rapid frame capture rate to minimize these artifacts. With a faster frame rate, the time between recording a signal (reading) each row or column is smaller. However, in systems and methods described herein, a rolling shutter method may be leveraged to generate images containing time-dependent information about an emissive material comprising an emissive species. For example, a rolling shutter method may enable the use of consumer-level electronics to obtain information based on the emission lifetimes of one or more emissive species even when using a broadband electromagnetic radiation source (e.g., a substantially white light source) to excite the species. To obtain this information, the exciting electromagnetic radiation may be pulsed and/or modulated to create a non-steady-state, time-dependent signal from the emissive species. In some cases, at least one characteristic of a detectable non-steady-state emission emitted and/or reflected/scattered by an emissive species varies over the image capture time period.

In some embodiments, an image sensor may be associated with an electronic hardware component (e.g., circuitry, one or more processors) configured to produce an image. In some embodiments, the electronic hardware component is configured to produce a single image comprising a first portion corresponding to a first portion of an emission time period of an emissive species and a second portion corresponding to a second portion of an emission time period of an emissive species.

In some embodiments, the electronic hardware component is configured to produce a single image comprising steady-state emission and a second portion corresponding to a non-steady-state emission of an emissive species. In some embodiments, the first portion of the emission time period is entirely distinct from the second portion of the emission time period. In certain other embodiments, the first portion of the emission time period at least partially overlaps with the second portion of the emission time period.

In some embodiments, the single image comprises subsequent portions corresponding to multiple other emission time periods (e.g., over which a non-steady state emission signal can be detected). The single image may, according to some embodiments, comprise at least 2, at least 3, at least 5, at least 10, or at least 20 portions, each corresponding to a different portion of the emission time period or a different emission time period. In some embodiments, the single image comprises 2-5 portions, 2-10 portions, 2-20 portions, 5-10 portions, 5-20 portions, or 10-20 portions. In some instances, the electronic hardware component configured to produce a single image may not necessarily produce an image and may instead provide a different output (e.g., electronic signals).

In some embodiments, the image sensor and/or electronic hardware component are incorporated into a camera (e.g., a digital camera) and/or a phone (e.g., a smartphone). In some embodiments, the camera and/or phone comprises a plurality of image sensors configured to detect electromagnetic radiation (e.g., emitted and/or reflected electromagnetic radiation). In certain instances, the camera and/or phone comprises one or more additional sensors (e.g., sensors configured to sense an individual's location and/or habits, sensors configured to sense light, acoustics, and/or magnetic fields). In some cases, the camera and/or phone may be used for mobile spectroscopy applications.

In an exemplary embodiment, a system is provided comprising an excitation component configured to excite a chemical or biological species, such that an emission produced by the chemical or biological species produces a detectable signal, an image sensor configured to sense the detectable signal, wherein the detectable signal comprises a time-dependent emission signal, and an electronic hardware component configured to convert the collected emission into a single image, wherein the single image includes the time-dependent emission signal.

In another exemplary embodiment, a method is provided for identifying a change in a chemical or biological species over a period of time, comprising stimulating the species such that it produces a detectable emission with an excited state lifetime greater than 10 nanoseconds, obtaining, using an image sensor, a single image of the detectable emission, wherein a first portion of the single image corresponds to a first time period after stimulating the species (e.g., comprising a steady-state photon emission, comprising a non-steady-state photon emission), and wherein a second portion of the single image corresponds to a second time period after stimulating the species, different than the first time period (e.g., comprising a non-steady-state photon emission), and determining, based upon a difference between the first portion and the second portion of the single image, the change in the chemical or biological species.

In another exemplary embodiment, a method is provided for identifying a characteristic of a chemical or biological species, comprising, stimulating the species such that the species produces a detectable emission with an excited state lifetime greater than 10 nanoseconds, obtaining, using an image sensor, a single image of the detectable emission, wherein a first portion of the single image corresponds to a first time period after stimulating the species, and wherein a second portion of the single image corresponds to a second time period after stimulating the species, different than the first time period, and determining, based upon a difference between the first portion and the second portion of the single image, the characteristic of the species. In some embodiments, a first portion of the single image corresponds to steady-state photon emission, and a second portion of the single image corresponds to a non-steady-state photon emission, different than the first steady-state photon emission. In some embodiments data from non-steady-state photon emission can produce multiple other portions of a single image, and determining, based upon a difference between the different portions the single image, the characteristic of the species.

In yet another exemplary embodiment, a method is provided for identifying a characteristic of an article, comprising positioning an image sensor proximate an article suspected of containing a chemical tag, stimulating the article such that the chemical tag, if present, produces a detectable emission, obtaining, using the image sensor, a single image of the detectable emission, wherein a first portion of the single image corresponds to a first time period after stimulating the analyte, and wherein a second portion of the single image corresponds to a second time period after stimulating the analyte, different than the first time period and determining, based upon a difference between the first portion and the second portion of the single image, the characteristic of the article.

In an exemplary embodiment, a method for detecting the presence of a stimulus is provided, comprising exposing an article comprising a chemical tag to a set of conditions comprising the stimulus, wherein the chemical tag undergoes a chemical and/or biological reaction and/or association in the presence of the stimulus, positioning an image sensor proximate the article, obtaining, using the image sensor, a single image of a portion of the article comprising the chemical tag, wherein a first portion of the single image corresponds to a first time period after exposing the article, and wherein a second portion of the single image corresponds to a second time period after exposing the article, different than the first time period and determining, based upon a difference between the first portion and the second portion of the single image, the characteristic of the article. In some embodiments, a first portion of the single image corresponds to steady-state photon emission, and a second portion of the single image corresponds to a non-steady-state photon emission, different than the first steady-state photon emission. In some embodiments, data from non-steady-state photon emission can produce multiple other portions of a single image, and determining, based upon a difference between the different portions the single image, the characteristic of the species. In other embodiments, multiple images can be collected under similar of different conditions to detect additional non-steady-state photon emission data that determine the characteristic of the article.

In another exemplary embodiment, a system is provided, the system configured for identification of a characteristic of an article, comprising a chemical tag associated with the article, the chemical tag capable of generating a detectable emission having an excited state lifetime more than 10 nanoseconds under a set of conditions, an image sensor configured to collect an emission produced by the chemical tag, an electronic hardware component configured to convert the collected emission into a single image, and a source configured to stimulate the chemical tag under the set of conditions, wherein the single image comprises a first portion and a second portion, wherein the second portion is obtained at a different time (and/or under non-steady-state conditions that are different) than the first portion obtained by stimulation of the chemical tag by the source, and wherein a difference between a property of the first portion and the second portion is associated with a characteristic of the article.

In yet another exemplary embodiment, a system configured for identification of a characteristic of a chemical tag is provided, the system comprising a chemical tag capable of generating a detectable emission having an excited state lifetime more than 10 nanoseconds under a set of conditions, an image sensor configured to collect an emission produced by the chemical tag, an electronic hardware component configured to convert the collected emission into a single image, and a source configured to stimulate the chemical tag, wherein the single image comprises a first portion and a second portion, wherein the second portion is obtained under different conditions and/or at a different time than the first portion after stimulation of the chemical tag by the source, and wherein a difference between a property of the first portion and the second portion is associated with a characteristic of the chemical tag. In other cases, images may be produced by combining a third, fourth, fifth, and sixth portion to the first and second portion. The number of portions may be higher yet and will be related to the desired level of complexity needed for the application at hand. Additionally, in a given reading of an article, it may be that only a subset of the potential emissive species are read as a result of their selective excitation, physical location, orientation, environment, orientation, lifetime, etc. It may be that with multiple readings of an article, different methods are used for each sequential reading.

In some exemplary embodiments, stimulation comprises electromagnetic radiation that is provided as a single pulse, a periodic pulse, a sequence of pulses, a continuously varying intensity, or combinations thereof. In some embodiments, a single pulse, a periodic pulse, a sequence of pulses, a continuously varying intensity, or combinations thereof are provided in addition to a constant stimulation of electromagnetic radiation. Exemplary pulse durations and pulse rates are described in more detail, below.

In some exemplary embodiments, stimulation comprises electromagnetic radiation of discrete wavelength ranges that excite select emissive species.

In some exemplary embodiments, stimulation is performed by a flash from a smartphone or camera, is modulated by a shutter, an electronic signal, refractory material, optical modular, mirror, or light valve, and/or is performed by fluorescent or LED lights.

In some exemplary embodiments, a characteristic is extracted from the analysis of a number of images taken with different excitations, and/or is extracted from collecting one or more images at different angles, distances, or orientations.

In some exemplary embodiments, the species is associated with a packaging component.

In some exemplary embodiments, the species undergoes a chemical and/or biological reaction upon stimulating the species.

In some exemplary embodiments, exposure to an analyte causes a change intensity of an emissive species and/or a change in the lifetime of a species with an excited state lifetime longer than 10 nanoseconds.

In some exemplary embodiments, a second stimulation causes a loss of emission or blockage of first stimulation of one or more emissive species contained within an object.

In some exemplary embodiments, a second simulation includes the generation of a color or change in absorption and/or emission.

In some exemplary embodiments, combinations of different first, second and additional stimulations can cause changes in the images that are acquired over the course of 100 nanoseconds to 100 milliseconds.

In some exemplary embodiments, the chemical tag undergoes a chemical and/or biological reaction upon stimulating the article, and/or stimulating the article comprises producing a chemical and/or biological reaction in the chemical tag.

In some exemplary embodiments, the chemical tag comprises at least one emissive dye having an excited state lifetime more than 10 nanoseconds.

In some exemplary embodiments, a rolling shutter component is associated with the image sensor.

In some exemplary embodiments, the chemical tag produces a detectable emission having an excited state lifetime more than 10 nanoseconds in the presence of the stimulus.

In some embodiments, lifetimes associated with different emissive materials as well as their other characteristics are used generate information. For example, the combination of images (or signals) taken under constant static illumination and/or those taken a time period after a flash of white light, or taken during a series of rapid flashes, or acquired during a continuously varying light intensity at one or more frequencies, can differentiate specific signals in the presence of complex or cluttered backgrounds. In some embodiments, light acquired while the emissive materials are excited by a constant intensity light source is referred to as steady-state photon emission. Without wishing to be bound by theory, in some embodiments, an emissive material will be activated in the steady-state photon emission process. In embodiments in which a detectable signal is acquired after the exciting source of electromagnetic radiation has been removed, or while the excitation is varied by pulsing, or by continuous modulation in intensity at frequencies similar to the rate at which the images are acquired by the rolling shutter, are referred to as non-steady-state photon emission events. For example, the materials associated with non-steady-state photon emission events generally have excited stated lifetimes longer then 10 nanoseconds.

In some embodiments, the time domains at which the exciting light is varied in non-steady-state photon emission events is in some cases within a factor of 10 (longer or shorter) than the time over which the image is collected. In some embodiments, however, the time is within a factor of 10 (longer or shorter) than the time over which the image is collected. In some embodiments, the time is within a factor of 100 (longer or shorter) than the time over which the image is collected. In some embodiments, the time is within a factor of 1,000 (longer or shorter) than the time over which the image is collected.

Advantageously, in some embodiments, the systems, compositions, and methods described herein may be used in conjunction with consumer electronics without further modification for the detection, identification, authentication, and/or characterization of a chemical/biological species (or an article with which the chemical/biological species is associated). For example, digital cameras, such as those incorporated into consumer electronics including, for example, smartphones, generally rely on light emitting diode (LED) source(s) designed to illuminate objects (e.g., with color balanced light that approximates natural daylight). Such light is generally referred to as white light. Advantageously, the use of white light in consumer electronics generally allows for recording of images that have substantially the same color balance as would be expected from natural light illumination. However, while the description herein generally refers to sources of electromagnetic radiation associated with consumer electronics, those of ordinary skill in the art would understand, based upon the teachings of this specifications, that other types of white light sources are possible. For example, the interior spaces of buildings are, in some cases, illuminated with white light sources. In some embodiments, a white light source is modulated and/or flickering at frequencies that are not generally detectable by the human eye. In some such embodiments, can provide a non-steady state excitation to an article. Advantageously, the systems, compositions, and methods described herein may be configured, in some embodiments, to utilize such ubiquitous white light sources (e.g., without the need for additional filters or components, in some embodiments). In some embodiments, such sources of electromagnetic radiation may be used to excite an emissive material(s).

The embodiments described herein are generally useful (e.g., using white light excitable materials as emissive elements), for example in, chemical sensing, biological sensing, environmental sensing, thermal exposure evaluation, light exposure, humidity exposure, radiation exposure, physical alterations, and/or product authentication. In an exemplary set of embodiments, the response of one or more emissive species may be captured by a consumer electronic device. In some embodiments, the consumer electronic device is a smartphone comprising a digital camera, (e.g., which functions as the reader and/or sensor). In some embodiments, the consumer electronic device comprises both a source of electromagnetic radiation for, and a sensor capable of detecting an emission from, one or more emissive species (e.g., a white light excitable emissive species).

Although smartphones are generally described herein as an exemplary consumer electronic device, those of ordinary skill in the art would understand, based upon the teachings of this specification, that other consumer electronic devices are also possible and/or the individual components that generally make up a consumer electronic device such as a smartphone's image capture electronics and/or associated light source may be used without the consumer electronic device. For example, the source of electromagnetic radiation (e.g., configured to generate white light) may be, in some cases, a white light excitation source (e.g., a light emitting diode (LED) not physically integrated into a consumer electronic device. In some embodiments, the source of electromagnetic radiation is a component integrated in a consumer electronic device. In some embodiments, the source of electromagnetic radiation is an external component to the consumer electronic device. Non-limiting examples of suitable sources of electromagnetic radiation include a flash, a flashlight, a torch, LEDs, optical fibers, lasers, ultraviolet-visible lamps (e.g., deuterium, tungsten halogen), incandescent bulbs, or the like. As described above and herein, advantageously and in some embodiments, use of the systems described herein may involve the use of an unmodified consumer electronic device such as a smartphone (or tablet, computer, digital camera, or the like) that when equipped with an application program (app), is used to excite an emissive species (i.e. emitter) and may also be used to read information derived from any resulting photon emission events (e.g., events that vary in wavelength and/or time). In some embodiments, such emission events (e.g., photon emissions) may convey important information such as the presence or absence of chemicals of interest, results of biological diagnostic assays, the quality of objects by detecting their cumulative thermal or optical exposure, evidence of physical manipulation, the presence of molecules of interest, and/or the products authenticity. In some embodiments of this invention, this information may be read in the presence of a complex background environment (e.g., comprising one or more sources of stray light in addition to the source of electromagnetic radiation). In some cases, it may be advantageous to read the photon emissions in a way that excludes all other sources of stray light.

As will be apparent from the description throughout this disclosure, the invention(s) includes many variations of the above description, not limited to any particular type of consumer electronic, source of electromagnetic radiation, sensor (e.g., CMOS sensor), etc.

In some embodiments, one or more of the electronic hardware components described herein comprises a controller and/or (micro)processor. In some embodiments, the controller is configured (e.g., programmed) to receive and transmit data commands to/from one or more components of the component and/or the smartphone (or other consumer electronic device). In some embodiments, the data includes one or more signals from one or more sensors. In some embodiments, the controller may be configured to adjust various parameters based on external metrics. For example, in some embodiments, the controller is configured adjust the wavelength of electromagnetic radiation, pulse, frequency, operation of the source of electromagnetic radiation, etc. in response to a signal from a sensor in electrical communication with the controller. In some embodiments, the controller adjusts the wavelength of electromagnetic radiation, pulse, frequency, operation of the source of electromagnetic radiation, etc. in response to an input from the user and/or a signal from the sensor.

The embodiments described herein can be implemented in any of numerous ways. For example, the embodiments may be implemented by any suitable type of analog and/or digital circuitry. In some embodiments, the embodiments may be implemented using hardware or a combination of hardware and software. When implemented using software, suitable software code can be executed on processing circuitry including any suitable processor (e.g., a microprocessor) or collection of processors, whether provided in a single computer or distributed among multiple computers (or other consumer electronic devices). It should be appreciated that any component or collection of components that perform the functions described above can be generically considered as one or more controllers that control the above-discussed functions. The one or more controllers can be implemented in numerous ways, such as with dedicated hardware or with one or more processors programmed using microcode or software to perform the functions recited above. The one or more embodiments can be implemented in numerous ways, such as with dedicated hardware, or with general purpose hardware (e.g., one or more processors) that is programmed using microcode or software to perform the functions recited above.

In some embodiments, the embodiments described herein comprise wireless capabilities for enabling suitable communication with other devices/systems (e.g., for controlling aspects of the electronic component(s), controlling a source of electromagnetic radiation, controlling a sensor or other component). Wireless devices are generally known in the art and may include, in some cases, LTE, WiFi and/or Bluetooth systems. In some embodiments, the systems and/or devices described herein comprise such a wireless device.

In some embodiments, the embodiments described herein may be configured to adjust various parameters based on external metrics. For example, in some embodiments, the system is configured to adjust the rate, wavelength, pulse, modulation, intensity, etc. of electromagnetic radiation from the source of electromagnetic radiation (e.g., in response to a signal from a sensor and/or consumer electronic device in electrical or wireless communication with and/or associated with the system). In some embodiments, the system adjusts the rate, wavelength, pulse, modulation, intensity, etc. of electromagnetic radiation from the source of electromagnetic radiation in response to an input from the user and/or a signal from the sensor and/or consumer electronic device.

In some embodiments, the system is associated with and/or comprises a power source. The power source may include any appropriate material(s), such as one or more batteries, photovoltaic cells, etc. Non-limiting examples of suitable batteries include Li-polymer (e.g., with between 100 and 1000 mAh of battery life), Li-ion, nickel cadmium, nickel metal hydride, silver oxide, or the like. In some cases, the battery may apply a voltage (e.g., to a degradable material as described herein) in response to a physiological and/or external metric and/or signal (e.g., by a user). For example, the voltage may be used to trigger the exit of the resident structure by e.g., applying a voltage to thermally sensitive degradable component as described herein. For example, the average magnitude of the voltage applied to the degradable component(s) may be between 0.001 to 0.01 V, between 0.01 to 0.1 V, between 0.1 V and 10.0 V, between 1.0 V and 8.0 V, between 2.0 V and 5.0 V, between 0.1 V and 5.0 V, between 0.1 V and 1.5 V, between 0.1 V and 1.0 V, between 1.0 V and 3.0 V, between 3.0 V and 8.0 V, or any other appropriate range.

Any electronic component circuitry may be implemented by any suitable type of analog and/or digital circuitry. For example, the electronic component circuitry may be implemented using hardware or a combination of hardware and software. When implemented using software, suitable software code can be executed on any suitable processor (e.g., a microprocessor) or collection of processors. The one or more electronic components can be implemented in numerous ways, such as with dedicated hardware, or with general purpose hardware (e.g., one or more processors) that is programmed using microcode or software to perform the functions recited above.

In this respect, it should be appreciated that one implementation of the embodiments described herein comprises at least one computer-readable storage medium (e.g., RAM, ROM, EEPROM, flash memory or other memory technology, or other tangible, non-transitory computer-readable storage medium) encoded with a computer program (i.e., a plurality of executable instructions) that, when executed on one or more processors, performs the above-discussed functions of one or more embodiments. In addition, it should be appreciated that the reference to a computer program which, when executed, performs any of the above-discussed functions, is not limited to an application program running on a host computer. Rather, the terms computer program and software are used herein in a generic sense to reference any type of computer code (e.g., application software, firmware, microcode, or any other form of computer instruction) that can be employed to program one or more processors to implement aspects of the techniques discussed herein.

In some embodiments, the systems and devices described herein comprise one or more optical detectors such as photodetectors (also referred to as "photosensors" or "photodetection elements") and may include any component that converts light or other electromagnetic radiation into an electrical signal (e.g., current, voltage). Non-limiting examples of suitable photodetectors include phototransistors and photodiodes. Non-limiting examples of image sensor arrays (which include photodetectors) include charge-coupled device (CCD) arrays and complementary metal oxide semiconductor (CMOS) arrays.

By way of example, smartphones currently generally leverage CMOS based optical detectors (imaging chips) to detect light. The sensitivity (ISO) of these chips and the time periods over which they collect light (exposure time) may vary, with these functions typically performed automatically by a smartphone (or other consumer electronic device) when taking a photograph. The speed by which the optical detection system acquires an image is generally referred to as the shutter speed. In previous film-based cameras the shutter was a physical device, whereas in smartphones the camera's shutter is typically electronic in nature. One exemplary method of producing an electronic shutter event is generally referred to as a rolling shutter because the image collection is accomplished by reading the output of different rows, or columns, of photo-detection elements in series. As a result of the manner in which these signals are accumulated, there may, in some cases, be a slight time delay between the reading of sequential rows (or columns) during acquisition of the image. In some embodiments, this time-encoded signal may provide information to identify a characteristic of an emissive species (or an article associated with an emissive species).

Another exemplary method of producing an electronic shutter is generally referred to as a global shutter. This method may also be used, for example, to capture non-steady-state photon emission information if the cycle time of the image collection method is configured to capture data at different time points of the emission lifetime.

Advantageously, embodiments described herein leverage the time delay and the ability to produce composite information by using emissive elements that give off light at characteristic rates and produce information that can be captured by the time delay associated with image acquisition using the rolling shutter mechanism.

An image is a collection of one or more pixels from the detection system and the ability to see patterns through collections of pixels or to signal average by using multiple pixel outputs will be used in some embodiments of this disclosure. In these methods images can be acquired at the same time as the light is exciting the emissive species and combined with images that are acquired after the illumination has been removed or has changed in intensity. Some photons resulting from reflected or scattered light will be observable with concurrent illumination, and the light source can be ambient in nature. In many instances in which images are obtained (one example is taking a photo with a smartphone), a single image is not simply obtained at one moment in time, but portions of the single image are taken at different times (although over a very short time span) to construct the single image. For example, one portion of the image (for example, the top portion) is obtained at a very slightly different time than another portion of the image (for example, the bottom portion). With a smartphone (or other consumer electronic device) camera, a "shutter" (e.g., an electronic shutter) may block portions of the image from forming at different times depending on location in the image, so that the entire image is not over-exposed, and at any particular time, some portion but not the entire image is being recorded, but over time (very short) the entire image is constructed. With knowledge of when specific portions of the image were obtained, one can identify information about what happened with a subject of that image at those two (or more) different times and/or over the entire time period of image formation (or a portion of that time period). For example, if a feature of an emissive species (chemical or biological species, emissive tag, or the like) changes on the timescale of image formation, then the single image formed may be used to determine something about that change(s). In some embodiments, an entire image (or images) comprise a considerable amount of data that is not relevant to the signals of interest and that analysis may depend on a select number of pixels. In some such embodiments, a select feature or number of pixels may constitute the image and/or information from the measurement. In some embodiments, pixels are combined to produce data that represents the spatial distribution of a signal. For example, an image may reveal a vertical line of signal with regards to a horizontal direction. In some embodiments, the vertical and horizontal are relative directions and not generally absolute. The spatial patterning of the different emissive species can inform a device on how to computationally analyze the information collected. In some embodiments, analysis of the signal may comprise a sum of the intensity of the pixels along the vertical direction. In some embodiments, a plot of these summed intensities in the horizontal dimension provides a method to analyze the total intensity of the line relative to the background. Such an analysis in concert with calibration signals may be used, in some cases, to produce quantitative measurements.

Advantageously, photons from scattered and reflected light can be intensified when illuminated with a white light source. In the case where there is no stray (background or ambient) light; no image will be detected from materials that are purely reflective or scattering when the excitation light is turned off. When a white light excitable emitter with an excited state lifetime of similar magnitude to the rate at which the image is acquired by sequential reading of individual rows or columns of optical detectors as performed by the rolling shutter, it is possible to extract information from the resulting image (e.g., provided that the excitation is not in a steady-state mode). These longer-lived signals persist after the excitation light is removed and the timescale over which the photon emission occurs is related to the excited state lifetime of the material. For a modulated non-steady-state excitation, longer-lived signals may, in some cases, provide a phase shift in the phase of the photon emission associated with the longer-lived species.

As will be apparent from the description throughout this disclosure, the invention(s) includes many variations of the above description, not limited to any particular type of image, number of images, type of equipment used to obtain an image, etc.

The methods in this invention detect light emitted that is characteristic of an article. For example, a first portion of the emitted light may be, in some embodiments, reflected or scattered light that is not absorbed by the article and a second portion of the emitted light that is absorbed may be dissipated as heat or create an excited state that can emit a photon at a characteristic rate. The emitted light may be measured, in some cases, at the same time as a constant intensity excitation is applied (e.g., such that the stationary signal is a steady-state photon emission event). In some embodiments, if a time component is present in the excitation relative to the collection of the emitted light, a non-steady-state emission is produced. The time component may be, for example, a time modulation of the excitation intensity at all or different wavelengths, time dependent changes in polarization, or a delay after the excitation light is removed. In some embodiments, an article is associated with an emissive material comprising an emissive species. In some cases, the emissive species has an emission lifetime as described herein. A person of ordinary skill in the art would understand that suitable emission timelines may be selected, for example, based on the time resolution of the image sensor. For some image sensors, a suitable lifetime may be on the order of milliseconds, while for other image sensors, a suitable lifetime may be on the order of microseconds. For example, image sensors with faster time responses will generally allow for lifetime-based images to be obtained using emissive species with shorter excited state lifetimes.

In some cases, a characteristic of an emissive species (e.g., identity, authenticity, age, quality, purity, presence) may be determined by obtaining an image (or series of images) comprising time-dependent information related to an emissive species. In certain instances, for example, the emission lifetime of an emissive species may be determined from an image (or series of images). Since the emission lifetime of an emissive species may be modified by a number of factors, including but not limited to binding or proximity to other molecules (e.g., water, oxygen, carbon monoxide), physical alteration, temperature, pH, and radiation exposure, the measured length of the emission lifetime (e.g., the observed emission lifetime, the emission time period) may provide information regarding a characteristic of an associated article. In some instances, an emissive material comprising one or more emissive species may be used to identify and/or authenticate an associated article. However, in some embodiments, the system need not produce an image. For example, data collected from a sensor may be used to provide information corresponding to a characteristic/identity of an emissive species, as described herein.

In some embodiments, a shutter mechanism is used that can provide time resolution using what is referred to as the rolling shutter, which is used in many smartphones and digital cameras. This non-steady-state photon emission data/image may be combined, in some embodiments, with steady-state photon emission data/image to provide a characteristic about an article. The rolling shutter is generally an electronic mechanism and is related to the electronic reading of the imaging chip. Similar to a classical shutter used in older cameras, the rate over which the chips are read may be varied. In smartphones or digital cameras a chip detects the light projected onto it by sequentially reading rows or columns of the photo-detection elements in rapid succession. The time delay with this reading allows for the device to behave in a way that can extract information as a function of the lifetime of the emissive species. This information may be extracted from a single image by reading the different rows or columns or could be extracted from the overlay of many images collected with different types of excitation and rolling shutter reading conditions. For example, it is possible that an excitation wherein the intensity changes with time may be used in conjunction with a rolling shutter to acquire lifetime data. In some embodiments, the rates at which the excitations are modulated may vary over a large range and will ideally approach similar cycle periods in time to the excited state lifetimes of the different emissive species. By varying the rates of image collection (rolling shutter) rates and the excitation conditions, it is possible, in some embodiments, to selectively detect different emissive species and minimize background signals. It is also noteworthy that this method allows for the selective detection of multiple different species having different excited state lifetimes within a biological assay. In some embodiments, images and/or data are collected such that information is produced by analysis of both steady-state photon emission events and non-steady-state photon emission events. This feature may be combined with the chromaticity (wavelengths) of the emissive species as well as methods that use polarization of light to decrease optical noise. In some embodiments the reader is a conventional smartphone that uses a rolling shutter. An aspect of the smartphone is the timing between the excitation and the speed of the rolling shutter. An excitation may be pulsed and entire images collected after a single pulse. Alternatively, the excitation may be pulsed multiple times during the collection of a single image. Additionally, the excitation may be continuously modulated at one or more varying frequencies throughout the collection of the images using the rolling shutter mechanism. It is also possible that a series of images may be determined that have combinations of different excitation frequencies and rolling shutter speeds. In some cases, a reader will initially collect data under many different excitation conditions and rolling shutter conditions. Computational methods may be used to determine which combination of these trial excitation and rolling shutter conditions produces the superior signal. This signal may be extracted or the reader can make additional measurements under the optimal conditions. By way of example to illustrate this concept, if a single analysis (or trial measurement) takes 10 milliseconds, it is possible to make 100 separate measurements in a second. In these ways the smartphone, digital camera, or detection device (reader) may advantageously be used to selectively detect signals with particular lifetimes in a complex background. For example, under some conditions the devices may be used to detect delayed-phosphorescence to the large exclusion of delayed-fluorescence, prompt-phosphorescence, and colorimetric signals. Alternatively, under other conditions the devices may be used to preferentially detect delayed-fluorescence and prompt-phosphorescence over delayed-phosphorescence and colorimetric signals. However, it is clear that these selective detection events, although useful in their own right, are advantageously greatly enhanced when used in conjunction with other images that contains additional information. For example, pairwise combinations of any of the image analysis techniques described herein may be used. Multiple images (e.g., from steady-state and non-steady-state photon emission events) may be fused that are collected for the detection of any of the signals. In some contexts, the use of multiple images (and/or data sets) may be considered as signal averaging, which generally increases the signal to noise ratio at a rate equal to the square root of the number of signals averaged.

In some embodiments, the combination of optical images that vary in wavelength and lifetime allows information to be extracted and/or encoded. When an article is being optically excited, emission(s) may be detected, in some embodiments, that are comprised of reflected photons and those resulting from the relaxation of excited state(s) generated by the optical excitation. For example, if the exciting light is of constant intensity, the emission may be invariant while the exciting light is on. Such a static situation is generally a steady-state photon emission event, as described herein. The color of the light in the steady-state mode will generally be a combination of that generated by what is generally referred to as subtractive color and the colors that are emitted by the relaxation of the excited states of the emissive material. Without wishing to be bound by theory, subtractive color is generally the result of certain wavelengths being absorbed by a material and some or all of the excited state relaxing to a ground state by a thermal mechanism. In some embodiments, the conversion of light to heat results in increased emission in the infrared region of the electromagnetic spectrum, but not at wavelengths detected by a CMOS imaging system.

In some cases, when the exciting light is turned off, the only reflected light may be caused by ambient stray light. In some embodiments stray light will be present. In an exemplary set of embodiments, it is advantageous to prevent stray light and eliminate substantially all forms of reflected light.

In some embodiments, images (or the equivalent) collected with varying excitation, or after an exciting light source has been removed (turned off), may vary in intensity as a function of time and are generally non-steady-state photon emission events. Generally, excited emissive materials that have excited state lifetimes<10 nanoseconds (ns) will also not be efficiently detected with CMOS imaging methods e.g., after an exciting light source has been turned off. Without wishing to be bound by theory, this is a result of the rolling shutter mechanism being unable to efficiently capture light within 10 ns of a light source being turned off. In some embodiments, emissive species that have lifetimes<10 ns are said to display prompt fluorescence and may be detected as steady-state photon emission events. Longer-lived emissive species may, in some cases, however be detected by a CMOS imaging system after the light source has been turned off and are generally non-steady-state photon emission events. There are multiple types of suitable materials that display longer lived emissions that can be detected as non-steady-state photon emission events, in accordance with the embodiments described herein. By way of example, and without wishing to be limited as such, with a continuously modulated excitation source scattering/reflection/prompt-fluorescence and non-steady-state photon emissions may be present throughout the measurement, however the scattering/reflection/prompt-fluorescence photon emission may have the same modulated waveform as the modulated excitation and the non-steady-state may have differences in the waveform of its modulated emission that reflect a delay in the photons being emitted relative to the excitation. The waveforms from modulated emissions need not necessarily be detected directly, but may produce features in an image collected over a time period by, for example, a rolling shutter mechanism.

For example, materials that exhibit delayed-emission include systems that undergo what is generally referred to as thermally activated delayed fluorescence (TADF). These materials generally have a singlet (electron spins aligned antiparallel) and triplet (electron spins aligned parallel) excited states that are very close in energy. Without wishing to be bound by theory, when the energy separating these states is small enough, they are in thermal equilibrium and in this equilibrium the electron spins may flip by a spin-orbit coupling mechanism. In the case that there are no heavy atoms that are capable of providing the large spin-orbit coupling necessary for efficient emissive relaxation from the excited state triplet directly to the ground state singlet, the triplet state may be said to be very weakly emissive, or in a substantially dark state. The triplet state is generally lower in energy than the singlet state and hence the equilibrium population of this state will be higher than the singlet state. However, when the excited state is in the singlet electronic configuration, the emissive relaxation to the ground state is efficient. As a result, the delay in the emission is the result of the excited state spending a portion of time in the dark triplet state.

Other methods for the generation of delayed fluorescence include the use of twisted charge transfer excited states and systems wherein other metastable charge-separated states are produced that may recombine to generate an excited singlet electronic state in an emissive material.

In some embodiments, the TADF process can occur within a single molecule. In some such embodiments, a π-conjugated organic molecule generally has substitution patterns of electron-donating and electron accepting groups. Certain patterns of molecules can allow for the highest occupied molecular orbital (HOMO) to have a special distribution over the molecule that has low overlap with the lowest unoccupied molecular orbital (LUMO). The molecule can be excited with light and it will rapidly thermally equilibrate to the lowest energy excited singlet state. In some cases, there is one electron occupying an orbital that resembles the original HOMO and one electron occupying an orbital that resembles the original LUMO. Without wishing to be bound by theory, the low orbital overlap between these two electrons results in the triplet state being very close in energy to the singlet. This energy proximity generally can allow for thermal interconversion between the singlet and triplet states, which is responsible for the TADF effect.

An alternative approach, in some embodiments, to create a TADF system is to bring two separate molecules together. In some such embodiments, one of the molecules behaves as an electron donor and the other behaves as an electron acceptor. If they are placed relative to each other such that their π-orbitals can interact, then the donor molecule may donate a small amount of its electron density to the acceptor molecule. Such an interaction is generally said to be a ground-state charge-transfer complex. In some embodiments, the HOMO is on the donor molecule and the LUMO is on the acceptor molecule. Upon absorption of a photon the charge-transfer may be greatly enhanced and it is often approximated, in some cases, that an electron from the donor transfers to the acceptor. The excited-state complex formed with such a photon absorption is generally referred to as an exciplex. Without wishing to be bound by theory, the excited-state has two half-filled orbitals, with one orbital resembling the original HOMO of the donor molecule and the other orbital the resembles the original LUMO of the acceptor molecule. This situation generally results in low overlap between the two half-filled orbitals, which results in a small energy difference between the singlet and triplet excited states. For example, the small energy separation of the singlet and triplet states of the exciplex allows for their equilibration, and is generally responsible for the TADF effect.

In some embodiments, the lifetimes of efficient TADF emitters are longer than 10 ns and less than 50 microseconds (e.g., 10 ns to 20 ns, 10 ns to 50 ns, 10 ns to 100 ns, 10 ns to 500 ns, 10 ns to 1 µs, 10 ns to 5 µs, 10 ns to 10 µs, 10 ns to 50 µs, 10 ns to 100 µs, 10 ns to 500 µs, 10 ns to 1 ms, 10 ns to 5 ms, 10 ns to 10 ms, 10 ns to 50 ms, 10 ns to 100 ms, 10 ns to 500 ms, 10 ns to 1 s, 10 ns to 5 s, 10 ns to 10 s, 50 ns to 100 ns, 50 ns to 500 ns, 50 ns to 1 µs, 50 ns to 5 µs, 50 ns to 10 µs, 50 ns to 50 µs), although longer lifetimes are possible. In general, and without wishing to be bound by theory, shorter lifetimes correspond to higher emissive quantum yields. For example, competing non-radiative relaxation processes may result in conversion of the excited state to the ground state without emission of an optical photon. The emission efficiency, generally referred to as the quantum yield, is related to the ratio of the radiative rate to all of the radiative and non-radiative relaxation rates. For example, if the emission lifetime is shorter, this can result in the radiative rate being the dominate deactivation process. As a result, a time domain of 10 ns to 50 microseconds (or longer) is the approximate lifetime over which materials with more efficient emissions will be observed. Longer lifetimes indicate that the materials are spending more time in the non-emissive triplet state and non-emissive processes can dominate. The equilibrium between the singlet and triplet states may depend, in some embodiments, on the environment as well as the intrinsic properties of the TADF materials.

Advantageously, a delayed-fluorescent signal generally allows for emissions to be detected after the removal of an exciting light source in a non-steady state photon emission event or under modulated light wherein differences between the waveform of the exciting light and the waveform associated with the modulated photon emission are present. One exemplary advantage of this process is that background emission(s) from reflection or scattering and prompt fluorescence are not present at longer lifetimes. In an exemplary set of embodiments, the delayed fluorescent signal can be read by a smartphone (or other consumer electronic device). For example, the rolling shutter mechanism may enable image capture to occur over the lifetime of the emission. In some embodiments, the rolling shutter captures the signal decaying from the time the light is removed and thereby detects the emission in the absence of the exciting light. The ability to detect signals that are decaying after the light is removed is generally a non-steady-state measurement and the emission is said to be a non-steady-state emission. In some cases, pulsing or continuously modulated light may be used to differentiate between signals coming from the non-steady state photon emission events and those coming from the steady-state photon emission events. In some embodiments, calibration and/or matching of a shutter speed (exposure time), a sensitivity of the photon detection elements (ISO), and characteristics of the exciting light source (flash with specific delay, flashing rate, or frequency over which the intensity is modulated) may be performed. Advantageously, in some embodiments, absolute timing of the light source and reading of the CMOS imaging chip is not needed. For example, the relative rates may be reflected in the data and analyzed computationally. This latter feature advantageously allows for an independent light source that is not electronically connected to the CMOS rolling shutter image acquisition to be used.

In some embodiments, phosphorescent materials with lifetimes over the period of 10 ns to 50 microseconds are used. In some such embodiments, these materials are generally referred to as prompt-phosphorescent materials. In some embodiments, heavy atoms present in the phosphorescent material, or in its immediate environment, facilitate the spin transition process. In some embodiments, the heavy atoms promote two different electron spin interconversion processes. Firstly, they may promote what is called inter-system crossing by converting the initially created singlet excited-state into a triplet excited-state by a spin orbit coupling mechanism. In some cases, the triplet is sufficiently lower in energy that there is no thermal equilibrium with the singlet. To achieve prompt-phosphorescence, which generally involves the emissive relaxation of the excited triplet state to the ground singlet state, the heavy atom may, in some cases, produce a mechanism that allows for a spin flip. Without wishing to be bound by theory, this is often accomplished by spin-orbit coupling achieved by electronic coupling to the heavy atom(s). Non-limiting examples of heavy atoms are elements heavier than e.g., neon and examples of main group heavy atoms include, but are not limited to, Al, Si, P, S, Cl, Ga, Ge, Sb, Se, Br, In, Sn, Sb, Te, and I. The heavier atoms generally provide for stronger spin orbit coupling and, in some embodiments, by attaching multiple heavy atoms to an organic base chromophore, the efficiency of the phosphorescence may be increased.

Many organometallic (molecules with metal-carbon bonds) and metallo-organic (molecules wherein the metals are bound to organic ligands though elements other than carbon) may, in some embodiments, exhibit prompt-phosphorescence. For example, the bonding may be though phosphorous, sulfur, oxygen, or nitrogen groups on the organic ligand. Non-limiting examples of suitable materials having prompt-phosphorescent behavior include those having metal centers are Cu, Zn, Ru, Rh, Pd, Ag, Cd, Re, Os, Ir, Pt, Au, and Hg. Post transition metal elements including Pb and Bi may also be used in systems displaying prompt-phosphorescence. These materials may also be detected using a smartphone and rolling shutter, in accordance with embodiments described herein. For example, in some embodiments, the rolling shutter mechanism allows for the prompt-phosphorescence emission to be recorded after removal of the excitation light thought non-steady-state photon emission events.

Another class of material are those displaying emission lifetimes longer than 50 microseconds that may extend to many seconds (e.g., at least 50 µs, at least 100 µs, at least 500 µs, at least 1 ms, at least 5 ms, at least 10 ms, at least 50 ms, at least 100 ms, at least 500 ms, at least 1 s, at least 2 s, at least 3 s, at least 4 s, at least 5 s, at least 6 s, at least 7 s, at least 8 s, at least 9 s, or at least 10 s), and these materials are generally referred to a delayed-phosphorescent emitters. To have significant emission over these times the materials generally comprise very rigid structures that attenuate non-radiative processes and/or have f-block elements wherein the orbitals involved in the emission are contracted and hence may be influenced minimally by the dynamics of the coordinating ligands. Non-limiting examples of rigid materials are ruby structures comprising Cr+3 doped $Al_2O_3$ (a ceramic material with a very high melting temperature and excited state lifetimes of 3.4 milliseconds). Other examples include, but are not limited to, rigid organic molecules in appropriate matrix materials. For example, examples of suitable f-block element-based materials are inorganic and metalloorganic materials containing Eu, Tb, Er, and Gd. The rolling shutter mechanism generally allows, in some embodiments, for the delayed-phosphorescence emission to be recorded to create images after removal of the excitation light from non-steady-state photon emission events.

In some embodiments, a smartphone or a system having similar components to a smartphone, is used to read both steady-state and non-steady-state photon emission events from emissive species described herein. There are a number of applications wherein the emission signal may be used e.g., to indicate the presence of a molecule or biomolecule, determine the thermal history of a material, if a material has been physically altered, the authenticity of a material, if a material has been exposed to ionizing radiation, if a material has been exposed to a chemical or biological analyte, and/or if a material has been exposed to ultraviolet radiation. As described above and herein, the excitation source need not be part of the smartphone and may be an external source that is controlled to produce steady-state and non-steady-state emissive signals.

However, in an exemplary set of embodiments, the smartphone (or other consumer electronic device) does not require augmentation and performs the necessary excitation to acquire steady-state and/or non-steady-state signals as a stand-alone system (e.g., with appropriate software). The camera function of the smartphone is designed to capture images, and although images will be very useful in some applications, the device need not produce an image. Specifically, individual pixels or collections of pixels can be used to collect the necessary signals to obtain the information of interest. Alternatively, the signal produced by a sensor (e.g., an image sensor) may be read directly without the production of pixels and/or an image.

To pair combinations of materials that will produce emissions as a result of reflection, scattering, prompt-fluorescence, delayed-fluorescence, prompt-phosphorescence, and/or delayed-phosphorescence that may be excited and read by a smartphone, the characteristics of the light sources (flashes) used in smartphones may be considered. In general, most smartphone light sources (LEDs) have their highest intensity output around 450 nm and depending on the exact make and model this peak intensity can be at higher or lower wavelengths. For example, Apple Corporation's iPhone 11 has a peak intensity very close to 450 nm, but their iPhone X and iPhone 6S models have peak light outputs closer to 440 nm. While a Google Pixel 2 Android smartphone has its peak light output closer to 460 nm. The light output of these light sources are finite, but minimal at 400 nm. They also exhibit lower intensity outputs that extends beyond 650 nm and in some cases beyond 700 nm. See, for example, FIGS. 17A-17I. The combined total output of a smartphone light source produces light that is perceived to the human eye to be similar to sunlight and is generally referred to as white light.

An exemplary condition to achieve an excited state of a compound by photon absorption may include excitation photons with an energy equal to or greater than the energy thereby separating the material's ground electronic state and its first excited electronic state. An approximation to this energy, without wishing to be bound by theory, is the difference in energy between the HOMO and the LUMO of a material. Those of ordinary skill in the art would be capable, based upon the teachings of this specification, to use the computation of HOMO and LUMO levels to gain valuable insights into materials selection. Those of ordinary kill in the art would be capable of measuring the optical absorption spectra of materials to gain valuable insight into materials selection based upon the teachings of this specification. The efficiency of excitation of the material by a given light source may depend, for example, upon the optical absorption characteristics of the absorbing emissive material and the intensity of the light from the exciting light source at the same wavelength. The amount of the material excited is generally related to the product of these values. Another approximation that is widely used to understand the characteristics of the absorptions of materials is generally referred to as the Born Oppenheimer approximation. One of the tenants of this approximation is generally that with the absorption of a photon an electron is virtually instantaneously transferred to a higher energy state and all of the nuclei in the system appear as if they are fixed in place during this process. The consequences of this are, in some cases, that an excitation event will be the composite of a number of unique structural configurations in an emissive material. As a result, the absorptions of emissive materials may also have ranges of energy, in some embodiments, that are a result of the different environments and structural configurations that the materials experience. This term, reflected in the description of the energy range over which the material absorbs light to populate a given excited state, is described as an absorption band. For example, in solution there may be many configurations of solvent molecules around an emissive material. In a solid form there can be a distribution of different organizations of a matrix that supports an emissive material. The internal dynamics of the emissive materials may also play a role and different thermal vibrations can lead to many different geometries of an emissive material that are instantaneously excited by the absorption of a photon.

Optical absorption bands of a material are generally characterized by the absorption maxima. This refers to the wavelength (energy) of the peaks in a plot of photon absorption efficiency as a function of wavelength. If a material has an absorption maximum close to 450 nm then a very efficient excitation can be expected when illuminated with a smartphone light source. The width of an optical absorption band is often described by its full width at half maximum (FWHM) and can be reported in nanometers. Without wishing to be bound by theory, as a result of the fact that the absorption occurs over a range of wavelengths, it is possible that a material with an absorption maximum that is of higher energy than 450 nm can be excited by the light source of a smartphone (or other consumer electronics). The FWHM of a material can in some cases be more than 20 nm, in other cases, more than 40 nm, in others more than 60 nm, in others more than 100 nm. As a result, the absorption maximum need not be precisely at the same wavelength as the smartphone light source output, but a component of the absorption may overlap with the spectral output of the smartphone's light source. For example, a finite intensity of the light source at a region where there is a finite absorption of the emissive material, is suitable in some embodiments. A material exhibiting an optical absorption that overlaps with the light output of a smartphone is said, in some embodiments, to be smartphone excitable. Without wishing to be bound by theory, the more photons absorbed by a material the brighter the emission from the excited material. In some embodiments, it can be an advantageous to create the brightest emission possible using the smartphone's light source. However, when the smartphone is used to detect non-steady-state emissions, signals may be detected even from very weak emission intensities as a consequence of the methods ability to eliminate or discriminate from background optical signals. Different emissive materials may also have different emission efficiencies for the conversion of the absorbed photons to fluorescence and phosphorescence signals. The efficiency may depend, for example, on one or both of the material and the environment.

Variations in emission efficiencies can be used, in some embodiments, to create information about the immediate environment of the emissive material or its previous history. The efficiency of the fluorescence and phosphorescence is referred to as the quantum yield. A quantum yield of 1.0 implies that 100% of the absorbed photons are converted to photons emitted as fluorescence and phosphorescence. A quantum yield of 0.1 implies that 10% of the absorbed photons are converted to photons emitted as fluorescence and phosphorescence. There are typically losses, but there are materials that approach quantum yields of 1.0, which is the theoretical limit for simple processes. As such, it is generally possible to have materials that can undergo what is generally referred to as singlet fission, wherein an initial excitation produces a singlet state that can separate to give two triplet states. Hence, it is theoretically possible to get multiple photons emitted from a single photon absorbed. It is also possible for a photon to trigger a reaction that can cause the release of multiple photons. In some embodiments, there may be a chemical or electrical potential built up in the material that is released with the absorption of a photon. For example, a photon triggered chemiluminescence reaction may, in some embodiments, produce a large number of emitted photons from a single absorption event.

Beyond the overlap of the emissive material's absorption bands with the smartphone's light source, other desirable properties that are application specific include, but are not limited to, lack of toxicity, low cost, excited state lifetime, chemical stability, interactions with specific chemical signals, optical anisotropy, efficiency of the conversion, charge transfer character, resistance or susceptibility to degradation via optical excitation, thermal sensitivity or insensitivity, sensitivity or insensitivity to the nature of its surroundings, thermal stability or instability, ability to fabricate objects in a process that can be readily implemented in an existing manufacturing process, and the inability of a third party to deduce the true identity of the emissive material.

In some embodiments, the use of signals acquired under the combined conditions of steady-state and non-steady-state emission, or alternatively under non-steady-state, are combined with a conventional smartphone operated by a program (app). Articles, sensors, and assays that can be read and analyzed using commercial smartphones in this manner will find wide utility (e.g., considering the fact that most adults and teenagers worldwide currently have personal smartphones). The inventors of the embodiments described herein have recognized that selection of appropriate emissive materials that provide informative signals is advantageous to realizing the potential of smartphones as readers in the described applications.

For example, there is an abundance of suitable organic dyes capable of efficient prompt-fluorescence and many of these materials are commercially available. Prompt-fluorescent dyes are often used to provide brighter colors in articles. For example, bright fabrics can have emissive dyes. There are dyes that can even be applied to food, and hence safe to eat, that display prompt-fluorescence in the visible range. The use of prompt-fluorescent dyes in commercial products and related methods to integrate these materials into articles is sufficiently established that one skilled it the art would be able, based upon the teachings of this specification, select other candidate materials and fabrication methods. Such materials and methods are described in more detail, below.

A number of materials that comprise a delayed-fluorescence by the Thermally Activated Delayed Fluorescence (TADF) mechanism may be suitable in accordance with embodiments described herein. TADF materials are described in more detail, below. In some embodiments, the TADF materials may be organic in nature and/or may be systematically designed/modified and fabricated to produce compositions with the desired absorption and emission properties. Under the conditions of optical excitation, TADF materials generally initially display prompt-fluorescence as a result of the fact that the initial excited state is a singlet state. However, without wishing to be bound by theory, conversion to the triplet state competes with direct prompt-fluorescence and produces an additional relaxation channel by delayed-fluorescence. In some cases, the delayed-fluorescence of the TADF material is the dominate method by which the excited states radiatively relax to the ground state. In other cases, the prompt-fluorescence is the dominate method by which the molecule emits photons. However, in the latter case there may still be a measurable, and hence informative, delayed-fluorescence signal. The dual processes observed in TADF materials may be important and may provide additional information. In particular it is found that the properties of TADF molecules may vary based on solvent and the rigidity, polarizability, and dipoles of the host matrix material. Specifically, the fact that the HOMO and LUMO are generally localized to different portions of molecules undergoing TADF, creates charge transfer character in the excited state. As a result, TADF materials may produce steady-state photon emission events as well as non-steady-state photon emission events, in some embodiments.

Prompt-fluorescence materials, and delayed-fluorescence materials, including TADF materials, are described in more detail, below.

In some embodiments, the articles and methods described herein use capture emission events having different timing. Advantageously, some embodiments demonstrate how the fusion of information produces enhancements in the sensitivity and fidelity of biological diagnostics, including, but not limited to, lateral flow assays (LFAs) and other assays used to determine, for example if a biomarker is present. Embodiments described herein may be adapted to work with other methods, for example with loop-mediated isothermal amplification (LAMP) for nucleic acid detection and/or vertical flow assays. Different optical features, which may be in the form of images, portions of images (e.g., one or more pixels), and any other signals captured by one or more photosensitive elements, may be captured, in some embodiments, in a way that provides complementary information. For example, detected photons associated with the diagnostic assay may be, in some embodiments, collected within different time domains ranging from those collected immediately, with or without external excitation, to those collected after a time delay (e.g., ranging from 10 nanoseconds to seconds or more) e.g., relative to an optical excitation. Advantageously, the combination of data and/or images taken under these different conditions provides for superior methods as compared to some traditional diagnostic assays. Various classes of materials and processes that enable the different timed processes in such embodiments are also described herein.

In some embodiments, the embodiments described herein may advantageously be used to monitor compliance of a medical subject (e.g., of a subject taking a pharmaceutical agent, of a subject participating in a clinical trial). For example, in some embodiments, the article and/or emissive species may comprise or be associated with an compound from the FDA's "Generally Recognized as Safe" Substances (GRAS) database and/or listed in 21 C.F.R. § 182, each of which are incorporated by reference herein in their entirety for all purposes. By way of example only and without wishing to be limited as such, in some embodiments the GRAS is riboflavin. Such GRAS molecules may be incorporated e.g., into a capsule (e.g., comprising a pharmaceutical agent) such that the molecule may be detected in a fluid produced by a subject (e.g., saliva, urine, etc.).

The term "subject," as used herein, refers to an individual organism such as a human or an animal. In some embodiments, the subject is a mammal (e.g., a human, a non-human primate, or a non-human mammal), a vertebrate, a laboratory animal, a domesticated animal, an agricultural animal, or a companion animal. In some embodiments, the subject is a human. In some embodiments, the subject is a rodent, a mouse, a rat, a hamster, a rabbit, a dog, a cat, a cow, a goat, a sheep, or a pig.

In an exemplary set of embodiments, an identity or characteristic of a chemical and/or biological species (e.g., reaction, presence, etc.) is determined by combining a first and second electromagnetic radiation signal. In some embodiments, the first signal comprises at least a first photon emission event. In some embodiments, the second signal comprises at least a second photon emission event. In some embodiments, the first photon emission event and the second photon emission event may occur over different time scales. For example, in some embodiments, the first photon emission event may occur during less than or equal to 10 nanoseconds of an excitation event that caused the first photon emission event. In some embodiments, the second photon emission event may occur at least 10 nanoseconds after the excitation event that caused the second photon emission event.

In some embodiments, the steady-state photon emission occurs while an emissive material is being continuously excited by a light source that stable and/or static (e.g., static relative to the rate at which a photon emission is collected). In some embodiments, a light source could be flickering at a very high frequency, which on average will produce a relatively static excitation over the time period that a photon emission is collected. In some such embodiments, the emissive material produces a relatively constant intensity emission. In some embodiments, the steady-state nature of the emission is substantially lost within less than or equal to 10 nanoseconds (e.g., less than or equal to 10 nanoseconds, less than or equal to 8 nanoseconds, less than or equal to 6 nanoseconds, less than or equal to 4 nanoseconds, less than or equal to 2 nanoseconds, less than or equal to 1 nanosecond, less than or equal to 0.5 nanoseconds) after removal of the excitation that caused the emission. In some embodiments, the non-steady state photon emission comprises a continued emission of photons from an emissive material, where the continued emission occurs at least 10 nanoseconds (at least 10 ns, at least 20 ns, at least 50 ns, at least 100 ns, at least 200 ns, at least 500 ns, at least 1 µs, at least 10 µs, at least 50 µs, at least 100 µs, at least 500 µs, at least 1 ms, at least 5 ms, at least 10 ms, at least 50 ms, at least 100 ms, at least 500 ms, at least 1 s, at least 2 s, at least 3 s, at least 4 s, at least 5 s, at least 6 s, at least 7 s, at least 8 s, at least 9 s, or at least 10 s) after the excitation that caused the emission is removed. For example, in some cases, after removal of the excitation that caused the emission, the intensity of the emission may change (e.g., decrease, increase) and/or is in a non-steady-state.

Emissions, as described herein, generally refer to photons produced in any way (e.g., including the product of fluorescence, phosphorescence, chemiluminescence, scattering, and/or reflection) where the photons defining the emission are measured in the system/process of the invention. In some embodiments, the first emission event is produced (e.g., in part, in whole) by a species which may be isolated or in a mixture, including a minor component in a mixture, where the species has a less than 10 nanosecond excited state lifetime. For example, in some embodiments, the first photon emission event comprises an emission from an emissive species having an excited state lifetime of less than or equal to 10 nanoseconds, less than or equal to 8 nanoseconds, less than or equal to 6 nanoseconds, less than or equal to 4 nanoseconds, less than or equal to 2 nanoseconds, less than or equal to 1 nanosecond, less than or equal to 0.5 nanoseconds. In some embodiments, the first photon emission event comprises an emission from an emissive species having an excited state lifetime of greater than 0.1 nanoseconds, greater than 0.5 nanoseconds, greater than 1 nanosecond, greater than 2 nanoseconds, greater than 4 nanoseconds, greater than 6 nanoseconds, or greater than 8 nanoseconds. Combinations of the above-referenced ranges are also possible (e.g., less than or equal to 10 nanoseconds and greater than 0.1 nanoseconds). Other ranges are also possible.

In some embodiments, the first photon emission event comprises a steady-state emission (e.g., a steady-state photon emission event). Those of ordinary skill in the art would understand, based upon the teachings of the specification, that the first signal may comprise reflection (e.g., reflected electromagnetic radiation, scattered electromagnetic radiation) such that the first photon emission event is a result of reflection. Signals comprising reflection are described in more detail, below.

In some embodiments, the first photon emission event and the second photon emission event are caused by the same excitation event. In some embodiments, the first photon emission is caused by a first excitation event and the second photon emission is caused by a second excitation event, different than the first excitation event (e.g., different in wavelength, different in intensity, starting and/or occurring at different times, occurring for different lengths of time, oscillating in intensity as a function of time).

In some embodiments, the first photon emission event corresponds to a steady-state emission (e.g., caused by the excitation event).

In some embodiments, at least a portion of the first photon emission event occurs substantially instantaneously (e.g., in response to an excitation event that causes the first photon emission event). In some embodiments, at least a portion of the first photon emission event occurs within less than or equal to 10 nanoseconds, less than or equal to 8 nanoseconds, less than or equal to 6 nanoseconds, less than or equal to 4 nanoseconds, less than or equal to 2 nanoseconds, less than or equal to 1 nanosecond, less than or equal to 0.5 nanoseconds of the excitation event that causes the first photon emission. In some embodiments, at least a portion of the first photon emission event occurs within greater than 0.1 nanoseconds, greater than 0.5 nanoseconds, greater than 1 nanosecond, greater than 2 nanoseconds, greater than 4 nanoseconds, greater than 6 nanoseconds, or greater than 8 nanoseconds of the excitation event that causes the first photon emission. Combinations of the above-referenced ranges are also possible (e.g., less than or equal to 10 nanoseconds and greater than 0.1 nanoseconds). Other ranges are also possible.

In some embodiments, the second photon emission event comprises an emission from an emissive species having an excited state lifetime (e.g., an emissive time period) of at least 10 ns, at least 20 ns, at least 50 ns, at least 100 ns, at least 200 ns, at least 500 ns, at least 1 µs, at least 10 µs, at least 50 µs, at least 100 µs, at least 500 µs, at least 1 ms, at least 5 ms, at least 10 ms, at least 50 ms, at least 100 ms, at least 500 ms, at least 1 s, at least 2 s, at least 3 s, at least 4 s, at least 5 s, at least 6 s, at least 7 s, at least 8 s, at least 9 s, or at least 10. In some embodiments, the second photon emission event comprises an emission from an emissive species having an excited state lifetime of 10 s or less, 5 s or less, 2 s or less, 1 s or less, 500 ms or less, 100 ms or less, 50 ms or less, 10 ms or less, 5 ms or less, 1 ms or less, 500 µs or less, 100 µs or less, 50 µs or less, 10 µs or less, 1 µs or less, 500 ns or less, 200 ns or less, 100 ns or less, 50 ns or less, 10 ns or less, 5 ns or less, or 1 ns or less. Combinations of the above referenced ranges are also possible (e.g., at least 10 ns and 10 s or less). Other ranges are also possible.

In some embodiments, the second photon emission event comprises a non-steady state emission (e.g., a non-steady-state photon emission event).

In some embodiments, the second photon emission event occurs at least 10 ns, at least 20 ns, at least 50 ns, at least 100 ns, at least 200 ns, at least 500 ns, at least 1 µs, at least 10 µs, at least 50 µs, at least 100 µs, at least 500 µs, at least 1 ms, at least 5 ms, at least 10 ms, at least 50 ms, at least 100 ms, at least 500 ms, at least 1 s, at least 2 s, at least 3 s, at least 4 s, at least 5 s, at least 6 s, at least 7 s, at least 8 s, at least 9 s, or at least 10 s after removal of the excitation event that caused the second photon emission event. In some embodiments, the second photon emission event occurs. 10 s or less, 5 s or less, 2 s or less, 1 s or less, 500 ms or less, 100 ms or less, 50 ms or less, 10 ms or less, 5 ms or less, 1 ms or less, 500 µs or less, 100 µs or less, 50 µs or less, 10 µs or less, 1 µs or less, 500 ns or less, 200 ns or less, 100 ns or less, 50 ns or less, 10 ns or less, 5 ns or less, or 1 ns or less after removal of the excitation event that caused the second photon emission event. In some embodiments, the second photon emission event occurs. Combinations of the above referenced ranges are also possible (e.g., at least 10 ns and 10 s or less). Other ranges are also possible.

In some embodiments, removal of the excitation event refers to a decrease in intensity and/or change in wavelength of the electromagnetic radiation source that produces the excitation event. In some embodiments, removal of the excitation event comprises complete removal (e.g., turning off) of the excitation source.

Generally, smartphones provide access to both high-resolution cameras and powerful computational resources for image analysis. To this end, smartphone readers have been developed to improve the accuracy of colorimetric assays; however, these approaches leverage temporally static data—the image is collected solely from reflected/scattered light. For example, and without wishing to be bound by theory, reflected/scattered light is generally time invariant with a static light source and is said to be steady-state. With suitable excitation and potentially filters a steady state fluorescence signal may also be obtained, in some embodiments. As described herein, the inventors discovered and recognized that combining e.g., the reflected/scattered and emitted light in a time-sequenced (steady state and non-steady state) processes provides access to richer information which may be used to significantly improve the sensitivity and accuracy of assays. For example, fusing steady-state and non-steady-state emission information in accordance with some embodiments dramatically enhances assay fidelity beyond what is possible with current smartphone and portable reader methods resulting in improved biological diagnostics.

As described herein, in some embodiments, optical detection of one or more emissions is performed using a smartphone, optionally in combination with separate excitation sources or a single excitation source.

In some embodiments, the excitation source(s) are a component of the consumer electronic device (e.g., integrated with the consumer electronic device).

Advantageously, such systems described herein provide for more robust assays with increased sensitivity compared to assays that require visual analysis or utilize simple readers configured to analyze only a single type of signal. The term "signal" as used herein refers to a measurement of the intensity of light, it impinging on the reader and also a processed version (e.g., an image) of such measurements. In some embodiments, the wavelength of the light, its polarization, and/or its spatial distribution provide key information (e.g., a characteristic or identity of an emissive species). Embodiments described herein are not generally limited to use with a smartphone and any suitable reader including electronics and optics that are used to capture and process emissions from an assay in accordance with the techniques described herein may instead be used. In some embodiments, there are advantages to using a smartphone (or other consumer electronic device) as it leverages existing hardware, contains an array of onboard sensors for data fusion, provides facile location tracking and communications, and that smartphones have become ubiquitous.

One of ordinary skill in the art would understand, based upon the teachings of this specification, that a smartphone or related equipment may not necessarily capture an image, and/or might not even have the ability to create an image. In some embodiments, the presence of a steady-state and non-steady state emission, from one or more species, provides data from at least the non-steady state emission signal, and optionally from both the steady state (photon) emission signal and the non-steady state (photon) emission signal (e.g., fusion of signals), which corresponds to desired data (e.g., corresponding to a characteristic and/or identity of a desired species).

In an exemplary set of embodiments, a smartphone reader modality in lateral flow assays (LFAs) is colorimetric detection. Although this method may be used with light sources, the images are generally created as a result of subtractive color and the smartphone is configured to detect reflected (or scattered) light. In some cases, reflected light may comprise a relatively noisy signal. Without wishing to be bound by theory, such a noisy signal may be due to the presence of reflected light from elements beyond the relevant signal for which the diagnostic is based. In some cases, these stray non-specific signals may vary e.g., as a consequence of the direction of the incident light and dynamic changes in incident light intensity. Colorimetric signals nevertheless can provide other useful information including images of the assay cartridge, markers that may be used for alignment, text, numbers, pictures, logos, bar codes, or QR codes. Images, in some embodiments, are the result of subtractive color, wherein part of the electromagnetic spectrum is absorbed. Colorimetric analysis may be used, in some cases, with materials that are substantially reflective and/or produce color by reflection of particular wavelengths. In the case of colorimetric reflected light, there is generally no detectable delay between the light interacting with the dye, nanoparticles, or reflectors in the assay and the arrival of the light at the reader (smartphone). An exemplary suitable alternative to pure colorimetric readers are those that make use of luminescent signals. For example, to create an luminescent state, a photon may be absorbed by the material to create an excited state that has a finite lifetime. There are different types of luminescent materials and excited state lifetimes that are used to create signals.

Some embodiments described herein generally are related to methods of fusing different types of signals and the time sequences thereof to create methods to read biological assays in ways that provide for superior sensitivity and accuracy to existing methods. According to some embodiments, a component of a system (e.g., an image sensor, a photosensitive component) detects at least a portion of a detectable emission produced by an emissive species over the time period wherein the emitting species is being illuminated (excited). In some cases, the component detects light after the illumination is removed over an emission time period the length of which is related to the emission lifetimes of the emissive species in the composition. A person of ordinary skill in the art would understand that an emissive species may produce a detectable emission through, for example, phosphorescence or fluorescence. An emissive species may also be detected by reflected/scattered light in the case that it has an absorption in the regions of the electromagnetic spectrum that are being excited. It is the case that many emissive species have color and hence may be detected in this way. A person of ordinary skill in the art would also understand that an emission time period or emission lifetime characterizes the rate at which an emissive species emits electromagnetic radiation after any excitation radiation has been removed (e.g., after a pulse of electromagnetic radiation has been emitted by an excitation component).

In some embodiments, prompt-fluorescent signals are generated by emissive materials that have excited state lifetimes less than or equal to 10 nanoseconds (e.g., less than or equal to 10 ns, less than or equal to 5 ns, less than or equal to 2 ns, less than or equal to 1 ns). Prompt-fluorescent materials represent the most common type of emissive materials, and dye molecules displaying prompt-fluorescence are widely available. Although the excited state of these materials has a measurable lifetime, the times are sufficiently short such that resolution of signals based on lifetime is not readily performed with the inexpensive hardware of a smartphone. To collect prompt-fluorescence with a smartphone the materials would generally be simultaneously excited by a light source, while the image is collected by standard optical detectors (for example CMOS imaging chips) commonly found in digital cameras or smartphones. When the excitation is removed the materials, in some embodiments, will relax within a few nanoseconds and the post illumination signal will go away before a time gated detection with these devices can capture substantial amounts of emitted light. As a result, to accurately record a prompt-fluorescence signal with a smartphone of digital camera, the excitation may be sustained during the duration of the measurement. This effect generally yields a constant (steady-state) emission, provided the excitation source is stable and the emissive molecule doesn't optically/chemically degrade (irreversibly bleach out) over the timescale of the measurement.

In the context of this invention the measurement of an emissive signal coming from a source with a lifetime that is less than or equal 10 nanoseconds in duration is detected while simultaneously exciting the emissive material and is said to be a steady-state measurement.

An exemplary fluorescent material that displays an excited state lifetime longer than 10 nanoseconds and up to 50 microseconds in the context of this invention is said to be a delayed-fluorescence signal. Similar to prompt-fluorescence, the major component of the emission generally comes from the relaxation of a singlet (electron spin paired) excited state and generally doesn't require a spin interconversion during the emission process. Organic materials, which generally lack heavy atoms from the third row or lower in the periodic table, are capable of delayed-fluorescence provided there is a mechanism for the delay. The delay mechanisms may be, in some cases, the result of equilibrium processes that occur in an excited material. One mechanism is known as thermally activated delayed-fluorescence (TADF). TADF materials are described in more detail, below. In this process, without wishing to be bound by theory, a material will have singlet (spins aligned antiparallel) and triplet (spins aligned parallel) excited electronic states that are sufficiently close in energy that they are in thermal equilibrium under ambient conditions. In the vast majority of materials, the triplet state may be lower in energy and hence for a majority of the time the material's excited state resides in the triplet state. In materials that lack heavy atoms, there is generally insufficient spin-orbit coupling to facilitate efficient direct emission from the triplet state, and hence the triplet state is a long lived low emissive (dark) state. However, and without wishing to be bound by theory, in TADF materials there is generally an equilibrium wherein the excited state can convert back to the singlet and then rapidly relax to the ground state by emitting a photon. The time spent in the triplet produces a delay and hence a delayed-fluorescence with excited state lifetimes larger than 10 nanoseconds up to 50 microseconds. Other methods to create delayed-fluorescence are also possible including, for example, processes wherein charge separated states are generated by electron transfer or alternatively conformational changes such as a twisted charge separated excited state. In some embodiments, the recombination of the charges can create a singlet state after a delay that yields delayed-fluorescence. The upper limit on the time scale of delayed-fluorescence is not a firm number, but in practice there are often competing non-emissive thermal relaxation processes. These processes depopulate the excited state under ambient conditions and thereby result in relatively very weak signals being produced at longer timescales because only a small fraction of the excited state will survive for that length of time with competing relaxation processes. The competing relaxation methods may be attenuated by lowering the temperature or placing the emissive species in a rigid matrix.

Delayed-fluorescence as described herein may, in some embodiments, be read (detected) by a smartphone, digital camera, or equivalent image capture device providing the detector used for image capture can collect data over the time period with sufficient emission intensity to allow detection. For example, in this process the optical input (excitation) used to create excited states with lifetimes greater than 10 nanoseconds is time synchronized with the image capture hardware using pulsed light flashes, rapid flashing, or frequency modulation of the excitation source. It is important to note that the time synchronization between the image capture and the excitation in the context of this invention is not necessarily absolute, but may be relative. In other words, in some cases, there may be no need for a precise absolute timing of pulses or the phase of the frequency of a modulated excitation and the rate of image capture of the image capture device. For example, the frequency of a pulsed or modulated light source need not be commensurate with the image capture device. The signals may be affected, in some cases, by both the time periods of the image capture and the excitation. In some embodiments, relative times and/or frequencies may be deduced computationally Advantageously, such a feature negates the need for precision in the absolute timing of these events. Complex excitation profiles may be applied that involve mixtures of these processes. In the context of this invention, time synchronization of the input exciting light generally refers to light intensity that varies as a function of time. In some embodiments, the detection system is capable of and configured to detect(ing) these non-steady state process to extract information pertaining to the time domain. These methods may allow, in some cases, for time phased (delayed) capture of the emitted light such that the delayed emission may be selectively detected and background signals may be eliminated. In some embodiments, the emitted light is detected after the excitation light is turned off and when shielded from ambient (stray light) the delayed signal is captured on a substantially or completely dark background. Alternatively, the time variance of the exciting light may be used to select signals coming from the emissive state of interest in a complex background containing stray and scattered light.

A number of suitable materials have highly emissive excited triplet states, which in the context of this invention display prompt-phosphorescence with excited state lifetimes of 10 nanoseconds to 50 microseconds (e.g., 10 ns to 20 ns, 10 ns to 50 ns, 10 ns to 100 ns, 10 ns to 500 ns, 10 ns to 1 µs, 10 ns to 5 µs, 10 ns to 10 µs, 10 ns to 50 µs, 10 ns to 100 µs, 10 ns to 500 µs, 10 ns to 1 ms, 10 ns to 5 ms, 10 ns to 10 ms, 10 ns to 50 ms, 10 ns to 100 ms, 10 ns to 500 ms, 10 ns to 1 s, 10 ns to 5 s, 10 ns to 10 s, 50 ns to 100 ns, 50 ns to 500 ns, 50 ns to 1 µs, 50 ns to 5 µs, 50 ns to 10 µs, 50 ns to 50 µs). In this context, the materials contain heavy atoms that interact with the excited state. The heavy atom effect as described herein generally refers to the ability of these elements to provide spin-orbit coupling sufficient to allow an excited state to undergo a facile spin interconversion during the emission process. In this method a triplet excited state relaxes directly to a singlet ground state with the emission of a photon. The initial excited state that is populated by light absorption will generally be a singlet in nature, because, without wishing to be bound by theory, singlet to singlet electronic transitions are much more efficient in the absorption of light. Once the first excited singlet state of a material is created, the heavy atom effect will, in some embodiments, produce fast intersystem crossing and create a lower energy triplet state. Without wishing to be bound by theory, for triplet states to directly emit light, one of the electron spins may flip during the emissive relaxation to the singlet ground state and the spin-orbit coupling provided by the heavy atoms can make this process highly efficient. Heavy atoms are generally defined as elements that have a nuclear core structure larger than neon. For example, phosphorous, sulfur and chlorine may all, in some contexts, produce some level of a heavy atom effect. However, heavier elements with nuclear cores bigger than argon may generally yield larger heavy atom effects. The heavy atom effect may also be enhanced, in some cases, by attaching additional heavy atoms to a molecule. For example, the attachment of halogens such as Cl, Br, or I to aromatic molecules with the addition of more halogens enhancing spin interconversion processes, may result in this effect. A number of transition metal containing materials display prompt-phosphorescence and there are many examples of materials that contain metal-carbon bonds (organometallics) as well as materials that contain metal-nitrogen, metal-sulfur, metal-phosphorous, or metal-oxygen bonds (metallo-organics) that connect them with electronically delocalized organic molecular subunits and are suitable for use with the embodiments described herein. The heavy atoms also need not be covalently bound to the materials and physical contact between the electron clouds of the heavy atoms and emitting materials may also give prompt-phosphorescence. Similar to delayed-fluorescence the emissive signals may be read by a smartphone, digital camera, or equivalent image capture device when paired with a time sequenomptced excitation.

Another class of molecules relevant to this disclosure are those displaying prompt-phosphorescence. In order to have sufficient radiative rates for the conversion of the triplet excited state to the singlet ground state, which generally requires a spin interconversion process, most materials need a spin orbit coupling component that is afforded by electronic coupling with heavy elements. It is possible to obtain efficient prompt-phosphorescence in organic compounds bearing heavy atoms. One such exemplary material is Erythrosin B shown below, which has four iodine atoms attached to the chromophore that promotes phosphorescence. Advantageously, this material is particularly attractive as it is used as a food dye and is considered non-toxic. However, embodiments described herein are not intended to be limited as such and other materials are also possible. Erythrosin B generally displays two different forms and in its deprotonated anionic state is emissive and excitable by the light sources associated with smartphones. Upon protonation to its neutral state, the most favored isomer is one that lacks extended conjugation and is non-emissive. There are other related halogenated dyes, such as the bromide derivative of Erythrosin B known as Eosin, that display similar behavior. Additionally, Rose Bengal (4,5,6,7-tetrachloro-2',4',5',7'-tetraiodofluorescein) has a closely related structure with the addition of four chlorine atoms to the pendant phenyl. The acid-base reactivity of these systems can be used to switch between emissive smartphone excitable and non-emissive materials that cannot be excited by a smartphone. This property may be used, for example, in applications for the detection of molecular signatures, thermal history, ionizing radiation, physical alteration, mechanical stress, fractures, oxygen, moisture, and/or UV radiation.

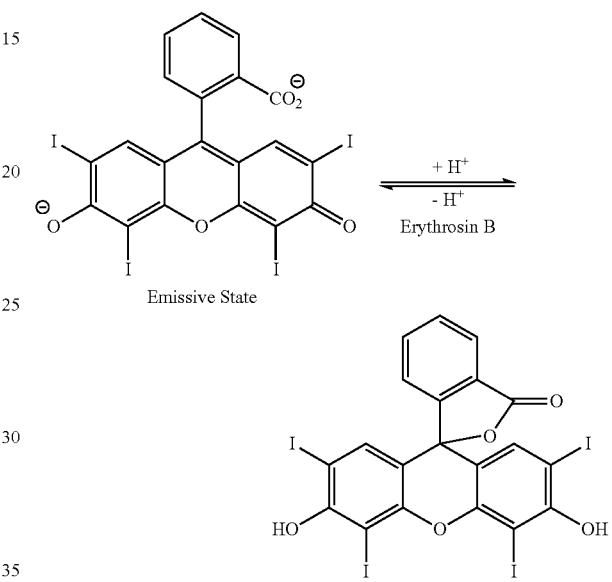

Although the heavy iodine atoms are covalently bound to chromophores in Erythrosin B, non-covalent interactions may also give significant phosphorescence. For example, physical mixtures of an organo-iodide material and another chromophore of interest that may be excited by the light source of a smartphone can display phosphorescence, in some embodiments. These interactions can occur through van der Waals type interactions or stronger interactions (e.g., using what is generally referred to as halogen bonding). In this latter scheme, without wishing to be bound by theory, a halide (typically iodine) generally behaves as a Lewis acid and forms a weak complex with the Lewis basic groups of the selected chromophore. Non-covalent associations may be promoted in solids and thin films and thereby produce higher phosphorescence intensities, which again can be modulated by interaction with their surroundings or different stimuli.

The incorporation of halides, such as bromine and iodine, into organic chromophores may be an advantageous approach to create different organic phosphors, in some embodiments. When the lifetimes are very long, it may be advantageous for the materials to be located in a rigid matrix, e.g., which can optionally be microcrystals of the emissive material in some cases. Alternatively, such materials may be embedded in other molecular polymeric or inorganic hosts. Examples of halogen containing phosphors that can be excited by the light sources of a smartphone are shown below. It should be noted that the sulfur groups may also produce heavy atom effects and thereby promote phosphorescence.

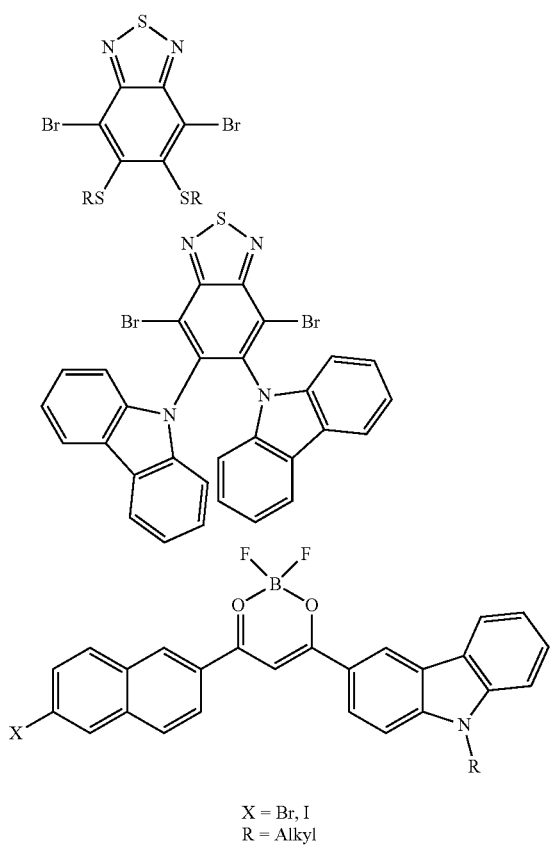

X = Br, I
R = Alkyl

Carbon dots are another class of emissive materials which may be suitable for use with the embodiments described herein. These materials are complex and their chemical structures are non-uniform and as a consequence are not precisely known. They are, in some cases, produced by different types of thermolysis and often contain nitrogen and oxygen heteroatoms. The compositions thereof may be determined by the starting materials and the thermolysis or combustion method. Carbon nanodots may be produced, for example, by laser-ablation of carbon materials, electrolysis of carbon materials, heating organic materials at high temperature, pyrolysis of nanocomposites or organic materials with other materials including silicates, hydrothermal/solvothermal treatments of organic materials, and microwave heating of organic materials. The fact that carbon dots are often created under high temperature may, in some cases, generally impart high thermal stability to these materials. As such, carbon dots are often suitable for relatively high temperature manufacturing processes or in materials, such as engine oil, that will encounter high temperatures. In some cases, such materials display what is generally considered to be singlet emission (fluorescence) with excited state lifetimes longer than 10 nanoseconds. These longer singlet emissions are generally referred to as delayed-fluorescence. It is possible that different symmetry electronic states within the materials produce sufficient spin-orbit coupling to allow for prompt-phosphorescence. In other cases, the lifetimes may exceed those typically associated with prompt-phosphorescence. In these systems, the spin orbit coupling is generally not strong and the radiative relaxation of the triplet states is slow. However, without wishing to be bound by theory, as a result of their rigid character, other non-radiative processes are attenuated such that significant emission is observed in the delayed-phosphorescence time regime. Alternatively, such materials may undergo TADF type processes as a result of thermal equilibrium between closely spaced singlet and triplet states. The energy levels in carbon dots generally have considerable dispersion and some variants can be effectively excited by the light sources of smartphones to create steady-state photon emission events as well as non-steady-state photon emission events.

A general class of prompt-phosphorescent materials include, for example, organometallic compounds that have what are known as ortho-metallated ring structures. Such materials generally comprise cyclic ring structures that involve an organic ligand and have at least one carbon-metal bond. Such a combination may, in some cases, give rise to favorable electronic states and a strong heavy atom effect from the transition metal. There are a number of materials that can be readily excitable by the light sources of smartphones. Non-limiting examples based on Os, Ir, and Pt are described herein. Such compounds can be optionally substituted to produce the desired properties and compatibilities. Similar ligands may be used to create other prompt-phosphorescent compounds with these metals and others. In some cases, the ortho-metalated compounds are selected to be stable under ambient conditions. For example, heavier transition metal elements and post transition metal elements such as Pb and Bi may provide stable carbon-metal bonds.

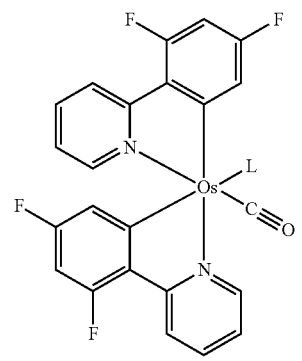

L = P(Ph)$_2$CH$_3$, P(Ph)(CH$_3$)$_2$

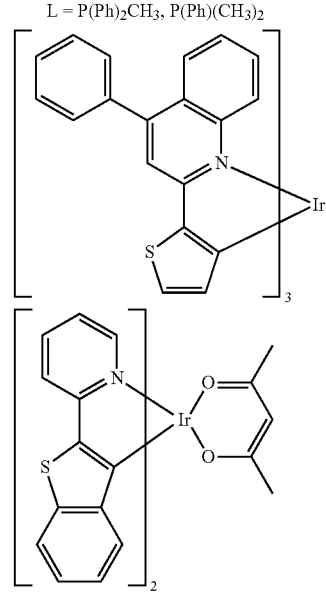

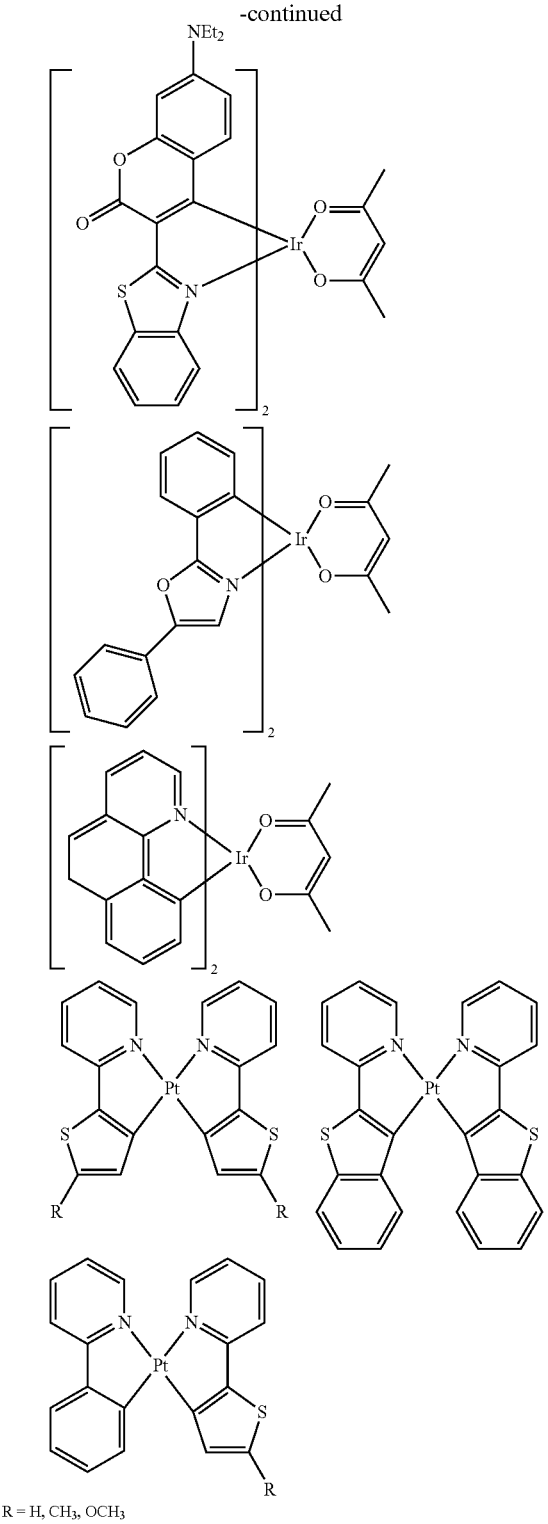

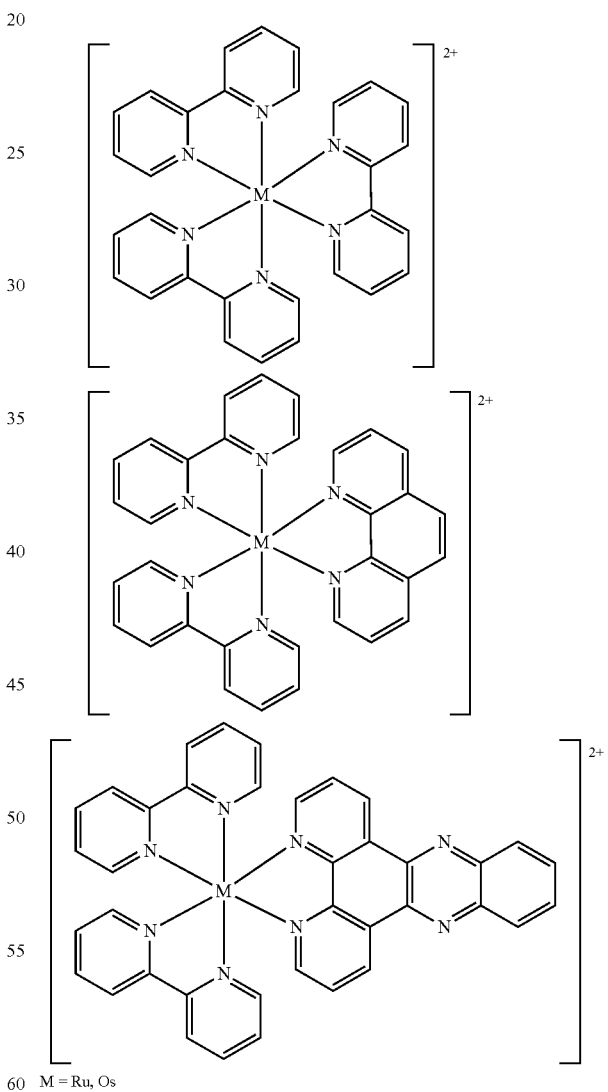

groups, different materials may be produced that are excitable by the light sources of smartphones.

Metallo-organic compounds, wherein metals are bound to organic ligands through non-carbon-based groups, may also display efficient prompt-phosphorescence. Non-limiting suitable examples are based on Ru and Os and the compounds described below are non-limiting examples of prompt-phosphorescent compounds that may be excited by smartphone light sources to create non-steady-state photon emissions. There are many other potential variations of compounds containing nitrogen bound ligands to transition metals that display prompt-phosphorescence and are excitable by the light sources of smartphones (or other consumer electronic devices). The charged nature of the compounds shown allow, in some embodiments, for electrostatic assembly processes and/or the use of functional counterions that can enable specific applications.

M = Ru, Os

Metallo-porphyrins are another suitable class of metallo-organic materials that display prompt phosphorescence and can be excited by the light source of a smartphone to create non-steady-state photon emission events. Porphyrins have a rich coordination chemistry and may be complexed by many There are also other classes of organometallic emitters that can be designed to have absorbances capable of being excited by the light sources of smartphones. Carbon compounds wherein the C-M bonds are strong are non-limiting examples. For example, stable Au and Pt compounds containing "M-CC—Ar" linkages are generally very stable and many are emissive. By selecting appropriate alkynes and Ar different transition metals. The porphyrins can be designed to be anionic and these compounds can create electrostatic assemblies. Pd and Pt porphyrins, for example, display high sensitivities to oxygen quenching, thereby enabling emissive sensors to be produced.

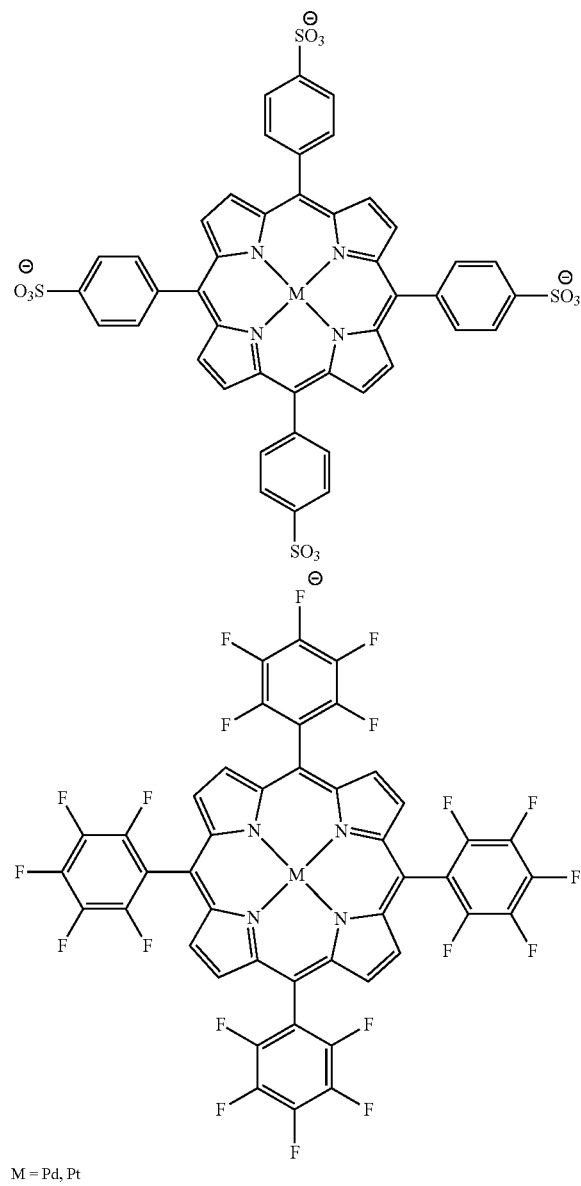

M = Pd, Pt

Other porphyrins are also possible and may be excited with the light source of a smartphone (or other consumer electronic device). The base structure may be substituted with a wide variety of functionalities at all of the ring carbon centers. For example, the pyrrole rings may be halogenated and oxygenated, in some embodiments. Oxygenation may give rise to systems having ketones such as the non-limiting examples shown below, which can display prompt-phosphorescence and are generally capable of creating non-steady-state photon emission events. Although Pt and Pd porphyrin compounds are described herein, a number of other metals and in some cases even the metal free porphyrins and their derivatives may be used as smartphone excitable emissive elements. Like all of the other chromophores, these materials may be used, in some embodiments, to produce steady-state photon emission events.

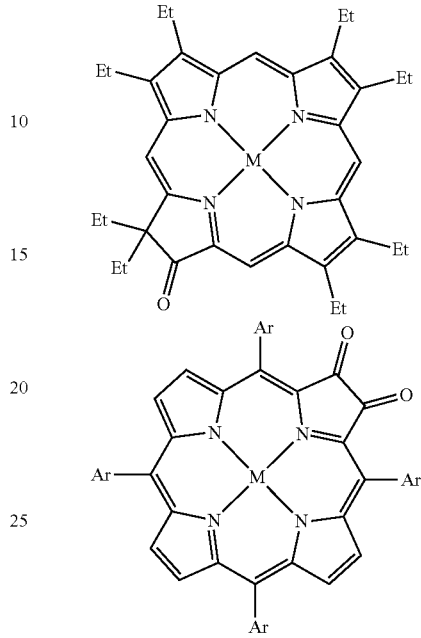

Other suitable classes of prompt-phosphorescent metallo-organic compounds and the metals may be bound to the organic ligands by groups other than nitrogen. For example, they may be bound through oxygen, phosphine, or sulfur, in some cases. Those skilled in the art would understand, based upon the teachings of this specification, that a number of potential binding modalities between the metals and organic ligands may be used to produce electronic transitions with sufficient coupling to enable effective phosphorescence. It is also possible for carbophilic metals, in some embodiments, to bind directly to the pi-systems of organic chromophores and facilitate phosphorescence. For example, silver ions may be useful as carbophilic cations and to create phosphorescent compositions.

Another suitable type of emissive material suitable for use with embodiments described herein display what is generally referred to in the context of this invention as delayed-phosphorescence, which is defined as an emissive material having an excited state lifetime of more than 50 microseconds (e.g., at least 50 μs, at least 100 μs, at least 500 μs, at least 1 ms, at least 5 ms, at least 10 ms, at least 50 ms, at least 100 ms, at least 500 ms, at least 1 s, at least 2 s, at least 3 s, at least 4 s, at least 5 s, at least 6 s, at least 7 s, at least 8 s, at least 9 s, or at least 10 s). In this case, and for all of the emissive materials discussed in the context of this invention, the ranges of excited state lifetimes stated are not exclusive. For example, there will be materials that span the excited state lifetimes defined for prompt-phosphorescence and delayed-phosphorescence. To achieve such long lifetimes the excited states of delayed-phosphorescent materials must not have other processes that cause rapid non-radiative relaxation. For many emissive materials the rate of non-radiative processes will deplete the excited states prior to emitting a significant fraction of the photons. As such, in some delayed-phosphorescent materials the emissive sites are embedded in very rigid environments such as solid-state inorganic matrices, with a number of inorganic phosphors displaying delayed phosphorescence. Other constructions that display delayed-phosphorescence include emissive sites based on heavy elements that have f-orbitals as their frontier orbitals, such as elements from the lanthanide and actinide series. In these materials the electron clouds (defined by their orbitals) involved in the emission are contracted and the electrons are held sufficiently close to the nuclei that they do not interact strongly with the electrons of the coordinating ligands. This feature tends to insulate the excited states from the surrounding dynamics and vibrations that contribute to non-radiative relaxation of the excited states. However, these materials are not completely immune from their environment and care must be taken to design emissive species that produce bright emissions in the context of a biological diagnostic test. For example, in many cases the coordination of water ($H_2O$) to the metal ions can give rise to rapid relaxation. In some embodiments, substitution of $H_2O$ in these compositions for $D_2O$ (heavy water) results in a reduction in the non-radiative rates and an increase in the intensity of the delayed phosphorescence. Typical elements displaying delayed phosphorescence include but are not limited to europium, terbium, gadolinium, and erbium. Similar to delayed-fluorescence and prompt-phosphorescence, delayed-phosphorescence may be selectively detected by a smartphone, digital camera, or equivalent image capture device when paired with time synchronized excitation of the material to create an emissive state.

In some embodiments, a light signal that may be of use in these methods is that of chemiluminescence. In this process a chemical reaction is generally triggered either by the addition of reagents or the in situ activation of a reaction pathway to give an excited state. In this case, the timing is caused by a trigger that releases a reagent or activates a pathway for chemiluminescence. The trigger may be part of the biological assay or performed at the end of the assay. The trigger could be performed physically, photochemically, or by an electrical impulse. There is, in some embodiments, no need for an optical excitation in this case and the signal generated after the trigger of the chemiluminescence will be collected in steady-state mode by the smartphone, digital camera, or equivalent image capture device.

The different optical signals described above and herein may be used in a number of combinations to enhance the sensitivity and fidelity of biological diagnostic assays including lateral flow, vertical flow and LAMP assays. Advantageously, the methods and signals described herein serve to minimize the effects of small movements (jitter) and/or reduce optical noise e.g., caused by non-specific signals and stray light. The ability to combine images may, in some embodiments, need precision in the alignment of the images that may be provided by optical (fiducial) markers, reference signals, image analysis, information about the assay, and computational methods. The combination of images collected from different optical elements collected under alternative illumination or collected over various time domains is used to determine and mitigate optical noise.

In some embodiments, color-based (colorimetric) signals are created by either subtractive color or selective reflection of light and may be collected under ambient conditions or with additional illumination. This steady-state signal is time invariant, without wishing to be bound by theory, if, for example, the incident light remains constant. In some embodiments, time sequencing between the incident light and detected signal is not used. In some cases, color changes will accompany the biological diagnostic as a result of a reaction or the localization of a colored material during the assay. The colorimetric signal may be used in conjunction with luminescent signals that are all collected e.g., by the smartphone, digital camera, or other image capture device or component. The images may alternatively, in some embodiments, encode information about the assay including instructions as to the nature of the assay, the method that should be used to optimally read the assay, and/or the physical location on the device where the signals of interest are expected. For example, the image may comprise fiducial markers. Images may also be collected, in some embodiments, that provide critical information for calibration and can for example include intensity and/or lifetime data from reference signals that are invariant in the assay. The relative intensities or lifetimes of the assay signals relative to these reference signals may be used, in some embodiments, to account for other differences that can limit the accuracy of the assay. For example, it could be that the light source used in one assay is brighter than that of another. An internal reference may be used, in some cases, to account for such variance and provide greater precision and quantitation of the signal. The references may be read separately, before or after measuring the measurement of the signal associated with detecting the signal of interest, or alternatively could be collected simultaneously from the same image. In some such embodiments, the reference signal is separated from the signal associated with the detection event, by having a different emission wavelength, different location in the image (assay), and/or different excited state lifetime.

Collecting and combining information from multiple images and spatial, wavelength, and time domains advantageously allows for a greater ability to discern signals from background noise and quantitate signals, in some embodiments. For example, biological diagnostic assays may be conducted in environments that have stray light. In some such cases, the ability of these methods to differentiate signals from background will advantageously allow for computational methods to be applied that increase the assay's sensitivity and fidelity. In some cases, the colorimetric signal is collected in response to (external) illumination. In some embodiments, such illumination may be produced by the flash of the same smartphone that is reading the assay. In other cases, the illumination is provided by an additional light source. In some cases, the direction of the light source may be used to provide a signal that minimizes or takes advantage of reflections/scattering or differences in the optical properties of the assay to enhance the signal. In some cases, the signals read may vary with the polarization of the incident and/or detected light. In some embodiments, information from the color and its chromaticity may be collected, which may be measured in different ways including, for example, the position on a diagram, the relative intensity of the different color pixels collected with a smartphone, or the intensity as a function of wavelength.

A colorimetric signal may be used, in some embodiments, in conjunction with one or more different luminescent signals. For example, when combined with prompt-fluorescence, both signals may be acquired in a steady-state mode. In some embodiments, the colorimetric signal may be collected under white light illumination and the prompt-fluorescence may be differentiated by collecting this signal under a different optical stimulation wherein the luminescent material is excited. This type of process may be used to provide complimentary information. For example, it is possible, in some cases, to selectively excite the prompt-fluorescent material by applying a light source of a particular wavelength.

In some embodiments (e.g., to create a high contrast fluorescence signal), the light used to excite the prompt-fluorescent material is selected such that it is not detected by the smartphone, digital camera, or other detector. In some cases, there may be a detection advantage if the fluorescent signal is detected on a dark background. For example, the excitation may be performed, in some cases, using light that may be excluded from the detection device by added filters, an absorptive support, or by the intrinsic absorption of the optical elements (lenses) in the detection system. One exemplary way to accomplish this feature is, in some embodiments, to use higher energy ultraviolet (UV) light to excite the fluorescent materials. In some cases, a diagnostic assay may be read using a colorimetric signal under either ambient light or under white light illumination and then combined with the prompt-fluorescence signal. Advantageously, the colorimetric signal need not be the direct result of a biomolecular detection event but could (in addition or alternatively) provide information about the location wherein the fluorescent signals are expected and/or provide fiducial markers that may be used to identify the areas that are to be analyzed. Such image(s) may be collected with or without the aid of illumination and/or in rapid succession the prompt-fluorescent material is excited and the signal is collected. The combined signals may be used, in some embodiments, to ensure accurate registration of all signals (mitigate any jitter and provide calibration) as well as compensate for other optical noise, thereby creating an improved signal. In some cases, the measurement will be made using a box or other device to prevent stray light from the surroundings from impinging on the assay. In some cases, both the colorimetric and fluorescent images will be collected under illumination, with the former using white light and the latter using light that will excite the prompt-fluorescent materials, but is filtered from the detection device, comprising a smartphone, digital camera, or other optical detection system. The prompt-fluorescence signals may also be produced, in some cases, by excitation with a white light source and optical filters positioned before the detector may be used to reject the white light background. The prompt-fluorescence signals also need not be directly related to a biological event but could also be used to provide fiducial spatial or calibration information. Colorimetric signals may be used, in some embodiments, in conjunction with chemiluminescent signals. The chemiluminescent signal may not require illumination in such embodiments, and advantageously may be detected in a background that excludes stray light.

Colorimetric, prompt-fluorescence, or chemiluminescence signals may also be used in conjunction with delayed-fluorescence, prompt-phosphorescence, or delayed-phosphorescence, in some embodiments. For example, the delayed-fluorescence, prompt-phosphorescence, or delayed-phosphorescence signals may be selectively detected using time synchronized light excitation in conjunction with the smartphone camera, digital camera, or other detection system. In some cases, the detection of light in these devices makes use of a shutter mechanism that allows for time gated detection of light, as described in more detail, below. Depending upon the lifetime of the emissive species, parameters on the smartphone or equivalent device may be chosen such that a single image may contain information about the lifetime of the emissive species. In this way, for example, the signal may evolve throughout the image capture. With delayed-phosphorescence a smartphone or digital camera that can capture entire images may also be used with a simple delay between the excitation and the image collection. In some cases, the images may be captured by using a video (frame) capture option that is common to these devices. These images, in some embodiments, are combined with other imagery to provide information on the assay, fiducial spatial information, calibration, or complementary signals to produce a robust assay.

In many instances in which images are obtained (one example is taking a photo with a cellphone), a single image is not simply obtained at one moment in time, but portions of the single image are taken at different times (although over a very short time span) to construct the single image. For example, one portion of the image (for example, the top portion) is obtained at a very slightly different time than another portion of the image (for example, the bottom portion). With a cellphone camera, a "shutter" (e.g., an electronic shutter) may block portions of the image from forming at different times depending on location in the image, so that the entire image is not over-exposed, and at any particular time, some portion but not the entire image is being recorded, but over time (very short) the entire image is constructed. With knowledge of when specific portions of the image were obtained, one can identify information about what happened with a subject of that image at those two (or more) different times and/or over the entire time period of image formation (or a portion of that time period). For example, if a feature of an emissive species (chemical or biological species, emissive tag, or the like) changes on the timescale of image formation, then the single image formed may be used to determine something about that change(s). In some embodiments, an entire image (or images) comprise a considerable amount of data that is not relevant to the signals of interest and that analysis may depend on a select number of pixels. In some such embodiments, a select feature or number of pixels may constitute the image and/or information from the measurement. In some embodiments, pixels are combined to produce data that represents the spatial distribution of a signal. For example, an image may reveal a vertical line of signal with regards to a horizontal direction. In this case, the vertical and horizontal are relative directions and not generally absolute. In some embodiments, analysis of the signal may comprise a sum of the intensity of the pixels along the vertical direction. In some embodiments, a plot of these summed intensities in the horizontal dimension provides a method to analyze the total intensity of the line relative to the background. Such an analysis in concert with calibration signals may be used, in some cases, to produce quantitative measurements in assays.

As will be apparent from the description throughout this disclosure, the invention(s) includes many variations of the above description, not limited to any particular type of image, number of images, type of equipment used to obtain an image, etc.

In some embodiments, an article (such as a diagnostic assay) is associated with an emissive material comprising an emissive species. In some cases, the emissive species has an emission lifetime as described above and herein. A person of ordinary skill in the art would understand that suitable emission timelines may be selected, for example, based on the time resolution of the image sensor. For some image sensors, a suitable lifetime may be on the order of milliseconds, while for other image sensors, a suitable lifetime may be on the order of microseconds. Image sensors with faster time responses will generally allow for lifetime-based images to be obtained using emissive species with shorter lifetimes. In some cases, a characteristic of an emissive species (e.g., identity, authenticity, age, quality, purity, presence) may be determined by obtaining an image (or series of images) comprising time-dependent information related to an emissive species. In certain instances, for example, the emission lifetime of an emissive species may be determined from an image (or series of images). Since the emission lifetime of an emissive species may be modified by a number of factors, including but not limited to binding or proximity to other molecules (e.g., water, oxygen, carbon dioxide, carbon monoxide), temperature, pH, and radiation exposure, the measured length of the emission lifetime (e.g., the observed emission lifetime, the emission time period) may provide information regarding a characteristic of an associated article. In some instances, an emissive material comprising one or more emissive species may be used to identify and/or authenticate an associated article.

According to some embodiments, an article (e.g., diagnostic assay) is associated with an emissive material comprising an emissive species. In some embodiments, the emissive species is a chemical and/or biological species. In some instances, an excitation component emits non-steady-state pulsed and/or modulated electromagnetic radiation, at least a portion of which is absorbed by the emissive species. In some cases, a pulsed and/or modulated excitation component can have polarization, or one or more bands of wavelengths. In some cases, multiple excitation components may be used in sequence and/or may be overlapping in the time they are applied to an article. In certain cases, the absorbed electromagnetic radiation excites one or more electrons of the emissive species to a higher energy state. The one or more excited states are generally metastable and may, in some cases, relax to a lower energy state (e.g., the ground state) through emission of electromagnetic radiation, thermal dissipation (e.g., through vibrational energy transfer), and/or a chemical reaction. The one or more excited states may, in some cases, also transfer energy to neighboring species, which can be emissive species with different emission wavelengths, polarizations, and/or lifetimes. When an excited state relaxes by emitting electromagnetic radiation, it may produce a detectable emission over a period of time (also referred to as an "emission time period" or "emission lifetime"). In some cases, an image sensor may detect at least a portion of the detectable emission. In certain cases, an electronic hardware component (e.g., circuitry, one or more processors) may subsequently generate an image (or series of images) comprising a first portion corresponding to a first portion of the emission time period and a second portion corresponding to a second portion of the emission time period.

In certain cases, an electronic hardware component can generate an image by capturing electromagnetic radiation (e.g., visible light or other light) from different portions of emissions at a number of different lifetimes. The sequence and time periods over which the image is captured may be variable and may be controlled by programing or modification of the electronic hardware. In this manner, an image (or series of images) may be used to obtain time-dependent information regarding the emissive species and/or a characteristic of the article. By collecting different parts of an image at different time periods in relation to the excitation component, unique images may be produced. These images may be used to convey information about the article and serve as an authentication code. As one non-limiting example, an image (or series of images) may be used to determine the emission lifetime of the emissive species. In some cases, the emission lifetime of an emissive species may be modified by binding and/or proximity to other molecules (e.g., water, oxygen, carbon dioxide, carbon monoxide), temperature, physical alteration, pH, radiation exposure, and/or other environmental factors. In some instances, therefore, the particular emission lifetime value may provide information about a characteristic of the associated article (e.g., the presence or absence of a label, a characteristic of the environment, information about prior chemical, physical, or other exposures). As another non-limiting example, a difference between a property of the first portion of an image and a property of the second portion of the image may provide information about a characteristic of the article (e.g., the presence or absence of a label, a characteristic of the environment, information about prior chemical, physical, or other exposures).

In some embodiments, the emissive species is selected such that the emissive species is present (or produces an emission) if a target analyte, is present.

In some embodiments, a shutter mechanism is used that can provide time resolution using what is known as the rolling shutter, which is used in many smartphones and digital cameras. The rolling shutter is generally an electronic mechanism and is related to the electronic reading of the imaging chip. Similar to a classical shutter used in older cameras, the rate over which the chips are read may be varied. In smartphones or digital cameras, a chip detects the light projected onto it by sequentially by reading rows or columns of the photo-detection elements in rapid succession. The time delay with this reading allows for the device to behave in a way that can extract information as a function of the lifetime of the emissive species. This information may be extracted from a single image by reading the different rows or columns or could be extracted from the overlay of many images collected with different types of excitation and rolling shutter reading conditions. For example, it is possible that an excitation wherein the intensity changes with time may be used in conjunction with a rolling shutter to acquire lifetime data. In this case, the rates at which the excitations are modulated may vary over a large range and will ideally approach similar cycle periods in time to the excited state lifetimes of the different emissive species. By varying the rates of image collection (rolling shutter) rates and the excitation conditions, it is possible, in some embodiments, to selectively detect different emissive species and minimize background signals. It is also noteworthy that this method allows for the selective detection of multiple different species having different excited state lifetimes within a biological assay. This feature may be combined with the chromaticity (wavelengths) of the emissive species as well as methods that use polarization of light to decrease optical noise. In some embodiments the reader is a conventional smartphone that uses a rolling shutter. A critical aspect of the smartphone is the timing between the excitation and the speed of the rolling shutter. An excitation may be pulsed and entire images collected after a single pulse. Alternatively, the excitation may be pulsed multiple times during the collection of a single image. Additionally, the excitation may be continuously modulated at one or more varying frequencies throughout the collection of the images using the rolling shutter mechanism. It is also possible that a series of images may be determined that have combinations of different excitation frequencies and rolling shutter speeds. In some cases, a reader will initially collect data under many different excitation conditions and rolling shutter conditions. Computational methods may be used to determine which combination of these trial excitation and rolling shutter conditions produces the superior signal. This signal may be extracted or the reader can make additional measurements under the optimal conditions. By way of example to illustrate this concept, if a single analysis (or trial measurement)

takes 10 milliseconds, it is possible to make 100 separate measurements in a second. In these ways the smartphone, digital camera, or detection device (reader) may advantageously be used to selectively detect signals with particular lifetimes in a complex background. For example, under some conditions the devices may be used to detect delayed-phosphorescence to the large exclusion of delayed-fluorescence, prompt-phosphorescence, and colorimetric signals. Alternatively, under other conditions the devices may be used to preferentially detect delayed-fluorescence and prompt-phosphorescence over delayed-phosphorescence and colorimetric signals. However, it is clear that these selective detection events, although useful in their own right, are advantageously greatly enhanced when used in conjunction with other images that contains additional information. For example, pairwise combinations of any of the image analysis techniques described herein may be used. Multiple images may be fused that are collected for the detection of any of the signals. In some contexts, this process may be considered as signal averaging, which generally increases the signal to noise ratio at a rate equal to the square root of the number of signals averaged.

One of ordinary skill in the art will also recognize, based upon the teachings of this specification, that an electronic global shutter may, in some embodiments, be used to produce time dependent emission data (non-steady state photon emission data). In some such embodiments, the cycle time (the time over which each image is exposed and read) is fast enough to capture differences in a non-steady-state emission. Selection of an appropriate excited state lifetime of an emissive species with a photon detection device operating with a global shutter may be useful for producing a non-steady-state photon emission signal in accordance with some embodiments described herein. In some embodiments, a global shutter based device may achieve the time resolution of the non-steady-state photon emission detection through multiple images that are read separately. In some embodiments, suitable delays between the turning off of a pulsed excitation and an image being collected under global shutter conditions is used to create the time information. In some embodiments, only a single delay is used. In some embodiments, multiple images are collected at one or more different delays. Electronic global shutters may also be used, in some embodiments, to detect non-steady-state emission produced by a modulated excitation. In some such embodiments, the global shutter device will detect emissions at different points in time relative to the modulated emission. The delayed emission may be detected, for example, as a result of its difference in phase from the excitation waveform or a difference in wavelength from the prompt fluorescence, reflection, and/or scattering.

Optical signals may also be added to biological diagnostic assays that provide additional information that may be read using the digital camera of a smartphone. For example, temperature sensitive emissive materials may be added to indicate the temperature at which the assay was performed and/or indicate that the assay has not been exposed to detrimental hot or cold conditions. This information can provide key information about the expected accuracy of the assay. In some cases, it may be useful to track or validate the authenticity of the assay to prevent fraud or misuse. In this case an optical code that encodes complex information for authentication may be included. In some cases, internal controls for facile calibration or fiducial registration of the assay may be included. For example, emissive materials of known performance may be incorporated into the assay as an internal reference for results calibration.

To increase the throughput of biological assay results interpretation, multiple assays may be simultaneously imaged and analyzed. For example, simultaneously imaging and analyzing four LFAs can quadruple the throughput resulting in significant time, labor, equipment, and cost savings; particularly in time sensitive and/or resource limited environments.

The fusion of various images described herein may advantageously provide improved sensitivity and fidelity in biological diagnostic assays. In some cases, this data may be collected in rapid succession e.g., to minimize the effect of physical movement or the lighting conditions that occur during the course of a measurement. The composite data resulting from the fusion of signals from different optical elements or the same optical element measured multiple times provide improved signal to noise ratios as compared to some conventional techniques. In some cases, a smartphone or digital camera is configured to read an assay without any additional light source or optical filters. In some embodiments, images are collected using ambient light and/or with illumination by the smartphone's or digital camera's flash (onboard white light LED). The flash, which is generally designed to provide white light, may be used to excite emissive materials with white light excitable chromophores and one or more of the previously mentioned classes of materials. Excitation by the flash may be performed in steady-state wherein images are taken under the conditions of continuous illumination, with this method preferred for collection of colorimetric and prompt-fluorescence signals from a biological diagnostic assay. By pulsing or modulating the flash intensity in time and applying the rolling shutter or video capture capabilities of the smartphone, digital camera or other optical imaging device, delayed-fluorescence, prompt-phosphorescence, or delayed-phosphorescence may be detected.

For example, in some cases, it may be advantageous to make use of an external light source such as a light emitting diode (LED) to excite the emissive species. This light source may be used in either steady-state mode or to create time sequenced detection in pulsed/modulated mode. The LED may be selected to generate ultraviolet light that is higher energy than the light output from a smartphone or digital camera's flash. The ultraviolet light may be intrinsically excluded from detection because of the lack of transparency of the optical elements to this wavelength of light. The excitation light used to excite the prompt-fluorescence may be removed from impinging on the detector by use of a filter. It is possible that multiple LEDs may be used to selectively excite different emitters and these light sources may be independently operated in a steady state, pulsed, or modulated fashion.

In addition to filters, polarizers may be used to create specific signals, in some embodiments. Polarizers may be used in conjunction with the excitation to give polarized excitation and additional polarizers may be placed between the assay and the detector for selective detection of different polarizers. The combined use of polarizers on both the excitation and detection elements may be used and the relative arrangement of the polarizers may be used to create improved signal contrast and eliminate stray light (optical noise). As a result, polarizers may be used to create enhanced signal to noise and hence improved sensitivity in biological diagnostic assays. Polarizers may also be used to eliminate stray light and allow for improved performance in assays performed under ambient light. The degree of depolarization of emissive species may also be used in biological diagnostic assays. In this case a polarized excitation is applied and the degree to which the emitted light has the same polarization provides relevant information. Depolarization can occur as a result of motions of the emissive material prior to emission or as a result of energy transfer between multiple emissive species. The degree of depolarization may also be related to the lifetime of the emissive material.

The excited state lifetimes of the emissive materials used in this invention can vary as a function of their environment. The rolling shutter method when paired with different time synchronized optical excitations may be used to reveal information about the absolute or relative excited state lifetimes of the emissive materials. Given that the excited state lifetime is a function of the material's local environment, there may be changes in this value as a result of proximate biomolecular recognition processes. In some cases, a biomolecular recognition event can trigger the formation of a new complex. Such an event can yield new emissions that are distinct in both the intensity as a function of wavelength as well as the lifetime. It is also common that changes in the solvation of an emissive material that are associated with a biological assay give rise to changes in lifetime. For example, many emissive materials have excited state lifetimes that change in polar aqueous environments relative to nonpolar environments.

The same hardware can optionally be used for both steady-state and time-gated (non-steady-state) measurements by firmware and/or software changes.

In delayed-fluorescence, prompt-phosphorescence, and delayed-phosphorescence, there may be, in some cases, optimal parameters for reading biological diagnostic assays. Optimization in these cases may involve creating a set of parameters that maximizes the signal and/or minimizes (suppresses) the background (e.g., including stray light) signals. These parameters generally depend on the particular assay and conditions under which the reading is conducted. When deployed on a smartphone a colorimetric signal may be used to provide information that directs the user to orient the smartphone in a particular manner relative to the assay to generate a desired signal. In some cases, this information, which may be contained in a logo, QR code, or bar code on the assay informs the smartphone about the optimal camera settings such as shutter speed (exposure time) and/or sensitivity (ISO) setting and the excitation profile. In some cases, the phone may perform measurements that rapidly explore a range of values for the shutter speed/ISO and the type/duration of excitation to be used. Computationally, the smartphone may be used to determine imaging conditions that produce desired signals (e.g., by providing high definition/contrast, the rejection of artifacts and stray light, and producing bright emissive signals). It may be that the data collected during this survey is adequate and optimal signals may be extracted from many images. It may be that all images are fused together, in some embodiments, such that only a fraction of the images are used to create the measurement. It may also be the case that guided by a quick survey method, computational methods yield imaging parameters that configure the smartphone to make subsequent measurements using a particular set of parameters to create an optimal measurement. For example, this may be used to determine if the assay is moved away from a bright interfering light source or change the time over which each image is collected by the detection chip (shutter speed or exposure time), or how best to configure the excitation. The latter may be pulsed light flashes or a frequency modulated method. In some cases, the smartphone may instruct the user to seek conditions that limit ambient light. This may be accomplished, for example, by going into a dark room or closet or using a dark cover over the camera and assay to eliminate light. The latter may comprise a dark cloth, piece of black plastic, or a box capable of positioning the camera relative to the assay while blocking stray light from interfering with the measurement. The latter may comprise a disposable element provided as part of product packaging.

In some cases, it may be advantageous to incorporate some or all of the diagnostic reader components or design features into the product packaging. These components can include, but are not limited to: UV, blue, or white light LED(s) for diagnostic assay excitation or status indicator functions such as power or diagnostic read-time alerts; optical filters, polarizers or lenses; a battery; and support electronics/PCB. In preferred embodiments, product packaging for the diagnostic assay may be used to block stray light and position the smartphone's camera relative to the diagnostic assay during results acquisition by simply resting the smartphone on top of the box. In one particularly preferred embodiment, the interior of the product packaging optionally includes an LED for excitation; optical filter(s), lens(es) or polarizer(s) for excitation and emission light optimization; a lightweight disposable battery; a PCB incorporating the support electronics; calibration, authentication or fiducial markings; and physical feature(s) such as guardrails to reliably orient the diagnostic assay relative to the imaging optics. In this preferred embodiment, the exterior of the product packaging optionally includes printed product information; authentication or tamperproof features; alignment features such as printed outlines of different smartphone make and models; and perforated regions that may be removed based on the smartphone make and model to enable the smartphone's camera to image the diagnostic assay located in the interior of the product packaging. The product packaging can either be disposable or reusable. Optionally, a solar cell may be located on the product packaging exterior to supply power and eliminate the battery requirement.

In some embodiments, an enclosure is configured to receive a consumer electronic device (e.g., smartphone). For example, the enclosure may comprise one or more features which correspond to the shape, size, and/or configuration of the consumer electronic device. In some embodiments, the features may be adjustable (e.g., such that different consumer electronic devices may be integrated with the enclosure, such that the positioning of the consumer electronic device may be adjusted). The enclosure may receive the entirety of the consumer electronic device, or only a portion of the consumer electronic device. For example, the enclosure may be adapted and arranged such that it encloses the image sensor and/or source of electromagnetic radiation of the consumer electronic device.

In some embodiments, the enclosure comprises a source of electromagnetic radiation. In some embodiments, the source of electromagnetic radiation is a component of the enclosure. In some embodiments, the source of electromagnetic radiation is a component of the consumer electronic device. In some embodiments, the source of electromagnetic radiation is in communication with the consumer electronic device (e.g., via one or more of circuitry, electrical communication, processor(s), and the like). For example, the source of electromagnetic radiation may receive a signal from the consumer electronic device such that electromagnetic radiation is produced. In some embodiments, a user interacts with the enclosure such that the source of electromagnetic radiation produces electromagnetic radiation.

In some embodiments, the enclosure is configured to position the consumer electronic device relative to an article (e.g., a diagnostic assay, an article associated with an emissive species). In some embodiments, positioning the consumer electronic device comprises positioning a sensor of the consumer electronic device, such that it can detect and detectable emission from the article (or emissive species).

In some embodiments, at least a portion of the enclosure is closed once the consumer electronic device is positioned. For example, in some embodiments, upon receiving the consumer electronic device, the enclosure is configured such that light external to the enclosure is prevented from interacting with a portion of the article, with the emissive species, and/or with the sensor. In some embodiments, preventing external light from interacting with the sensor means that the sensor will generally only receive electromagnetic radiation generated by the source of electromagnetic radiation and/or emitted by the emissive species. Advantageously, a closed enclosure may reduce or eliminate background signals and/or noise, and/or prevent exposure of the emissive species to undesired electromagnetic radiation.

In some embodiments, the enclosure is configured to receive an assay component (e.g., a lateral flow assay, a vertical flow assay, a chip, a cassette, a cartridge, an article containing a sample). Exemplary enclosures and exemplary components thereof are shown in FIGS. 14A-14F. In some embodiments, the enclosures are designed such that a user may interact with the consumer electronic device while performing an assay. Enclosures and/or assays may be useful in conjunction with various applications described herein including, but not limited to, diagnostics, authentication, detection, identification, purity, and quality control.

In some embodiments, the embodiments described herein are used in conjunction with an integrated sampling and/or analysis cassette. In some embodiments, the methods and systems described herein may be used to analyze s sample provided on the sampling and/or analysis cassette. In some embodiments, all components needed for sampling and analysis are provided in a kit. For example, as shown in FIG. 14F, the kit may comprise, in some cases, an integrated cassette, a sample collection component (e.g., a swab, a collection reservoir, a vial), an optional adapter for a consumer electronic device (e.g., a smartphone), and an optional tray (e.g., for sample prep). In some cases, instructions for use of the kit may be provided (e.g., on one or more components of the kit such as the tray).

The combination of different images generally allows for additional information to be stored with the results of an assay. This may include the individual assay, type of assay, the location where the assay was conducted, and the time of the assay.

In an exemplary embodiment, delayed-phosphors based on europium chelates may be used in LFAs, with stand-alone readers to read such assays. Smartphone readers using the methods described herein may be configured to read these assays. In the case that the europium cannot be optimally excited using the white light flash (onboard LED) of the smartphone's camera, a supplemental light source that has shorter wavelength excitation frequencies (UV or blue light) is used in conjunction with the smartphone.

In some embodiments, the combination of an off the shelf smartphone and blue LED is a useful alternative compared to a dedicated reader. Smartphones have considerable computation power, may be connected to the cloud for additional computational resources and/or results reporting purposes, provide spatial-temporal data, and/or may be configured to capture and read other imagery (QR codes, text, bar codes). A smartphone system may also be deployed more broadly and rapidly. The applications (apps) that convert the smartphone to a lateral flow reader can be easily downloaded and upgraded on the phone. If pairing with an external LED, the devices may be readily paired with the smartphone synchronizing with the pulsed or frequency modulated LED excitation. The rolling shutter along with the time synchronized excitation may be used to eliminate or identify noise from stray light that can be compensated for in the measurement through baseline correction. In some embodiments, the smartphone need not rely on a blue LED excitation and will be able to read the assay using its onboard white light flash. Advantageously, the smartphone synchronizing with the pulsed or frequency modulated LED excitation may not, in some cases, require that the data acquisition and the excitation be synchronized, but that the relative times can be deduced, and hence synchronized, computationally from the data/image acquired.

The smartphone reader may provide biological diagnostic assays to be read more widely than custom hardware and may serve, in some embodiments, to enable deployment scenarios including point-of-care, near-home, and at-home testing with facile cross-referencing of the results.

In some embodiments, an optical method is described that may be used to monitor the thermal degradation of a product. In some embodiments, a smartphone may be used to make a determination of the degree of thermal degradation, which will be a function of the cumulative time and temperature exposure. In some embodiments, the optical methods may be used to determine a peak temperature. In some embodiments, the measurement is used to determine if a product has exceeded a recommended thermal exposure. These determinations may be used, in some cases, in combination with other information such as authentication of the product, its date of manufacture, or exposure to light.

Advantageously, some embodiments described herein may provide greater precision and/or are readily integrated with information or sensing by optical interrogation of a product, e.g., as compared to traditional time temperature indicators and/or dosimetric labels. For example, considering the nature of degradation processes and the statistical nature of the thermal activation that control the degradation processes in materials, there may not be a clear linear relationship between the product of temperature and time and the degree to which a product is degraded with traditional methods. In some embodiments described herein, advantageously, monitoring other thermally activated processes that may behave as an "integration device" to quantify the thermal exposure may be used. Without wishing to be bound by theory, these processes need not be the same types of process as those that lead to the degradation of the product, but may be correlated to the degree of thermal degradation and provide a measure thereof. As such, in some embodiments, the components and methods described herein provide a temporal thermal profile which corresponds to the quality (and/or authentication) of a product.

In some embodiments, the components and methods described herein use thermally activated changes in the delayed emission of materials to determine temperature exposure for monitoring the thermal degradation of products. The delayed emission, defined as light emitted from an excited material after 10 nanoseconds, advantageously provides for the collection of high-fidelity signals that may be read by any detector system (e.g., capable of differentiating light emitted after 10 nanoseconds, from light emitted in less than 10 nanoseconds, capable of detecting a non-steady state emission). In some embodiments, the light is collected at least 1 microsecond after the emissive material is excited and, in some cases, the excitation light has been removed. In some embodiments, a smartphone (and/or component associated with the smartphone) may be used as the detector of the delayed emission, and is described in more detail below. The delayed emission from the designed emissive material system may, in some cases, report on the thermal history of a product (and, in some embodiments, in multiple ways). Responses to thermal exposures may include, for example, optical absorption and emission wavelength changes, new physical patterns of optical absorption and/or emission, changes in the emissive lifetimes, changes in intensities, and/or combinations thereof. The emissive signals may, in some embodiments, be used in conjunction with other optical codes including methods to allow for serial tracking, authentication, recording expiration dates, determining total light exposure, etc.

In some embodiments, a composition comprises an emissive species configured to be associated with an article. In some embodiments, excitation of the emissive species produces a detectable signal (e.g., having one or more delayed emissions of greater than or equal to 10 nanoseconds). As described herein, in some embodiments, the detectable signal corresponds to a temporal thermal history of the article.

In some embodiments, a label comprises one or more emissive species. In some embodiments, the label is associated with an article. For example, labels described herein may be useful in determining the temporal thermal history of an article. In some embodiments, the label comprises an emissive species optionally having one or more first detectable delayed emission(s) of greater than or equal to 10 nanoseconds in duration corresponding to a first temporal thermal history of the emissive species. In some embodiments, the label comprises one or more, two or more, three or more, four or more five or more, six or more, eight or more, ten or more, twenty or more, or fifty or more emissive species (e.g., each corresponding to a temporal thermal history).

In some embodiments, the detectable delayed emission, if present upon excitation of the first emissive species, corresponds to identification of the emissive species being exposed to the temporal thermal history.

In some embodiments, as described herein, the label is configured to be proactively added to an article, such that the label provides a temporal thermal profile of the article.

In some embodiments, an excitation component is configured to excite, using electromagnetic radiation, an emissive species such that, if single or multiple emissive species, or their precursors, were exposed to a temporal thermal history, produces a detectable delayed emission (e.g., non-steady-state emission) of greater than or equal to 10 nanoseconds. In some embodiments, a detector is configured to detect at least a portion of the detectable delayed (e.g., non-steady-state) emission. The detector may be, in some cases, associated with the excitation component.

As described in more detail below, in some embodiments, the detector comprises a rolling shutter mechanism.

In some embodiments, the detectable delayed emission comprises a peak intensity, emission lifetime, absorption wavelength, and/or emission wavelength.

In some embodiments, the response to excitation involves a change in the wavelength of the absorption or emission related to the delayed emission. In some embodiments, the response involves a change in intensity of a detectable signal. In some embodiments, the response involves a change in the delayed emission lifetime. In some embodiments, the response involves the creation of a new delayed emission. In some embodiments, the response involves the removal of a delayed emission. In some embodiments, the response involves two components combining to produce or remove a delayed emission.

In some embodiments, the response involves a matrix that changes its physical properties to create changes in the delayed emission signal. In some embodiments, the response involves the diffusion of one or more materials to create changes in the delayed emission signal. In some embodiments, the response involves a matrix that undergoes a phase change that produces or changes the delayed emission signal. In some embodiments, the response involves chemical reaction to produce the delayed emission signal. In some embodiments, the response involves changes in aggregation to produce or change the delayed emission signal. In some embodiments, the response is produced by an enhancement in energy transfer from an antenna molecule or polymer to a delayed emission component. In some embodiments, the response produces a pattern from the delayed emission signal. In some embodiments, the response is produced from materials that are safe for humans consume.

In some embodiments, the label is produced by the deposition of second material onto a delayed emission material in order to produce a system capable of displaying a temporal thermal history.

In some embodiments, the composition is produced with components proximate to each other. In some embodiments, one of the components of the composition, label, and/or system is fused onto or into glass. In some embodiments, components are separated physically from each other.

In some embodiments, the composition, label, and/or system is produced by spray deposition, ink jet printing, printing, or lamination.

In some embodiments, the delayed emission has a lifetime greater than 10 nanoseconds, greater than 100 nanoseconds, greater than 1 microsecond, greater than 100 microseconds, or greater than 1 millisecond. In some embodiments, the delayed emission has a lifetime less than 10 milliseconds, less than 1 millisecond, less than 100 microseconds, less than 1 microsecond, or less than 100 nanoseconds. Combinations of the above-referenced ranges are also possible (e.g., greater than 10 nanoseconds and less than 10 milliseconds). Other ranges are also possible.

In some embodiments, the delayed emission species contains a metal ion. In some embodiments, the delayed emission species is an organic molecule. In some embodiments, the delayed emission species is a nanoparticle. In some embodiments, the delayed emission species is a crystal. In some embodiments, the delayed emission species is a microparticle. In some embodiments, the delayed emission species is an organic molecule containing heavy atoms.

In some embodiments, excitation of the emissive species is accomplished by a light source with modulated intensity at different frequencies. In some embodiments, excitation of the emissive species is accomplished by a light flash or a laser pulse.

In some embodiments, the detector (e.g., reader) is a smartphone component. In some embodiments, the detector is a component of a streak camera. In some embodiments, the detector is a component of a device capable of selectively detecting a delayed emission. In some embodiments, the detector is a component of a device capable of selectively detecting a delayed emission in a complex environment with non-delayed emission, ambient, and reflected light present. In some embodiments, the detector is a component of is a device capable of selectively detecting a delayed emission and is also capable of detecting prompt-fluorescence, ambient, and reflected/scattered light. In some embodiments, the detector is capable of detecting patterns of delayed emission to produce information about a thermal or cold exposure. In some embodiments, the detector is capable of detecting patterns of delayed emission as well as patterns from reflected/scattered, ambient, or non-delayed emission to produce information about a thermal or cold exposure. In some embodiments, the detector is capable of integrating information of a thermal or cold exposure with other information optically encoded on the product.

In some embodiments, the detector comprises a CMOS imaging chip.

In some embodiments, the detector is configured to use a rolling shutter effect to collect the delayed emission data.

In some embodiments, the detector is configured to use a global shutter to collect images that may be sequenced at various times (e.g., with regard to a non-steady-state excitation).

In some embodiments, the temporal thermal history is the cumulative amount of time that an article (and/or label and/or composition) experiences a particular temperature or range of temperatures and that shorter times at higher (or lower) temperatures could be equivalent to longer times at less high (or less low) temperatures.

There are a number of ways to translate a thermal exposure into a detectable change in the delayed emission in this invention. For many emitters (emissive materials) the emission intensity is generally reduced with increasing temperature. Without wishing to be bound by theory, this is generally a result of the internal dynamics including molecular motions wherein rotational, vibrational, rocking, aggregation, collisional, and/or combinations of these processes cause a material to relax faster from an excited state to a ground state without giving off an optical photon. These thermal relaxation processes are collectively referred to as a non-radiative processes and result in the relaxation of an excited material to its ground state (non-excited form). In non-radiative processes the energy is often dissipated as local heat that is absorbed by the local environment. The rate at which a material undergoes a non-radiative process may, in some cases, depend on the environment. For example, if the internal dynamics (motions) enhance the non-radiative rate then an environment that restricts a material's physical dynamics, will affect the rate the non-radiative processes. An increased rate of non-radiative relaxation as a result of a particular thermal history may produce a decreased intensity of an emission signal, but may be used to create a time temperature indicator (TTI) is to detect changes in the emission lifetime of the emissive materials. This is because the intensity of an emission is dependent on the amount of material initially excited and will at a minimum require a reference signal. It is also possible that other secondary processes not related to the TTI response will cause degradation of the emissive materials to give a non-emissive material and thereby lower the emission intensity. Monitoring of the emission lifetime may, in some cases, be independent of the amount of the active emissive material and the degree to which it is excited. The emission lifetime is generally related to the time that the molecule remains in its excited state. The emission lifetime is, in some embodiments, inversely related to the additive rates of all non-radiative and radiative processes. Increases in either the non-radiative or radiative rates of a dye may, in some cases, give a reduction in a dye's emission lifetime. Conversely decreases in non-radiative or radiative rates may, in some cases, increase an increase a material's emission lifetime. However, the emission intensities and lifetimes may not give the same information. For example, a faster emission rate may, in some cases, allow for brighter emission and still cause a reduction in a material's lifetime. Alternatively, a faster non-radiative rate may, in some cases, reduce both the brightness of the emission and the material's lifetime. As a result, the emission intensity and emission lifetime may, in some cases, in some cases vary independently and other information may, in some cases, be necessary to produce a useful TTI that may, in some cases, be imparted by having multiple delayed emissions from different emitters or locations on a product or its packaging.

An additional advantage of lifetime sensing is that it may, in some cases, be used to remove interfering fluorescent signals from materials found in products and their packaging that typically display lifetimes less than 10 nanoseconds from the time wherein the material is put in an electronically excited state. In some cases, it may be advantageous to exclude emissions with lifetimes that are less than 100 nanoseconds from the time of excitation, and in yet other cases it may be advantageous to exclude emissive signals that are less than 1 microsecond from the time of excitation. However, some embodiments described herein are not intended to be limited as such.

By detecting longer lived emissive signals, it is possible to remove intrinsic background emission and depending upon the context of the measurement and the product, measuring the emission at different time periods may be desired. Many products have intrinsic fluorescence, and it is typical to add emissive dyes to products to make them appealing. However, by detecting delayed emissions, only selected emissive materials are being recorded. It is also clear that more information may, in some cases, be produced by having multiple emissive signals with different emission colors and lifetimes or changes thereof. For example, it may be desirable in some TTI applications to have a high-performance reader that may, in some cases, make use of very short-lived signals that are only slightly longer than 10 nanoseconds. In other applications that involve consumers it will be best to use signals that may, in some cases, be read by a smart phone for TTI. In some embodiments the emissive signals of interest may, in some cases, be patterned to create additional TTI information and in yet other cases the emissive signals may, in some cases, be used in coordination with other optical patterns, including trade-marked logos, QR codes, bar codes, and pictures or patterns on a products packaging.

Smart phones may, in some cases, be used to read TTI devices based on a delayed emission. In some embodiments, pulsed or modulated excitation light, is used in conjunction with detection using the rolling shutter effect in the smartphones camera unit. In some cases, it will be sufficient to detect only light coming from a delayed (e.g., non-steady-state photon) emission. In other cases, capturing images of delayed emission will be useful and the rolling shutter mechanism may, in some cases, be used to resolve both the spatial position and the emission lifetime.

An emissive species may have any suitable structure. The emissive material may, in some cases, be any suitably emissive material including polymers, waxes, pigments, metal complexes, main group complexes, lanthanide complexes, inorganic oxides, inorganic sulfides, inorganic salts, metallo-organic molecules, organometallic molecules, organic molecules, organic semiconductors, inorganic semiconductors, halogenated organic molecules, supramolecular complexes of multiple molecules, molecular aggregates, nanoparticles, or nanostructured materials. Those skilled in the art will recognize, based upon the teachings of this specification, that there are many emissive materials that fall in these general classifications as well as others that will have the necessary optical properties to be used in this invention. The excitation of the material may, in some cases, be performed by light, by electrical methods, or by chemical methods, as described in more detail below. The excitation may be performed in a fashion that may, in some cases, be used to determine the lifetime of the emissive material. For example, optical excitation of a flash may, in some cases, be used and the emission collected over one or more time periods thereafter. Alternatively, excitation may, in some cases, be used provided that the intensity is modulated. In general, frequencies (Hertz=cycles/second) over which the light intensity is modulated may correspond cycle times that are similar or shorter than the lifetime of the emissive signal. It may be advantageous to use multiple different frequencies for a TTI measurement.

In some embodiments, the emissive species is a chemical and/or biological species. In some cases, the emissive species is a fluorophore, a phosphor, or a thermally activated delayed fluorescence (TADF) molecule or molecular complex. In some embodiments, the emissive species is configured to bind to a chemical and/or biological species.

The method of construction of this TTI invention or equivalent thermal exposure measuring device requires one or more emissive materials or materials that may, in some cases, transform into emissive materials and supporting compositions that may or may not be active. In some cases, the supporting composition will include a cofactor, which is a material, which may, in some cases, also be emissive, that modulates the light coming from the TTI. The cofactor may, in some cases, change the materials emission lifetime, optical absorption characteristics, emission intensity, or spatial patterning of the emission from the TTI. In some cases, a cofactor is required to create the emissive material though a reaction or association. In some cases, structuring of the fabricated materials that provide for the TTI indicator is important. For example, it may be possible to have emissive materials physically separated initially from the cofactors. In some cases, the relative concentrations of the emissive materials and various cofactors will be important. In other cases, variations in material compositions and physical separations will be used to create unique patterns that provide TTI information. In other cases, the physical characteristics of the materials will be important such as their melting/freezing point or glass-transition temperature ($T_g$). Fabrication methods to accomplish these features include lamination, screen printing, spray coating, inkjet printing, roll to roll methods, or anyway that a solvent of dispersion may, in some cases, be applied to a surface.

The context of how an emissive material or an emissive material precursor is positioned in a TTI composition and the degree to which thermal exposures change the properties through the mechanical properties of the matrix, chemical reactions, concentration, and spatial diffusion may, in some cases, be used independently or in combination to determine a thermal exposure. In some embodiments, there is detectable change in the delayed emission. In some cases, thermal exposures to a composition create new delayed emissions and in other cases delayed emissions are reduced or removed by thermal exposure. In other cases, the wavelengths where the emissive species absorb or emit light change in response to a thermal exposure to create a TTI. In other cases, changes in the lifetime of the emissive species may, in some cases, be used to create a TTI. In other cases, special locations are selected where emissive species will change to create a TTI. In yet other cases, combinations of any or all of these respective effects may, in some cases, be used to create a TTI. The organization of the emissive materials and other cofactors in a composition is critical to produce a response to a thermal exposure that meets the requirements of a product. The temperatures of interest range from below −80° C. to above 100° C. with many anticipated applications ranging from −20° C. to 60° C. The matrix may, in some cases, be a single material or contain multiple components. For example, the matrix may, in some cases, be composed of a wax, polymer, inorganic oxide, silica, gel, a fluid, natural fibers, fatty acid or ester, or combinations thereof. The different active elements (emitters, cofactors and their precursors) may, in some cases, be uniformly distributed in the matrix or display compositional variations either laterally of vertically with regard to a surface. In many cases, different materials will be co-fabricated to form stratified compositions. The physical separation of different elements in a matrix material may, in some cases, allow for responses to occur if materials may, in some cases, be made to diffuse with thermal exposures. The matrix in some embodiments will display a change in its mechanical properties, which could include a phase change, softening, or interdiffusion (mixing) with other materials in the composition in response to a thermal exposure. In other cases, the matrix is simply a medium that other processes, including chemical reactions and diffusion, occur under thermal exposure. In some cases, different components that come together to create a TTI may, in some cases, be produced by lamination of one or more layers onto a product. In other cases, the compositions that produce a TTI may, in some cases, be printed and positioned proximate to each other. The physical dimensions and spatial patterning of the different elements of the composition may, in some cases, used to give a specific TTI. For example, when a thermal exposure allows for emissive species, emissive precursors and/or cofactors to diffuse over a given distance, the different elements need to be patterned to produce a readable response relevant to the targeted TTI. The distance over which diffusion occurs will be highly dependent on the thermal exposure. In most cases diffusion distances will increase with higher temperatures and longer durations. The physical spacing and patterns of the new emissive characteristics (lifetime, wavelength, intensity changes) generated as a result of a thermal exposure may, in some cases, be used to produce a TTI. In some cases, the pattern of emissive species may, in some cases, also be used to authenticate a product. In this method, measurement of the characteristics of the emissive species provides an identification code that is not easily reproduced.

The dynamics and mobility of a material may, in some cases, be influenced by its local environment and hence the properties of the matrix. Increased rigidity may, in some cases, reduce degrees of freedom in a material such as rotations about chemical bonds, bending motions, wagging motions and collisions with other molecules. In some cases, a molecule will have a reduced non-radiative rate in a more rigid environment as a result of reductions in these processes. This reduction in the non-radiative rate will yield an increased emissive lifetime relative to a more dynamic state. In some other cases, a material may, in some cases, be trapped in a particular configuration in a rigid environment and have an emission behavior with a different lifetime, wavelength, or brightness than it will have in a less constrained less rigid environment. In some cases, the thermal process will result in diffusion of materials that give rise to changes in the emission lifetime. It is also possible that a material may, in some cases, be trapped in a non-equilibrium higher energy state or conformation in a matrix such that it emits light at a different wavelength, lacks a delayed emission, is non-emissive, has a very different excited state lifetime, or combinations thereof. A thermal exposure may, in some cases, allow the material to relax to a lower energy state and give changes in its emission efficiency, excited state lifetime, wavelengths of emission and absorption, or combinations thereof.

A material or matrix material may with thermal exposure diffuse (move) from one micro-environment/phase to another or two separate phases may, in some cases, become one. In other cases, increased temperature may, in some cases, result in phase separation. In other cases, the increased temperature may, in some cases, cause solid phases to be melt into liquids. In other cases, a polymer or solute may, in some cases, be dissolved in a solution that precipitates with a thermal exposure. Such a polymer or solute has what is known as an upper critical solution temperature and there are a number of examples in water. For example, phenol and water have an upper critical solution temperature and many copolymers of N-isopropyl acrylamide are known to have a range of upper critical solution temperatures. The matrix that creates the micro-environments may, in some cases, have compositional gradients or separate domains of different materials and be a wax, fatty acid or ester, polymer, gel, paper, fluid, or other solid. For example, an emissive material may, in some cases, be positioned in a higher rigidity matrix and with thermal activation a softening material may, in some cases, diffuse into the rigid matrix and cause it to become less rigid. There are many potential matrix materials that will soften as a result of thermal processes, such as changes in the materials conformation, reduction of internal stresses in the matrix, disruption of physical interactions, or even thermal breaking of bonds. If the changes in the matrix materials allow for the internal dynamics of the emissive material to be enhanced then a decrease in the emissive lifetime may, in some cases, be detected.

It is also possible that thermal exposures may, in some cases, give rise to an increase in the effective rigidity of the local environment around an emissive material and thereby decrease the rate of non-radiative processes. In these situations, the emission lifetime may, in some cases, increase. For example, a matrix material may be captured in a meta-stable phase and transition to a more stable higher rigidity phase with a thermal exposure. An emissive material may be dissolved in a solution or melt of a matrix material and rapid removal of solvent or rapid cooling may, in some cases, be used to create a higher energy composite of the matrix and emissive material. This phase may, in some cases, be what is known as a solid solution wherein a solid contains relative composition uniformity just as would be expected for a solution. Solid solutions may, in some cases, be stable indefinitely, and are in many cases thermodynamically unstable. Heating a solid solution may, in some cases, allow for diffusion of the components and cause phase separation, reactions, and/or aggregation. In such a way the local environment around an emissive material may, in some cases, change in a dramatic way. If the two components crystallize it may, in some cases, result in a change in the local environment and change the dynamics, and hence the non-radiative rates, of the emissive material. It is also possible that a precipitation, cooling, or evaporation process creates a matrix that is characterized as having an amorphous glassy state, wherein there are some small local dynamics in the matrix. A glassy state may, in some cases, be stable for extended periods of time, and for many materials either stress or thermal treatments may, in some cases, initiate crystallization. All of the processes just discussed may, in some cases, be used to create different dynamic environments around an emissive material that may, in some cases, produce measurable changes in the emissive lifetime that may, in some cases, be used to determine a product's thermal history.

There are abundant examples of materials that display changes in lifetimes as a function of their internal dynamics. One class of molecules are those that exhibit that is known as thermally delayed activated fluorescence. The molecules shown display this process and have reduced non-radiative processes, which gives longer lifetimes when in a more rigid aggregated environment. (ref. Tsujimoto, H.; Ha, D.-G., Markopoulos, G.; Chae, H. S.; Baldo, M. A.; Swager, T. M. "Thermally Activated Delayed Fluorescence and Aggregation Induced Emission with Through-Space Charge Transfer" *J. Am. Chem. Soc.* 2017, 139, 4894-1900, which is incorporated herein by reference in its entirety for all purposes).

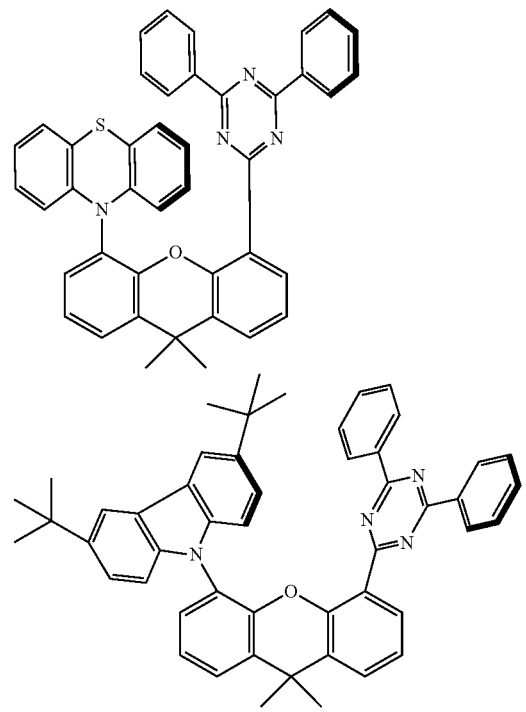

Without wishing to be bound by theory, a number of molecules have reduced non-radiative rates (longer lifetimes) when aggregated and this general process is known as aggregation induced emission. Key for this invention is that the emissive materials as well as the aggregated emissive molecules have a lifetime over 10 microseconds. Longer lifetimes arise from thermally delayed activated fluorescence, emission from a triplet excited state, or as a result of other dynamic equilibria within an emissive material. There are many materials that display temperature dependent emission (ref. Wang, X-Dong; Wolfbeis, O. S.; Meier, R. "Luminescent Probes and Sensors for Temperature" *Chem. Soc. Rev.*, 2013, 42, 7834, which is incorporated herein by reference in its entirety for all purposes). These materials have been utilized for measuring a temperature at a specific time however, delayed emissive materials have not been used to give an analysis of thermal exposure with a single measurement as a TTI as is the subject of this invention. To monitor a thermal exposure, the emissive temperature sensitive materials would require continuous monitoring or at least a number of measurements over time. Such a method would not be appropriate for the anticipated applications of this invention wherein a product's thermal exposure (or its thermal history) will be determined by a single measurement. For example, before administering a drug, a single measurement that selectively detects emission lifetime(s) may, in some cases, be used to ensure that the product has not be subject to thermal degradation. Materials and molecules that are known to be thermally responsive and have delayed emission are relevant to this invention, may, in some cases, be used to create TTI devices capable of determining a product's thermal history. In this case changes in the structure and properties of the matrix material surrounding the emissive material may, in some cases, produce changes in the emissive lifetime, color, or intensity.

Energetic disorder caused by trapping materials in different high energy states may, in some cases, have a large effect on the ability of a material to transport energy over distances. Semiconductive/conjugated polymers are well known to behave as antennas to transfer energy over distances. It has been found that these materials are more efficient at transmitting energy when they are in more regular states or when they are placed into aggregated states. A TTI may, in some cases, be created by using a thermal exposure to promote either a change in the organization of the conjugated polymer to have a more planar structure with greater delocalization or thermally induced phase separation of the conjugated polymer from a matrix. Most purely emissive conjugated polymers have excited state lifetimes less than 10 nanoseconds and incorporating a small percentage of a delayed emission component into the polymer mixture, either by direct conjugation, as a pendant, or as a physical mixture may, in some cases, be used to create a response. Either a transition of the conjugated polymer with a delayed emissive component from a disordered to an ordered state, phase separation of the conjugated polymer delayed emissive component from the matrix material, or combinations thereof may, in some cases, be used to create a TTI. Disordered states of the conjugated polymer and the emissive component may, in some cases, be generated by rapid quenching of a heated sample, by rapid dissolution caused by precipitation, by mechanical actions, by rapid evaporation of solvent, or combinations thereof. Additionally, it is possible that a delayed emission component or species capable of causing a delayed emission, may, in some cases, diffuse into a film of a conjugated polymer as a result of thermal exposure and also create a new delayed emission signal to constitute a TTI.

Thermal processes may, in some cases, be used to create disorder in materials. For example, a polymer may be stretched such that its chains are in a higher energy conformation. If the polymer is below a temperature wherein it may, in some cases, relax then it may, in some cases, retain the alignment that is associated with the polymer chains for extended periods. Chain alignment may, in some cases, be used to orient a dye or anisotropic nanoparticle with delayed emission that is within the stretched polymer host materials. As a result of this effect the material will have an emission that is polarized and as a result will have angle specific optical properties such as reflection and absorption. In a simple scheme, the emission may, in some cases, be attenuated by use of a polarizing component that limits light of the polarization of the aligned material with the delayed emission. Without wishing to be bound by theory, with thermal activation the entropy driven relaxation of the host polymer will, in some embodiments, promote a more random orientation of the emissive material and the light intensity may increase if the polymer has a decreased non-radiative rate in the disordered state. The host material may, in some cases, be many things, including polyolefins, acrylates, vinyl polymers, polyarylethers, polysulfones, or the like that may, in some cases, be drawn at select temperatures and align the guest delayed emission materials. It is also possible to stretch an elastomeric polymeric material and cool it down in it to have it retain the orientation of the polymer chains. Here again thermal exposure may, in some cases, be used to erode the chain alignment and the alignment of the guest delayed emissive species. It is also possible that a bonding to a solid surface may, in some cases, be used to "hold" the host polymer in an aligned structure. The bonding to the surface may, in some cases, be through physical linkages such as corrugations and roughened surfaces, through electrostatics, or through the application of an adhesive. In these cases, a stretched material is applied to the article while under mechanical stress. Thermal exposures may, in some embodiments, weaken the anchoring to the surface, or allow for realization of the stressed polymer, and allow for the polymer chains to randomize and again reduce the alignment of the guest materials displaying delayed emission. It is also possible that a delayed emissive materials that do not align in a stretched polymer or have alternative alignments may, in some cases, be used to create TTI.

An alternative method to create aligned materials with delayed emission in a variety of host materials by an active photolysis. For example, emissive materials may be activated (created) or deactivated (destroyed) by photolysis. In this case a higher energy (lower wavelength) light source will be used and polarized photolysis will activate or deactivate a population of the emissive materials that are aligned such that they efficiently interact with the polarized light. In most cases the light source used to activate/deactivate the delayed emissive materials will be in the UV part of the electromagnetic spectrum. This photolysis treatment will then create a delayed emissive species, but with thermal exposure the emissive material can randomize and loose its polarization. As with any of the schemes the choice of the host material and the emissive material will be key to create a TTI with the desired performance for an article.

Thermal processes may, in some cases, also be used to change the local concentrations of emissive materials and other cofactors that affect the emissive lifetime. Thermally initiated crystallization and/or phase separation process from a solid solution may, in some cases, create compositional heterogeneity. These may, in some cases, result in emissive materials and other cofactors concentrating in one phase, at grain boundaries, at interfaces, and/or at surfaces. In some cases, these events may, in some cases, be used to create an emissive species with a longer lifetime. For example, two molecules that are components of a solid solution may, in some cases, be concentrated by crystallization or phase separation to form an aggregate. The molecules may, in some cases, be the same or different and one of the molecules could be an emissive material and the other may, in some cases, be a cofactor. These processes may, in some cases, be used to produce compositions wherein upon illumination a new excited state complex may, in some cases, be formed known as an exciplex. When formed by molecules with different characteristics an exciplex may, in some cases, have what is known as charge transfer character. This generally results in the partial transfer of an electron from the donor molecule to the acceptor molecule. As a result of the low overlap of the respective orbitals on the donor and acceptor molecules, these types of materials may, in some cases, display thermally activated delayed fluorescence. The delayed emission of these species will allow for use as a TTI in the context of this invention. In other cases, an emissive material and a quencher may, in some cases, be brought into proximity by a thermal exposure. The quencher is a cofactor that modulates the lifetime of the emissive material. The quenching event may, in some cases, occur as a result of a binding event, such as a ligand binding a metal center, acid base reaction, hydrogen bonding, excited state proton transfer, metal chelation, electron transfer, and/or energy transfer. By the different mechanisms described, emissive materials with changes in excited state lifetimes, emission intensity, absorption and emission wavelengths, or combinations thereof may, in some cases, be generated. These delayed emission features, or lack thereof in the case of quenching, may, in some cases, be used in patterns that are designed to determine the degree of a thermal exposure.

Diffusion of different materials into each other may, in some cases, affect the local environment around molecules in many other ways. If an emissive molecule is placed in an environment with proximate free space and is co-deposited with another material to give a phase separated mixture. The environment may, in some cases, change by heating wherein materials will move in a way to fill the free space. For example, if the lower density part of the mixture contains an emissive dye/material the material may, in some cases, densify by the diffusion of another material to fills empty space proximate to the dye/material and thereby restricts the internal movement of the emissive material. More restricted movement may, in some cases, reduce the rate of non-radiative processes and give an increase in the emission lifetime. Alternatively, if the densification results in bringing a quencher molecule proximate to the emissive material, then the rate of the non-radiative processes may, in some cases, increase and the lifetime may, in some cases, be lowered. Emissive materials may, in some cases, form complexes with themselves or with other molecules that may, in some cases, reduce their internal dynamics and result in decreased non-radiative rates. In the context of molecular emitters is also possible that a second dye or the same dye may, in some cases, diffuse into a material having free volume and form a complex with a guest dye. These processes may, in some cases, create species that have different lifetimes. The free volume in all of these situations may, in some cases, be created in a polymer or through host guest interactions. For example, polymers containing bicyclic ring systems are known to promote free volume. Alternatively, emissive molecules may, in some cases, form supramolecular host-guest complexes in macrocyclic cavity forming molecules such as calixarenes, cyclodextrins, cucurbit[n]urils, or pillaranes. If the cavities of the macrocycles are larger than the emissive guests, then other molecules may, in some cases, diffuse in under thermal activation and become proximate and change the emission lifetime. It is also possible that the emissive guests will be displaced by an incoming molecule under thermal activation and once the guest is released it will have a different emissive lifetime.

Thermally activated chemical reactions may, in some cases, be used to create changes in the emissive lifetime of a material or create a new material with a delayed emission. Similar to what was previously discussed, a material may, in some cases, contain multiple components that upon thermal activation diffusion is enhanced and different components are brought proximate to each other. Beyond non-covalent associations, the proximity of a cofactor may, in some cases, facilitate a chemical reaction. These reactions may, in some cases, be simple and catalyzed when the cofactor is an acid or base. Alternatively, two elements, which need not be emissive in their own right, may, in some cases, combine to form or destroy an emissive material with an emissive lifetime more than 10 nanoseconds for detection. For example, a reaction may, in some cases, result in the coordination of an organic molecule to a metal center or metal nanoparticle. The coordination event may, in some cases, result in a dramatic change in the emission lifetime of the organic molecule or alternatively the organic molecule may, in some cases, transfer energy into the local states of the metal ion and essentially serve as an antenna. For example, an $Eu^{+3}$ metal center may, in some cases, coordinate with a ligand containing a nitrogen atom such as a pyridine or phosphine oxide ligands that is also a chromophore capable of capturing light. In this case the antenna ligand may, in some cases, transfer energy to the $Eu^{+3}$ core states to produce a new emission with a lifetime greater than 10 ns. One who is skilled in the art will recognize that there are many metal ligand combinations and interactions with other heavy atoms from the main group, including iodides, bismuth, telluride, lead, etc., that may, in some cases, also promote different lifetimes. For many applications it is important that the emissive materials and the metal ions/heavy atom containing materials are non-toxic. Non-toxic materials of note include dyes used as food additives. These materials may, in some cases, have intrinsic emissive properties and examples include Allura Red, Riboflaven, Fisetin, Quinine, Curcumin, Vanillen, Sunset Yellow, 4,4'-bis(2-benzoxazolyl)stilbene, and Erythrosin B. The case of Erythrosin B is highly relevant as this molecule may, in some cases, be converted between a longer wavelength emissive form and a colorless form with base as shown.

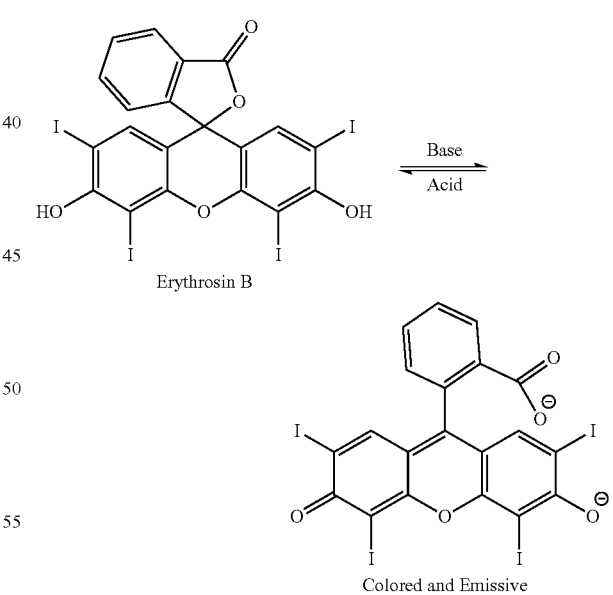

Erythrosin B

Colored and Emissive

For example, when Erythrosin B is in its neutral state the delocalization is restricted and it not an effective chromophore. However, with deprotonation the spirolactone opens to create a very effective chromophore. The additional presence of iodines, which are heavy atoms, in the structure promotes intersystem crossing in the excited state and this molecule has a long-lived excited state as a result of the triplet state produced. For this system, base will create an emission with an extended lifetime that may, in some cases, be detected and acid will deactivate the chromophore to remove the long lived excited state. Erythrosin B may, in some cases, for example be deposited in a matrix material in its closed non-emissive form and a base capable of causing it to convert to the emissive state deposited in the same or different matrix in a pattern on top of this material. The matrix materials may, in some cases, be chosen to allow for diffusion of the base upon a prescribed thermal activation. The result of diffusion of the base to the molecule will create a new emission that has a lifetime more than 10 ns that may, in some cases, be detected. The duration and temperature of the thermal exposure may, in some cases, be determined by the degree of diffusion of the base and this feature may, in some cases, be determined by accessing the length of the diffusion in either the lateral or vertical dimensions. The thickness of the matrix materials for both the dye and the base need not be the same and may, in some cases, have gradients in thickness. It is also possible that the diffusion will be determined by an additional layer of material that is inserted between the dye matrix and the base. It is also possible to print the dye and base in an laterally offset geometry, in some embodiments. It is also possible to start with the colored negatively charged form of Erythrosin B and quench the emission by reacting it with acid that may, in some cases, diffuse. It is also possible that Erythrosin B or its base form may, in some cases, actively diffuse upon thermal activation. The base and acid may, in some cases, be part of the matrix or covalently linked to the matrix. For example, one of the matrix materials may, in some cases, be a polymeric acid or polymeric base. The Erythrosin B and the acid or base may, in some cases, also be co-deposited on a product provided that each is in microparticle form within the matrix. In this way dispersions, potentially in a continuous phase of water, based on small micelles, or colloids may, in some cases, be deposited where the materials diffuse to give changes in lifetime upon thermal exposure. There are other base catalyzed reactions, including elimination reactions that produce extended $\pi$-electron conjugation that may, in some cases, be used to create species with delayed emissions. It should also be noted that all of the different mechanisms suggested here may, in some cases, be applicable to many other dyes and also need not be limited to acids and bases. These mechanisms may, in some cases, be applied to many of the general materials sets described in this invention.

Purely thermal reactions may, in some cases, also be used to create new materials with delayed emissions. These processes may, in some cases, be as simple as dehydration. For example, $Eu^{+3}$ species have reduced lifetimes in the presence of water. Hydrated metal complexes may condense with dehydration to give new emissive complexes or nanoparticles. Hydrates of organic molecules such as aldehyde hydrates may, in some cases, lose water to create or quench delayed emission species. There are a variety of elimination reactions that may, in some cases, proceed thermally to create extended conjugation and cause a change in the optical absorption and emission wavelengths of delayed emission species. For example, molecules may, in some cases, eliminate halide acids such as HBr, HI or HCl. Additionally, reactions such as the Cope elimination may, in some cases, be used to create new double bonds. A variety of pericyclic reactions are possible, including thermal ring-opening of cyclobutenes to create conjugated dienes, which when integrated with heavy atoms of some other material capable of creating a delayed emission may, in some cases, be used to create a composition capable of functioning as a TTI with this invention. Similarly, a Diels-Alder or retro-Diels-Alder reaction may, in some cases, be used to create a new emission. The Diels-Alder reaction is one of the most commonly used reactions in chemistry and there are abundant ways that this reaction may, in some cases, be used to create or destroy molecules displaying a delayed emission.

The emissive materials may, in some cases, be purely inorganic and applied to a product by way of a dispersion in water or other solvent. Purely inorganic materials may, in some cases, be considered ceramics and are capable of withstanding high temperatures. For example, it is possible that a precursor material may, in some cases, be applied to a surface with other materials such as surfactants to allow for precision printing of a pattern and then heated to high temperatures (>300° C.) wherein the organic materials are removed and with sufficient heating on a surface such as glass these materials may, in some cases, become fused to the glass. The fact that the inorganic emissive materials do not melt may, in some cases, result in nanoparticles or isolated elements that are bound (fused) to the surface of a glass support. This process may, in some cases, be performed in conjunction with other particles that form a pattern such as a bar code or QR code. A TTI may be formed, in some cases, using inorganic materials processed at high temperature if a laminate with an element designed to produce a TTI is added once the article is cooled. It should also be noted although some applications of inorganic chromophores require high temperature processes, the methods described here are not required to have a high temperature processing step. The processes to create TTI's detailed here are general and the inorganic materials may, in some cases, be deposited on plastics, wood, paper, ceramics or glass without heating. In some cases, some of the inorganic emissive materials may, in some cases, be optionally passivated and provide for a reference signal with a lifetime that is invariant upon chemical exposure. Passivation may, in some cases, occur by producing structured inorganic emissive materials wherein a particle has a protective inorganic shell, as well as other ways. To produce a TTI device from these materials fabricated under the conditions of high heat will require a final over-coating step of a cofactor which may, in some cases, be performed at a later stage. The cofactor may, in some cases, be a quencher or a light harvesting antenna or a material that binds to the particle or combinations thereof. In some cases, a cofactor may, in some cases, be applied that quenches the inorganic emissive material and may, in some cases, be lost by thermal volatilization or diffusion into an overcoating material. In this case a thermal event will give an increase in the intensity of the inorganic emitter and/or its emissive lifetime. The quencher need not be applied evenly across the areas containing the inorganic emitter. In some cases, only part of the inorganic emitter need be treated with the quencher and in this way a reference emissive material is produced in conjunction with thermally responsive emissive material. It is also possible to apply variable amounts of quencher in a known pattern with the locations on the product where the quencher is applied more sparingly activated (display an increase in the emission intensity and/or lifetime) by lower degrees of thermal exposure. Locations on the product wherein the quencher is applied in a larger quantity will activate at higher temperature time dosages. Comparisons of these effects may, in some cases, yield TTI information of interest for a given product.

It is also possible to use cofactors that behave as antennas with inorganic emitters that have been fused to surfaces at high temperatures. For example, isolated $Eu^{+3}$ ions without coordinated organic ligands have very limited absorption, particularly in the visible region of the electromagnetic spectrum. Europium ions may, in some cases, be embedded into a glass or similar substrate by heating nanoparticles or heating materials applied from a dispersion of $EuCl_3$. Application of a cofactor that is capable of absorbing light and binding to the $Eu^{+3}$ ions may, in some cases, then be used to produce an emissive state with an appropriate emissive lifetime. The antenna chromophores are behaving as ligands and other added ligands that either bind stronger to the $Eu^{+3}$ or are in greater abundance may, in some cases, be used to produce a TTI. For example, a pyridine containing chromophore may, in some cases, be bound to an $Eu^{+3}$ species and in the presence of a stronger binding ligand may, in some cases, be displaced with a thermal treatment. If the displacing ligand, which may, in some cases, include phosphine oxides, 4,4'-bipyridyls, terpyridyls, or 1,10-phenanthrolines, do not produce $Eu^{+3}$ complexes that absorb at the wavelength of the excitation, then the europium based emissive species will diminish. The amount of displacing ligand may, in some cases, be varied and there may, in some cases, be an excess of the starting antenna ligand. As with other methods, variations in the matrix, concentration, and other aspects of the environment may, in some cases, be used to produce a thermally activated response that produces the desired TTI.

It is also possible to have an initial state wherein some or all of the $Eu^{+3}$ sites are bound with ligands that do not allow for excitation at the applied wavelengths. Application of an antenna chromophore that may, in some cases, displace these ligands under the desired thermal exposure conditions may, in some cases, then produce a means to produce a TTI. Combinations of ligand concentration, matrix material, spatial positioning and the like may, in some cases, be used to produce a TTI with the proper response profile for a given product.

Similar schemes may, in some cases, be anticipated for other metal ions, including terbium ($Tb^{+3}$), erbium ($Er^{+3}$), yttrium ($Yb^{+3}$) and a variety of other metals including gold, silver, palladium, platinum, manganese, titanium, and ruthenium. Main group elements including tin, lead, bismuth, cadmium, indium and other heavy elements may, in some cases, also be used to create responsive materials capable of producing emission behaviors in response to a thermal exposure to create a TTI. Nanoparticle systems may, in some cases, also be used containing main group or transition metal ions with fluoride, oxygen, sulfur, selenium, and telluride.

Some products may, in some cases, be damaged by excessively cold temperatures and freezing of samples may, in some cases, cause irreversible damage to the product. Products may be unstable upon freezing and not return to their initial state. In many cases these are products involving aqueous solutions or aqueous gels, but the products may, in some cases, have many forms. For example, it may be of interest to determine if fish has been frozen prior to selling it in a retail store. Similarly, freezing will compromise many beverages. Freezing of a solution of gel will often cause phase separation when one of the components crystallizes. Such a process may, in some cases, lead to the assembly or deconstruction of a material displaying a delayed emission. Detecting changes in the emission intensities, absorption and emission wavelengths, and excited state lifetimes may, in some cases, be used to produce a TTI that reflects the cold exposure of a product. Gel materials may, in some cases, be used to host the components to create these cold exposure TTIs and these materials have the advantage that they may, in some cases, be patterned to create more information.

The analysis of spatial patterns of materials displaying delayed emission may, in some cases, be used to quantify a thermal exposure. Compositions fabricated from phase separated materials may, in some cases, be patterned in ways able to produce a TTI code providing more information than a simple threshold exposure. For example, by creating patterns of the components needed to produce a TTI with different spacing between multiple active elements that must diffuse together to produce the signal, a gradation of thermal exposures may, in some cases, then be determined yielding more granular data. Materials wherein the pattern requires only short-range diffusion will respond first and only with longer thermal exposures will the wider spaced materials achieve the required diffusion. Similar to optical bar codes and QR codes the delayed emissive signatures created by thermal exposure or cold exposure may, in some cases, be used to provide information. This same information may, in some cases, also be used in product authentication and in many cases the patterns collected from delayed emission may, in some cases, be used in conjunction with other optical codes that provide information about the product (lot number, date of manufacture, place of origin, etc.) that may, in some cases, be integrated with the information from the TTI. The patterns may, in some cases, be complex and need not be limited to a single delayed emission species as the TTI but may, in some cases, contain multiple delayed emission species as well as different mechanisms for the TTI response. Reference emissions may, in some cases, also be integrated into the materials that provide for spatial positioning, excited state lifetimes, and intensity information. The delayed emission readers that capture information from the TTIs may, in some cases, also vary. Readers may, in some cases, range from a fast laser pulse with time resolved lifetimes, to devices that use shutters to gate both the excitation and emission collection. Readers may, in some cases, be used that resolve lifetimes and wavelengths and in this case the reader may, in some cases, be a streak camera. Smart phones and other devices incorporating CMOS imaging chips such as digital cameras may, in some cases, also be used to read TTIs via the rolling shutter effect.

As described above, in some embodiments, a system comprises an excitation component. In some instances, the excitation component comprises a source of electromagnetic radiation. The source of electromagnetic radiation may be a source of any type of electromagnetic radiation (i.e., electromagnetic radiation of any wavelength). Suitable types of electromagnetic radiation that may be emitted by the source of electromagnetic radiation include, but are not limited to, ultraviolet radiation (e.g., having a wavelength in a range from about 10 nm to about 380 nm), visible light (e.g., having a wavelength in a range from about 380 nm to about 740 nm), near-infrared radiation (e.g., having a wavelength in a range from about 700 nm to about 800 nm), and infrared radiation (e.g., having a wavelength in a range from about 740 nm to about 3 μm).

In some embodiments, the source of electromagnetic radiation is configured to emit broadband radiation. In certain instances, the source of electromagnetic radiation is configured to emit electromagnetic radiation in a wavelength range spanning at least 350 nm, at least 360 nm, at least 370 nm, at least 380 nm, at least 390 nm, at least 400 nm, at least 500 nm, at least 1 μm, at least 2 μm, or at least 3 μm. In certain instances, the source of electromagnetic radiation is configured to emit electromagnetic radiation in a wavelength range spanning 350 nm to 400 nm, 350 nm to 500 nm, 350 nm to 1 μm, 350 nm to 2 μm, 350 nm to 3 μm, 400 nm to 500 nm, 400 nm to 1 μm, 400 nm to 2 μm, 400 nm to 3 μm, 500 nm to 1 µm, 500 nm to 2 µm, 500 nm to 3 µm, 1 µm to 2 µm, or 1 µm to 3 µm. In some embodiments, the source of electromagnetic radiation is configured to emit substantially white light.

In some embodiments, the source of electromagnetic radiation is configured to emit electromagnetic radiation in a wavelength range spanning at least 350 nm, at least 360 nm, at least 370 nm, at least 380 nm, at least 390 nm, at least 400 nm, at least 500 nm, at least 600 nm, at least 700 nm, or at least 800 nm. In certain instances, the source of electromagnetic radiation is configured to emit electromagnetic radiation in a wavelength range of greater than or equal to 350 nm, greater than or equal to 400 nm, greater than or equal to 450 nm, greater than or equal to 500 nm, greater than or equal to 550 nm, greater than or equal to 600 nm, greater than or equal to 650 nm, greater than or equal to 700 nm, or greater than or equal to 750 nm and less than or equal to 800 nm, less than or equal to 750 nm, less than or equal to 700 nm, less than or equal to 650 nm, less than or equal to 600 nm, less than or equal to 550 nm, less than or equal to 500 nm, less than or equal to 450 nm, or less than or equal to 400 nm. Combinations of the above referenced ranges are also possible (e.g., greater than or equal to 350 nm and less than or equal to 800 nm). Other ranges are also possible.

In some embodiments, the source of electromagnetic radiation is configured to emit electromagnetic radiation in relatively narrow ranges of wavelengths. In certain cases, for example, the source of electromagnetic radiation is configured to emit electromagnetic radiation in a discrete wavelength range that selectively excites particular emissive species. In some embodiments, the source of electromagnetic radiation is configured to emit electromagnetic radiation in a discrete wavelength range spanning 350 nm or less, 300 nm or less, 200 nm or less, 100 nm or less, 90 nm or less, 80 nm or less, 70 nm or less, 60 nm or less, 50 nm or less, 40 nm or less, 30 nm or less, 20 nm or less, or 10 nm or less. In some embodiments, the source of electromagnetic radiation is configured to emit electromagnetic radiation in a discrete wavelength range spanning 10 nm to 20 nm, 10 nm to 40 nm, 10 nm to 50 nm, 10 nm to 60 nm, 10 nm to 80 nm, 10 nm to 100 nm, 10 nm to 200 nm, 10 nm to 300 nm, 10 nm to 350 nm, 20 nm to 40 nm, 20 nm to 50 nm, 20 nm to 60 nm, 20 nm to 80 nm, 20 nm to 100 nm, 20 nm to 200 nm, 20 nm to 300 nm, 20 nm to 350 nm, 40 nm to 60 nm, 40 nm to 80 nm, 40 nm to 100 nm, 40 nm to 200 nm, 40 nm to 300 nm, 40 nm to 350 nm, 50 nm to 100 nm, 50 nm to 200 nm, 50 nm to 300 nm, 50 nm to 350 nm, 100 nm to 200 nm, 100 nm to 300 nm, or 100 nm to 350 nm.

In some embodiments, the source of electromagnetic radiation is configured to emit electromagnetic radiation in a discrete wavelength range spanning 500 nm or less, 400 nm or less, 350 nm or less, 300 nm or less, 200 nm or less, 100 nm or less, 90 nm or less, 80 nm or less, 70 nm or less, 60 nm or less, 50 nm or less, 40 nm or less, 30 nm or less, 20 nm or less, or 200 nm or less. In some embodiments, the source of electromagnetic radiation is configured to emit electromagnetic radiation in a discrete wavelength range spanning 200 nm to 20 nm, 200 nm to 40 nm, 200 nm to 50 nm, 200 nm to 60 nm, 200 nm to 80 nm, 200 nm to 100 nm, 200 nm to 200 nm, 200 nm to 300 nm, 200 nm to 350 nm, 20 nm to 40 nm, 20 nm to 50 nm, 20 nm to 60 nm, 20 nm to 80 nm, 20 nm to 100 nm, 20 nm to 200 nm, 20 nm to 300 nm, 20 nm to 350 nm, 40 nm to 60 nm, 40 nm to 80 nm, 40 nm to 100 nm, 40 nm to 200 nm, 40 nm to 300 nm, 40 nm to 350 nm, 50 nm to 100 nm, 50 nm to 200 nm, 50 nm to 300 nm, 50 nm to 350 nm, 100 nm to 200 nm, 100 nm to 300 nm, or 100 nm to 500 nm.

In some embodiments, the source of electromagnetic radiation is configured to emit substantially violet light (e.g., light having a peak wavelength in a range of 400 nm to 450 nm), substantially blue light (e.g., light having a peak wavelength in a range from 450 nm to 490 nm), substantially cyan light (e.g., light having a peak wavelength in a range from 490 nm to 520 nm), substantially green light (e.g., light having a peak wavelength in a range from 520 nm to 560 nm), substantially yellow light (e.g., light having a peak wavelength in a range from 560 nm to 590 nm), substantially orange light (e.g., light having a peak wavelength in a range from 590 nm to 635 nm), and/or substantially red light (e.g., light having a peak wavelength in a range from 635 nm to 700 nm). In some embodiments, the source of electromagnetic radiation is configured to emit electromagnetic radiation in a plurality of relatively narrow ranges of wavelengths. In certain instances, the source of electromagnetic radiation is configured to emit electromagnetic radiation in at least 2 discrete ranges, at least 3 discrete ranges, at least 4 discrete ranges, or at least 5 discrete ranges.

In some embodiments, the source of electromagnetic radiation has at least a first portion of the electromagnetic radiation spectrum comprising a wavelength of between greater than or equal to 425 nm and less than or equal to 475 nm (e.g., greater than or equal to 425 nm and less than or equal to 450 nm). In some embodiments, a second portion of the electromagnetic radiation spectrum produced by the source of electromagnetic radiation comprises a wavelength of greater than or equal to 525 nm and less than or equal to 725 nm (e.g., greater than or equal to 600 nm and less than or equal to 725 nm, greater than or equal to 600 nm and less than or equal to 700 nm). In some embodiments, the source of electromagnetic radiation has at least a first portion of the electromagnetic radiation spectrum comprising a wavelength of between greater than or equal to 425 nm and less than or equal to 525 nm (e.g., greater than or equal to 425 nm and less than or equal to 525 nm). In some embodiments, a second portion of the electromagnetic radiation spectrum produced by the source of electromagnetic radiation comprises a wavelength of greater than or equal to 525 nm and less than or equal to 725 nm. In some embodiments, the source of electromagnetic radiation produces white light.

In an exemplary set of embodiments, the source of electromagnetic radiation is configured to emit substantially white light. For example, the source of electromagnetic radiation emits light having a range between at least 350 nm and less than or equal to 800 nm and has a peak in the range of spanning at least 350 nm, at least 360 nm, at least 370 nm, at least 380 nm, at least 390 nm, at least 400 nm, at least 500 nm, at least 600 nm, at least 700 nm, or at least 800 nm. In certain instances, the source of electromagnetic radiation is configured to emit electromagnetic radiation in a wavelength range of greater than or equal to 350 nm, greater than or equal to 400 nm, greater than or equal to 450 nm, greater than or equal to 500 nm, greater than or equal to 550 nm, greater than or equal to 600 nm, greater than or equal to 650 nm, greater than or equal to 700 nm, or greater than or equal to 750 nm and less than or equal to 800 nm, less than or equal to 750 nm, less than or equal to 700 nm, less than or equal to 650 nm, less than or equal to 600 nm, less than or equal to 550 nm, less than or equal to 500 nm, less than or equal to 450 nm, or less than or equal to 400 nm.

In some embodiments, the source produces a wavelength of electromagnetic radiation that interacts with the emissive species such that the emissive species produces a detectable signal having one or more delayed emissions of greater than or equal to 10 nanoseconds, as described herein.

The excitation component may comprise one or more sources of electromagnetic radiation, and the one or more sources of electromagnetic radiation may comprise any suitable source of electromagnetic radiation. Examples of suitable sources of electromagnetic radiation include, but are not limited to, light-emitting diodes (LEDs), organic light-emitting diodes (OLEDs), flash bulbs, emissive species (e.g., fluorescent dyes, inorganic phosphors), room lights, and electrical discharge sources. In some embodiments, the excitation component comprises a plurality of sources of electromagnetic radiation (e.g., a plurality of LEDs, OLEDs, flash bulbs, emissive species, and/or electrical discharge sources). In some cases, two or more sources of electromagnetic radiation are configured to emit electromagnetic radiation in the same range of wavelengths. In some instances, each electromagnetic radiation source of the plurality of electromagnetic radiation sources is configured to emit electromagnetic radiation in the same range of wavelengths. In some cases, two or more sources of electromagnetic radiation are configured to emit electromagnetic radiation in different ranges of wavelengths. In some instances, each electromagnetic radiation source of the plurality of electromagnetic radiation sources is configured to emit electromagnetic radiation in different ranges of wavelengths.

In some embodiments, the electromagnetic radiation emitted by an excitation component is pulsed and/or modulated. Time varying excitation is generally said to be a non-steady-state excitation. In some embodiments, an excitation component is configured to emit electromagnetic radiation such that at least one characteristic of the electromagnetic radiation (e.g., intensity, wavelength, polarization) is modulated over time. In some embodiments, an excitation component is configured to emit one or more pulses of electromagnetic radiation. In some embodiments, the excitation component emits a complex pattern of pulses and modulated electromagnetic radiation that may be in sequence or overlapping in time, polarization, spatial position on the article, and/or wavelength. The excitation component may emit one or more pulses of any duration at any pulse rate. In some embodiments, the excitation component is configured to emit one or more pulses of electromagnetic radiation having a duration of 10 milliseconds (ms) or less, 1 ms or less, 100 microseconds (μm) or less, 10 μm or less, 1 μm or less, 100 nanoseconds (ns) or less, 10 ns or less, 5 ns or less, 2 ns or less, 1 ns or less, 500 picoseconds (ps) or less, 200 ps or less, 100 ps or less, 50 ps or less, 20 ps or less, 10 ps or less, or 1 ps or less. In some embodiments, the excitation component is configured to emit one or more pulses of electromagnetic radiation having a duration in a range from 1 ps to 10 ps, 1 ps to 20 ps, 1 ps to 50 ps, 1 ps to 100 ps, 1 ps to 200 ps, 1 ps to 500 ps, 1 ps to 1 ns, 1 ps to 2 ns, 1 ps to 5 ns, 1 ps to 10 ns, 10 ps to 50 ps, 10 ps to 100 ps, 10 ps to 200 ps, 10 ps to 500 ps, 10 ps to 1 ns, 10 ps to 2 ns, 10 ps to 5 ns, 10 ps to 10 ns, 100 ps to 500 ps, 100 ps to 1 ns, 100 ps to 2 ns, 100 ps to 5 ns, 100 ps to 10 ns, 1 ns to 5 ns, or 1 ns to 10 ns.

In some embodiments, an excitation component is configured to emit one or more pulses of electromagnetic radiation at a relatively high pulse rate (e.g., similar or higher than an image capture rate of an image sensor). In some cases, an excitation component is configured to emit one or more pulses of electromagnetic radiation within a single cycle of image capture by an image sensor (or, in some cases, within multiple image capture cycles). In some cases, an excitation component is configured to produce a modulated intensity of electromagnetic radiation that varies over a single cycle of image capture by an image sensor (or, in some cases, within multiple image capture cycles). In some cases, an excitation component is timed with an image capture such that images created from photon emissions at different delay times with regard to the excitation pulse or modulation are produced.

After emission of the one or more pulses of electromagnetic radiation, any electromagnetic radiation emitted by an emissive species may be monitored by the image sensor as a function of time.

In some embodiments, the excitation component is configured to emit one or more pulses of electromagnetic radiation at a pulse rate of at least 1 pulse/s, at least 2 pulses/s, at least 5 pulses/s, at least 10 pulses/s, at least 15 pulses/s, at least 20 pulses/s, at least 50 pulses/s, or at least 100 pulses/s. In some embodiments, the excitation component is configured to emit one or more pulses of electromagnetic radiation at a pulse rate in a range from 1 to 5 pulses/s, 1 to 10 pulses/s, 1 to 15 pulses/s, 1 to 20 pulses/s, 1 to 50 pulses/s, 1 to 100 pulses/s, 5 to 10 pulses/s, 5 to 15 pulses/s, 5 to 20 pulses/s, 5 to 50 pulses/s, 5 to 100 pulses/s, 10 to 20 pulses/s, 10 to 50 pulses/s, 10 to 100 pulses/s, 20 to 50 pulses/s, 20 to 100 pulses/s, or 50 to 100 pulses/s.

In some embodiments, an excitation component comprises a source of electromagnetic radiation that is configured to emit pulsed and/or modulated electromagnetic radiation. In some embodiments, an excitation component comprises a source of electromagnetic radiation that is configured to emit a substantially continuous stream of electromagnetic radiation.

In some embodiments, an excitation component comprises a component configured to facilitate pulsing and/or modulation of electromagnetic radiation emitted by a source of electromagnetic radiation. The component may be a mechanical and/or electronic. Non-limiting examples of suitable mechanical and/or electronic components include optical shutters, rotating elements (e.g., choppers), lasers, moving mirrors, dynamic refractory materials, and other optical modulators. Examples of suitable optical shutters include mechanical shutters, light valves (e.g., liquid crystal light modulators), and molecular crystals that respond to mechanical and/or thermal stresses and/or to electrical fields, but a person of ordinary skill in the art would understand that other types of shutters may be used. The frequency or time period of the modulated electromagnetic radiation can, in some cases, be paired with the response time (frame rate) of the imaging device. The modulation time period will, in some embodiments, often be faster than the overall frame rate, but may be close to the time between reading of the rows or columns of image pixels with the rolling shutter mechanism. In some cases, having the modulation time period close in time to delays between reading of the rows or columns will create information when paired with a time dependent emission with a similar time period.

In some embodiments, systems and methods described herein couple the pulse profile (e.g., rate, shape) of electromagnetic radiation emitted by an excitation component with the lifetime of an emissive species and the image capture rate of an image sensor. Advantageously, the coupling of these components enables, in some embodiments, determination of the characteristic of a particular emissive species (e.g., emission lifetime), which may in turn provide information about a characteristic of an associated article. By way of example, the measured emission lifetime of a particular emissive species may provide information about the environment (e.g., presence of certain molecules, temperature, pH) in which the emissive species is located.

Figure 4:
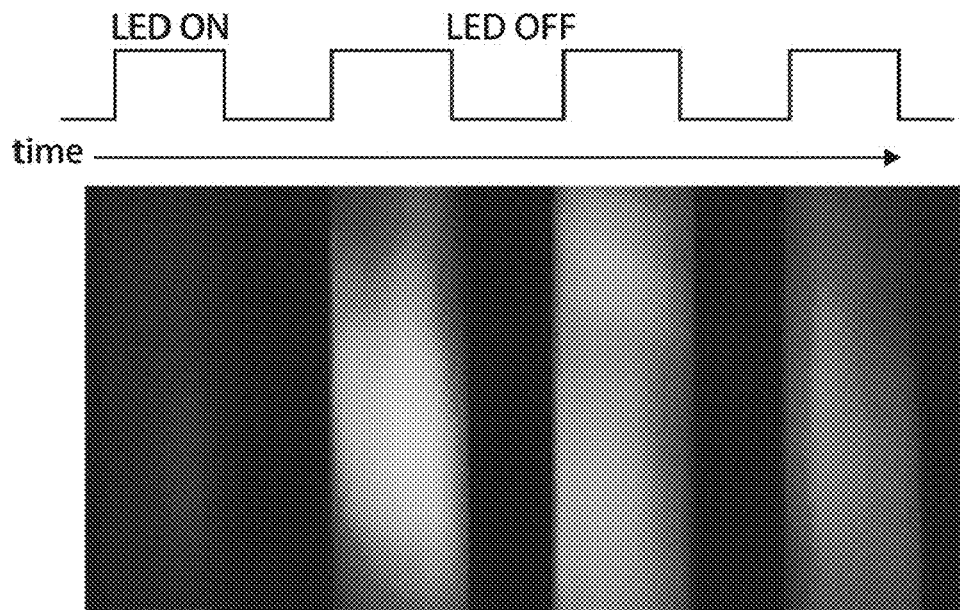
FIG. 4 shows, according to some embodiments, a single image of a pulsing LED captured by a smartphone using a rolling shutter method and a top caption indicating whether the LED was on or off.

As an illustrative embodiment, FIG. 4 shows a single image of a pulsing LED captured by a smartphone using a rolling shutter method and a top caption indicating whether the LED was on or off. In FIG. 4, the pulse rate of the LED is faster than the total image capture rate of the smartphone, and a banding structure is visible. In particular, some rows of the image capture the LED in its "on" state, while subsequent rows capture the LED in its "off" state.

Figure 5:
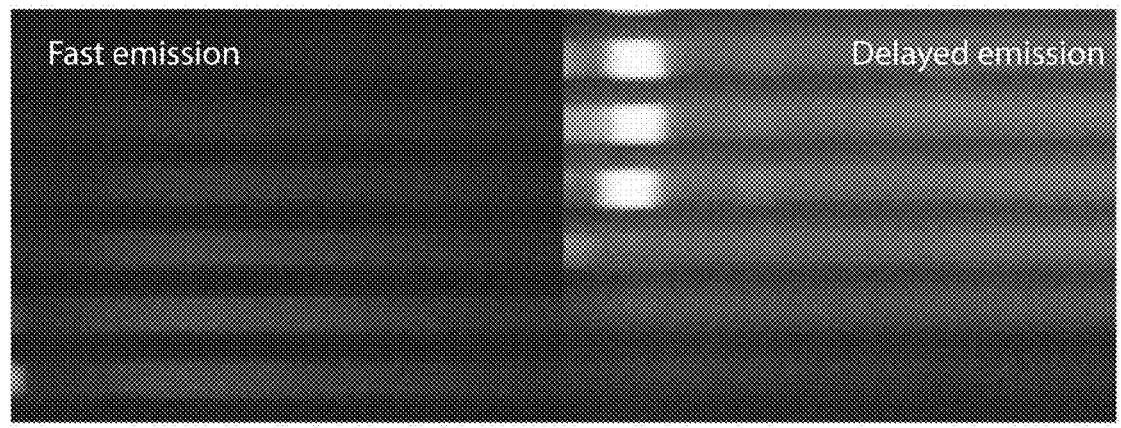
FIG. 5 shows images of a pulsing UV-LED exciting a fast emissive species (left) and a delayed emission species (right), according to some embodiments.
Figure 5:
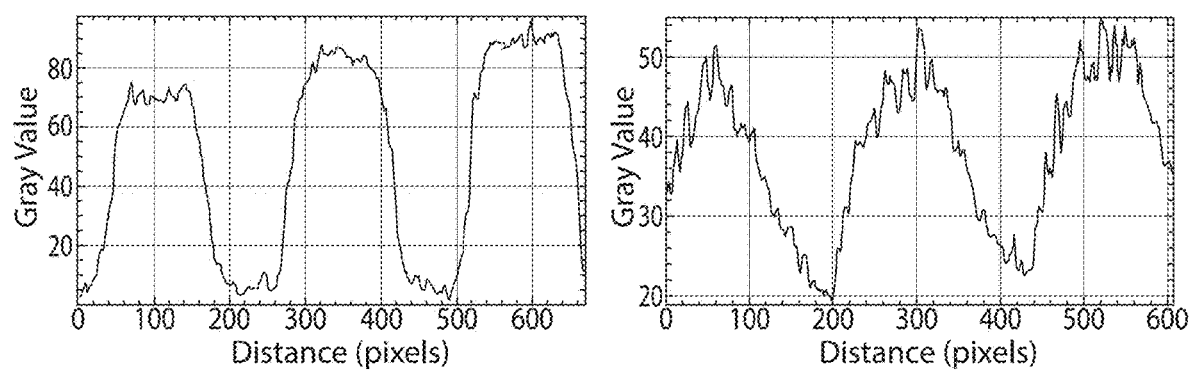

To further illustrate, FIG. 5 shows an image of a pulsing UV-LED exciting a fast emissive species (left), as captured by a smartphone using a rolling shutter method. The image of the fast emissive species is accompanied by a plot of pixel intensity. FIG. 5 also shows an image of a pulsing UV-LED exciting a delayed emissive species (right), as captured by a smartphone using a rolling shutter method. The image of the delayed emissive species is also accompanied by a plot of pixel intensity. From FIG. 5, it may be seen that the image of the delayed emissive species contains bands that appear "fuzzy." This "fuzziness" may be due at least in part to delayed emission occurring after the UV-LED was turned off.

According to some embodiments, a component of a system (e.g., an image sensor) detects at least a portion of a detectable emission (e.g., a detectable non-steady-state emission) produced by an emissive species during an emission time period (also referred to as an emission lifetime). A person of ordinary skill in the art would understand that an emissive species may produce a detectable emission through phosphorescence, fluorescence, and/or reflection/scattering (e.g., reflection of ambient electromagnetic radiation and/or electromagnetic radiation emitted by an excitation component). A person of ordinary skill in the art would also understand that an emission time period or emission lifetime generally refers to the time during which an emissive species emits electromagnetic radiation after any excitation radiation has been removed (e.g., after a pulse of electromagnetic radiation has been emitted by an excitation component).

An emissive species generally has an intrinsic emission lifetime, also referred to as an excited state lifetime, that may be determined by intrinsic radiative and non-radiative decay rates, as represented by the following formula:

$$k_{radiative} + k_{non-radiative} = 1/\text{intrinsic emission lifetime}$$

However, the emission lifetime is generally dependent on the context and values may change with different solvents or solid forms. For example, the observed emission lifetime of a species may differ from the intrinsic emission lifetime. For example, when other quenching processes are present, the observed emission lifetime may be calculated according to the following formula:

$$k_{radiative} + k_{non-radiative} + k_{quenching} = 1/\text{observed emission lifetime}$$

Thus, the observed emission lifetime would be shorter than the intrinsic emission lifetime. As discussed below, numerous factors (e.g., presence of other molecules, temperature, radiation exposure) may affect the emission lifetime of an emissive species such that an observed emission lifetime is different than (e.g., greater than, less than) the intrinsic emission lifetime of the emissive species. The radiative rate ($k_{radiative}$) contains all of the different emission processes and may be measured as the weighted average of processes that have different rates of emission. The measured emission rate may, in some cases, vary within a measurement of a species. For example, in TADF delayed-fluorescence with excitation there may be prompt-fluorescence followed by a transition to the TADF process wherein the excited state displays the singlet-triplet equilibrium.

In systems and methods described herein, an emissive species has an intrinsic emission lifetime of any suitable length. In certain cases, an emissive species has a relatively long intrinsic emission lifetime. In some embodiments, an emissive species has an intrinsic emission lifetime of at least 1 nanosecond (ns), at least 5 ns, at least 10 ns, at least 20 ns, at least 50 ns, at least 100 ns, at least 200 ns, at least 500 ns, at least 1 μs, at least 10 μs, at least 50 μs, at least 100 μs, at least 500 μs, at least 1 ms, at least 5 ms, at least 10 ms, at least 50 ms, at least 100 ms, at least 500 ms, at least 1 s, at least 2 s, at least 3 s, at least 4 s, at least 5 s, at least 6 s, at least 7 s, at least 8 s, at least 9 s, or at least 10 s. In some embodiments, an emissive species has an intrinsic emission lifetime in a range from 1 ns to 10 ns, 1 ns to 20 ns, 1 ns to 50 ns, 1 ns to 100 ns, 1 ns to 500 ns, 1 ns to 1 μs, 1 ns to 5 μs, 1 ns to 10 μs, 1 ns to 50 μs, 1 ns to 100 μs, 1 ns to 500 μs, 1 ns to 1 ms, 1 ns to 5 ms, 1 ns to 10 ms, 1 ns to 50 ms, 1 ns to 100 ms, 1 ns to 500 ms, 1 ns to 1 s, 1 ns to 5 s, 1 ns to 10 s, 10 ns to 20 ns, 10 ns to 50 ns, 10 ns to 100 ns, 10 ns to 500 ns, 10 ns to 1 μs, 10 ns to 5 μs, 10 ns to 10 μs, 10 ns to 50 μs, 10 ns to 100 μs, 10 ns to 500 μs, 10 ns to 1 ms, 10 ns to 5 ms, 10 ns to 10 ms, 10 ns to 50 ms, 10 ns to 100 ms, 10 ns to 500 ms, 10 ns to 1 s, 10 ns to 5 s, 10 ns to 10 s, 50 ns to 100 ns, 50 ns to 500 ns, 50 ns to 1 μs, 50 ns to 5 μs, 50 ns to 10 μs, 50 ns to 50 μs, 50 ns to 100 μs, 50 ns to 500 μs, 50 ns to 1 ms, 50 ns to 5 ms, 50 ns to 10 ms, 50 ns to 50 ms, 50 ns to 100 ms, 50 ns to 500 ms, 50 ns to 1 s, 50 ns to 5 s, 50 ns to 10 s, 100 ns to 500 ns, 100 ns to 1 μs, 100 ns to 5 μs, 100 ns to 10 μs, 100 ns to 50 μs, 100 ns to 100 μs, 100 ns to 500 μs, 100 ns to 1 ms, 100 ns to 5 ms, 100 ns to 10 ms, 100 ns to 50 ms, 100 ns to 100 ms, 100 ns to 500 ms, 100 ns to 1 s, 100 ns to 5 s, or 100 ns to 10 s. Other ranges are also possible.

In some embodiments, an emissive species has an observed emission lifetime (e.g., a measured emission time period) of any suitable length. In certain cases, an emissive species has a relatively long observed emission lifetime relative to typical fluorescent dyes that are present in many articles or in natural systems (e.g., at least 10 ns). A relatively long observed emission lifetime may, in some cases, allow a single image to show emission from an emissive species when an excitation source is turned off. In so doing, the slower emissions may be observed once the faster emissions are absent. In certain instances, an emissive species has an observed emission lifetime that may be measured using consumer-level electronics (e.g., a smartphone, a digital camera). In some embodiments, an emissive species has an observed emission lifetime (e.g., a measured emission time period) of at least 1 nanosecond (ns), at least 5 ns, at least 10 ns, at least 20 ns, at least 50 ns, at least 100 ns, at least 200 ns, at least 500 ns, at least 1 μs, at least 10 μs, at least 50 μs, at least 100 μs, at least 500 μs, at least 1 ms, at least 5 ms, at least 10 ms, at least 50 ms, at least 100 ms, at least 500 ms, at least 1 s, at least 2 s, at least 5 s, or at least 10 s.

In some embodiments, an emissive species has an observed emission lifetime (e.g., a measured emission time period) of 10 s or less, 5 s or less, 2 s or less, 1 s or less, 500 ms or less, 100 ms or less, 50 ms or less, 10 ms or less, 5 ms or less, 1 ms or less, 500 μs or less, 100 μs or less, 50 μs or less, 10 μs or less, 1 μs or less, 500 ns or less, 200 ns or less, 100 ns or less, 50 ns or less, 10 ns or less, 5 ns or less, or 1 ns or less. In certain cases, an emissive species having a shorter observed emission lifetime (e.g., 0.1 second or less) may provide higher average signals than an emissive species having a longer observed emission lifetime because the electromagnetic radiation emission is spread over a shorter period. In addition, an emissive species having a shorter observed emission lifetime (e.g., 0.1 second or less) may advantageously allow collection of lifetime images to occur at a faster rate than an emissive species having a longer observed emission lifetime.

In some embodiments, an emissive species has an observed emission lifetime (e.g., a measured emission time period) in a range from 1 ns to 10 ns, 1 ns to 20 ns, 1 ns to 50 ns, 1 ns to 100 ns, 1 ns to 500 ns, 1 ns to 1 µs, 1 ns to 5 µs, 1 ns to 10 µs, 1 ns to 50 µs, 1 ns to 100 µs, 1 ns to 500 µs, 1 ns to 1 ms, 1 ns to 5 ms, 1 ns to 10 ms, 1 ns to 50 ms, 1 ns to 100 ms, 1 ns to 500 ms, 1 ns to 1 s, 1 ns to 5 s, 1 ns to 10 s, 10 ns to 20 ns, 10 ns to 50 ns, 10 ns to 100 ns, 10 ns to 500 ns, 10 ns to 1 µs, 10 ns to 5 µs, 10 ns to 10 µs, 10 ns to 50 µs, 10 ns to 100 µs, 10 ns to 500 µs, 10 ns to 1 ms, 10 ns to 5 ms, 10 ns to 10 ms, 10 ns to 50 ms, 10 ns to 100 ms, 10 ns to 500 ms, 10 ns to 1 s, 10 ns to 5 s, 10 ns to 10 s, 50 ns to 100 ns, 50 ns to 500 ns, 50 ns to 1 µs, 50 ns to 5 µs, 50 ns to 10 µs, 50 ns to 50 µs, 50 ns to 100 µs, 50 ns to 500 µs, 50 ns to 1 ms, 50 ns to 5 ms, 50 ns to 10 ms, 50 ns to 50 ms, 50 ns to 100 ms, 50 ns to 500 ms, 50 ns to 1 s, 50 ns to 5 s, 50 ns to 10 s, 100 ns to 500 ns, 100 ns to 1 µs, 100 ns to 5 µs, 100 ns to 10 µs, 100 ns to 50 µs, 100 ns to 100 µs, 100 ns to 500 µs, 100 ns to 1 ms, 100 ns to 5 ms, 100 ns to 10 ms, 100 ns to 50 ms, 100 ns to 100 ms, 100 ns to 500 ms, 100 ns to 1 s, 100 ns to 5 s, 100 ns to 10 s, 1 µs to 5 µs, 1 µs to 10 µs, 1 µs to 50 µs, 1 µs to 100 µs, 1 µs to 500 µs, 1 µs to 1 ms, 1 µs to 5 ms, 1 µs to 10 ms, 1 µs to 50 ms, 1 µs to 100 ms, 1 µs to 500 ms, 1 µs to 1 s, 1 µs to 5 s, 1 µs to 10 s, 10 µs to 50 µs, 10 µs to 100 µs, 10 µs to 500 µs, 10 µs to 1 ms, 10 µs to 5 ms, 10 µs to 10 ms, 10 µs to 50 ms, 10 µs to 100 ms, 10 µs to 500 ms, 10 µs to 1 s, 10 µs to 5 s, 10 µs to 10 s, 100 µs to 500 µs, 100 µs to 1 ms, 100 µs to 5 ms, 100 µs to 10 ms, 100 µs to 50 ms, 100 µs to 100 ms, 100 µs to 500 ms, 100 µs to 1 s, 100 µs to 5 s, 100 µs to 10 s, 1 ms to 5 ms, 1 ms to 10 ms, 1 ms to 50 ms, 1 ms to 100 ms, 1 ms to 500 ms, 1 ms to 1 s, 1 ms to 5 s, 1 ms to 10 s, 10 ms to 50 ms, 10 ms to 100 ms, 10 ms to 500 ms, 10 ms to 1 s, 10 ms to 5 s, 10 ms to 10 s, 100 ms to 500 ms, 100 ms to 1 s, 100 ms to 5 s, 100 ms to 10 s, 1 s to 5 s, or 1 s to 10 s.

An emissive species may be selected to emit any suitable type of electromagnetic radiation (i.e., electromagnetic radiation of any wavelength). Suitable types of electromagnetic radiation that may be emitted by an emissive species include, but are not limited to, ultraviolet radiation (e.g., having a wavelength in a range from about 10 nm to about 380 nm), visible light (e.g., having a wavelength in a range from about 380 nm to about 740 nm), near-infrared radiation (e.g., having a wavelength in a range from about 700 nm to about 800 nm), and infrared radiation (e.g., having a wavelength in a range from about 740 nm to about 3 µm). In some embodiments, an emissive species is configured to emit electromagnetic radiation having a wavelength in a range from 200 nm to 380 nm, 200 nm to 400 nm, 200 nm to 600 nm, 200 nm to 740 nm, 200 nm to 800 nm, 200 nm to 1 µm, 200 nm to 2 µm, 200 nm to 3 µm, 380 nm to 600 nm, 380 nm to 740 nm, 380 nm to 800 nm, 380 nm to 1 µm, 380 nm to 2 µm, 380 nm to 3 µm, 400 nm to 600 nm, 400 nm to 740 nm, 400 nm to 800 nm, 400 nm to 1 µm, 400 nm to 2 µm, 400 nm to 3 µm, 600 nm to 740 nm, 600 nm to 800 nm, 600 nm to 1 µm, 600 nm to 2 µm, 600 nm to 3 µm, 700 nm to 800 nm, 740 nm to 1 µm, 740 nm to 2 µm, 740 nm to 3 µm, 800 nm to 1 µm, 800 nm to 2 µm, 800 nm to 3 µm, 1 µm to 2 µm, or 1 µm to 3 µm.

In some embodiments, an emissive species is configured to emit visible light. In certain cases, an emissive species is configured to emit substantially violet light (e.g., light having a peak wavelength in a range of 400 nm to 450 nm), substantially blue light (e.g., light having a peak wavelength in a range from 450 nm to 490 nm), substantially cyan light (e.g., light having a peak wavelength in a range from 490 nm to 520 nm), substantially green light (e.g., light having a peak wavelength in a range from 520 nm to 560 nm), substantially yellow light (e.g., light having a peak wavelength in a range from 560 nm to 590 nm), substantially orange light (e.g., light having a peak wavelength in a range from 590 nm to 635 nm), and/or substantially red light (e.g., light having a peak wavelength in a range from 635 nm to 700 nm). In certain instances, an emissive species is configured to emit electromagnetic radiation that is detectable by consumer-level electronics (e.g., a smartphone, a digital camera).

In some cases, an emission profile (i.e., a plot of intensity of electromagnetic radiation emitted by an emissive species as a function of time) of an emissive species may be fit to one or more functions (e.g., exponential functions). Multiple lifetimes can result from different environments around an emissive species and/or have multiple radiative rates. These environments can change with exposure to chemicals, heat, mechanical stress, moisture, cooling, gases, light, and ionizing radiation. In certain instances, when an excitation component emits electromagnetic radiation of oscillating intensity at a fixed or varying frequency, emission from an emissive species absorbing that electromagnetic radiation may exhibit variations resulting from the complex excitation profile. In an illustrative, non-limiting example, if electromagnetic radiation emitted by an excitation component has a sinusoidal profile at a frequency close to the emission lifetime of the emissive species, the resulting electromagnetic radiation emitted by the emissive species (i.e., the species excited by the excitation radiation) will generally have an oscillating intensity that is at the same frequency, but phase-shifted from the excitation radiation. That is, in some cases, the oscillating intensity of photons emitted by an emissive species may be delayed from the oscillating intensity of photons emitted by an excitation component. In some instances, there may be distortion of the intensity of the emitted radiation from the pure sine waveform of the exciting radiation.

In some cases, waveform and delay information from an emission profile may be used to calculate or estimate the emission lifetime of an emissive species. According to some embodiments, an emissive species may be exposed to a number of different excitation frequencies, and different emission responses may be detected. In some cases, the use of a standard emitter that has a known and invariant emission lifetime will be used to determine or estimate an absolute or relative lifetime of an emissive species. In some cases, an excitation component may emit electromagnetic radiation having complex waveforms, and an emissive species absorbing the electromagnetic radiation may produce emissions having complex modulations in intensity.

Figure 6:
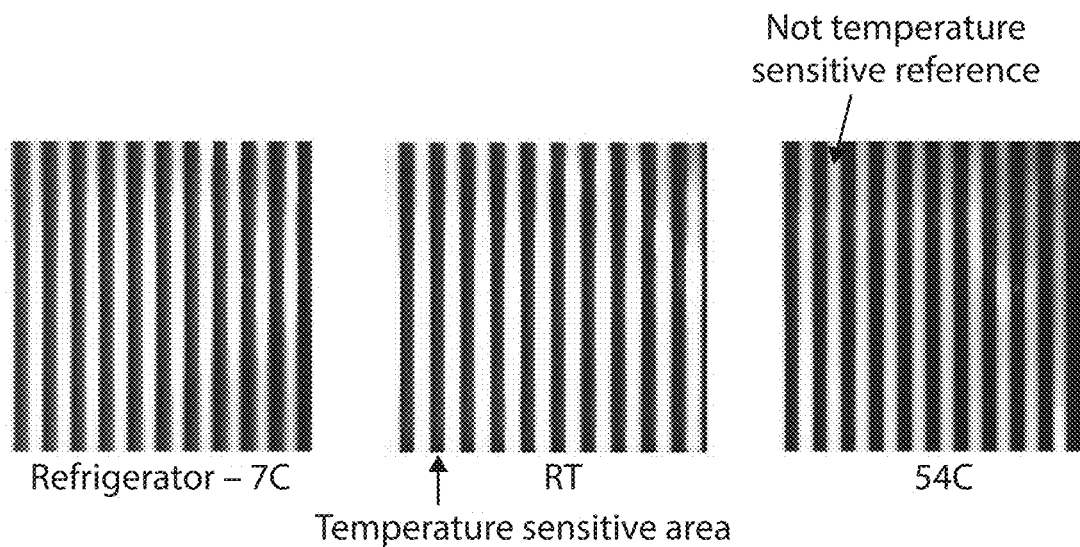
FIG. 6 shows, according to some embodiments, optical micrographs of a thin film comprising two emissive species at 7° C., under refrigeration (left), at room temperature (center), and at 54° C., under heating (right)

In some embodiments, the emission time period (e.g., observed emission lifetime) of an emissive species may vary based on environmental conditions, including but not limited to binding or proximity to other molecules (e.g., oxygen, water, carbon dioxide, carbon monoxide, quenching molecules), physical alteration, temperature, pH, and radiation exposure. As an illustrative example, FIG. 6 shows optical micrographs of a thin film comprising two emissive species exposed to different temperatures during image acquisition using rolling shutter. In particular, FIG. 6 shows an image of a thin film at 7° C., under refrigeration (left), at room temperature (center), and at 54° C., under heating (right). As the temperature increases, the amount of emission attributable to the emissive species during the "off" state of the LED decreases. Without wishing to be bound by a particular theory, this may be due to the lifetime of the emissive species decreasing as a result of additional deactivation pathways.

In some embodiments, a quenching molecule or material is added to the environment of an emissive species. A quencher molecule or material may act as a dynamic and/or static quencher. In certain cases, the quenching molecule or material forms a static complex with the emissive species by binding to the emissive species or being persistently proximate to the emissive species. In some instances, binding or persistent proximity of a quenching molecule or material to an emissive species changes at least one characteristic (e.g., wavelength, intensity, emission lifetime) of electromagnetic radiation emitted by the emissive species. In some instances, binding or persistent proximity of a quenching molecule or material to an emissive species quenches emission from the emissive species, such that no emission from the emissive species is detected.

In some embodiments, a quenching molecule or material dynamically interacts with an emissive species. In some such embodiments, dynamic interaction between a quenching molecule or material and an emissive species may be controlled by diffusion or other motion. This extra quenching rate of deactivation ($k_Q$) can reduce the observed emission lifetime the emitting species. In some cases, dynamic interaction between a quenching molecule or material and an emissive species changes at least one characteristic (e.g., wavelength, intensity, emission lifetime, or polarization) of electromagnetic radiation emitted by the emissive species. In some instances, dynamic interaction between a quenching molecule or material and an emissive species quenches emission from the emissive species, such that no emission from the emissive species is detected. This may be referred to as saturated dynamic quenching as it requires all of the quenching interactions to happen at faster times than the lifetime of the emissive species. In an illustrative, non-limiting example, oxygen is present in an environment surrounding an emissive species but is not bound to the emissive species. Through diffusion, an oxygen molecule may become sufficiently proximate to an emissive species to quench emission of the emissive species (e.g., the distance between the oxygen molecule and the emissive species may be small enough that electron or energy transfer can occur). The likelihood that an oxygen molecule will, through diffusion, become sufficiently proximate to an emissive species to quench emission of the emissive species may depend on factors such as oxygen concentration in the environment and temperature. For example, a higher oxygen concentration and/or higher temperature may increase the likelihood that an oxygen molecule would quench an emissive species. In some cases, therefore, an observed emission lifetime of an emissive species may provide information about oxygen concentration and/or temperature. In certain instances, for example, an emissive species exposed to the interior of a package may be used to determine oxygen content within the package without opening the package. In other cases, a package or capsule can contain a gas or molecule that quenches or prevents quenching of an emissive molecule. Opening the package or capsule, or compromises in their containment, may be detected through changes in the lifetime and intensity of emissive species.

A non-limiting example of a suitable quenching molecule is a molecule comprising an amine. Amines may act as dynamic or static quenchers. In some cases, amines may react as Lewis or Bronsted bases to create static complexes that change the color and/or intensity of an emissive species. In some cases, amines engage in electron transfer processes that give rise to a dynamic quenching process that may reduce emission lifetime. In certain cases, amines can react with other species to create new dynamic quenchers. As one example, an amine may deprotonate a molecule to make it more electron rich and capable of dynamically quenching an emissive species through diffusion and electron transfer process. Amines are indicators of food spoilage and can allow for the detection of the quality of food without opening the packaging. In some cases, an amine may be a primary diffusive quencher that may be modified by binding to carbon dioxide to make a carbamic acid, which may alter its quenching characteristics. In some embodiments, a system comprising a dynamic quencher that may be modified by binding to carbon dioxide may be used to measure carbon dioxide. Such a system or method may be useful in many biological and packaging contexts.

In some cases, an emissive species may be characterized by an emission quantum yield. A person of ordinary skill in the art would understand the emission quantum yield to refer to the ratio of the number of photons absorbed by an emissive species to the number of photons emitted by the emissive species. This ratio generally depends on the relative rates of the various deactivation processes. As one example, if the emissive process for an emissive species is fast relative to the non-emissive processes, the emission quantum yield will be relatively high. In some cases, emission quantum yield may be affected by one or more intrinsic properties of an emissive species. In some cases, emission quantum yield may be affected by one or more extrinsic properties (e.g., properties related to a matrix, a solvent, and/or a reactive molecule). In certain instances, a quenching molecule or material may completely quench an emissive species, which generally means that the emission quantum yield of the emissive species is below detection limits.

In some embodiments, at least one characteristic (e.g., emission quantum yield, emission lifetime, intensive, wavelength, polarization) of an emissive species changes as a function of its environment. As an illustrative, non-limiting example, an emissive species may have a higher emission quantum yield in a hydrophobic environment than in an aqueous environment. Without wishing to be bound by a particular theory, this effect may be related to changes in the solvation of the excited state of the emissive species, which may have a different charge distribution than the ground state. In other cases, water bound to luminescent metal ions or far red emitting dyes can absorb energy through vibrational states and quench luminescence. In some cases, heavy water ($D_2O$) may be used to prevent these processes. As another example, aggregation of certain emissive species may increase emission intensity and/or change observed emission lifetime. As yet another example, binding of certain molecules to an emissive species may affect the observed emission lifetime of the emissive species. For example, a gamma cyclodextrin molecular complex may exhibit a particular observed emission lifetime when a single chromophore is bound in its cavity but may exhibit a different observed emission lifetime when a secondary molecule binds in the cavity.

An emissive species may have any suitable structure. In some embodiments, the emissive species is a chemical and/or biological species. In some cases, the emissive species is a fluorophore, a phosphor, an inorganic solid, a salt, or a thermally activated delayed fluorescence (TADF) molecule or molecular complex.

In some embodiments, an emissive species is a TADF molecule or molecular complex. A TADF molecule or molecular complex generally refers to one or more molecules configured to have low spin (i.e., singlet) and high spin (i.e., triplet) states that are sufficiently close in energy that they undergo dynamic equilibration at room temperature. In some cases, this dynamic equilibration process involves spin orbit coupling. In some cases, this dynamic equilibration process results in a much slower rate of emission than expected for a singlet state at least in part because the triplet state acts as a holding reservoir for excited electrons. In some instances, a photon may be absorbed by a TADF molecule or molecular complex and may initially create a singlet state having a high rate of emission. The singlet state may be in rapid equilibrium with a lower-energy triplet state having a low rate of emission. When the molecule thermally reverts to the singlet state, there is a chance for the molecule to emit a photon before it converts back to the lower-energy triplet state. As a result, electromagnetic radiation may leak out of the minority singlet state through fluorescence, but the rate of emission is much slower than expected for a singlet state.

In some embodiments, a TADF molecule has a structure that comprises an electron-rich region and an electron-deficient region. Examples of a suitable electron-rich region include, but are not limited to, amine groups. Examples of a suitable electron-deficient region include, but are not limited to, imine groups and nitrile groups. In the ground state, the highest occupied molecular orbital (HOMO) may be localized on the electron-rich region, and the lowest unoccupied molecular orbital (LUMO) may be localized on the electron-deficient region. To create efficient emission, the half-filled orbitals in the excited state have finite overlap. In some embodiments, the TADF molecule is in a twisted nonplanar state. In some embodiments, the TADF molecule is arranged such that the electron-rich and electron-deficient regions are in a co-facial arrangement (i.e., the π-electron systems of the electron-rich and electron-deficient regions interact in a face-to-face arrangement). Non-limiting examples of TADF molecules are illustrated in the following structures.

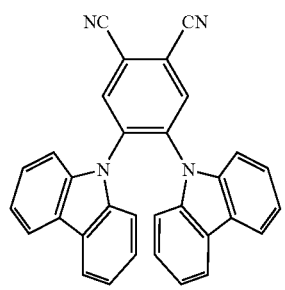

-continued

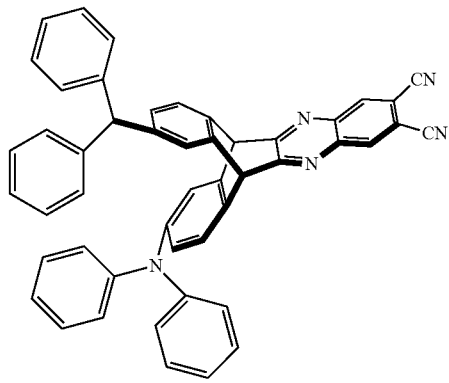

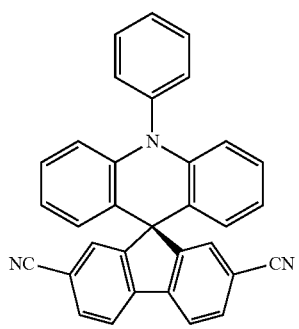

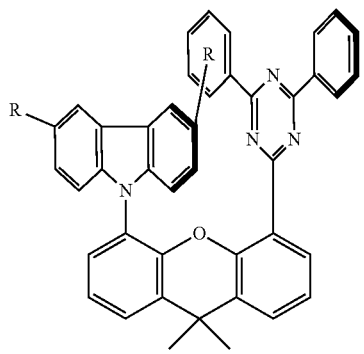

Non-limiting examples of materials displaying TADF behavior that have suitable absorption bands to allow for excitation by the light source of a smartphone are described below. The absorption bands of such materials can be shifted by the addition of different substituents for optimal overlap of their absorbance bands with the light intensity profile produced by smartphone light sources. Systematic changes in structure can shift the absorptions to longer wavelengths either by raising the HOMO energy, by lowering the LUMO energy, or both.

103
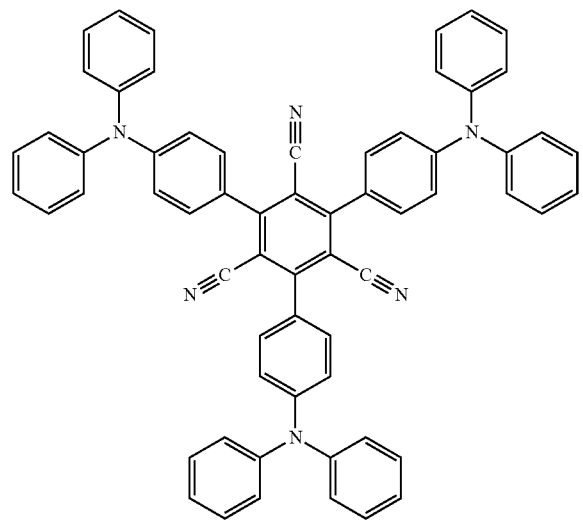
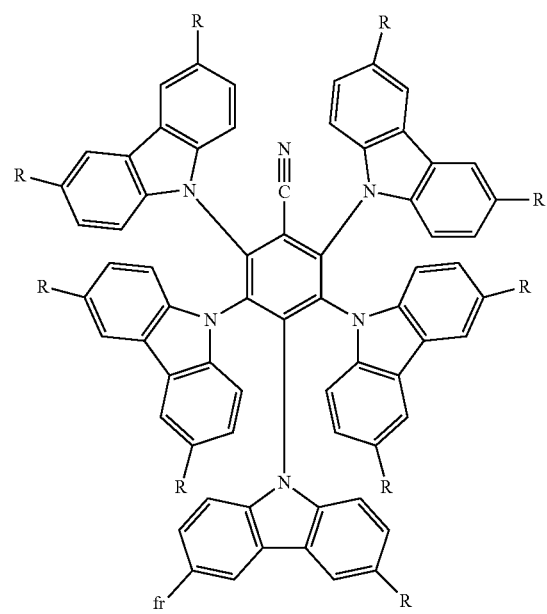
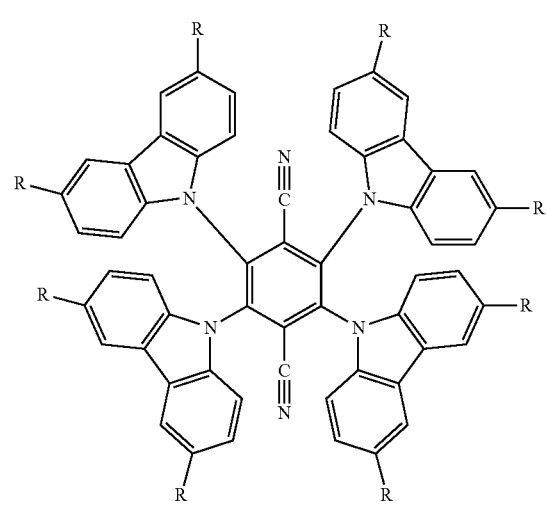
104
-continued
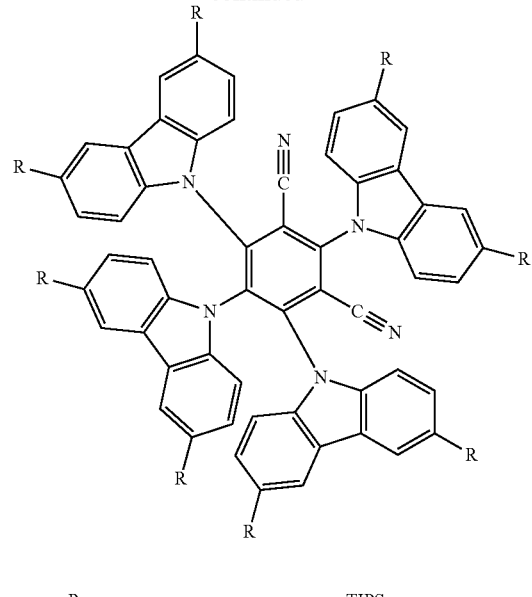
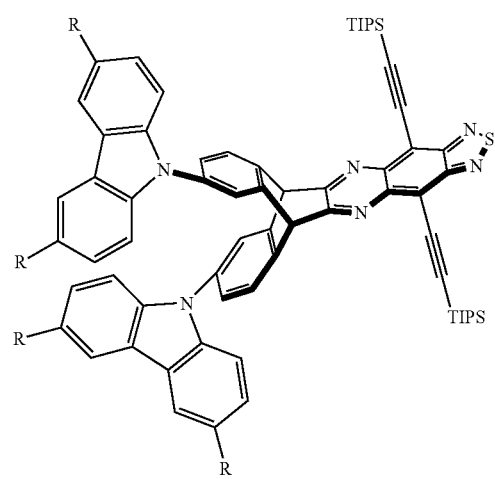
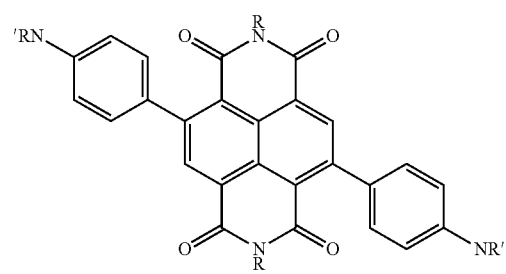
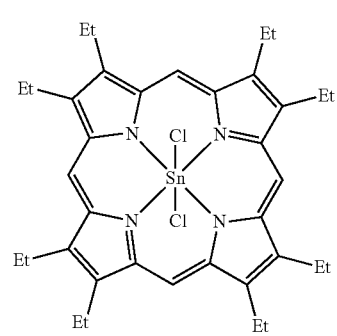

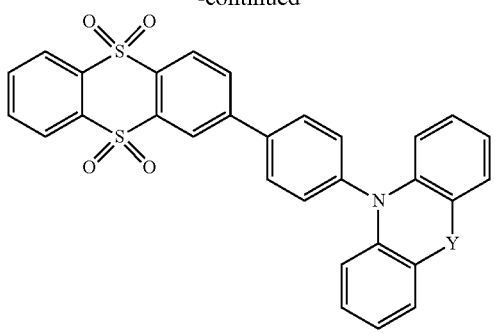

R = H, Alkyl, or Ph
R' = Alkyl, or Ph
Y = C(CH$_3$)$_2$ or O
varied independently TADF materials may also be produced be the association of dissimilar materials. For example, an electron donating material with a high energy HOMO can be complexed with an electron accepting material that has a low energy LUMO. In these types of materials, without wishing to be bound by theory, the donor and acceptor molecules interact such that their π-orbitals mix and a ground state charge-transfer interaction is observed. The inter-material interaction may be greatly enhanced in the excited state when an exciplex excited state is produced. The fact that the HOMO and LUMO orbitals largely reside on the donor and acceptor materials, respectively, may result in some exciplex materials displaying TADF behavior. The fact that there are two separate materials involved in the production of these exciplexes, it is possible to create a number of pairwise combinations to create a diversity of exciplex structures. The exciplex structures may form, in some cases, by the diffusion of molecules to each other and may be useful for creating TTIs described above. The emission efficiency and the lifetimes of the excited state exciplex structures will vary with environment and the pairs of materials. Additionally, the ability to produce the ground state charge transfer complex as well as the exciplex will vary based on the environment. Creating combinations capable of being excited to create TADF active exciplexes will involve selecting pairs of donors and acceptors.

Suitable non-limiting examples of acceptor molecules that can be used to produce compositions with suitable donor molecules to produce TADF behavior are described below. X substituents can be chosen to produce LUMO states that can be paired with a selected donor material. Additionally, the X substituents may be used to control the structure of the exciplex either by restricting the geometries for interacting with the donor through interactions with the matrix. The X substituents may be varied independently and the Ar groups indicate an aromatic fragment that has functionality that supports the desired properties. The aromatic group could be a heterocycle or a substituted hydrocarbon.

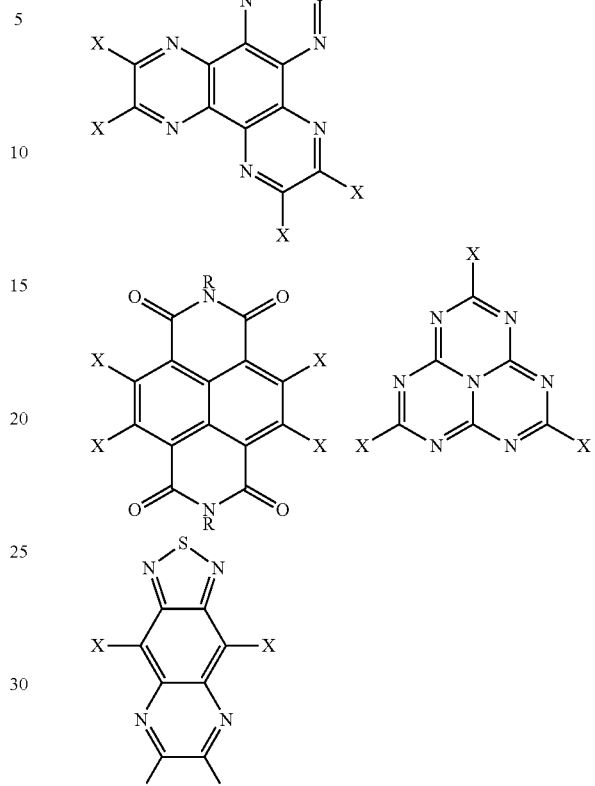

X = H, CN, CC—Ar, F, Ar
R = Alkyl or Ar,
all can be varied independently

Non-limiting examples of suitable donor molecules that can be used to produce TADF behavior in exciplexes with suitable acceptor molecules are described below. The Ar (aromatic) groups may, in some embodiments, include heterocycles. The Ar groups may be, in some embodiments, substituted with groups that promote the TADF behavior by changing the HOMO energies and/or through promoting/directing particular structural arrangements.

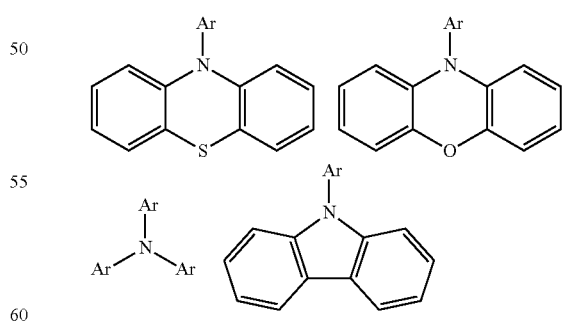

The structures described herein are only intended to be representative and there are many other possible acceptor and donor molecules that can be paired to produce TADF in particular contexts/environments. The inventors of the instant application have recognized that choosing particular donor and acceptor combinations that may be excited by the light sources of smartphones (or other consumer electronic devices) may be approached by consideration of the fact that the π-electron systems may be capable of orbital overlap. For example, if the steric bulk of the substituents prevent geometries that allow for these interactions, the ability to produce an exciplex may be compromised. Additionally, the relative energy levels of the donor and acceptor molecules need to have the proper levels to create absorption features that overlap with the output of the light sources of the smartphone. To a first approximation, suitable pairs may include those that have a difference in the energy of the donor's HOMO and the acceptor's LUMO of approximately 2.75 eV or less. Photons at 450 nm, which is close to the peak photon output of many smartphone light sources, generally have an energy of about 2.75 eV (although other energies are also possible). It is possible that the HOMO and LUMO be separated slightly more than 2.75 eV, in some embodiments, for example because of the intrinsic bandwidth of the absorptions will still allow for finite absorption at 450 nm. It should also be noted that the HOMO and LUMO states of the respective ground state molecules are generally only an approximation. Charge transfer ground state complexes typically shift the energy levels with the absorption involving a change in the electronic levels of the constituents. The complexities of the environment may also change the energy levels of the absorptions as well as those of the emissions. The individual donor and acceptor materials may also be independently emissive and display prompt-fluorescence that can produce a non-steady-state photon emission event.

In some embodiments, non-limiting examples of the TADF materials described herein are low molar mass molecules. The TADF effect is however not limited to small molecules. The active TADF components may be, for example, pendant groups on polymers, or be integrated directly into a polymer backbone. They may be part of an organized or amorphous solid. They may be constituents of a covalent crystalline or amorphous framework material, which may or may not have porosity. They may be guests in a receptor. For example, a cyclodextrin molecule may host both a donor and acceptor chromophore in its cavity to promote an TADF exciplex. Alternatively, interactions with a receptor, or a matrix, may be used to enhance or reduce TADF behavior of a material by promoting conformations, by presenting a dipolar potential, by the proximate placement of a material capable of quenching the excited state, or preventing quenching by effectively insulating the molecule from its surroundings. The TADF materials also need not be purely organic in nature and may have many other elements including but not limited to boron, silicon, phosphorous, selenium, as well as other main group elements. Organometallic, metallo-organic, or purely inorganic materials may also present as active or structural components in a TADF composition.

In some embodiments, an emissive species comprises a TADF molecular complex formed from two or more molecules. In some cases, a TADF molecular complex comprises an exciplex. An exciplex may be formed by two or more molecules in which the π-electron systems of the molecules have some degree of co-facial arrangement. Advantageously, forming TADF exciplexes through combinations of molecules (e.g., pairwise combinations of molecules) can result in a wide variety of emission lifetimes, emission wavelengths, and responsiveness to environmental factors. In exciplexes, the emission efficiency often depends on the dynamics of the component molecules relative to each other. For at least this reason, the rigidity of the medium and/or the presence of other molecules may substantially affect emission rates and/or quantum yields.

The TADF materials may be, in some cases, attached to biological species, or immobilized on particles, and/or bound to surfaces to produce a desired signal in an assay.

In some cases, a TADF exciplex may have a substantially longer wavelength and/or a substantially longer emission lifetime than the component molecules. In certain instances, for example, each component molecule may be intrinsically fluorescent with a relatively short emission lifetime (e.g., on the order of nanoseconds). Once the TADF exciplex is formed, the TADF exciplex may have a longer emission lifetime (e.g., on the order of microseconds). In some cases, forming a TADF exciplex advantageously increases the emission lifetime by hundreds to thousands of times.

In some cases, the fact that TADF exciplexes are formed by at least two separate molecules may allow for the molecules to be initially separated by a certain distance and then allowed to interact and form a TADF exciplex by diffusion. Thus, a thermal dosimeter may be developed that images materials based the lifetime and wavelength of their emissions. In some cases, TADF exciplex formation may be induced by physical processes (e.g., breaking capsules) and/or changes in viscosity or other physical characteristics.

In some embodiments, intermolecular TADF exciplexes are produced in response to biomolecular or molecular associations of the localization of components at a particular location. In some such embodiments, the exciplex is promoted by a co-localization of the two components, which can be designed into an assay.

Additional non-limiting examples of pairs of molecules that display TADF behavior are shown below. In these illustrative examples, the molecules with amines are the electron-rich element and the molecules with imines are the electron-deficient element.

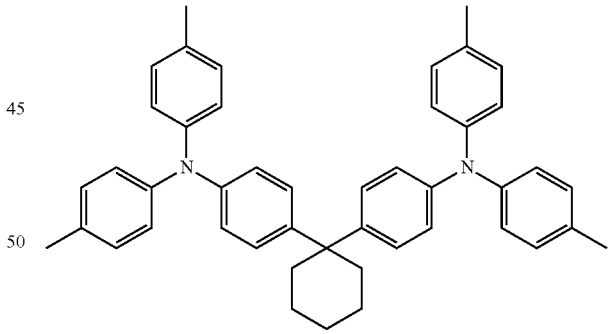

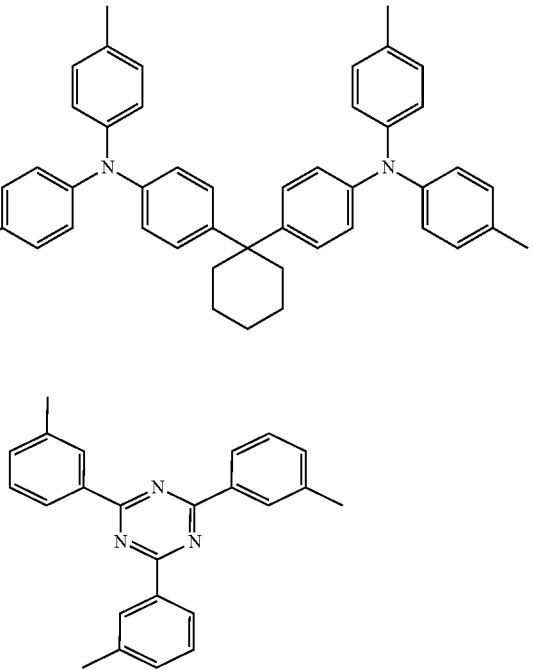

-continued

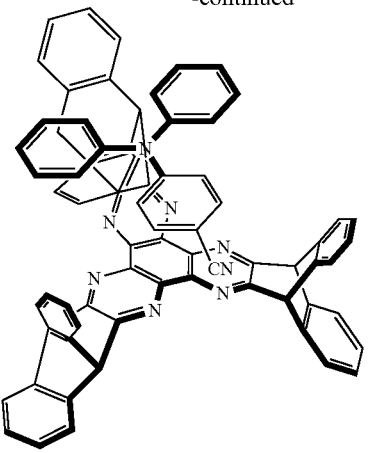

One of ordinary skill in the art would understand that modifying the substituents and scaffolds of TADF molecules or molecular complexes can change the lifetimes and wavelengths of any emissions. In some embodiments, a TADF molecule or molecular complex has an intrinsic emission lifetime of at least 100 ns, at least 1 μs, at least 10 μs, at least 50 μs, at least 100 μs, at least 500 μs, or at least 1 ms. In some embodiments, a TADF molecule or molecular complex has an intrinsic emission lifetime in a range from 1 μs to 5 μs, 1 μs to 10 μs, 1 μs to 50 μs, 1 μs to 100 μs, 1 μs to 500 μs, 1 μs to 1 ms, 10 μs to 50 μs, 10 μs to 100 μs, 10 μs to 500 μs, 10 μs to 1 ms, 100 μs to 500 μs, 100 μs to 1 ms, or 500 μs to 1 ms.

In some embodiments, a TADF molecule or molecular complex has an observed emission lifetime (e.g., a measured emission time period) of at least 1 μs, at least 10 μs, at least 50 μs, at least 100 μs, at least 500 μs, or at least 1 ms. In some embodiments, a TADF molecule or molecular complex has an observed emission lifetime (e.g., a measured emission time period) in a range from 1 μs to 5 μs, 1 μs to 10 μs, 1 μs to 50 μs, 1 μs to 100 μs, 1 μs to 500 μs, 1 μs to 1 ms, 10 μs to 50 μs, 10 μs to 100 μs, 10 μs to 500 μs, 10 μs to 1 ms, 100 μs to 500 μs, 100 μs to 1 ms, or 500 μs to 1 ms.

In some embodiments, a TADF molecule or molecular complex has a relatively high emission quantum yield. In some embodiments, a TADF molecule or molecular complex has an emission quantum yield of at least 0.3, at least 0.4, at least 0.5, at least 0.6, at least 0.7, at least 0.8, at least 0.9, or about 0.95. In some embodiments, a TADF molecular or molecular complex has an emission quantum yield in a range from 0.8 to 0.9, 0.8 to 0.95, 0.8 to 0.95, 0.8 to 0.95, 0.9 to 0.95.

In some embodiments, an emissive species is substantially phosphorescent. In some embodiments, a phosphorescent emissive species comprises a heavy atom. In some embodiments, a phosphorescent emissive species comprises an organometallic compound.

In some embodiments, an emissive species comprises a heavy atom. Examples of suitable main-group heavy atoms include, but are not limited to, chlorine, bromine, iodine, sulfur, selenium, tellurium, phosphorus, silicon, and tin. Without wishing to be bound by a particular theory, a heavy atom may convert primary singlet states produced by absorption of a photon to a triplet state and/or increase the rate of emission such that emission lifetimes are in an optimally detectable range. In some embodiments, the heavy atom may be associated with an organic scaffold.

In some embodiments, an emissive species comprises an organometallic or metallo-organic compound. An organometallic compound generally has a metal ion bound covalently to one or more ligands. In some cases, an organometallic compound comprises one or more metal-carbon bonds. Non-limiting examples of suitable metals include gold, silver, platinum, iridium, rhenium, ruthenium, and osmium. Non-limiting examples of suitable ligands include alkynyl, aryl, heteroaryl, carbonyl, pyridyl, bipyridyl, terpyridyl, porphyrin, thiols, and phthalocyanine groups. Examples of suitable organometallic compounds include, but are not limited to, rhenium carbonyl bipyridyl compounds, platinum acetylide compounds, ruthenium bipyridyl compounds, ruthenium terpyridyl compounds, platinum porphyrin compounds, and platinum phthalocyanine compounds. In some cases, an organometallic compound may be used for oxygen sensing. In some embodiments, for example, platinum porphyrin and/or platinum phthalocyanine compounds may be used for oxygen sensing.

In some embodiments, an emissive species comprises bismuth. A person of ordinary skill in the art would recognize bismuth as a nontoxic heavy metal that is considered a post-transition-metal element. In some embodiments, bismuth forms a phosphorescent compound with one or more ligands (e.g., pyridyl ligands). In other cases, bismuth forms phosphorescent materials of a purely inorganic nature. In certain cases, bismuth forms a biologically friendly salt. In some cases, the biologically friendly salt may be formulated with dyes.

In some embodiments, an emissive species comprises a lanthanide and/or actinide. Lanthanide and/or actinides generally have highly contracted electronic states and often produce atomic-like emission profiles with narrow emission lines. In some embodiments, a lanthanide and/or actinide forms a complex with a ligand (e.g., an organic ligand). In some cases, the ligands may be used to provide different electromagnetic radiation absorption and/or emission profiles. In certain instances, one or more ligands bound to the lanthanide and/or actinide act as antennas harvesting electromagnetic radiation. In some instances, the emissive properties of an emissive species comprising a lanthanide may vary upon the binding of water. In certain cases, the effects of water may be mitigated by substituting heavy water (i.e., $D_2O$) for $H_2O$. In certain cases, an emissive species may be prepared by binding heavy water to a lanthanide and/or actinide, and the emission lifetime may be reduced to different degrees by exchange with water. Such a process may be used, in some cases, to determine if a material has been exposed to an atmosphere containing water vapor.

Purely inorganic phosphors may also be excited by the light sources of a smartphone. In some cases, the absorption efficiency on a weight basis may be lower than some of the organic materials, however these materials may advantageously display high thermal and chemical stability. Purely inorganic phosphors often contain different oxide materials (aluminate, silicate, borates) that have high melting points and can be classified as ceramics. They may also be dispersed in other salts, including fluorides or sulfates. The luminescent properties may arise, in some cases, from the integration of active metal ions into inorganic materials. Such structures can be organized as single crystals or may be considered to be solid solutions. For example, $Cr^{+3}$ can be incorporated into a matrix of $Al_2O_3$ and these compositions, generally referred to as ruby, display phosphorescence and can be excited by the light source of a smartphone. There are many other active elements that can be placed in inorganic materials, and some can be in different oxidation states.

Non-limiting examples of suitable metal ions that can be used to create inorganic phosphors include Eu, Bi, Ce, Cr, Nd, Yb, Pb, Gd, Dy, Er, L, U, Ta, Sr, and Y.

In some embodiments, multiple metal ions are incorporated into a composition to create an inorganic phosphor. The excited state lifetimes of these materials, depending upon the material, may be characterized as prompt-phosphorescence or delayed-phosphorescence and thereby may be useful for producing non-steady-state photon emission events. Different elemental substitutions may affect lifetimes and as a non-limiting example the substitution of $Mn^{+2}$ into different compositions may be used to create extended excited state lifetimes.

A number of inorganic phosphors belong to the structural class of compounds called perovskites and may also be suitable in accordance with embodiments described herein. In these types of compounds, there is often an atom that is viewed as a cation between different polyhedral groups, often composed of metal oxides or halides. A sub-area of perovskites are materials wherein the cations are organic ammonium ions. Some of these organic/inorganic hybrid salt complexes, which are readily synthesized at low temperature, and may be excitable by smartphones. Non-limiting examples of smartphone excitable crystals include (n-butylammonium)$_2$PbI$_4$ and (N-methylpropane-1,3-diammonium)PbBr$_4$. The excited lifetimes of these organic/inorganic hybrid perovskites may vary from those corresponding to prompt-fluorescence and prompt-phosphorescence and are generally capable of producing non-steady-state photon emission events. Longer excited state lifetimes may also be possible with different compositions (e.g., with elements more environmentally friendly than lead).

Another class of purely inorganic emissive species are those created from nanostructured semiconductors and may also be suitable in accordance with embodiments described herein. There are many different types of these materials and without wishing to be bound by theory, as a result of their delocalized electronic states, the size of the nanoparticles may be correlated with their absorption characteristics. As such, in some embodiments, selected sizes of these materials may be used to create smartphone excitable materials. A non-limiting list of semiconductor nanomaterials include nanoparticles comprising one of more of the following, CdS, CdSe, CdTe, ZnSe, InP, Ge, PbS, and PbSe. The excited state lifetimes of these materials may vary with size and composition and materials displaying excited state lifetimes corresponding to those of prompt-fluorescence to prompt-phosphorescence have been observed.

Metallo-organic analogs of $Eu^{+3}$, $Tb^{+3}$, and other lanthanide or actinide elements may display delayed-phosphorescence, in some cases. In some embodiments, the organic ligands interacting with the metal center behave as antennas for the capture of photons. Without wishing to be bound by theory, the ligands once excited to their singlet excited states, generally undergo a rapid intersystem crossing to a triplet state, and then transfer triplet energy to the metal center. The relative energies of the triplet states and those on the metal center may affect the efficiency of the energy transfer. As a result, care should be taken to select ligands that are excitable by a smartphone and may efficiently participate in triplet energy transfer to the metal center. The orbitals on the metal centers are contracted and the electronic states may be considered to be heavily localized on the metal centers, in some cases. As a result, the emission spectra may be very similar from different complexes of a particular metal, even with very different antenna ligands and coordination environments. Ligands may be selected to have other desirable properties, including sensitivity to different chemical, thermal, optical, environmental, and/or optical stimuli.

Europium ($Eu^{+3}$) based emitters are of particular note in accordance with embodiments described herein as they generally display red light emission. Antenna ligands capable of absorbing light from the light source of a smartphone may be used. A non-limiting example is the ketone complex described below. The ketone is generally a non-ionic ligand and is generally more weakly bound than the other three anionic 1,3-diketonate ligands. In some cases, the coordination sphere around the $Eu^{+3}$ may be dynamic and additional ligands, shown as L, may also coordinate to the metal center. Without wishing to be bound by theory, the degree of coordination is generally subject to the steric constraints around the metal center and those imposed by the ligands. The steric influence of matrix materials may also play a role, in some cases. For example, in some embodiments, two ketones may be interacting with the $Eu^{+3}$ center or that there is no L coordinated. The L groups may be anionic and, for example, may be a carboxylate, sulfate, or halide ion. The weakly bound nature of the ketone generally causes it to be susceptible to substitution. In cases where a more robust association is required, the matrix material may be used to enforce a strong association by restricting the geometry and/or by placing the materials in a highly rigid environment. In some applications, it may be useful to have the ketone metal interactions be subject to modulation by chemical, optical, thermal, environmental, ionizing radiation, and/or mechanical stimulation. These applications may, for example, take advantage of the weak binding of the ketone to the Eu metal center. Such changes can be irreversible or reversible, depending on the application. Other ketones beyond those shown, as well as other ionic ligands, may also be used to create smartphone excitable complexes.

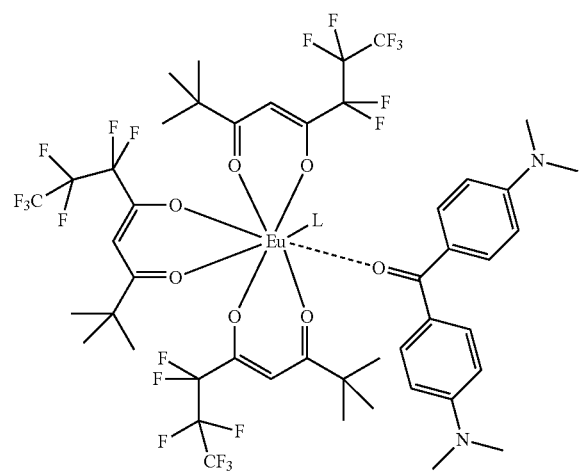

Anionic ligands associated with the metal centers may be used, in some cases, to create a diversity of materials with delayed-phosphorescence. A non-limiting example of a smartphone excitable $Eu^{+3}$ complex that has a carbazole integrated into the ionic 1,3-diketonate ligand is shown below. In some embodiments, without wishing to be bound by theory, the extension of the π-electron system by the carbazole allows this compound to be excited by a smartphone. The neutral 1,10-phenanthroline ligand generally occupies two coordination sites on the $Eu^{+3}$ as shown. An additional ligand to be bound to the Eu site is also possible. In some embodiments, a number of other ligands may be paired with the carbazole 1,3-diketonate ligand shown (e.g., enhancing the absorption of light from the smartphone, and/or create the opportunity to excite the complex at an alternative wavelength).

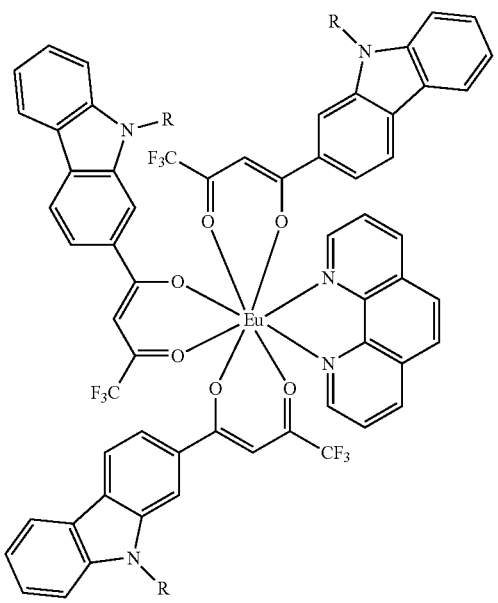

R = Alkyl or Aryl

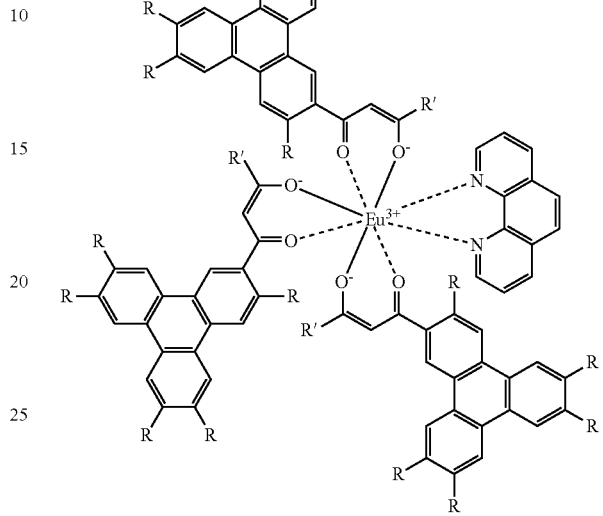

Non-limiting examples of Europium complexes with anionic ligands containing fused aromatic rings (such as phenanthrenes and triphenylenes) that may be excited by visible light are shown below. Without wishing to be bound by theory, incorporation of visible-light-absorbing moieties into anionic ligands yields generally improves white light activated phosphors since the ionic ligands are more tightly bound to the Eu$^{+3}$ than neutral ligands.

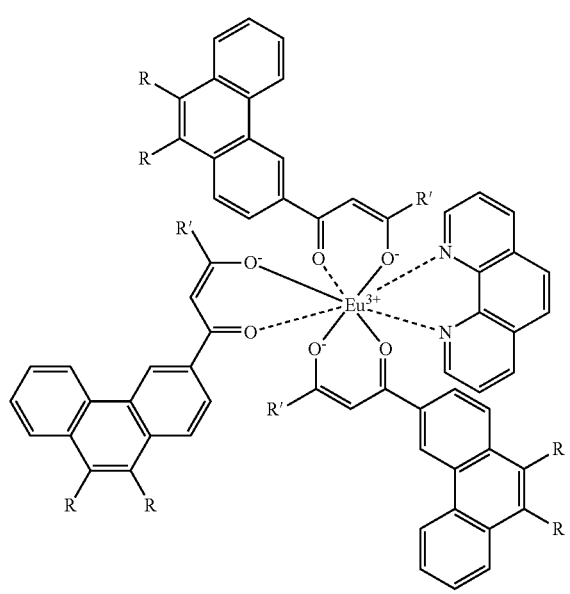

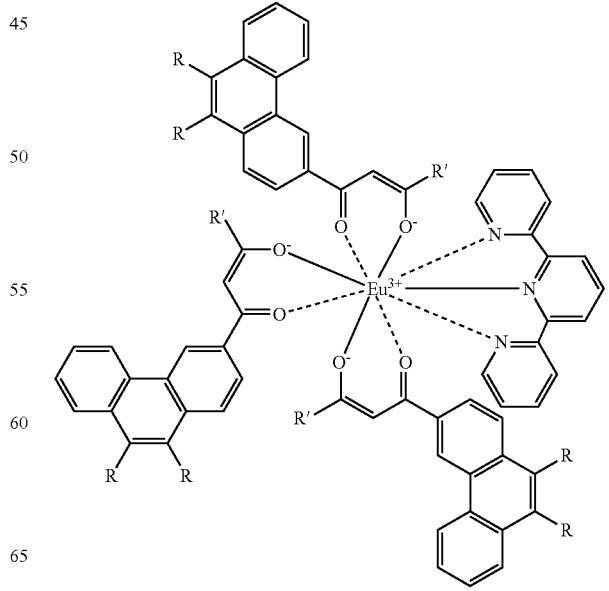

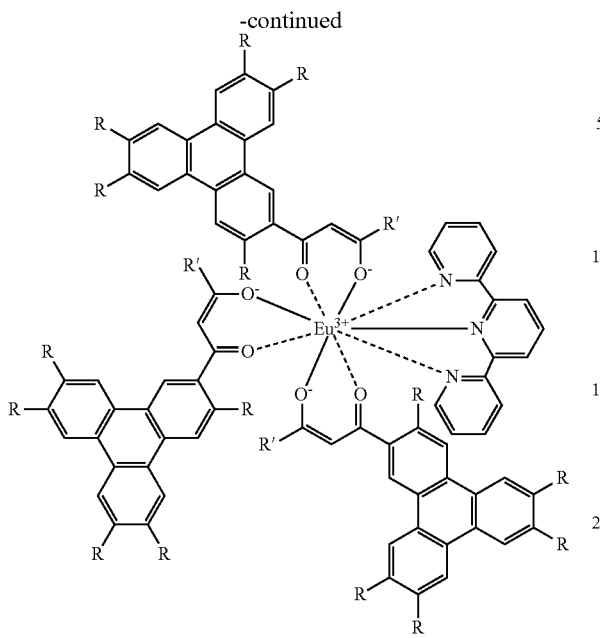

R = H, Alkyl, or Alkoxy
R' = $C_nF_{2n+1}$

A non-limiting example of an $Eu^{+3}$ complex having a tricoordinate antenna ligand is shown below. This is only one of a number of potential analogs that are possible and one of ordinary skill in the art will understand based upon the teachings of this specification that different substitutions may be used to enhance the absorption of light from a smartphone (or other consumer electronic device), the compatibility with matrix materials, the stability of the complex, prevent unwanted quenching, and/or enhance the quantum yield of the delayed-phosphorescence.

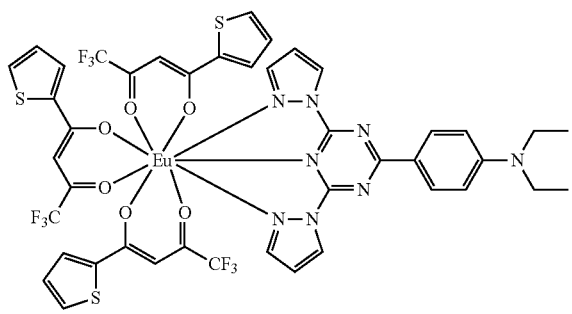

Figure 35A:
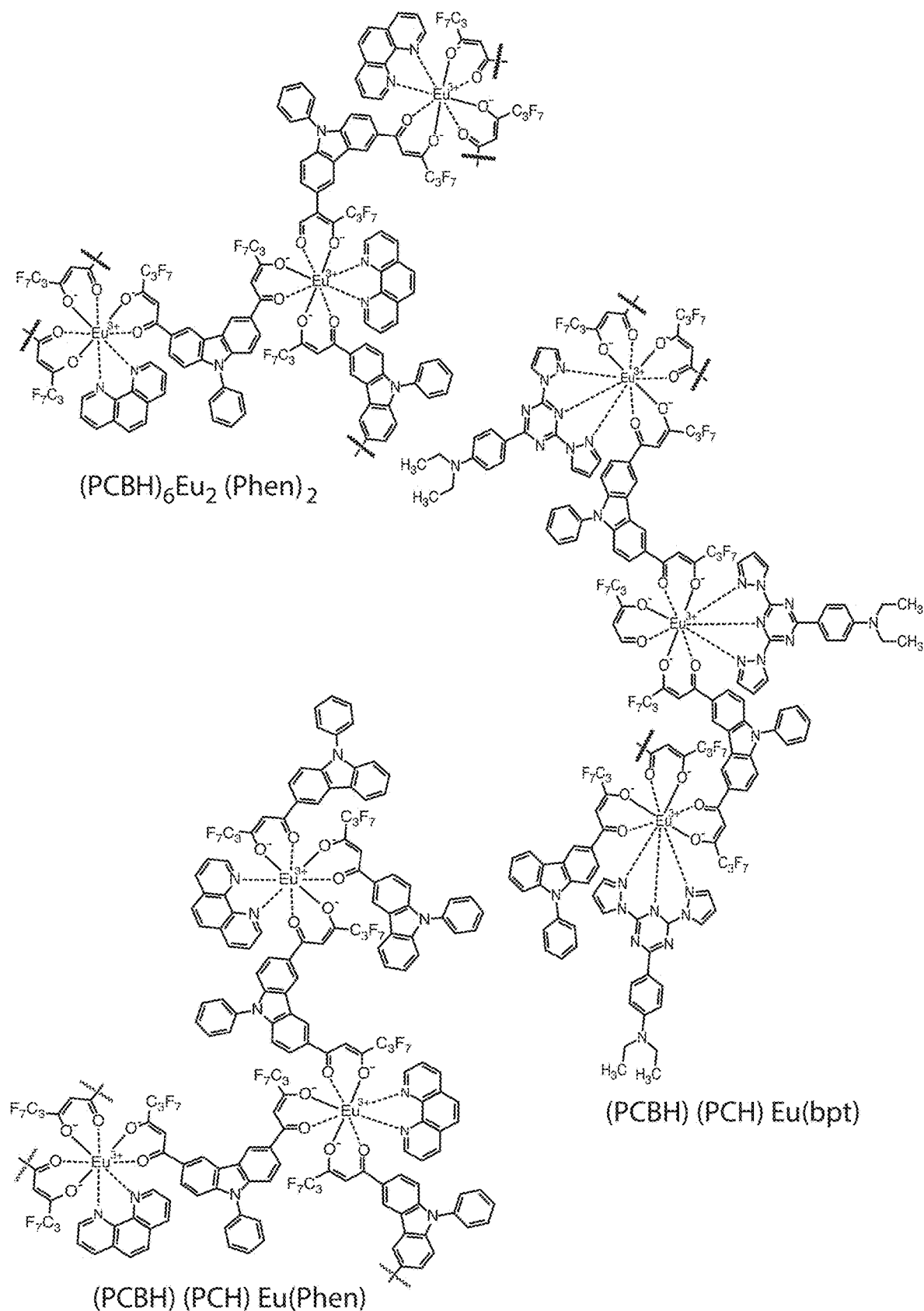
FIG. 35A shows chemical structures of exemplary oligomeric/polymeric white light excitable Eu-based delayed emitters $(PCBH)_6Eu_2(Phen)_2$, (PCBH)(PCH)Eu(Phen), and (PCBH)(PCH)Eu(bpt), according to some embodiments.

Additional suitable non-limiting examples of Europium based emitters are provided herein, in Examples 8-21 below, and some exemplary structures are shown in FIG. 35A.

Other smartphone excitable materials capable of displaying delayed-phosphorescence include the boron and aluminum complexes shown below. These materials generally have very rigid structures that restrict non-radiative relaxation of their excited electronic states to the ground state. Without wishing to be bound by theory, the lack of heavy atoms generally results in slower emission rates than would be expected with the incorporated heavy atoms. Nevertheless, such materials may display strong luminescence if incorporated into an appropriate matrix. The long lifetimes of these compounds give rise to oxygen quenching and these materials may therefore be used, for example, as oxygen sensors.

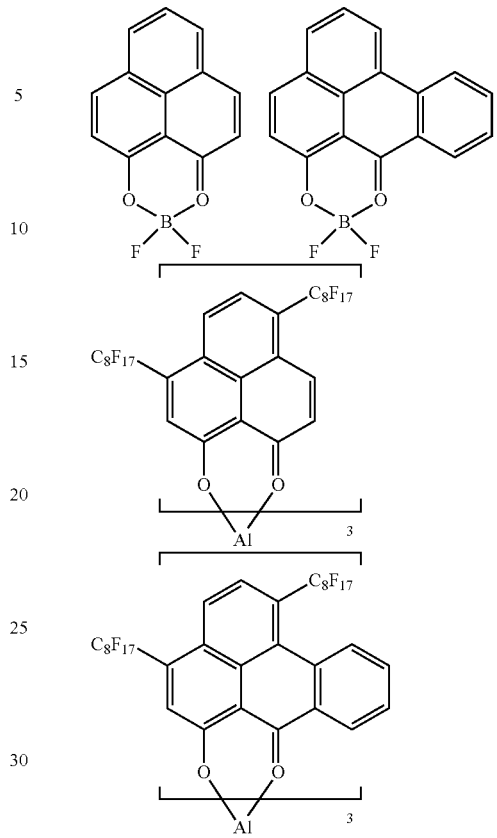

In many applications the smartphone excitable luminescent materials (e.g., emissive species) may be suspended in another material (e.g., a matrix). The luminescent materials may be in a fluid or solid solution wherein they are randomly dissolved at the molecular level. Crystals or particles of the luminescent materials may be dispersed in a solid, thin film, liquid crystal, oil, or solution. Luminescent materials can be co-crystallized with another material. Luminescent materials may be imbibed into a polymer or plastic by thermally promoted diffusion, by physical pressure, and/or by solvent assisted transport into the material. Materials may be prepared by polymerization of monomers incasing the materials in a dispersion or as a bulk material/film. Luminescent materials may be attached to materials by adhesives, including pressure sensitive adhesives, epoxy resins, polyurethanes, or thermoplastics. Polymer encapsulants may be applied to dispersions of luminescent materials to create coated particles. Luminescent materials may be synthesized in a matrix material that may be either organic or inorganic in nature.

In some embodiments, luminescent materials may be used in aqueous environments and may be connected (conjugated) to other species, including biological recognition elements such as proteins, antibodies, DNA, and RNA. They may also be directly connected to fungi, bacteria, tissue, or cells. Materials may be dispersed in solutions or powder form and polymers may be assembled around them to create coated polymers. For example, if a luminescent material is relatively non-polar it may be dispersed in water using polymer, molecular, or polymerizable surfactants. Polymers of the structure $Z(OCH_2CH_2)_x(OCH(CH_3)CH_2)_y(OCH_2CH_2)_xOZ$ may be used to disperse materials. This block copolymer has a hydrophobic group in the center that may interact with the hydrophobic luminescent material, while the $(OCH_2CH_2)_x$ groups are generally hydrophilic allowing for water dispersibility. The Z groups, which may be more than one functionality may be used to crosslink the materials to form robust coatings and/or to conjugate them to another material, such as an antibody, protein, or DNA/RNA. There are many types of suitable polymer surfactants and diblock copolymers of polystyrene with other polar materials including acrylates of poly(ethylene oxide) that represent non-limiting examples. It is also possible to disperse luminescent materials in a polymerizable monomer to create polymer encapsulated materials. For example, a luminescent material may be dispersed in water by the use of a surfactant with styrene to create particles. The luminescent material may be dispersed uniformly in the polymer particle as a solid solution or separated into small crystals or aggregates. In some cases, the act of polymerizing a material hosting the luminescent material may cause the material to separate to give embedded crystals or aggregates. Comonomers may be used to crosslink the polymers or to create functional groups on the surface of the particles that may participate in bioconjugation reactions. The functional groups may also be added post polymerization as needed. Preferred, non-limiting functional groups that may be placed on the surface of a particle incorporating a luminescent material include carboxylic acid groups, amines, thiols, esters, alkenes, strained cyclic alkenes, strained cyclic alkynes, electrophilic alkenes, maleimides, tetrazines, isothiocyanates, blocked isocyanates, oxazolines, carbodiimides, or azides. A diversity of methods (reaction sequences) are available that use these groups to create linkages to different biomolecular species.

In some embodiments, a pre-existing polymer particle may be functionalized with a luminescent material. An illustrative but non-limiting example is the case of polystyrene particles that have carboxylate groups on their surface. Dispersing these particles in a solvent that swells the polymer, such as methylene chloride, chloroform, tetrahydrofuran, toluene or 1,2-dichlorobenzene but also contains the luminescent material may be used to make luminescent particles. In some embodiments, once the particles are swollen with the organic solution containing the luminescent material, the materials are dried. If none of the materials are soluble in water, the particles may be dissolved in water and methods for conjugation to different biomolecular recognition elements applied. Conjugation methods include reactions of amines with reactive esters, thiol additions to alkene acceptor molecules (thio-Michael reactions), click reactions between tetrazine and reactive alkenes, amine additions to isothiocyanates, copper-catalyzed click reactions of organic azides with terminal alkynes, and/or click reactions of organic azides with strained cyclic alkenes and alkynes.

Functional groups may be added to the materials, or particles containing the materials, that may covalently link the materials to the object of interest. Luminescent materials may be bound to a tape and added to an article by lamination. High temperature processes may be applied to purely inorganic materials that allow for reaction or fusion with glass, ceramics, or polymers. Some materials may be capable of sufficiently high temperatures such that they may be thermally imbibed into glass. In some applications, mixtures of multiple luminescent materials are desired. In other cases, one or more luminescent materials may be spatially patterned on an article. Spatial patterning may be done in all three dimensions and may be accomplished by, for example, lamination, spray coating, screen printing, gravure printing, ink jet printing, embossing, stamping, or 3D printing.

After fabrication, the materials may potentially be locked in a final stable form by heating, polymerization, photolysis, lamination, or by overcoating. The materials may also be passivated via encapsulation.

In some cases, electron transfer processes may be used to create materials with emission lifetimes that may be used to encode information in or on articles. In some cases, these processes include the use of electron transfer processes to create excited states.

In some embodiments, an emissive species may be used as crystals, ceramics, particles, in polymer composites, and/or encased in glass. In some embodiments, an emissive species is deposited on an object with a continuous composition, gradient, or pattern. In certain instances, a pattern may be similar to linear bar codes or matrix codes that are readable by laser scanners or image analysis. In some embodiments, one or more emissive species are directly integrated into a printed image or mixed with other dyes. In some embodiments, one or more emissive species are homogeneously deposited on a solid, surface, or solution. A person of ordinary skill in the art will recognize that emissive species may be added to compositions or deposited in patterns with other emissive or colored materials to create unique and complex information content.

The emissions detected may depend on the excitation method, frequencies, delays, wavelengths, and intensities of the emissive species that are present. Delays after a pulse may change the image, which may be particularly apparent if multiple emissive species are spatially patterned. In some cases, all emissive species may be excited simultaneously. In some cases, certain emissive species may be electively excited by the choice of wavelength of electromagnetic radiation used. In some cases, an article may have an intrinsic emission. For example, a printed object may use blue dye to prevent paper or fabric from appearing yellow. Emission from these brighteners may be blocked by printing or depositing materials over them. For example, carbon-based inks may be deposited on white paper. Similarly, longer lived emissive species may be deposited on paper and then patterned by printing carbon inks on top of them.

In some embodiments, a secondary process may occur that quenches an emission. In some embodiments, an emissive material may contain an emissive species that may be read only once or a few times. For example, a secondary process could be initiated by the reading process that causes an irreversible change in the article containing the emissive species. This change may be immediate or take some time to develop. Such changes may be activated by photochromic molecules, and/or the photogeneration of acid, base, radicals, or quenchers. In some cases, an emissive species may be configured to produce a detectable emission, but a secondary process may change the material such that the detectable emission is not present with repeated reading. In some cases, a secondary process may be triggered by photochemical generation of reactive molecules, colored dyes, radicals, acids, bases, reduced or oxidized species, and/or causing a chemical cascade. Secondary processes may also be initiated by mechanical stress, air exposure, moisture exposure, or ionizing radiation such as gamma rays or x-rays.

The abundance of different emissive species makes it possible to create many different response mechanisms for not only determining the intrinsic identity of a material, but its chemical state. Many of the emissive species described herein are multicomponent with bonds, associations, and/or linkages that may be modified to give a reversible or irreversible response to light, temperature, radiation, a molecule of interest, an enzyme, a nucleic acid, a protein, a cell, a bacteria, a virus, a spore or other biomolecule, physical modification, pressure, gas, oxygen, moisture, carbon dioxide, pollen, environmental pollutant, particulate, drug, pH, allergens and the like.

In some embodiments, one or more, two or more, three or more, four or more, five or more, six or more, seven or more, eight or more, nine or more, ten or more, fifteen or more, or twenty or more (different) emissive species may be present (e.g., associated with an article, in the system, on a chemical tag, on a label) and/or excited by an excitation component. In some embodiments, the number of different emissive species associated with an article is in a range from 1 to 2, 1 to 5, 1 to 7, 1 to 10, 1 to 15, 1 to 20, 2 to 5, 2 to 7, 2 to 10, 2 to 15, 2 to 20, 5 to 7, 5 to 10, 5 to 15, 5 to 20, 10 to 15, or 10 to 20. In some embodiments, each emissive species may be responsive (e.g., may change in one or more of an intensity of the emitted light, a polarization of the emitted light, a spatial profile of the emitted light or a change in the emission lifetime of the emissive species) to different stimuli (e.g., change to a particular temperature, pH, solvent, chemical reagent, type of atmosphere (e.g., nitrogen, argon, oxygen, etc.), electromagnetic radiation). In some such embodiments, a characteristic of the stimuli (e.g., presence, identity, etc.) and/or article may be determined based upon which one or more emissive species produce(s) a detectable signal.

By way of illustrative example and without wishing to be limited as such, in some embodiments, a system comprises a first emissive species and a second emissive species. In some embodiments, a determinable change in the first emissive species (but not the second emissive species) corresponds to a particular characteristic (e.g., of an article associated with the emissive species). In some embodiments, a determinable change in the second emissive species (but not the first emissive species) corresponds to a particular characteristic. In some embodiments, a determinable change in both the first emissive species and the second emissive species corresponds to a particular characteristic. In some embodiments, no determinable change in either the first emissive species or the second emissive species corresponds to a particular characteristic. In some embodiments, a third emissive species is present. In some embodiments, a change in one of the three emissive species corresponds to a particular characteristic. In some embodiments, a change in two of the three emissive species corresponds to a particular characteristic. In some embodiments, a change in three of the three emissive species corresponds to a particular characteristic. In some embodiments, no change in three of the three emissive species corresponds to a particular characteristic. Those of ordinary skill in the art would understand, based upon the teachings of this specification, that higher order combinations of emissive species (four or more, five or more, etc.) may be used and that select changes in select emissive species may corresponds to a particular characteristic(s) (e.g., of an article associated with the emissive species).

By way of a further illustrative example and without wishing to be limited as such, in some embodiments, a system comprises a plurality of emissive species (e.g., at least a first emissive species, a second emissive species, and a third emissive species) such that each emissive species is selected to be responsive to a particular stimulus. For example, the stimulus may be concentration of an analyte, pH, and/or temperature. In an exemplary set of embodiments, each emissive species may be responsive (e.g., the emissive species undergoes a property change such as wavelength and/or intensity) to a different temperature. In some such embodiments, a change in one or more emissive species is indicative of exposure to a particular temperature (or set of temperatures). For example, a change in the first emissive species indicates exposure to at least a first temperature, and a change in the second emissive species indicates exposure to at least a second temperature, different than the first temperature. Other stimuli are also possible, as described herein.

In some cases, information may be extracted from a subset of the different emissive species by the use of complex excitation methods, polarization, spatial patterning, time delays, and/or secondary exposures.

Figure 7:
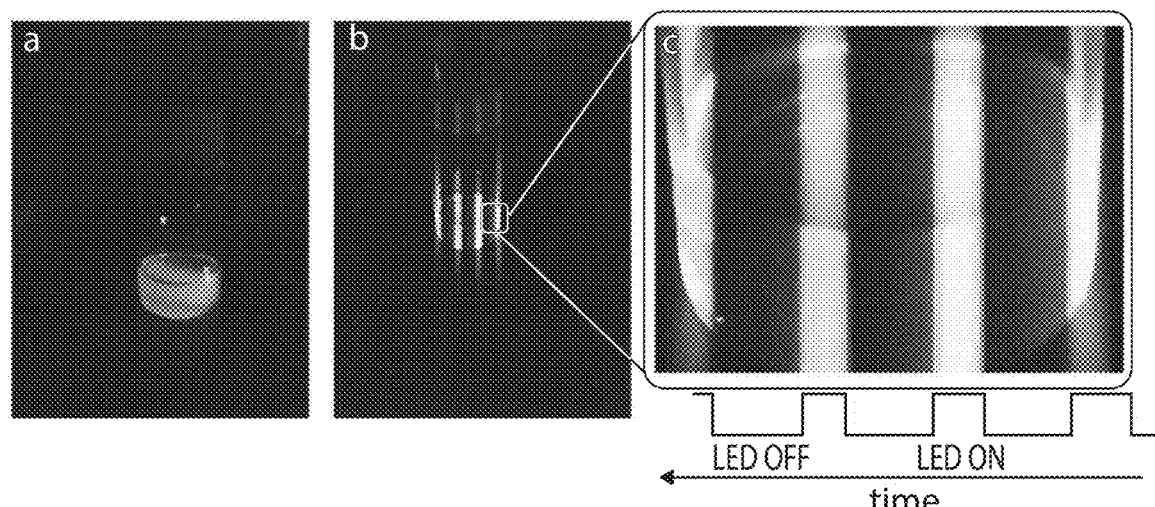
FIG. 7 shows an optical micrograph of a vial containing multiple emissive species under steady illumination (left), an optical micrograph of the same vial under pulsed illumination as imaged using rolling shutter (middle), and a magnified view of the middle optical micrograph (right), according to some embodiments.

FIG. 7 shows an exemplary system comprising two emissive species. In the exemplary system shown in FIG. 7, one emissive species has an emission lifetime greater than 10 ns, and one emissive species has an emission lifetime less than 10 ns. As shown in FIG. 7, the rolling shutter effect may be combined with a pulsed electromagnetic radiation source to resolve the individual components. FIG. 7 (left) shows an optical micrograph of a vial containing two emissive species. FIG. 7 (middle) shows an optical micrograph of the same vial under pulsed illumination imaged using rolling shutter. As shown in FIG. 7 (middle), during the "on" state, emission from both species is observed, and during the "off" state, only emission from the species with an emission lifetime greater than 10 ns is observed. As may be seen from the magnified image shown in FIG. 7 (right), the rolling shutter method superimposes the time domain on the spatial domain.

The systems and methods described herein may be useful for a number of applications. For example, in some embodiments, the systems and methods described herein may be used for product identification, product authentication, or the like. In some embodiments, the systems and methods described herein may be used to determine a characteristic of an article. In some instances, the characteristic of the article may include the identity of the article, point of origin of the article, the location of the article, the authenticity (or counterfeit nature) of the article, the quality of the article, the age of the article, whether the article is new or used, deterioration of the article, mishandling of the article, tampering of the article, contamination of the article, or the like. Such characteristics may be useful for, for example, detecting theft, detecting unauthorized distribution, identifying illegal sales, identifying counterfeit products, identifying adulterated products, quality control, quality assurance, tampering with, and tracking of the article.

Optimization may involve, in some embodiments, creating a set of parameters that maximizes the signal and/or minimizes (suppresses) the background (e.g., including stray light) signals. These parameters generally depend on the particular assay and conditions under which the reading is conducted. When deployed on a smartphone a colorimetric signal may be used to provide information that directs the user to orient the smartphone in a particular manner relative to the assay to generate a desired signal. In some cases, this information, which can be contained in a picture, logo, QR code, or bar code on the assay informs the smartphone about the optimal camera settings such as shutter speed (exposure time) and/or sensitivity (ISO) setting and the excitation profile. In some cases, the phone may perform measurements that rapidly explore a range of values for the shutter speed/ISO and the type/duration of excitation to be used. Computationally, the smartphone may be used to determine imaging conditions that produce desired signals (e.g., by providing high definition/contrast, the rejection of artifacts and stray light, and producing bright emissive signals). It may be that the data collected during this survey is adequate and optimal signals can be extracted from many images. It may be that all images are fused together, in some embodiments, such that only a fraction of the images are used to create the measurement. It may also be the case that guided by a quick survey method, computational methods yield imaging parameters that configure the smartphone to make subsequent measurements using a particular set of parameters to create an optimal measurement. For example, this may be used to determine if the assay is moved away from a bright interfering light source or change the time over which each image is collected by the detection chip (shutter speed or exposure time), or how best to configure the excitation. The latter may be pulsed light flashes or a frequency modulated method. In some cases, the smartphone may instruct the user to seek conditions that limit ambient light. This may be accomplished, for example, by going into a dark room or closet or using a dark cover over the camera and assay to eliminate light. The latter may comprise a dark cloth, piece of black plastic, or a box capable of positioning the camera relative to the assay while blocking stray light from interfering with the measurement. The latter may comprise a disposable element provided as part of product packaging.

In some embodiments, an emissive species (e.g., a phosphor) may be used to detect the presence of a heavy metal (e.g., lead, mercury). As an illustrative example, an emissive species (e.g., a lumophore) may be coated on a strip of paper, and the coated paper may be inserted in a water sample. If heavy metals are present, they may bind to the coated paper and may modify the emission lifetimes of the emissive species. The emission lifetime of each species may be measured using lifetime imaging as described above.

In some cases, a test strip (e.g., an emissive species coated on a strip of paper) may be used to detect a molecular signature of a product. As one non-limiting example, a perfume may be sprayed on a test strip to produce a new object that, when imaged over the lifetime of the emissive species, may be used to validate its identity. The molecular signature may be caused by selective enhancement or quenching of emissive species and/or changing the lifetime of emissive species.

In some cases, an emission tag (e.g., a chemical tag) may be used for labeling or information encoding. In some cases, such emission tags (e.g., chemical tags) may rely on patterning and different colors. The emission images may be prepared and read by a number of possible complex and variable excitation and measurement methods. In some cases, many different image patterns may be generated by a single emission tag. The measured lifetime images may be dynamically changed based on an application or from instructions transmitted to the reading device from a central source. Complex algorithms may be assigned to a given location or the time of day where the image is acquired. In some cases, secondary information (e.g., a one- or two-dimensional bar code on an object) may contain instructions on how to read a complex emissive lifetime image.

In some cases, a dynamic quencher that is capable of quenching select emissive species to produce a specific lifetime may be added to an emissive material. Emissive species and/or dynamic quenchers may be incorporated in films, bulk polymers, pastes, gels, or fluids (e.g., liquids, gases). For example, one or more emissive species may be printed on a surface, and one or more dynamic quenchers may be placed in a gas phase. In some cases, the rate of diffusion of the quencher may be modified by a secondary stimulus, and a lifetime image may be used to detect the presence of the secondary stimulus. The stimulus may be chemical, thermal, photochemical, radiative (e.g., involving exposure to ionizing radiation), or mechanical. The action of the secondary stimulus may be reversible or irreversible. If reversible, it may behave as a real-time sensor for the second stimulus. Non-limiting examples of a suitable secondary stimulus include the presence of water and heat. Heat is well known to modify the diffusion processes within materials and can modify the lifetime of an emissive species by changing the diffusion rates of dynamic quenchers. It may also involve selective excitation of a photochromic element. Electromagnetic radiation may be used to change the properties of the materials and their diffusion. The secondary stimulus may also be used to increase the concentration of the dynamic quenchers, which may increase the probability that the dynamic quenchers are close to the emissive species. In some cases, both the dynamic quencher and the emissive species may diffuse. In some cases, only the emissive species may diffuse. The encounter of the two species is generally controlled by diffusion rates and concentration.

In some cases, an article may be associated with an emissive tag (e.g., a chemical tag) that is difficult to reverse engineer or copy. In an emissive tag, a plurality of different emissive species may be placed in different environments, positions, or orientations by the way the compositions are assembled. In some embodiments, the process by which an emissive tag is assembled may be complex and may yield a unique signal. It is far easier to create a new unique signal in a highly multidimensional processing space, than it is to replicate this signal. Hence, it will be efficient to create new unique signals, and will be effectively futile to attempt to counterfeit copies of these compositions. In some embodiments, emissive species may be covalently bound and/or encased in materials that can only be disassembled by aggressive physical, thermal, and/or chemical processes that result in degradation of the emissive species. This may, in some cases, prevent easy identification of the emissive species. In addition, the patterns created may be sufficiently complex that significant effort would be required to reverse engineer or copy the patterns. Moreover, even if an emissive tag could be reverse engineered or copied, codes may be easily changed and require matching to other product information, such as linear barcodes and/or matrix codes.

One way to authenticate an article is to place specially designed emissive species directly within the article. Emissive species may be embedded in plastics, ceramics, glass, metals, paints, gels, waxes, liquids, or oils. In some cases, the emissive species may be homogeneously distributed. In some cases, the emissive species may be printed according to a pattern. Even in the absence of a complex pattern, given the possible variations in emissive species colors and emission lifetime, there is still considerable information available.

Additionally, a secondary label on the container that a product (e.g., an article) comes in may be used to give the reader (e.g., a smartphone) additional instructions on how the read is to be performed. For example, a fluid may be analyzed by first scanning an optical linear barcode or two-dimensional matrix code on its container or packaging and then scanning the fluid. In such a way there may be a variety of codes created for products with minimal expense. In another representative example, a liquid, gel, paste, or solid containing a taggant may be sprayed or deposited onto a linear barcode, two-dimensional matrix code, a test strip capable of creating a non-steady state photon emission to produce an image, or any other region of the container or packaging capable of recognizing the presence of the taggant. In such a way the authenticity of both the contents and its associated packaging may be easily verified.

A wide variety of emissive species may be produced from non-toxic organic and/or inert inorganic materials. Similarly, insoluble carbon-dot materials may be considered as non-toxic, thermally stable, and inert. In some embodiments, these materials need only be present in trace concentrations and may be applied to the skin in the case in perfumes and cosmetics. Alternatively, the emissive species may be part of the coating on a product. In the case of coated pills, tablets, or capsules, combinations of emissive species can uniquely encode the pill, tablet, or capsule while remaining safe for consumption. In some cases, one of more safe materials that are approved for human consumption or for application to the skin may be combined. For example, bismuth compounds are used in treating digestive problems. Bismuth may be used to create compositions with edible dyes to create long-lived emissive complexes. Other suitable non-limiting examples include food dyes that can have long-lived emissions. Advantageously, long-lived emissions may enable, in some cases, selective detection by non-steady-state methods.

Emissive species can be included in other consumable materials such as lubricating oils.

Emissive tags may be incorporated onto packaging, in the packaging material itself, integrated as part of a linear barcode or matrix code, or included in an image or trademark. The linear barcode or matrix code may provide instructions to the reader on how to excite the emissive species and where to read the code. For example, in a given package, a user may be instructed to place his or her reader (e.g., image sensor) over a particular symbol or word. It is possible that there could be multiple codes placed on a single package and the reader only redirected if there was data suggesting possible counterfeit activity. This could be the result of optical barcodes suggesting that a product was not distributed in a particular region, but there are multiple products being read in that area. It could be that other questionable codes that are potentially counterfeit have been detected. Thus, the use of emissive species may advantageously provide a low-cost way of incorporating authentication information into the packaging of a product that may also be used to obtain information to track the sources of counterfeit goods.

Packaging is often used to protect a product from the environment, and emissive tags may be used to determine the status of the product. In some cases, an emissive tag may be designed to respond to particular types of stimuli. For example, if an emissive tag is placed on the inside of food packaging, it may be used to determine the quality of the food. Biogenic amines produced by microbial activity could cause changes in emissive species responses (e.g., lifetime, intensity, wavelength of the emission, color) and the concentration of these amines determined by the captured image. In some cases, this measurement may be determined without ever opening the packaging provided the packaging is transparent at the tag excitation and read wavelengths. Similarly, for modified atmosphere packaging used for produce, tags may be developed that detect the levels of oxygen, carbon dioxide, and/or other microbial markers. The ingress of oxygen may be used to determine if the seal of a product has been broken.

In some embodiments, emissive tags may be used to sense gas and/or liquid states. In some embodiments where a product is a liquid, the emissive tag may be in contact with the liquid, and specific interactions between constituents of the liquid and the emissive tag may be used to generate a unique image read by emission wavelengths and lifetimes. For blister packaging and the like, an analyte may be incorporated into the contents of the item contained within the packaging for subsequent release, or actively added at the point of manufacture to the head-space of the packaging, such that the resultant head-space analyte interacts with an emissive tag located on the inside of the packaging to affect the emissive wavelengths and lifetimes of the tag. In one embodiment, this analyte-tag interaction may be reversible, such that the tag reverts to its original state upon opening the package and the subsequent evaporation or removal of the analyte.

In some cases, the thermal history of the product may be determined by the emissive authentication code placed in or on the packaging. This may be very useful for thermally sensitive medications such as biologics, insulin, and vaccines. Emissive tags may be used to determine the authenticity of products and ensure that the cold chain, needed to preserve their quality, has been observed. In one embodiment, an emissive tag located on a vial of insulin may be used to monitor the cumulative time-out-of-fridge. Thermal history tags may also be useful to monitor the quality of meat and fish as well as wine.

The combination of an emissive encoded tag, optical linear barcode or matrix code, hologram, embossed code, waveguided code, and a smartphone reader or similar interconnected device, may be used to obtain time, location, and authentication data. This data may be captured locally using a device application and periodically transmitted to a central location or, bandwidth permitting, be constantly transmitted. In some cases, manufacturers and/or retailers may be able to use this information to monitor where their products are located and, more importantly, where counterfeit products are infiltrating their supply or distribution chains.

In some embodiments, an emissive tag is optically anisotropic. In some embodiments, one or more emissive species of an emissive tag may emit electromagnetic radiation at a first set of wavelengths and emission lifetimes in one direction and a second set of wavelengths and emission lifetimes in a second direction. In some cases, this anisotropy may be produced by mechanical methods (e.g., blow molding, melt flow, extrusion, rubber, embossing, solvent flow, stretching) when the emissive species is a polymer or is embedded within a polymer. In some embodiments, emissive species may be part of a liquid crystal or dissolved in a liquid crystal. Alignment of emissive species within the liquid crystal may be accomplished by mechanical methods, optical methods, photochemical reactions, and/or the application of electrical and/or magnetic fields. In certain cases, circularly polarized electromagnetic radiation may be generated. In some cases, these alignments may be retained and persist in the emissive tag indefinitely or until other conditions are applied that cause a loss of alignment. In certain cases, an anisotropic optical material may be placed around and/or over an emissive species and may thereby generate a polarized image. In some cases, the addition of polarization and optical anisotropic character to an emissive tag may advantageously create additional complexity and provide more options for encoding information. In some cases, an increase in temperature may cause a decrease in optical alignment within a material. In some such cases, emissive lifetime image changes resulting from a change in the alignment of a material may be used to obtain information on the thermal history of an object.

In some embodiments, pills, tablets, and capsules may be placed in a blister package. Typically, one side of this package is hemispherical and transparent so that the product may be seen and the backing, often foil, is flat with the product removed by breaking the backing. These packages may contain atmospheres that result in specific lifetimes for emissive tags. The atmosphere may contain a gas such as carbon dioxide, which may interact with amines or other species in the emissive material to give a unique lifetime. This may yield a unique optical signature for the product. In some cases, if the product is compromised by breaking the seal, this may also be detected. In some embodiments, the atmosphere may be nitrogen or argon, and the emissive tag may be one that changes its lifetime in the presence of oxygen, which may infuse into the packaging if the seal is broken. In some instances, the atmosphere may contain heavy water, which may be replaced by water in the event of a broken seal.

In some embodiments, an emissive species and/or emissive tag may be combined with recognition entities such as RNA, DNA, PNA, chimeric nucleic acids, molecular beacons, antibodies, aptamers, lectins, proteins, engineered proteins, enzymes, intercalating agents and the like to produce assays (e.g., diagnostic assays, immunoassays). In some cases, the assays may be used for point-of-care, field, point-of-need, and/or in-home diagnostic use. In some embodiments, the assays may be based on high-throughput screening (HTS), time-resolved FRET, and/or time-resolved fluorescence quenching techniques. In certain cases, the assays may be combined with other diagnostic, sensing, and/or signal/analyte amplification techniques, including but not limited to polymerase chain reaction (PCR), quantitative polymerase chain reaction (qPCR), isothermal amplification, gene editing techniques, and the like. In certain cases, the assays may be combined with high-throughput array techniques, including but not limited to DNA microarrays, protein microarrays, organ-on-a-chip devices, and the like. In some cases, the assays may be used to test environmental samples (e.g., water, soil, mold, paint) and/or biological samples (e.g., blood, sweat, mucus, urine, stool). In some cases, these assays may be incorporated into wearable sensors designed to monitor pH, sweat rate/loss, the concentration of analytes (e.g., glucose, lactate, chloride, electrolytes, metabolites, small molecules). In some cases, the systems and methods described here may be fabricated into assays (e.g., diagnostic assays) to monitor analytes indicative of disease states such as bacterial, viral, or fungal infections, renal failure, or cancer. One who is skilled in the art will recognize that other assays are possible.

In some embodiments, emissive sprays, aerosols, liquids, particles and the like may be used to verify the presence or absence of allergens in food and drink samples.

In some embodiments, emissive solids, liquids, particles, aerosols, gels, pastes or the like may be widely distributed and remotely monitored to verify the presence or absence of analytes such as explosives, chemical agents, biological agents, toxic chemicals, heavy metals, narcotics, radiation and the like. Additionally, the aforementioned rolling shutter effect can yield distance information for range-finding applications.

In another embodiment, emissive tags capable of detecting analytes such as explosives, chemical agents, biological agents, toxic chemicals, heavy metals, narcotics, radiation and the like may be deployed on autonomous air, land, and sea based vehicles for remote monitoring.

In another embodiment, emissive tags may be used for friend/foe identification.

In another embodiment, emissive tags may be used in security badges or identification cards.

In another embodiment, emissive tags may be used in currency.

In some embodiments, an emissive species (e.g., a chemical and/or biological species) described herein may be associated with a point-of-care, field, point-of-need, or home diagnostic kit or related method.

In some embodiments, one or more emissive species may be incorporated into a solution that is drop-casted, spun-coat, or sprayed onto a variety of substrates. In some embodiments, an emissive species may be incorporated into a thin film.

In some embodiments, the systems and methods described herein may be used to detect degradation (e.g., a characteristic) of an article due to, for example, exposure to extreme temperatures, changes in moisture and/or humidity, exposure to light and/or chemical reactants). For example, in some such embodiments, the one or more chemical and/or biological species may have a time-dependent emission and/or reflection behavior that is altered by exposure to different temperatures, moisture, humidity, light, and/or reaction with particular chemicals. In other cases, the chemical and/or biological species may be used as a timer to ensure the quality of a material. For example, if the change in the characteristic of the species is triggered by exposure to gamma radiation, ethylene oxide, oxygen, or other sterilization agents as part of a sterilization process, then the emissive species may be used to indicate the exposure and/or how much time has expired after this process. Similarly, a physical opening of packaging around an article and exposure to ambient atmosphere may be identified (e.g., a characteristic) using the methods and systems described herein.

In some embodiments, as described herein, changes in the emission profile (e.g., amount, rate) of an emissive species (e.g., as identified in a single image), under a particular set(s) of conditions, correspond to one or more characteristics of an article or the species itself. That is to say, in some embodiments, one or more characteristics of an article may be identified based upon the luminescence and/or reflection/scattering profile of one or more chemical and/or biological species (e.g., chemical and/or biological species proactively added to the article).

In some embodiments, the species may be applied to an article and a record of the characteristic of the article associated with that species may be made. For example, in some embodiments, the identity of the article may be confirmed if a particular emission pattern is detected by an image system.

In some embodiments, the systems and methods described herein may be combined with one or more additional identifying components. For example, in some embodiments, a second identifying component, different than the chemical and/or biological species, may be present. For example, in some embodiments, the species may be further associated with a single or multidimensional optical barcode. Those of ordinary skill in the art would understand, based on the teachings of this specification, how to select additional identifying components for use with the methods and systems described herein. In some embodiments, the article is associated with a species and a second identifying component such as an optical barcode, hologram, RFID, and/or additional chemical markers and/or biological markers. Non-limiting examples of additional chemical markers and/or biological markers that may be used in conjunction with the systems described herein include, but are not limited to, colorimetric dyes, fluorescent dyes, IR dyes, watermarks, nanoparticles, nanorods, quantum dots, antibodies, proteins, nucleic acids, and combinations thereof.

The term "associated with" as used herein means generally held in close proximity, for example, a chemical tag associated with an article may be adjacent a surface of the article. As used herein, when an emissive species is referred to as being "adjacent" a surface, it may be directly adjacent to (e.g., in contact with) the surface, or one or more intervening components (e.g., a label) may also be present. A chemical tag that is "directly adjacent" a surface means that no intervening component(s) is present. In some embodiments, the chemical and/or biological species is adjacent a surface of the article. In some embodiments, the emissive species is directly adjacent a surface of the article. In some embodiments, the emissive species is incorporated into the article (e.g., is present within the bulk of at least a portion of the article but, absent the addition of the chemical and/or biological species to the article, would not be inherently present in the article itself or not present in an amount desirable for implementation of the systems and/or methods described herein).

In some embodiments, the emissive species passively emits electromagnetic radiation. In some embodiments, the emissive species does not emit electromagnetic radiation and may be stimulated (e.g., triggered) to luminesce and/or reflect electromagnetic radiation that may be detected (e.g., in a single image produced, for example, using a rolling shutter or the like).

In some embodiments, stimulation (e.g., triggering) of the species produces an emission and/or changes a lifetime of the emission. In some embodiments, the lifetime of the emission identifies a characteristic of the species and/or the article.

In some embodiments, a characteristic of an article may be determined by detecting a first (time-independent) steady-state photon emission by one or more species under a first set of conditions and detecting a second (time-dependent) non-steady-state photon emission by the one or more species under a second set of conditions, different that the first set of conditions, wherein the change between the first emission and the second emission identifies a characteristic of the article.

As described above and herein, a characteristic of an emission (e.g., the lifetime of the emission) of one or more species may be identified by obtaining a single image of the emission using a rolling shutter mechanism and an image sensor, such that a first portion of the image corresponds to a steady-state photon emission and a second portion of the image corresponds to a second time period after the same emission begins.

In some embodiments, a single pulse of electromagnetic radiation may be used to stimulate the species.

A characteristic of an emission may also be identified by exciting the emissive species by a modulated excitation, as described above. In some embodiments, advantageously, emissive species that have lifetimes substantially faster than the modulating cycle time(s) may be used to provide a first component of the detactable signal and those with long-lived lifetimes that are similar to the modulating cycle times may be used to provide a second component of the detectable signal.

In some embodiments, multiple pulses of electromagnetic radiation may be used to stimulate the species. In certain cases, multiple pulses of electromagnetic radiation may be useful for repeated authentication of an article. In some embodiments, the emissive species may be stimulated over a particular period of time such that the intensity, lifetime, and/or color of the signal produced by the image sensor in response to the emission may be monitored over time. In some such embodiments, the emission profile of the species may be used to determine a characteristic of an article (e.g. authenticity, freshness, whether the item had been used, etc.) In some embodiments, a plurality of pulses of electromagnetic radiation of one or more chemical and/or biological species may be used to generate, for example, a complex identifiable signal such that the time-domain of the identifiable signal corresponds to a characteristic of the article (e.g., identity, authenticity, etc.).

Generally, any stimulation that produces a detectable emission (and/or reflection) of electromagnetic radiation from a chemical and/or biological species may be used with the systems and methods described herein.

In some embodiments, the methods and systems described herein may utilize a sequential release of two or more emission profiles to identify one or more characteristics of an article.

In some cases, it may be desirable to have species that may be excited for months or even years. In some embodiments, electromagnetic emissions that occur in response to an added reactant, light, heat, radiation, or mechanochemical stimulus may be used.

The availability of luminescent materials that are smartphone excitable enables consumers to make measurements without the need for additional hardware. For example, advantageously, it is possible for a consumer to test if they are infected with a virus or if they have developed immunity to a disease by testing for antigens and antibodies. Some applications of luminescent materials imaged by collecting steady-state photon emission and non-steady-state photon emission events will make use of information read through conventional imagery such as a bar code, QR code, photograph, identification number, company logo, or other markings. The smartphone excitable and readable luminescent materials augment this conventional information and may combine, in some embodiments, to create valuable information on the authenticity, quality, or status of articles, as well as determination of the presence and quantity of biological or chemical materials.

In some embodiments, the image sensor is positioned proximate an article suspected of containing a chemical and/or biological species. In some embodiments, upon excitation of the chemical and/or biological species to produce an emission, the image sensor may be configured to produce a single image of the emission. In some such embodiments, the single image may correspond to one or more characteristics of an article.

In some embodiments, the chemical and/or biological (e.g., emissive) species may undergo a reaction (e.g., which may be detected using the systems and methods described herein) in the presence of an analyte. For example, the interaction between a species (e.g., an emissive species and/or a chemical and/or a biological species) and an analyte may include formation of a bond, such as a covalent bond (e.g. carbon-carbon, carbon-oxygen, oxygen-silicon, sulfur-sulfur, phosphorus-nitrogen, carbon-nitrogen, metal-oxygen or other covalent bonds), an ionic bond, a hydrogen bond (e.g., between hydroxyl, amine, carboxyl, thiol and/or similar functional groups, for example), a dative bond (e.g. complexation or chelation between metal ions and monodentate or multidentate ligands), and the like. The interaction may also comprise van der Waals interactions. In one embodiment, the interaction comprises forming a covalent bond with an analyte. In some cases, the interaction between the species and the analyte may comprise a reaction, such as a charge transfer reaction. In some other embodiments, the species may undergo a chemical or physical transformation upon a change in the surrounding environment (e.g., change in temperature) to produce a determinable emission profile (e.g., pattern) from the image sensor. The determinable signal may, in some cases, persist or subside over time.

The emissive species may also interact with an analyte via a binding event between pairs of biological molecules including proteins, nucleic acids, glycoproteins, carbohydrates, hormones, and the like. Specific examples include an antibody/peptide pair, an antibody/antigen pair, an antibody fragment/antigen pair, an antibody/antigen fragment pair, an antibody fragment/antigen fragment pair, an antibody/hapten pair, an enzyme/substrate pair, an enzyme/inhibitor pair, an enzyme/cofactor pair, a protein/substrate pair, a nucleic acid/nucleic acid pair, a protein/nucleic acid pair, a peptide/peptide pair, a protein/protein pair, a small molecule/protein pair, a glutathione/GST pair, an anti-GFP/GFP fusion protein pair, a Myc/Max pair, a maltose/maltose binding protein pair, a carbohydrate/protein pair, a carbohydrate derivative/protein pair, a metal binding tag/metal/chelate, a peptide tag/metal ion-metal chelate pair, a peptide/NTA pair, a lectin/carbohydrate pair, a receptor/hormone pair, a receptor/effector pair, a complementary nucleic acid/nucleic acid pair, a ligand/cell surface receptor pair, a virus/ligand pair, a Protein A/antibody pair, a Protein G/antibody pair, a Protein L/antibody pair, an Fc receptor/antibody pair, a biotin/avidin pair, a biotin/streptavidin pair, a drug/target pair, a zinc finger/nucleic acid pair, a small molecule/peptide pair, a small molecule/protein pair, a small molecule/target pair, a carbohydrate/protein pair such as maltose/MBP (maltose binding protein), a small molecule/target pair, or a metal ion/chelating agent pair. Specific non-limiting examples of species include peptides, proteins, DNA, RNA, PNA.

As used herein, an "analyte" or "chemical compound" may be any chemical, biochemical, or biological entity (e.g. a molecule) to be analyzed. The analyte may be in vapor phase, liquid phase, or solid phase. In some embodiments, the analyte is a vapor phase analyte. In some cases, the analyte may be a form of electromagnetic radiation. In some cases, the analyte may be airborne particles. In some cases, the device may be selected to have high specificity for the analyte, and may be a chemical, biological, or explosives sensor, for example. In some embodiments, the analyte comprises a functional group that is capable of interacting with at least a portion of the device (e.g., a species). In some cases, the device may determine changes in pH, moisture, temperature, and the like, of a surrounding medium. The analyte may be a chemical species, such as an explosive (e.g., TNT), toxin, or chemical warfare agent. In a specific example, the analytes are chemical warfare agents (e.g., sarin gas) or analogs of chemical warfare agents (e.g., dimethyl methylphosphonate, DMMP).

As used herein, the term "react" or "reacting" refers to the formation of a bond between two or more components to produce a stable, isolable compound. For example, a first component and a second component may react to form one reaction product comprising the first component and the second component joined by a covalent bond. The term "reacting" may also include the use of solvents, catalysts, bases, ligands, or other materials which may serve to promote the occurrence of the reaction between component(s).

A "stable, isolable compound" refers to isolated reaction products and does not refer to unstable intermediates or transition states.

In some embodiments, the chemical compound (i.e. analyte) may be an aromatic species, including optionally substituted aryl species and/or optionally substituted heteroaryl species, such as benzene, toluene, xylene, or polycyclic aromatic hydrocarbons such as benzo[a]pyrene. In some embodiments, the analyte may be an amine-containing species such as ammonia. In some embodiments, the analyte may be a nitrile-containing species such as acetonitrile. In some embodiments, the analyte may be an oxygen-containing species, such as a species comprising an alcohol, a ketone, an ester, a carboxylate, an aldehyde, other carbonyl groups, an ether, or the like. In some embodiments, the analyte may be a species comprising a ketone, an ester, an ether, or an aldehyde, such as cyclohexanone, ethyl acetate, THF, or hexanal. In some embodiments, the analyte is a phosphorus-containing analyte such as DMMP. In some embodiments, the analyte may be a nitro-containing species such as nitromethane or TNT. Other examples of analytes include alcohols, olefins, nitric oxide, thiols, thioesters, and the like.

In some cases, the sensor may determine changes in a condition, or set of conditions, of a surrounding medium. As used herein, a change in a "condition" or "set of conditions" may comprise, for example, change to a particular temperature, pH, solvent, chemical reagent, type of atmosphere (e.g., nitrogen, argon, oxygen, etc.), electromagnetic radiation, or the like. In some cases, the set of conditions may include a change in the temperature of the environment in which the sensor is placed. For example, the sensor may include a component (e.g., binding site) that undergoes a chemical or physical change upon a change in temperature, producing a determinable signal from the sensor.

Home tests for the presence or absence of viruses or antibodies generally use controls to ensure that the tests are performed and read properly. Such tests may provide key data used to monitor and model outbreaks of infectious diseases including contact tracing. In a non-limiting example, a delayed-phosphorescence material is conjugated to an antibody and used in a lateral flow assay. Delayed-phosphorescence may be used, for example, to eliminate background signals and create high-fidelity data. Specifically, detecting the luminescence in both steady-state and non-steady-state modes, or only in non-steady-state mode may be used to eliminate/subtract background signals, or to isolate signals from delayed-fluorescent, prompt-phosphorescent, and/or delayed-phosphorescent emissive materials. Although assays may be evaluated with the aid of article/structures that block stray light, detecting non-steady-state photon emission events may be also be used to selectively detect delayed-fluorescent, prompt-phosphorescent, and/or delayed-phosphorescent emissive materials in ambient light. These methods may also leverage other steady-state signals to augment the method including information used for image alignment and calibration.

Product authentication may be accomplished, for example, using a smartphone readable tag applied to an article. In some embodiments, the tag may be designed to encode highly complex information with different luminescent materials deposited in patterns that may be paired with optically read codes and instructions from cloud computing resources. The ability to create complexity in the tags stems from the ability to use combinations of excited state lifetimes, wavelengths (scattered, reflected, and luminescent light), patterning, and instructions on how the smartphone interrogates the tag. The latter may be determined by other product information (barcode or QR code) as well as location and time data. These instructions may include the position on the article to be analyzed, the sensitivity and exposure times used for signal detection, and the characteristics of the light source (pulse rate, delays, or the frequency of intensity modulation). Non-limiting examples of authentication uses include the validation of medicines, luxury goods, and replacement parts from a manufacturer.

Smartphone excitable and readable luminescent materials may also be used to sense the presence or absence of gases or other molecular species. Delayed-fluorescent, prompt-phosphorescent, and delayed-phosphorescent materials often have oxygen sensitivity, with molecular oxygen quenching their emission. Quenching reduces both the lifetime and emission intensity and combinations of parameters on the smartphone (light source and rolling shutter) may be configured to extract information used to detect and quantify oxygen levels. Modified atmosphere packaging is often used to limit the oxygen exposure of products and is widely used to maximize the shelf life of food in retail stores. Consumers and retailers may use the methods and materials presented here to verify that the integrity of the packaging is intact. Smartphone excitable and readable luminescent materials may also be used to detect other molecular signatures. A number of Europium delayed-phosphorescent luminescent materials have sensitivities to water resulting in quenching of their emission by energy transfer to the water molecules. Hence, moisture content may be monitored in packaging in this way. Additionally, there are other methods that may be used to design smartphone excitable and readable lumiphores for the detection of biogenic amines indicative of spoilage and/or microbial activity, or for the detection of sulfur compounds and carbon dioxide. All of these methods are relevant to packaging applications and the monitoring of perishable articles. It is possible using multiple lumiphores to determine one or more of these different molecular signatures simultaneously while authenticating with a smartphone. The ability to determine the status of the interior of a package without breaking the seal, is attractive for both consumers and retailers.

It is also possible to use smartphone excitable and readable luminescent materials to determine if an article has been altered. Anti-tampering methods may be developed that indicate when a seal has been broken. Breaking the seal may release a molecular signature that modifies the behavior of a lumiphore. Luminescent materials may also be designed to be sensitive to mechanical activity, cutting, resealing, heating, stretching, or any type of deformation. These may be used to detect if the packaging has been opened or somehow manipulated.

Smartphone excitable and readable luminescent materials may also be used to monitor the thermal history of a material. Changes that occur as a result of time spent at particular temperatures may be cumulative and designed to reveal if a material has exceeded a range that is too hot or too cold for a particular amount of time. Additional cumulative emissive indicators may be designed that allow for smartphone determination of ultraviolet light or ionizing radiation exposure. These may indicate damage or confirm treatments, for example as part of a sterilization protocol.

Other embodiments suitable for use in the context of some embodiments described herein are described in International Pat. Apl. Serial No.: PCT/US2009/001396, filed Mar. 4, 2009, entitled, "Devices and Methods for Determination of Species Including Chemical Warfare Agents"; International Pat. Apl. Serial No.: PCT/US2009/006512, filed Dec. 11, 2009, entitled, "High Charge Density Structures, Including Carbon-Based Nano structures and Applications Thereof"; U.S. patent application Ser. No. 12/474,415, filed May 29, 2009, entitled, "Field Emission Devices Including Nanotubes or Other Nanoscale Articles"; International Pat. Apl. Serial No.: PCT/US2011/051610, filed Oct. 6, 2010, entitled, "Method and Apparatus for Determining Radiation"; International Pat. Apl. Serial No.: PCT/US2010/055395, filed Nov. 4, 2010, entitled, "Nanostructured Devices including Analyte Detectors, and Related Methods"; International Pat. Apl. Serial No.: PCT/US2011/053899, filed Sep. 29, 2011, entitled, "COMPOSITIONS, METHODS, AND SYSTEMS COMPRISING POLY (THIOPHENES); International Pat. Apl. Serial No.: PCT/US2011/025863, filed Feb. 23, 2011, entitled, "Charged Polymers and Their Uses in Electronic Devices"; and International Pat. Apl. Serial No.: PCT/US2015/039971, filed Jul. 10, 2015, entitled "FORMULATIONS FOR ENHANCED CHEMIRESISTIVE SENSING", each of which are incorporated herein in their entireties for all purposes.

In some embodiments, the emissive species(s) has been proactively added to the article. That is to say, in some embodiments, the emissive species is not inherently associated with the article but is added in order to, for example, identify a characteristic of the article. In some embodiments, a label may be associated with the article. In some embodiments, the emissive species is inherently associated with the article but is not present in an amount desirable for implementation of the invention, thus more is added for this purpose. In some embodiments, the emissive species(s) are associated with the label such that the presence or absence of the chemical tag on the label identifies a characteristic of the associated article.

By way of an illustrative example only, and not intending to be limited as such, in some embodiments, one or more emissive species may be proactively added to an article that does not inherently comprise such emissive species (or, as noted above, may comprise such compounds but the additional of more facilitates the invention described herein). In some embodiments, the detection by a sensor of at least one of the one or more emissive species may identify a characteristic of the article. For example, two emissive species may be proactively added to the article. Detection, by a sensor, of both of the two emissive species may indicate the authenticity of the article. By contrast, a sensor which detects zero or one of the two emissive species may indicate that the article is not authentic. Those of ordinary skill in the art would understand, based upon the teachings of this specification, that the presence (or absence) of one or more emissive species associated with the article may identify one or more characteristics of the article as described in more detail herein (e.g., age, quality, origin, identity, etc.).

In some embodiments, a chemical tag comprises the one or more emissive species as described herein. In some embodiments, the chemical tag comprises one or more, two or more, three or more, four or more, five or more, six or more, seven or more, eight or more, nine or more or ten or more emissive species. In some embodiments, detection of the presence (or absence), of at least one of the one or more (or two or more, etc.) emissive species in the chemical tag identifies a characteristic of the article. For example, in some embodiments, detection of all of the emissive species present in the chemical tag identifies the characteristic of the article. In some embodiments, detection of at least a portion of the emissive species present in the chemical tag identifies the characteristic of the article. In some embodiments, the detection of none of the emissive species present in the chemical tag identifies the characteristic of the article In some embodiments, the chemical tag comprises a plurality of identifiable (e.g., by one or more sensors) emissive species. As described herein, in some embodiments, the chemical tag (and/or the one or more emissive species it comprises) is not inherently associated with the article. In some embodiments, the chemical tag may comprise one or more emissive species inherently associated with the article, but not present in an amount desirable for implementation of the systems and methods described herein, and thus more is added for this purpose. In some embodiments, the chemical tags described herein may be useful for additional applications. For example, in some embodiments, the chemical tag may be associated with an ink, a preservative, a flavoring, a fragrance, a colorant (e.g., a dye), and/or a structural element (e.g., glue, tape, strapping, packaging) associated with the article (or label).

The chemical tags described herein may be implemented in any suitable manner. For example, the chemical tag may be associated with a label. In some embodiments, the chemical tag and/or label may be single use or designed for multiple (e.g., repeated) use.

In some embodiments, the chemical tags described herein may be combined with one or more additional identifying components. For example, in some embodiments, a label may comprise a chemical tag (e.g. comprising one or more emissive species) and a second identifying component, different than the chemical tag. In some embodiments, a first label comprising the chemical tag and a second label comprising the identifying component may each be associated with an article. For example, in some embodiments, the chemical tag (or label) may be associated with a single or multidimensional optical barcode. Those of ordinary skill in the art would understand, based on the teachings of this specification, how to select additional identifying components for use with the chemical tags and systems described herein. In some embodiments, the article is associated with a chemical tag (or label comprising the chemical tag) and a second identifying component such as an optical barcode, hologram, RFID, and/or additional chemical markers and/or biological markers. Nonlimiting examples of additional chemical markers and/or biological markers that may be used in conjunction with the systems described herein include, but are not limited to, colorimetric dyes, fluorescent dyes, IR dyes, watermarks, nanoparticles, nanorods, quantum dots, antibodies, proteins, nucleic acids, and combinations thereof.

The term "label" as used herein is given its ordinary meaning in the art and generally refers to a component (e.g., comprising paper, fabric, plastic, ink, electronic device, or other material) associated with an article and giving information about said article. In an exemplary embodiment, the label is a sticker that contains functionality. In another exemplary embodiment, the label is a marker. In yet another exemplary embodiment, the label is a stamp. In other embodiments the label is printed or sprayed on an article. Other labels are also possible and means for associating labels with an article are described in more detail below.

The chemical tags and labels described herein may be applied to the article on any suitable manner. For example, in some embodiments, the chemical tag and/or label may be applied at one or more (e.g., two or more, three or more, four or more, five or more) or at a plurality of spatially distinct locations. For example, in some embodiments, the article comprises one or more (or two or more, etc.) chemical tags, wherein each chemical tag is the same or different. In some embodiments, each chemical tag may identify a same or different characteristic of the article.

In some embodiments, the chemical tag may be combined with one or more different materials. For example, polymerizations or polymer deposition may, in some cases, be used to form phase separation with polymers and thereby spontaneously form domains of a chemical tag or chemical tag precursor(s) with the polymer. The polymer may be inert and the chemical tag/chemical tag precursor may, in some cases, be released by mechanical disruption of the material. Alternatively, the polymer may be an active element and part of the triggered release, generation, or activation of the chemical tag. The polymer and chemical tag/chemical tag precursor and related elements may be deposited, in some cases, from solution onto a tag or made separately and applied in a lamination step. In some embodiments, the polymer may be produced in situ to make a film comprising the chemical tag. Those of ordinary skill in the art would understand, based upon the teachings of this specification, that the size and density of the chemical tag phase may be controlled by, for example, processing conditions, surfactants and the like. Crosslinking of the polymer host materials or the polymers encapsulants used in colloid production may be used, in some cases, to modulate the diffusion through these materials. Such crosslinks may be designed to be removed upon exposure to a chemical, photochemical, enzymatic, mechanical, electrochemical, or thermal process.

In some embodiments, the polymer is deformable such that deformation (e.g., stretching, bending) of the polymer releases the chemical compound(s) of the chemical tag.

Any suitable polymer may be used. For example, in some embodiments, the polymer may be kinetically stable (and thermodynamically unstable) such that it will generally spontaneously depolymerize with a bond rupture. An example of such a class of polymers are the poly(vinyl sulfones), which, without wishing to be bound by theory, when fragmented at room temperature will spontaneously depolymerize. Such materials have a broad compositional range and have generally been shown to be sensitive to radiation, base, electron transfer (redox), and thermal processes. Such polymers may be useful for the fabrication of polymer capsules comprising the chemical tags, described herein. Other polymers are also possible and those of ordinary skill in the art would be capable of selecting such polymers based upon the teachings of this specification.

The one or more chemical compounds may be applied to the article and/or label using any suitable means. Non-limiting examples of deposition methods include spray coating, dip coating, evaporative coating, ink jet printing, imbibing, screen printing, pad printing, gravure printing or lamination. In some embodiments, the one or more chemical compounds may be bound to the label or article via formation of a bond, such as an ionic bond, a covalent bond, a hydrogen bond, van der Waals interactions, and the like. The covalent bond may be, for example, carbon-carbon, carbon-oxygen, oxygen-silicon, sulfur-sulfur, phosphorus, nitrogen, carbon-nitrogen, metal-oxygen, or other covalent bonds. The hydrogen bond may be, for example, between hydroxyl, amine, carboxyl, thiol, and/or similar functional groups.

In some embodiments, the chemical tag and/or label are edible. That is to say, in some embodiments, the chemical tag and/or label may be safely consumed by a subject (e.g., a human, an animal). Non-limiting examples of chemical compounds that may be used in the chemical tag (or label) include compounds listed in the Sigma-Aldrich Ingredients Catalog: Flavors & Fragrances (2014) and Sigma-Aldrich and the Sigma-Aldrich Flavor & Fragrance Ingredients Supplement (2018), each of which are incorporated by reference in its entirety for all purposes.

In some embodiments, the chemical tag includes porous luminescent silicon (e.g., which, in some cases, may transform to silicon dioxide over time and therefore generally be considered harmless under some circumstances).

The labels described herein may comprise any suitable substrate for containing or otherwise associating the chemical tag with the article. For example, in some embodiments, the label may comprise a substrate, and a chemical tag (e.g. comprising one or more chemical compounds) associated with the substrate. Non-limiting examples of suitable substrates include silicone, silica, glass, metals, microporous materials, nanoporous materials, polymers, gels, and natural materials (e.g., paper, wood, rocks, tissues, hair, fur, leather).

In some embodiments, the label comprises a means for attaching the label to an article. Non-limiting examples of suitable means for attaching the label include adhesives, lamination, melt bonding, spray coating, spin coating, printing, strapping, and combinations thereof.

Any suitable type of sensor may be used to detect the presence (or absence) of a chemical tag (or one or more emissive species the chemical tag comprises). The sensor may comprise one or more components capable of detecting changes in optical properties such as wavelength, intensity, color, fluorescence, light scattering, or other features. Those of ordinary skill in the art would be capable of selecting suitable sensors based upon the teachings of this specification.

In some embodiments, the sensor is positioned proximate an article suspected of containing a chemical tag. In some embodiments, upon detection of the compound(s), the sensor may be configured to send a signal. In some such embodiments, the signal may correspond to one or more characteristics of the article (e.g., temporal thermal history). As described herein, in some embodiments, the chemical tag (or the one or more chemical compounds the chemical tag comprises) are not inherent to the article. For example, in some embodiments, a sensor will not detect the presence (e.g., amount, concentration, non-zero rate of release) of a chemical compound adjacent an article unless the chemical compound had been proactively associated with the article prior to sensing.

In an exemplary set of embodiments, an imaging device comprises a source of electromagnetic radiation configured to emit radiation to excite non-steady-state emission in emissive species during emission time periods of the emissive species, the emission time periods being at least 10 nanoseconds; an electromagnetic radiation sensor comprising a plurality of photodetectors arranged in an array of rows and columns, wherein the electromagnetic radiation sensor is configured to sense the non-steady-state emission from the emissive species during the emission time period; and processing circuitry configured to: sequentially read out rows or columns of the array to provide a plurality of time-encoded signals; and identify a characteristic of the emissive species based on a comparison of at least two of the plurality of time-encoded signals.

In some embodiments, the emissive time periods are at least 100 nanoseconds. In some embodiments, the emissive time periods are at least 1 microsecond.

In an exemplary set of embodiments, an imaging device comprises a source of electromagnetic radiation configured to emit radiation to excite non-steady-state emission in emissive species during emission time periods of the emissive species, the emission time periods being at least 10 nanoseconds; an electromagnetic radiation sensor, wherein the electromagnetic radiation sensor is configured to sense the non-steady-state emission from the emissive species during the emission time period; and processing circuitry configured to: globally expose and/or read data from the electromagnetic radiation sensor to provide a plurality of time-encoded signals and identify a characteristic of the emissive species based on a comparison of two or more of the plurality of time-encoded signals.

In some embodiments, the processing circuitry is further configured to generate one or more images based on the plurality of time-encoded signals, and wherein identifying the characteristic of the emissive species is based on the one or more images.

In some embodiments, the processing circuitry is further configured to: generate a first portion of an image based on time-encoded signals for one or more first rows or one or more first columns of the array; generate a second portion of the image based on time-encoded signals for one or more second rows or one or more second columns of the array, and wherein identifying the characteristic of the emissive species is based on a comparison of the first portion of the image and the second portion of the image.

In an exemplary set of embodiments, a system configured for identification of a characteristic of a chemical tag, comprises a chemical tag associated with an article, wherein the chemical tag comprises an emissive species, wherein the emissive species produces a detectable non-steady-state emission during an emission time period under a set of conditions, and wherein the emission time period is at least 10 nanoseconds; an excitation component configured to excite the emissive species under the set of conditions such that the detectable non-steady-state emission, which varies over the image capture time period, is produced; an image sensor configured to detect the detectable non-steady-state emission; and an electronic hardware component configured to convert the detected non-steady state emission into a single image, wherein the single image comprises a first portion corresponding to a first portion of the emission time period and a second portion corresponding to a second portion of the emission time period, and wherein a difference between a property of the first portion and the second portion is associated with a characteristic of the chemical tag.

In some embodiments, at least one characteristic of the detectable non-steady state emission varies during detection of the detectable non-steady state emission by an image sensor. In some embodiments, the emissive species is a chemical and/or biological species. In some embodiments, the chemical tag comprises a plurality of emissive species. In some embodiments, the excitation component is configured to excite a plurality of emissive species. In some embodiments, at least two emissive species of the plurality of emissive species are chemical and/or biological species. In some embodiments, the excitation component comprises a source of electromagnetic radiation. In some embodiments, the source of electromagnetic radiation is configured to emit substantially white light. In some embodiments, the source of electromagnetic radiation comprises an LED, an OLED, a fluorescent light, and/or an incandescent bulb. In some embodiments, the source of electromagnetic radiation comprises a flash lamp.

In some embodiments, the excitation component comprises an optical shutter, a light valve, an optical modulator, a dynamic refractory material, a rotating element that periodically blocks the electromagnetic radiation, and/or a moving mirror. In some embodiments, the excitation component is configured to excite the emissive species by electrical, mechanical, chemical, particle, or thermal stimulation. In some embodiments, the excitation component and the image sensor are integrated in a single component. In some embodiments, the excitation component and the image sensor are separate. In some embodiments, the image sensor comprises a CMOS sensor, charge coupled device, or photodiode. In some embodiments, the image sensor is associated with a rolling shutter mechanism. In some embodiments, the image sensor is associated with a global shutter. In some embodiments, the image sensor is incorporated in a smartphone. In some embodiments, the emissive species comprises one or more thermally activated delayed fluorescence (TADF) molecules or molecular complexes. In some embodiments, the emissive species comprises an inorganic phosphor. In some embodiments, the emissive species comprises bromine, iodine, sulfur, selenium, telluride, phosphorus, tin, lead, mercury, and/or cadmium. In some embodiments, the emissive species comprises bismuth, rhenium, iridium, platinum, gold, or copper. In some embodiments, the emissive species comprises a lanthanide or actinide. In some embodiments, the emissive species is associated with a pill, a capsule, or packaging of a product. In some embodiments, the article comprises a coating, wherein the coating comprises the emissive species. In some embodiments, the characteristic of the article and/or chemical tag is associated with the presence of a chemical agent, biological agent, explosive, toxic chemical, heavy metal, narcotic, xenobiotic, and/or radiation source. In some embodiments, the characteristic of the article is an authenticity of the article.

In some embodiments, the system comprises a second chemical tag. In some embodiments, the system comprises a second identifiable component. In some embodiments, the second identifiable component comprises an optical barcode, hologram, watermark, RFID, invisible ink, dyes, colorimetric markers, fluorescent markers, nanoparticles, nanorods, quantum dots, antibodies, proteins, nucleic acids, or combinations thereof. In some embodiments, the emissive species is associated with a point-of-care, field, or home diagnostic kit or method. In some embodiments, one or more components are in wireless communication with a component providing instructions for excitation of the emissive species and/or detection of the detectable emission.

In an exemplary set of embodiments, a method for identifying a change in an emissive species over a period of time, comprises exciting the species such that it produces a detectable non-steady-state emission during an emission time period, wherein the emission time period is at least 10 nanoseconds; obtaining, using an image sensor, data associated with the detectable non-steady state emission; optionally, create, based on at least a portion of the data obtained using the image sensor, a single image, wherein a first set of data used to create a first portion of the single image corresponds to a first portion of the emission time period, and wherein a second set of data used to create a second portion of the single image corresponds to a second portion of the emission time period; and determining, based upon a difference between the first portion and the second portion of the single image, the change in the emissive species.

In an exemplary set of embodiments, a method for identifying a change in an emissive species over a period of time, comprises causing the species to emit non-steady-state electromagnetic radiation during an emission time period; obtaining, using an image sensor, a single image of at least a portion of the electromagnetic radiation emitted by the emissive species; identifying information from a first image portion corresponding to emission of electromagnetic radiation by the emissive species at least at a first point in time; identifying information from a second image portion corresponding to emission of electromagnetic radiation by the emissive species at least at a second point in time; and determining, from at least the information from the first image portion and the information from the second image portion, the change in the emissive species.

In some embodiments, the method comprises identifying information from more than two image portions of the single image corresponding to emission of electromagnetic radiation by the emissive species at more than two points in time, and/or obtaining a plurality of images, each image being of at least a portion of the electromagnetic radiation emitted by the emissive species, and for each image identifying information from a first image portion corresponding to emission of electromagnetic radiation by the emissive species at least at a first point in time, and identifying information from a second image portion corresponding to emission of electromagnetic radiation by the emissive species at least at a second point in time; and from information identified from the more than two image portions, and/or from information from the plurality of images, determining a change in the emissive species.

In some embodiments, the emission time period is at least 10 nanoseconds. In some embodiments, exciting the species comprises exposing the species to electromagnetic radiation. In some embodiments, the exciting electromagnetic radiation is provided as a single pulse, a periodic pulse, a sequence of pulses, a pulse of continuously varying intensity, or any combination thereof. In some embodiments, the electromagnetic radiation is modulated by an electrical signal, shutter, refractory material, optical modulator, moving mirror, mechanical device, or light valve. In some embodiments, the electromagnetic radiation comprises visible light. In some embodiments, the electromagnetic radiation comprises substantially white light. In some embodiments, the electromagnetic radiation comprises discrete wavelength ranges. In some embodiments, exciting the species comprises exposing the species to pulsed and/or modulated light from an LED, an OLED, a fluorescent light, and/or an incandescent bulb. In some embodiments, exciting the species comprises exposing the species to a flash lamp. In some embodiments, exciting the species comprises applying a voltage, ionizing radiation, a physical force, or chemical reaction. In some embodiments, the species is associated with a packaging component.

In some embodiments, the species undergoes a chemical and/or biological reaction upon excitation. In some embodiments, exposure to an analyte causes a change in one or more of an intensity of the emitted light, a polarization of the emitted light, a spatial profile of the emitted light or a change in the emission lifetime of the emissive species.

In some embodiments, the method further comprises a second step of activating an article. In some embodiments, the second step of activating an article causes a change in emission lifetime, spatial profile, polarization, chemical sensitivity, intensity and/or blockage of the first step of exciting the species. In some embodiments, the second step of exciting the species produces generation of a color and/or change in absorption and/or emission. In some embodiments, combinations of different first, second and additional steps of exciting the species cause changes in the images that are acquired over the course of 100 nanoseconds to 100 milliseconds.

In an exemplary set of embodiments, a system comprises a radiation source configured to generate electromagnetic radiation for exciting an emissive species such that the emissive species produces a detectable non-steady-state emission during an emission time period, the emission time period being at least 10 nanoseconds; a sensor configured to: detect, during a first portion of the emission time period, a first emission from the emissive species, and detect, during a second portion of the emission time period, a second emission from the emissive species; and processing circuitry configured to identify a characteristic of the emissive species based on a difference between a property of the first emission detected during the first portion of the emission time period and a property of the second emission detected during the second portion of the emission time period.

In some embodiments, the radiation source is configured to generate electromagnetic radiation for exciting a second emissive species such that the second emissive species produces a second detectable non-steady-state emission during a second emission time period, the second emission time period being at least 10 nanoseconds. In some embodiments, the sensor is configured to detect, during a first portion of the second emission time period, a first emission from the second emissive species, and to detect, during a second portion of the second emission time period, a second emission from the second emissive species. In some embodiments, each emissive species comprises the same emitter. In some embodiments, each emissive species comprises a plurality of emitters. In some embodiments, the emission time period is less than 100 milliseconds, less than 50 milliseconds, less than 5 microseconds, less than 1 microsecond, or less than 0.1 microseconds.

In some embodiments, the system further comprises an article associated with the emissive species, wherein the characteristic of the emissive species corresponds to a characteristic of the article. In some embodiments, the characteristic of the emissive species corresponds to the presence or absence of an analyte. In some embodiments, the characteristic corresponds to exposure of the emissive species to temperature, thermal history, pH, UV radiation, humidity, a sterilization technique(s), a chemical(s), a pathogen(s), a biological species, and/or mechanical stress.

In an exemplary set of embodiments, a system comprises a radiation source configured to generate electromagnetic radiation for exciting an emissive species such that the emissive species produces a detectable non-steady-state emission during an emission time period; an electromagnetic radiation sensor configured to sense during a single exposure: first emission from the emissive species during a first portion of the emission time period, and second emission from the emissive species during a second portion of the emission time period, wherein the emission time period is at least 10 nanoseconds and is less than a duration of the single exposure; and processing circuitry configured to identify a characteristic of the emissive species based on a difference between a property of the first emissions detected during the first portion of the emission time period and a property of the second emissions detected during the second portion of the emission time period.

In an exemplary set of embodiments, a method for identifying a characteristic of an emissive species, comprises generating electromagnetic radiation; exciting, using the electromagnetic radiation, an emissive species such that the emissive species produces a detectable non-steady-state emission during an emission time period, the emission time period being at least 10 nanoseconds; detecting, during a first portion of the emission time period, a first emission from the emissive species, and detecting, during a second portion of the emission time period, a second emission from the emissive species; and identifying the characteristic of the emissive species based on a difference between a property of the first emission detected during the first portion of the emission time period and a property of the second emission detected during the second portion of the emission time period.

In some embodiments, detecting the first emission comprises exposing an electromagnetic radiation sensor to the detectable non-steady-state emission, the electromagnetic radiation sensor comprising a plurality of photodetectors arranged in an array of rows and columns. In some embodiments, the method comprises sequentially reading out rows or columns of the array to provide a plurality of time-encoded signals, wherein a first time-encoded signal corresponds to the first emission and to a second time-encoded signal corresponds to the second emission. In some embodiments, the step of identifying a characteristic of the emissive species comprises comparing the first and second time-encoded signals.

In an exemplary set of embodiments, a method for identifying a characteristic of an emissive species, comprises exciting the species such that the species produces a detectable emission during an emission time period, wherein the emission time period is at least 10 nanoseconds; obtaining, using an image sensor, a first image of the detectable emission, wherein a first portion of the first image corresponds to a first portion of the emission time period, and wherein a second portion of the first image corresponds to a second portion of the emission time period; and determining, based upon a difference between the first portion and the second portion of the first image, the characteristic of the species.

In some embodiments, exciting the species comprises exposing the species to electromagnetic radiation. In some embodiments, exciting electromagnetic radiation is provided as a single pulse, a periodic pulse, a sequence of pulses, a pulse of continuously varying intensity, or any combination thereof. In some embodiments, the electromagnetic radiation is modulated by an electrical signal, shutter, refractory material, optical modulator, moving mirror, mechanical device, or light valve. In some embodiments, the electromagnetic radiation comprises visible light. In some embodiments, the electromagnetic radiation comprises substantially white light. In some embodiments, the electromagnetic radiation comprises discrete wavelength ranges. In some embodiments, exciting the species comprises exposing the species to pulsed and/or modulated light from an LED, an OLED, a fluorescent light, and/or an incandescent bulb. In some embodiments, exciting the species comprises exposing the species to a flash lamp. In some embodiments, exciting the species comprises applying a voltage, ionizing radiation, a physical force, or chemical reaction.

In some embodiments, the species is associated with a packaging component. In some embodiments, the species undergoes a chemical and/or biological reaction upon excitation. In some embodiments, exposure to an analyte causes a change in the emitted light intensity, polarization, spatial profile, and/or a change in the emission lifetime of the emissive species. In some embodiments, the method further comprises a second step of activating an article. In some embodiments, the second step of activating an article causes a change in emission lifetime, spatial profile, polarization, chemical sensitivity, intensity and/or blockage of the first step of exciting the species. In some embodiments, the second step of exciting the species produces generation of a color and/or change in absorption and/or emission. In some embodiments, combinations of different first, second and additional steps of exciting the species cause changes in the images that are acquired over the course of 100 nanoseconds to 100 milliseconds.

In an exemplary set of embodiments, a method for identifying a characteristic of an article comprises: positioning an image sensor proximate an article suspected of containing an emissive tag; stimulating the article such that the emissive tag, if present, produces a detectable non-steady-state emission; obtaining, using the image sensor, a single image of the detectable non-steady-state emission, wherein a first portion of the single image corresponds to a first time period after stimulating the analyte, and wherein a second portion of the single image corresponds to a second time period after stimulating the analyte, different than the first time period; and determining, based upon a difference between the first portion and the second portion of the single image, the characteristic of the article.

In an exemplary set of embodiments, a system comprises a radiation source configured to generate electromagnetic radiation for exciting an emissive species such that the emissive species produces a detectable non-steady-state emission during an emission time period; an electromagnetic radiation sensor including a plurality of photodetectors configured to detect the non-steady state emission during the emission time period; a controller configured to control a timing of generation of the electromagnetic radiation by the radiation source such that pulsed or frequency modulated intensity electromagnetic radiation is generated during the capture of the one or more images; and processing circuitry configured to: generate, based on output of the plurality of photodetectors, one or more images, the emission time period being less than a time to capture a single image of the one or more images; and for each of the one or more images, determine a first property of a first portion of the image and a second property of a second portion of the image, and identify a characteristic of the emissive species based, at least in part, on the first property and the second property.

In some embodiments, the radiation source is configured to generate electromagnetic radiation for exciting a second emissive species such that the second emissive species produces a second detectable non-steady-state emission during a second emission time period, the second emission time period being at least 10 nanoseconds. In some embodiments, the sensor is configured to detect, during a first portion of the second emission time period, a first emission from the second emissive species, and to detect, during a second portion of the second emission time period, a second emission from the second emissive species. In some embodiments, each emissive species comprises the same emitter. In some embodiments, each emissive species comprises a plurality of emitters.

In some embodiments, the electromagnetic radiation sensor is configured to capture a plurality of images, and wherein the processing circuitry is further configured to: determine an average of the first property over the plurality of images; determine an average of the second property over the plurality of images; and identify a characteristic of the emissive species based, at least in part, on the average of the first property and the average of the second property. In some embodiments, a delayed emission can be detected in the same image with normal reflected light. In some embodiments, excitation is performed by pulsed light and/or frequency modulated light intensity. In some embodiments, the electromagnetic radiation sensor is configured to capture a plurality of images, and wherein the controller is further configured to control the radiation source to generate a pulse or intensity modulated at different frequencies of electromagnetic radiation prior to capture of each of the plurality of images.

In some embodiments, the plurality of photodetectors are arranged in an array of rows and columns, and wherein the processing circuitry is further configured to: sequentially read out rows or columns of the array to provide a plurality of time-encoded signals; and generate the one or more images based on the plurality of time-encoded signals. In some embodiments, the plurality of photodetectors are contained within a single integrated electronic chip. In some embodiments, the plurality of photodetectors are contained in multiple integrated electronic chips.

In an exemplary set of embodiments, a system comprises an excitation component configured to excite an emissive species such that the emissive species produces a detectable non-steady-state emission during an emission time period, wherein the emission time period is at least 10 nanoseconds; an image sensor configured to detect at least a portion of the detectable non-steady-state emission; and an electronic hardware component configured to produce a single image comprising a first portion corresponding to a first portion of the emission time period and a second portion corresponding to a second portion of the emission time period.

In some embodiments, the single image further comprises a third portion corresponding to a third portion of the emission time period. In some embodiments, the single image further comprises subsequent portions corresponding to multiple other portions of the emission time period. In some embodiments, the first portion of the emission time period is different from the second portion of the emission time period. In some embodiments, the first portion of the emission time period at least partially overlaps with the second portion of the emission time period.

In an exemplary set of embodiments, a system comprises an excitation component configured to expose an emissive species to non-steady-state electromagnetic radiation, an image sensor configured to detect at least a portion of electromagnetic radiation emitted by the emissive species, and an electronic hardware component configured to produce a single image comprising at least a first image portion corresponding to emission of electromagnetic radiation by the emissive species at least at a first point in time, and a second image portion corresponding to emission of electromagnetic radiation by the emissive species at least at a second point in time. In some embodiments, the electronic hardware component is configured to produce the single image comprising more than two image portions corresponding to emission of electromagnetic radiation by the emissive species at more than two respective points in time, and/or produce multiple images each comprising at least a first image portion corresponding to emission of electromagnetic radiation by the emissive species at least at a first point in time, and second image portion corresponding to emission of electromagnetic radiation by the emissive species at least at a second point in time.

In an exemplary set of embodiments, a system configured for identification of a characteristic of an article comprises a chemical tag associated with the article, wherein the chemical tag comprises an emissive species, wherein the emissive species produces a detectable non-steady-state emission during an emission time period under a set of conditions, and wherein the emission time period is at least 10 nanoseconds, an excitation component configured to excite the emissive species under the set of conditions such that the detectable non-steady-state emission, which varies over the image capture time period, is produced, an image sensor configured to detect the detectable non-steady-state emission, and an electronic hardware component configured to convert the detectable emission into a single image, wherein the single image comprises a first portion corresponding to a first portion of the emission time period and a second portion corresponding to a second portion of the emission time period, and wherein a difference between a property of the first portion and the second portion is associated with a characteristic of the article. In some embodiments, the single image further comprises subsequent portions corresponding to multiple other portions of the emission time period.

In an exemplary set of embodiments, a method for detecting the presence of a stimulus, comprises exposing an article comprising a chemical tag to a set of conditions comprising the stimulus, wherein the chemical tag undergoes a chemical and/or biological reaction in the presence of the stimulus that changes the lifetime, wavelength, and/or intensity of one or more emissive species in the tag, positioning an image sensor proximate the article, obtaining, using the image sensor, a single image of a portion of the article comprising the chemical tag, wherein a first portion of the single image corresponds to a first time period after exposing the article, and wherein a second portion of the single image corresponds to a second time period after exposing the article, different than the first time period, and determining, based upon a difference between the first portion and the second portion of the single image, the characteristic of the article.

In some embodiments, the method further comprises obtaining a second image of at least a portion of the detectable emission, wherein the second image is obtained at a different excitation method, position, angle, distance, and/or orientation than the first image. In some embodiments, the method further comprises determining, based upon a difference between the first image and the second image, the characteristic of the species.

In some embodiments, the chemical tag undergoes a chemical and/or biological reaction upon stimulating the article. In some embodiments, stimulating the article comprises producing a chemical and/or biological reaction in the chemical tag. In some embodiments, the chemical tag comprises at least one emissive dye having an excited state lifetime more than 10 nanoseconds. In some embodiments, the image sensor is associated with a rolling shutter mechanism. In some embodiments, the image sensor is associated with a global shutter. In some embodiments, the chemical tag produces a detectable emission having an excited state lifetime more than 10 nanoseconds in the presence of the stimulus. In some embodiments, a second stimulation of the article causes a process that changes the characteristics of the chemical tag by causing partial blockage of the excitation, quenching of one or more emissive species, changes in the physical properties of the matrix, activation of a new emissive species, and/or a change in the emissive characteristics of one of more emissive species. In some embodiments, the second stimulation is used to detect that an article has been previously subjected to an image sensor. In some embodiments, the second stimulation is used to produce a change in the tag that will change the optical image read in subsequent image sensors.

In an exemplary set of embodiments, a composition comprises an emissive species configured to be associated with an article, wherein excitation of the emissive species produces a detectable signal having one or more delayed emissions of greater than or equal to 10 nanoseconds, and wherein the detectable signal corresponds to a temporal thermal history of the article.

In an exemplary set of embodiments, a label, comprises a first emissive species optionally having one or more first detectable delayed emission(s) of greater than or equal to 10 nanoseconds corresponding to a first temporal thermal history of the first emissive species, and optionally a second emissive species having one or more second detectable delayed emission(s) of greater than or equal to 10 nanoseconds corresponding to a second temporal thermal history of the second emissive species, different than the first temporal thermal history, wherein the first detectable delayed emission, if present upon excitation of the first emissive species, corresponds to identification of the first emissive species being exposed to the first temporal thermal history and the second detectable delayed emission, if detectable, corresponds to identification of the second emissive species being exposed to the second temporal thermal history.

In some embodiments, the label is configured to be proactively added to an article, such that the label provides a temporal thermal profile of the article.

In an exemplary set of embodiments, a method comprises exciting one or more emissive species associated with an article, and detecting, using a detector, a detectable delayed emission of the emissive species, wherein the detectable delayed emission, if present, has a delayed emission of greater than or equal to 10 nanoseconds, and wherein the detectable delayed emission, if present, corresponds to an exposure of the article to a temporal thermal history.

In an exemplary set of embodiments, a method comprises exciting one or more first emissive species, optionally, exciting one or more second emissive species, detecting, using a detector, a first detectable delayed emission(s) produced by the first emissive species and/or a second detectable delayed emission(s) produced by the second emissive species, wherein, the first detectable delayed emission, if present, corresponds to exposure of the first emissive species to a first temperature, and wherein, the second detectable delayed emission, if present, corresponds to exposure of the second emissive species to a second temperature, different than the first temperature, wherein, at least one detectable delayed emission is present.

In an exemplary set of embodiments, a system comprises an excitation component configured to excite, using electromagnetic radiation, an emissive species such that, if single or multiple emissive species, or their precursors, were exposed to a temporal thermal history, produces a detectable delayed emission of greater than or equal to 10 nanoseconds, and a detector configured to detect at least a portion of the detectable delayed emission.

In some embodiments, detecting comprises a rolling shutter mechanism. In some embodiments, detecting comprises a global shutter. In some embodiments, the detectable delayed emission comprises a peak intensity, emission lifetime, absorption wavelength, and/or emission wavelength. In some embodiments, the response involves a change in the wavelength of the absorption or emission related to the delayed emission. In some embodiments, the response involves a change in intensity of a detectable signal. In some embodiments, the response involves a change in the delayed emission lifetime. In some embodiments, the response involves the creation of a new delayed emission. In some embodiments, the response involves the removal of a delayed emission. In some embodiments, the response involves two components combining to produce or remove a delayed emission.

In some embodiments, the label is produced by the deposition of second material onto a delayed emission material in order to produce a system capable of displaying a temporal thermal history. In some embodiments, the response involves a matrix that changes its physical properties to create changes in the delayed emission signal. In some embodiments, the response involves the diffusion of one or more materials to create changes in the delayed emission signal. In some embodiments, the response involves a matrix that undergoes a phase change that produces the delayed emission signal. In some embodiments, the response involves chemical reaction to produce the delayed emission signal. In some embodiments, the response involves changes in aggregation to produce the delayed emission signal. In some embodiments, the response is produced by an enhancement in energy transfer from an antenna molecule or polymer to a delayed emission component. In some embodiments, the response produces a pattern from the delayed emission signal. In some embodiments, the response is produced from materials that are safe for humans consume. In some embodiments, the response wherein the composition is produced with components proximate to each other. In some embodiments, one of the components is fused onto or into glass. In some embodiments, is produced with components separated physically from each other. In some embodiments, is produced by spray deposition, ink jet printing, printing, or lamination.

In some embodiments, the delayed emission has a lifetime greater than 10 nanoseconds, greater than 100 nanoseconds, greater than 1 microsecond, greater than 100 microseconds, or greater than 1 millisecond.

In some embodiments, the delayed emission species contains a metal ion, is an organic molecule, is a nanoparticle, or is an organic molecule containing heavy atoms.

In some embodiments, the detector is a smartphone component.

In some embodiments, excitation of the emissive species is accomplished by a light source with modulated intensity at different frequencies. In some embodiments, excitation of the emissive species is accomplished by a light flash or a laser pulse. In some embodiments, the reader is a streak camera. In some embodiments, the reader is a device capable of selectively detecting a delayed emission. In some embodiments, the reader is a device capable of selectively detecting a delayed emission in a complex environment with non-delayed emission, ambient, and reflected light present. In some embodiments, the reader is a device capable of selectively detecting a delayed emission and is also capable of detecting fluorescence, ambient, and reflected light. In some embodiments, the reader is capable of detecting patterns of delayed emission to produce information about a thermal or cold exposure. In some embodiments, the reader is capable of detecting patterns of delayed emission as well as patterns from reflected, ambient, or non-delayed emission to produce information about a thermal or cold exposure. In some embodiments, the reader is capable of integrating information of a thermal or cold exposure with other information optically encoded on the product. In some embodiments, the reader contains a CMOS imaging chip. In some embodiments, the reader uses the rolling shutter effect to collect the delayed emission data.

In an exemplary set of embodiments, a method comprises determining an identity or characteristic of a chemical/biological species by combining: a first electromagnetic radiation signal comprising at least a steady-state photon emission event, and a second electromagnetic radiation signal comprising at least a non-steady-state photon emission event.

In an exemplary set of embodiments, a method comprises determining an identity or characteristic of a chemical/biological species by combining: a first electromagnetic radiation signal and a second electromagnetic radiation signal, wherein the first electromagnetic signal comprises at least a first photon emission event occurring within 10 nanoseconds of an excitation event that caused the first photon emission event, and a second electromagnetic signal comprising at least a second photon emission event occurring after 10 nanoseconds of the excitation event that caused the second photon emission event.

In some embodiments, the first photon emission event comprises an emission produced by an emissive species having an excited state lifetime of less than or equal to 10 nanoseconds. In some embodiments, the second photon emission event comprises an emission produced by an emissive species having an excited state lifetime of at least 10 nanoseconds.

In an exemplary set of embodiments, a method of reading a biological diagnostic assay wherein an imaging device provides a readout from the assay comprises detecting two or more signals emanating from the assay, wherein each of the two or more signals are selected from a subtractive color, reflected color, chemiluminescence, prompt-fluorescence, delayed-fluorescence, prompt-phosphorescence, and delayed-phosphorescence emission.

In some embodiments, each signal is read using a smartphone or digital camera.

In an exemplary set of embodiments, a system comprises an excitation component configured to excite a first emissive species such that the first emissive species produces a detectable steady-state photon emission signal, the excitation component is configured to excite a second emissive species such that the second emissive species produces a detectable non-steady-state photon emission signal, and a sensor configured to detect at least a portion of the detectable steady-state photon emission signal and at least a portion of the detectable non-steady-state emission signal.

In some embodiments, the system further comprises an electronic hardware component configured to combine the detectable steady-state emission and the detectable non-steady-state emission into a determinable signal. In some embodiments, the detectable steady-state emission and/or the detectable non-steady-state emission correspond to a characteristic of the first emissive species and/or the second emissive species.

In some embodiments, the signal corresponds to a quantity of a target biological species. In some embodiments, at least one emission is selected from the group consisting of subtractive color, reflected color, chemiluminescence, prompt-fluorescence, delayed-fluorescence, prompt-phosphorescence, or delayed-phosphorescence. In some embodiments, the first electromagnetic radiation signal is a colorimetric signal and the second electromagnetic radiation signal is a prompt-fluorescence signal. In some embodiments, the first electromagnetic radiation signal is a colorimetric signal and the second electromagnetic radiation signal is a delayed-fluorescence signal. In some embodiments, the first electromagnetic radiation signal is a colorimetric signal and the second electromagnetic radiation signal is a prompt-phosphorescence signal. In some embodiments, the first electromagnetic radiation signal is a colorimetric signal and the second electromagnetic radiation signal is a delayed-phosphorescence signal. In some embodiments, the first electromagnetic radiation signal is a colorimetric signal and the second electromagnetic radiation signal is a chemiluminescence signal. In some embodiments, the first electromagnetic radiation signal is a prompt-fluorescence signal and the second electromagnetic radiation signal is a delayed-phosphorescence signal. In some embodiments, at least one signal is collected in a steady-state mode and at least one other signal is collected using a time synchronized light source. In some embodiments, at least one signal is collected when a time synchronized electromagnetic radiation source is off and at least another signal is collected when a time synchronized electromagnetic radiation source is on. In some embodiments, at least one signal is collected while the assay is illuminated by one or more LED light sources. In some embodiments, the excitation event is a source of electromagnetic radiation. In some embodiments, the source of electromagnetic radiation comprises a flash from a smartphone or digital camera.

In some embodiments, the system or method further comprises a biological diagnostic assay associated with the first electromagnetic radiation signal and/or second electromagnetic radiation signal. In some embodiments, the biological diagnostic assay is a lateral flow assay. In some embodiments, the biological diagnostic assay is a loop-mediated isothermal amplification (LAMP) for nucleic acid detection. In some embodiments, the delayed-phosphorescence is associated with a europium or terbium complex. In some embodiments, nanoparticles are used to provide a colorimetric signal. In some embodiments, nanoparticles are used to provide an emissive signal. In some embodiments, changes in local environment and/or a biomolecular recognition event changes at least one signal.

In some embodiments, a rolling shutter mechanism is associated with the method or system.

In an exemplary set of embodiments, a system comprises a radiation source configured to emit radiation having one or more wavelengths within an electromagnetic radiation spectrum, and an emissive species, wherein a first portion of the electromagnetic radiation spectrum comprises radiation having a wavelength between 425 nm and 475 nm, wherein a second portion of the electromagnetic radiation spectrum comprises radiation having a wavelength between 525 nm and 725 nm, and wherein the radiation source is configured to produce a wavelength of electromagnetic radiation that interacts with the emissive species such that the emissive species produces a detectable signal having one or more delayed emissions of greater than or equal to 10 nanoseconds.

In an exemplary set of embodiments, a system comprises a source of electromagnetic radiation having a plurality of wavelengths, and an emissive species, wherein the emissive species is configured to produce a detectable signal having one or more delayed emissions of greater than or equal to 10 nanoseconds, and wherein the plurality of wavelengths spans a wavelength range greater than or equal to 50 nm.

In some embodiments, the electromagnetic radiation produced by the source is unadulterated prior to exposure to the emissive species. In some embodiments, the system does not comprise a light filter positioned between the source and the emissive species. In some embodiments, the source is a component of a consumer electronic device. In some embodiments, the consumer electronic device is a smartphone, tablet, computer, digital camera, or the like.

In an exemplary set of embodiments, a system comprises an excitation component configured to produce a plurality of wavelengths of electromagnetic radiation, wherein: the excitation component is configured to excite a first emissive species such that the first emissive species produces a detectable stead-state photon emission signal, the excitation component is configured to excite a second emissive species such that the second emissive species produces a detectable non-steady-state photon emission signal, and a sensor configured to detect at least a portion of the detectable steady-state photon emission signal and at least a portion of the detectable non-steady-state emission signal.

In an exemplary set of embodiments, a system comprises a radiation source configured to generate a plurality of wavelengths of electromagnetic radiation for exciting an emissive species such that the emissive species produces a detectable non-steady-state emission during an emission time period, the emission time period being at least 10 nanoseconds, a sensor configured to: detect, during a first portion of the emission time period, a first emission from the emissive species, and detect, during a second portion of the emission time period, a second emission from the emissive species, and processing circuitry capable of identifying a characteristic of the emissive species based on a difference between a property of the first emission detected during the first portion of the emission time period and a property of the second emission detected during the second portion of the emission time period.

In an exemplary set of embodiments, a method comprises determining an identity or characteristic of a chemical/biological species by: exposing an emissive species to an electromagnetic radiation spectrum generated by a source of electromagnetic radiation and having a range that spans greater than or equal to 50 nm, the emissive species associated with the chemical/biological species, and detecting a detectable emission produced by the emissive species, wherein the detectable emission, if present, corresponds to the identity or characteristic of the chemical/biological species.

In an exemplary set of embodiments, a method comprises determining an identity or characteristic of a chemical/biological species by combining: a first electromagnetic radiation signal and a second electromagnetic radiation signal, wherein the first electromagnetic signal comprises at least a first photon emission event occurring within 10 nanoseconds of an excitation event that caused the first photon emission event, and a second electromagnetic signal comprising at least a second photon emission event occurring after 10 nanoseconds of the excitation event that caused the second photon emission event, wherein the excitation event comprises an electromagnetic radiation spectrum, wherein a first portion of the electromagnetic radiation spectrum comprises a wavelength of between 425 nm and 475 nm, and wherein a second portion of the electromagnetic radiation spectrum comprises a wavelength of between 525 nm and 725 nm.

In some embodiments, at least one emission is selected from the group consisting of subtractive color, reflected color, chemiluminescence, prompt-fluorescence, delayed-fluorescence, prompt-phosphorescence, or delayed-phosphorescence. In some embodiments, the source of electromagnetic radiation comprises an LED component.

In some embodiments, luminescent materials are excited and a smartphone detects a steady-state photon emission event and a non-steady-state emission event or optionally a non-steady-state photon emission event. In some embodiments, the emissive material absorbs light emitted from a smartphone. In some embodiments, the emissive material absorbs light at a wavelength of 440 nm or higher. In some embodiments, the detectable signal comprises subtractive color, reflected color, chemiluminescence, prompt-fluorescence, delayed-fluorescence, prompt-phosphorescence, or delayed-phosphorescence emission. In some embodiments, the emissive material comprises a TADF emission, an organometallic compound, a metalorganic material, a Europium complex, and/or an organic molecule containing iodine or bromine atoms.

In some embodiments, the emissive material is electronically coupled to or connected to a heavy atom. In some embodiments, the emissive material comprises metalloporphyrin. In some embodiments, the emissive material is excited by a white light source. In some embodiments, the emissive material is excited by an LED emitting between 440 and 700 nm. In some embodiments, the emissive material is used in a lateral flow assay or vertical flow assay. In some embodiments, the emissive material is used in product authentication.

In some embodiments, the emissive material is used to detect a gas, a chemical, an antibody, an antigen, a virus, a bacteria, an allergen, mold, spore, and/or a pathogen. In some embodiments, the emissive material is used to detect ionizing radiation. In some embodiments, the emissive material is used to detect a thermal exposure. In some embodiments, the emissive material is used to detect an ultraviolet light exposure. In some embodiments, the emissive material is used to detect moisture and/or oxygen exposure.

In an exemplary set of embodiments, a system comprises a source of electromagnetic radiation associated with a consumer electronic device, a sensor associated with the consumer electronic device, and an emissive species capable of producing a detectable signal by the sensor, the detectable signal having one or more delayed emissions of greater than or equal to 10 nanoseconds.

In an exemplary set of embodiments, a method comprises using a consumer electronic device to determine an identity or characteristic of a chemical/biological species, wherein the consumer electronic device comprises a source of a spectrum of electromagnetic radiation, and exposing an emissive species to the spectrum of electromagnetic radiation such that the emissive species produces a detectable emission which corresponds to the identity or characteristic of the chemical/biological species and which is detectable by the consumer electronic device.

In some embodiments, a first portion of the electromagnetic radiation spectrum comprises a wavelength of between 425 nm and 475 nm and wherein a second portion of the electromagnetic radiation spectrum comprises a wavelength of between 525 nm and 725 nm. In some embodiments, the detectable signal comprises one or more delayed emissions of greater than or equal to 10 nanoseconds. In some embodiments, at least one emission is selected from the group consisting of subtractive color, reflected color, chemiluminescence, prompt-fluorescence, delayed-fluorescence, prompt-phosphorescence, or delayed-phosphorescence. In some embodiments, the source of electromagnetic radiation comprises an LED component. In some embodiments, a rolling shutter mechanism associated with the system or method.

In some embodiments, luminescent materials are excited and a smartphone detects a steady-state photon emission event and a non-steady-state emission event or optionally a non-steady-state photon emission event. In some embodiments, the emissive material absorbs light emitted from a smartphone. In some embodiments, the emissive material absorbs light at a wavelength of 440 nm or higher. In some embodiments, the detectable signal comprises subtractive color, reflected color, chemiluminescence, prompt-fluorescence, delayed-fluorescence, prompt-phosphorescence, or delayed-phosphorescence emission. In some embodiments, the emissive material comprises a TADF emission. In some embodiments, the emissive material comprises an organometallic compound. In some embodiments, the emissive material comprises a metalorganic material. In some embodiments, the emissive material comprises Europium complex. In some embodiments, the emissive material comprises an organic molecule containing iodine or bromine atoms. In some embodiments, the emissive material is electronically coupled to or connected to a heavy atom. In some embodiments, the emissive material comprises metalloporphyrin. In some embodiments, the emissive material is excited by a white light source. In some embodiments, the emissive material is excited by an LED emitting between 440 and 700 nm. In some embodiments, the emissive material is used in a lateral flow assay. In some embodiments, the emissive material is used in product authentication. In some embodiments, the emissive material is used to detect a gas, a chemical, an antibody, an antigen, a virus, a bacteria, an allergen, mold, spore, and/or a pathogen. In some embodiments, the emissive material is used to detect ionizing radiation. In some embodiments, the emissive material is used to detect a thermal exposure.

In some embodiments, a global shutter associated with the method or system.

In some embodiments, an enclosure is provided and configured to receive the consumer electronic device. In some embodiments, the enclosure is configured to position the consumer electronic device relative to an emissive species. In some embodiments, the enclosure is configured to prevent external light from interacting with the sensor. In some embodiments, the enclosure contains a source of electromagnetic radiation capable of exciting the emissive species.

In an exemplary set of embodiments, a kit comprises an enclosure configured to receive a consumer electronic device, the consumer electronic device comprising a sensor and a source of electromagnetic radiation associated with the enclosure and/or consumer electronic device, wherein: the enclosure is configured to position the consumer electronic device relative to an emissive species, if present, such that the sensor can detect a detectable emission from the emissive species, and the enclosure is configured to prevent external light from interacting with the sensor.

Additional Exemplary Embodiments

The following embodiments are provided for exemplary purposes and are not intended to be limiting. Other embodiments as described herein are also possible.

1. A device capable of exciting an object and reading a pattern generated by luminescence and/or reflected/scattered electromagnetic radiation wherein at least one emissive species generates a signal that changes over the course of the reading of the pattern.

a. A device as in embodiment 1 wherein the excitation is produced by one of more bursts of electromagnetic radiation that excite all of the emissive species.

b. A device as in embodiment 1, wherein the reading of the pattern is accomplished by acquiring a single image.

c. A device as in embodiment 1, wherein the reading of the pattern is accomplished by acquiring multiple images.

d. A device as in embodiment 1 wherein the excitation is accomplished by pulsed and/or modulated electromagnetic radiation.
e. A device as in embodiment 1 wherein the excitation is accomplished by a flash lamp, LED, laser, and/or a fluorescent light.
f. A device as in embodiment 1 wherein the excitation method is controlled by an optical shutter, light valve, optical modulator, refractory material, or mirror.
g. A device as in embodiment 1 wherein excitation is performed at different wavelengths capable of independently exciting different emissive species.
h. A device as in embodiment 1 wherein one of more images are collected with different delays from a burst of electromagnetic radiation or modulated electromagnetic radiation at one or more wavelengths.
i. A device as in embodiment 1 wherein the excitation varies throughout the reading of the pattern,
j. A device as in embodiment 1 having an integrated excitation and image capture component
k. A device as in embodiment 1 wherein the excitation and image capture components are separate.
l. A device as in embodiment 1 wherein the device incorporates a CMOS imaging unit.
m. A device as in embodiment 1 wherein the device is a smartphone.
n. A device as in embodiment 1 wherein the device can dynamically change the method of excitation and reading of an object during the course of taking measurements.
o. A device as in embodiment 1 wherein the instructions for excitation and reading of an image are provided from another optical image, software, form an external source via wireless communication.
p. A device as in embodiment 1 wherein the device is capable of triggering a non-optical excitation of at least one emissive component by electrical, mechanical, particle, or chemical stimulation.
2. An article comprising one or more emissive species (e.g., dyes, materials) that have excited state lifetimes more than 10 nanoseconds.
a. An article as in embodiment 2 wherein a coating of the article has information that reveals the identity and/or status of a product that is associated with the article.
b. An article as in embodiment 2 that is a coating on a pill, a capsule, or the physical packaging of a product.
c. An article as in embodiment 2 wherein part of the article comprises a bar code or matrix code.
d. An article as in embodiment 2 wherein information on how the article is to be read is encoded.
e. An article as in embodiment 2 wherein the emissive dyes with lifetimes more than 10 nanoseconds respond to their environment to reveal information about the status of the product.
f. An article as in embodiment 2 wherein the emissive signal is created, changed, or enhanced with a lifetime greater than 10 nanoseconds in response to its environment or exposure history.
g. An article as in embodiment 2 wherein the emissive signal is created by an inorganic phosphor.
h. An article as in embodiment 2 wherein the emissive signal is created by an inorganic/organic composition.
i. An article as in embodiment 2 with an emissive material that contains bismuth.
j. An article as in embodiment 2 with an emissive material that contains iridium, platinum, rhenium, gold, or copper.
k. An article as in embodiment 2 with an emissive material that contains a lanthanide or actinide metal.
m. An article as in embodiment 2 with an emissive material contains bromide, iodide, sulfur, selenium, telluride, phosphorous, antimony, tin, lead, mercury, or cadmium.
n. An article as in embodiment 2 with an emissive material that displays a thermally activated delayed emission.
o. An article as in embodiment 2 with an emissive material that can diffuse to change its location in the article.
p. An article as in embodiment 2 which is a liquid.
q. An article as in embodiment 2 which is a gel.
r. An article as in embodiment 2 which is composite of solids, liquids, and/or gels.
s. An article as in embodiment 2 which has optical structures that focus or waveguide light.
u. An article as in embodiment 2 which contains a hologram
v. An article as in embodiment 2 which contains a bar or matrix code
w. An article as in embodiment 2 that is produced by the combination of an initial test strip that gives an emissive response after application of a material of interest to it.
x. An article as in embodiment 2 which has optical structures that result in directional emission or polarization of emitted light.
3. A method of reading a biological diagnostic assay wherein an imaging device provides a readout from the assay by detecting two or more signals emanating optionally from subtractive color, reflected color, scattering, chemiluminescence, prompt-fluorescence, delayed-fluorescence, prompt-phosphorescence, or delayed-phosphorescence.
4. A method as in embodiment 3, wherein the signal is an image captured by a smartphone, digital camera or equivalent.
5. A method as in embodiment 3, wherein the signal is used to create a digital intensity profile.
6. A method as in embodiment 3, wherein the signal can be used to give information about the quantity and/or presence of a biological species.
7. A method as in embodiment 3, wherein the two or more signals come from more than one of the following processes: subtractive color, reflected color, scattering, chemiluminescence, prompt-fluorescence, delayed-fluorescence, prompt-phosphorescence, or delayed-phosphorescence.
8. A method as in embodiment 3, wherein a colorimetric signal is used with a prompt-fluorescence signal.
9. A method as in embodiment 3, wherein a colorimetric signal is used with a delayed-fluorescence signal.
10. A method as in embodiment 3, wherein a colorimetric signal is used with a prompt-phosphorescence signal.
11. A method as in embodiment 3, wherein a colorimetric signal is used with a delayed-phosphorescence signal.
12. A method as in embodiment 3, wherein a colorimetric signal is used with a chemiluminescence signal.
13. A method as in embodiment 3, wherein a prompt-fluorescence signal is used with a delayed-phosphorescence signal.
14. A method as in embodiment 3, wherein at least one signal is collected in a steady-state mode and at least one other signal is collected using a time synchronized light source.
15. A method as in embodiment 3, wherein at least one signal is collected when the time synchronized light source is off and at least another signal is collected when the time synchronized light source is on.
16. A method as in any previous embodiment, wherein at least one signal is collected while the assay is illuminated by one or more LED light sources.

17. A method as in any previous embodiment, wherein at least one signal is characteristic of the cycle time of a modulated light excitation.

18. A method as in any previous embodiment, wherein at least one of the light sources is the flash from a smartphone or digital camera.

19. A method as in any previous embodiment, wherein the biological diagnostic is a lateral flow or vertical flow assay.

20. A method as in any previous embodiment, wherein the biological diagnostic is a loop-mediated isothermal amplification (LAMP) for nucleic acid detection 21. A method as in any previous embodiment, wherein the delayed-phosphorescence is associated with a europium or terbium complex.

22. A method as in any previous embodiment, wherein nanoparticles are used to provide a colorimetric signal.

23. A method as in any previous embodiment, wherein nanoparticles are used to provide an emissive signal.

24. A method as in any previous embodiment, wherein excited state lifetime information is part of the signal.

25. A method as in any previous embodiment, wherein polarized light is used.

26. A method as in any previous embodiment, wherein changes in the local environment affect the signal.

27. A method as in any previous embodiment, wherein a biomolecular recognition event affects the signal.

28. A method as in any previous embodiment, wherein more than one biological diagnostic assay can be simultaneously analyzed.

29. A method as in any previous embodiment, wherein the hardware can be used for both steady-state and time-gated measurements by changing the firmware or software.

30. A method of reading a biological diagnostic assay using non-steady state illumination and a smartphone or digital camera.

31. A method as in any previous embodiment, wherein a rolling shutter mechanism is used for the detection of signals.

32. A method as in any previous embodiment, wherein the non-steady state illumination is used to read a prompt-fluorescence, delayed-fluorescence, prompt-phosphorescence, or delayed-phosphorescence signal.

33. A method as in any previous embodiment, wherein the biological diagnostic assay is a lateral flow assay.

34. A method as in any previous embodiment, wherein changes in the lifetime, wavelength, intensity or polarization of emissive signals detected as a result of a binding event allows for discrimination between specific and non-specific binding events.

35. A method as in any previous embodiment, wherein image or images are optionally collected, one or more times, in different sequences to provide image orientation, ambient light correction, the signal or signals associated with the biological event of interest, a signal for calibration or quantification of the biological event, the temperature under which the assay is performed, authentication or tracking of the assay, the thermal history of the assay, and fiducial signals for image alignment.

36. A method as in any previous embodiment, wherein the signals collected can be performed a part of a personal health monitoring system, wherein an individual can perform tests that are transmitted to medical experts.

EXAMPLES

Example 1—Direct Capture System

Figure 8:
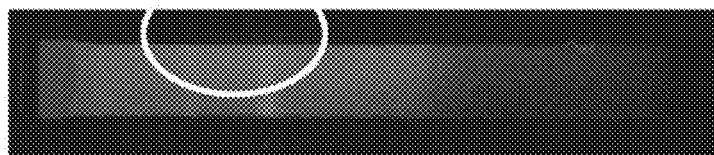
FIG. 8 shows chromatographic images of an exemplary system, according to one set of embodiments.
Figure 8:
Figure 8:
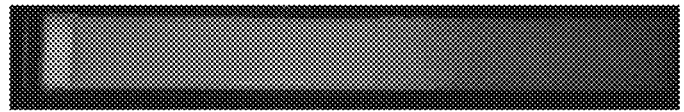
Figure 8:
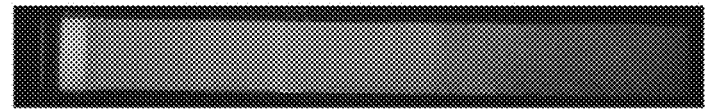
Figure 8:
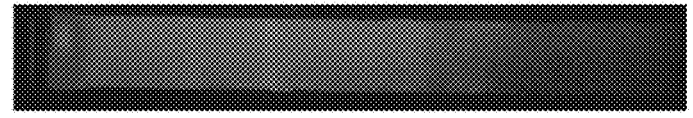
Figure 8:
Figure 8:

Human IgG was conjugated to 200 nm Europium (Eu) beads and Goat anti-human IgG/IgM was immobilized onto nitrocellulose. Lateral flow devices containing pre-treated glass fiber sample pads and cover tape were then assembled. Dilutions of the Eu-labeled Human IgG in buffer were deposited onto the sample/conjugate pad of the lateral flow device and the resultant developed by dipping into buffer. After a set time had elapsed, the chromatographic result was imaged/analyzed using a customized smartphone device, holder, and algorithm/app (FIG. 8).

Example 2—Serological Assay System—Antibody Detection

Figure 9:
FIG. 9 shows an exemplary negative assay result with a control line detected in accordance with one or more inventions described herein, according to one set of embodiments.
Figure 10:
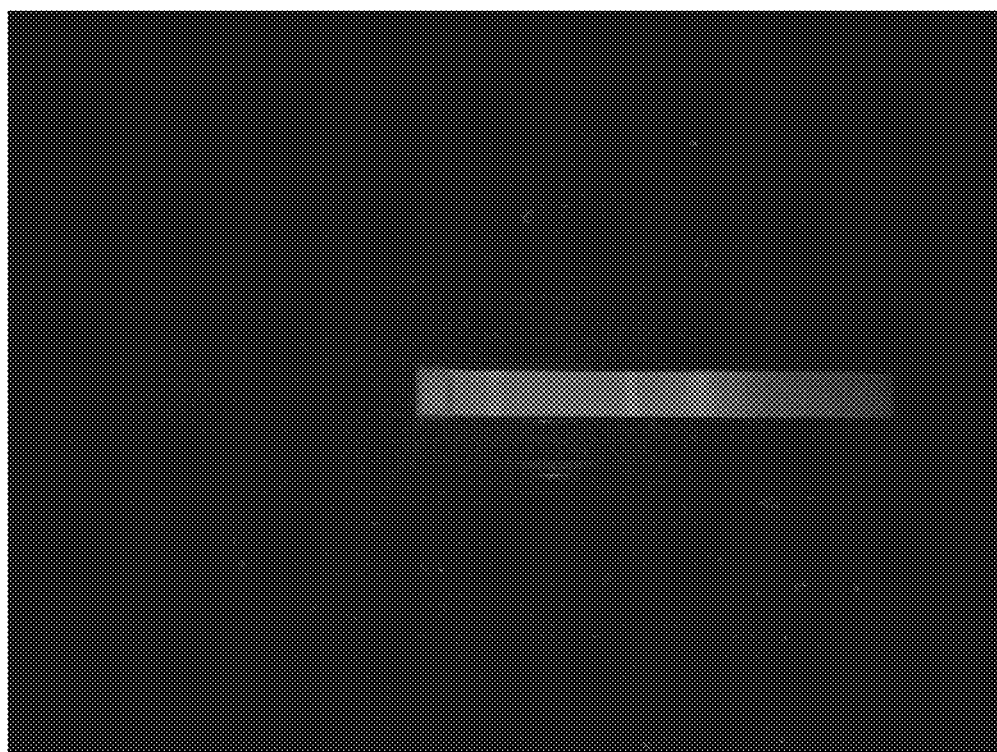
FIG. 10 shown an exemplary positive assay result with an IgG line detected in addition to a control line in accordance with one or more inventions described herein, according to one set of embodiments.

Chicken IgY (control line), Goat anti-Human IgA (test line 1), Donkey anti-Human IgM (test line 2), and Donkey anti-Human IgG (test line 3) were immobilized onto nitrocellulose and lateral flow devices assembled. Eu-labeled Donkey anti-Chicken and Eu-labeled Mouse anti-HIS were then deposited onto the sample/conjugate pad followed by specific COVID-19 antigen(s) such as HIS-tagged Nucleoprotein (NP) antigen. The resultant devices were then tested using clinical-derived Human COVID-19 antibody positive and negative saliva or blood/serum samples, imaged/analyzed using a customized smartphone device, holder, and algorithm/app. FIG. 9 shows an example of a negative assay with only the control line detected. FIG. 10 shows an example of a positive assay with the IgG line detected in addition to the control line.

Example 3—Sandwich Assay System—Antigen Detection

Figure 11:
FIG. 11 shows an exemplary negative assay result detected in accordance with one or more inventions described herein, according to one set of embodiments.
Figure 12:
FIG. 12 shows an exemplary positive assay result detected in accordance with one or more inventions described herein, according to one set of embodiments.

Coronavirus NP capture antibodies were immobilized onto nitrocellulose and lateral flow devices assembled. Coronavirus COVID-19 SARS NP detection antibodies, conjugated to 200 nm Eu beads were mixed with Coronavirus COVID-19 NP antigen in buffer or Human saliva, and the assay developed. The results were then imaged/analyzed using a customized smartphone device, holder, and algorithm/app. FIG. 11 shows an example of a negative assay with no line detected. FIG. 12 shows an example of a positive assay with a line detected.

Example 4—Europium Based Lateral Flow Assay

Figure 13:
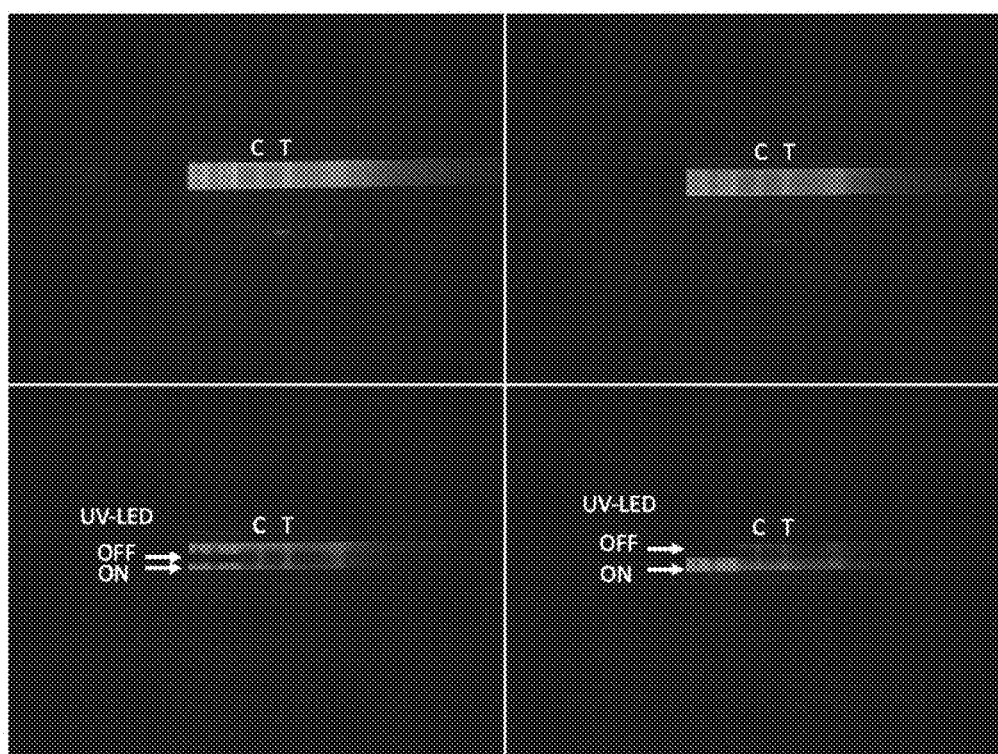
FIG. 13 shows representative photographs of a Europium-based lateral flow assay imaged using a customized system in accordance with one or more inventions described herein, according to one set of embodiments.

FIG. 13 shows representative photographs of a Europium-based lateral flow assay imaged using a customized smartphone device, holder, and algorithm/app under different camera settings. At faster shutter speeds (shorter exposures) the rolling shutter effect may be clearly observed eliminating background signals (prompt fluorescence) originating from the nitrocellulose, cover tape, etc. In this case the UV-LED off signal (image portion) represents a steady-state signal and the light off represents a time synchronized signal (image portion).

Example 5—Exemplary System

Figure 14A:
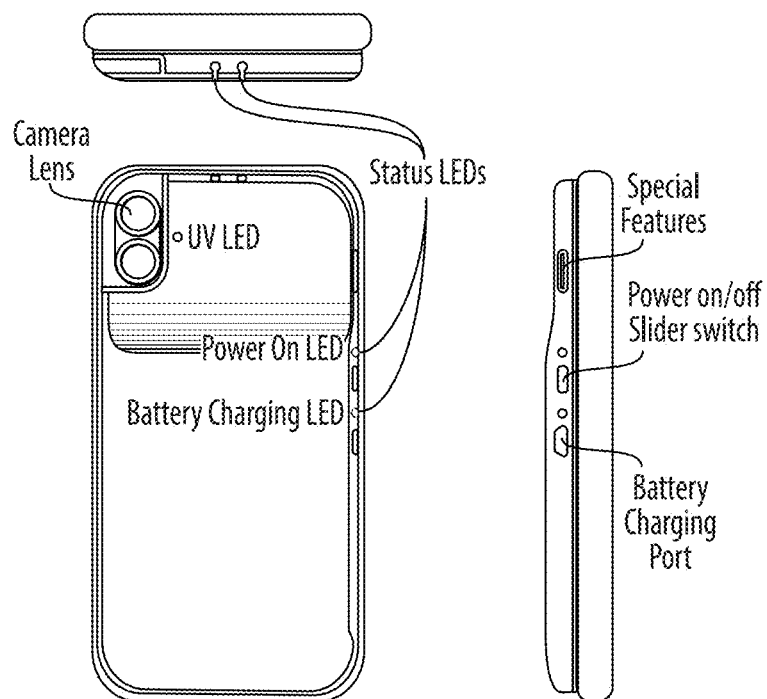
FIG. 14A shows a case configured to integrate with a smartphone, comprising a UV LED source and permits the camera of the smartphone to be exposed, according to one set of embodiments.
Figure 14B:
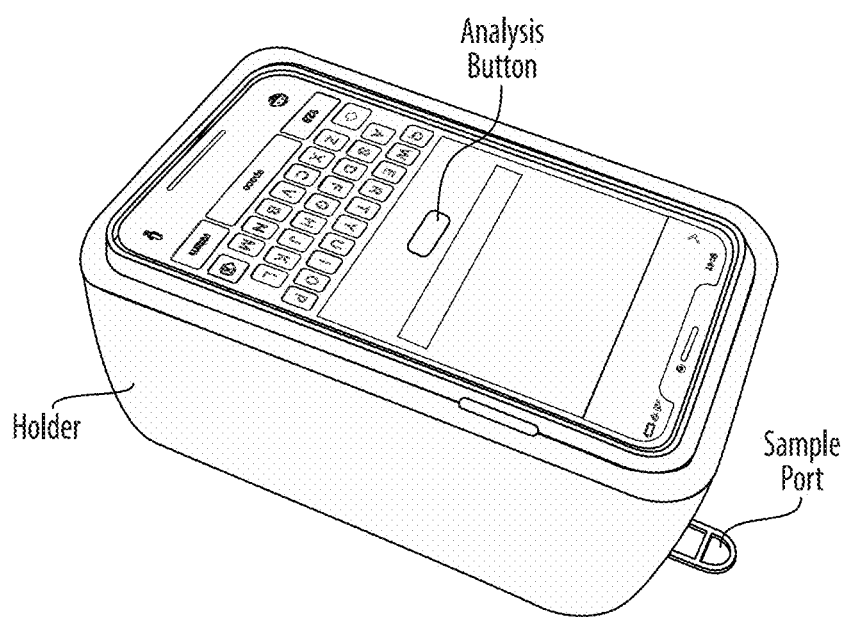
FIG. 14B shows an exemplary holder comprising a portion configured to receive the smartphone, and a sample port configure to receive a sample (e.g., an immunoassay cassette), according to one set of embodiments.
Figure 14C:
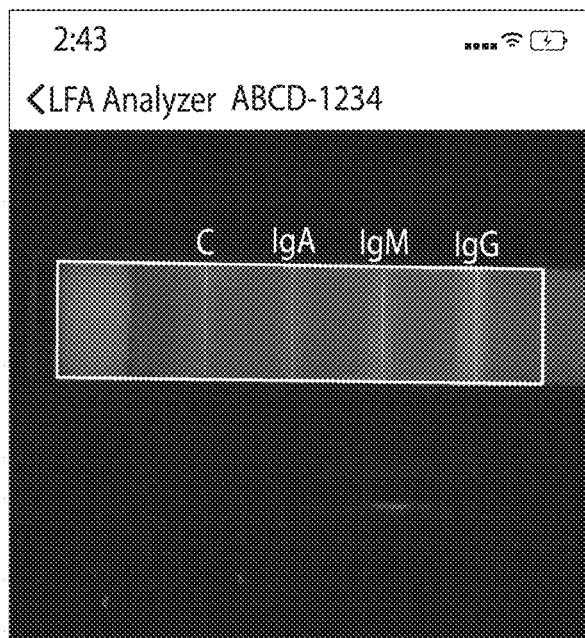
FIG. 14C shows an exemplary output from a custom smartphone software that provides, for example, an image of the sample and a corresponding plot of intensity, according to one set of embodiments.
Figure 14C:
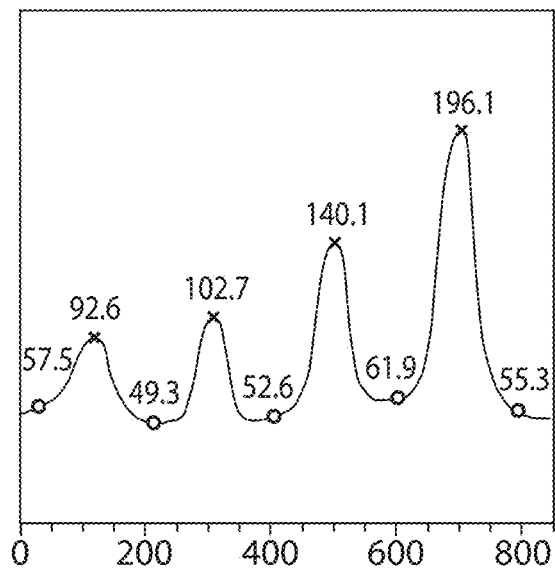
Figure 14D:
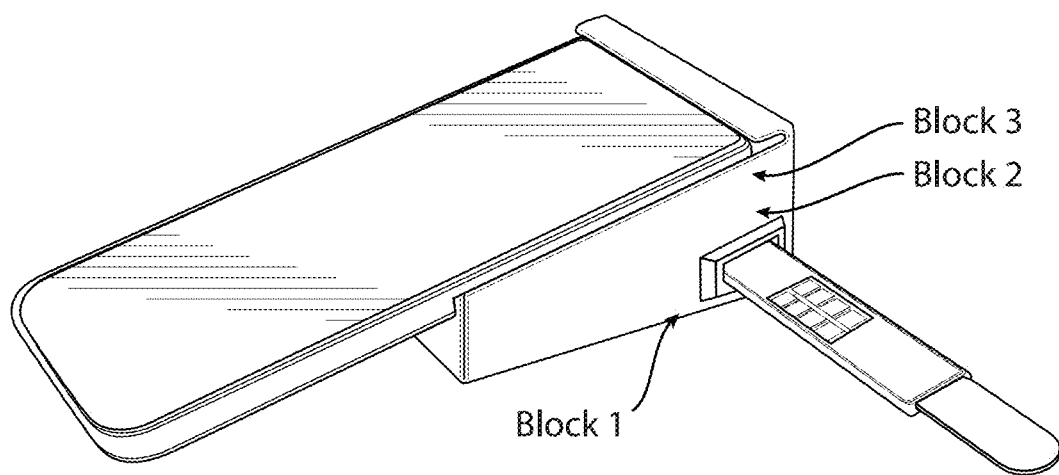
FIG. 14D shows an illustrative kit in accordance with one or more inventions described herein, according to one set of embodiments.
Figure 14E:
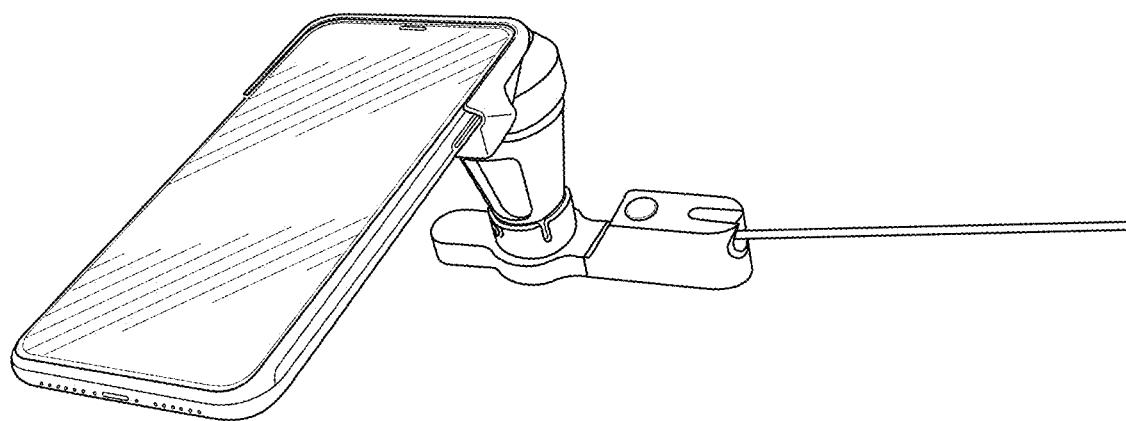
FIG. 14E shows schematics of a design rendering of the rapid, point of need diagnostic, according to some embodiments.
Figure 14F:
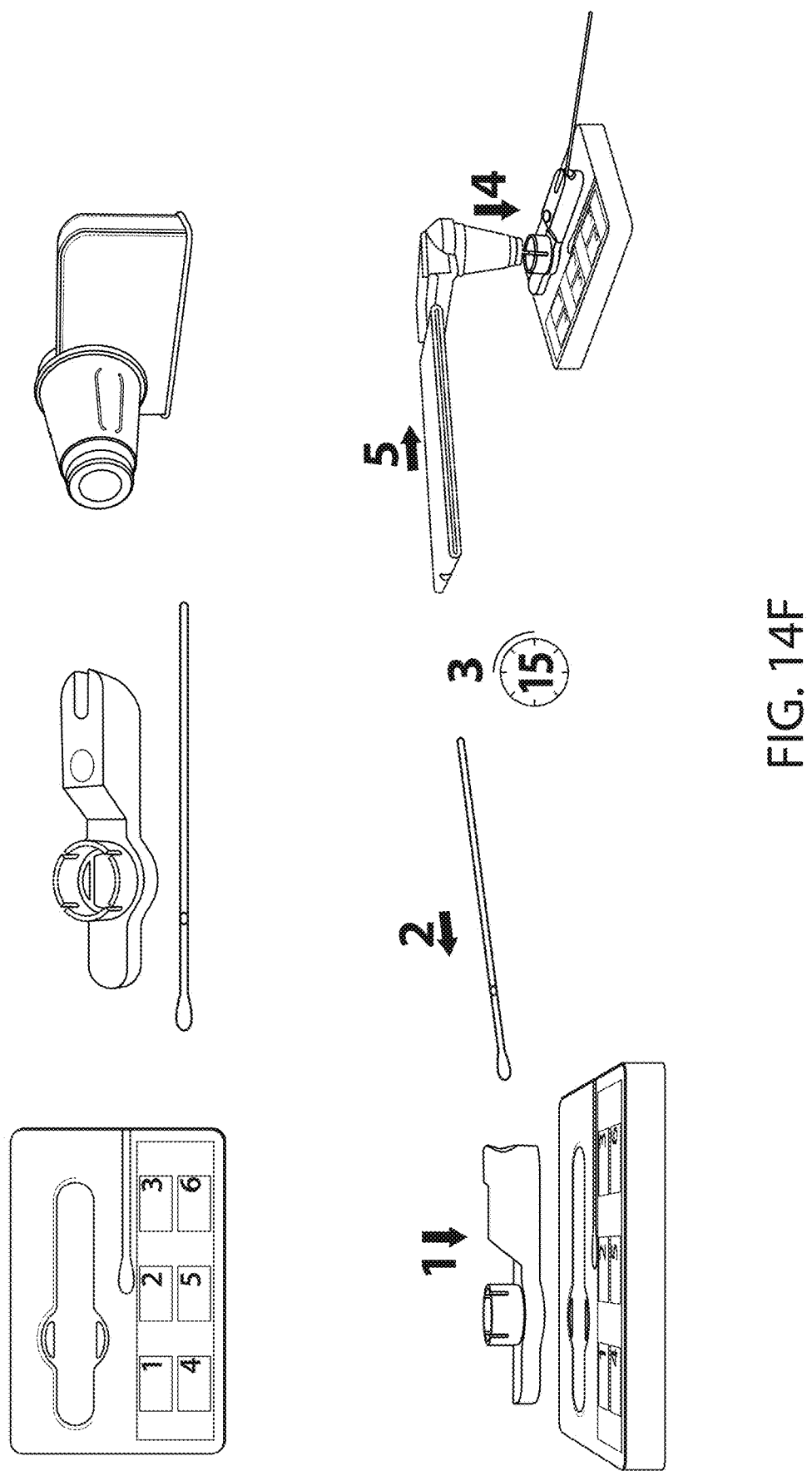
FIG. 14F shows a schematics of a design rendering of the components of the diagnostic: set up tray with instructions for use (top left), integrated cassette and sample collection swab (top middle), smartphone adapter (top right), and overall workflow (bottom), according to some embodiments.

FIGS. 14A-14C show an exemplary system for capturing data from an assay, according to some embodiments described herein. For example, FIG. 14A shows a case configured to integrate with a smartphone, comprising a UV LED source and permits the camera of the smartphone to be exposed. FIG. 14B shows an exemplary holder comprising a portion configured to receive the smartphone, and a sample port configure to receive a sample (e.g., an immunoassay cassette). FIG. 14C shows an exemplary output from a custom smartphone software that provides, for example, an image of the sample and a corresponding plot of intensity.

An illustrative device (FIG. 14D) that prevents stray light from interfering with the measurement of an immunoassay, accepts an immunoassay cassette, positions the camera of a smart phone relative to the assay for interrogation, and contains a combination of components such as a light emitting diode (LED), an optical filter, a polarizer, a lens, a battery, a diode (indicator light) and a PCB. The device design is modular to allow for: 1) the interchange of components to address different smartphone types and different assay cartridges; 2) efficiencies in manufacturing; and 3) reduction of waste and environmental impact. The device design may also be configured to read assays in either reflectance or transmission modes.

Another illustrative device (FIGS. 14E-14F) provides rapid, point of need diagnostics. For example, FIG. 14F shows a schematics of a design rendering of the components of the diagnostic: set up tray with instructions for use (top left), integrated cassette and sample collection swab (top middle), smartphone adapter (top right), and overall workflow (bottom). Other components are also possible.

Example 6—Exemplary Computational Analysis

Figure 15A:
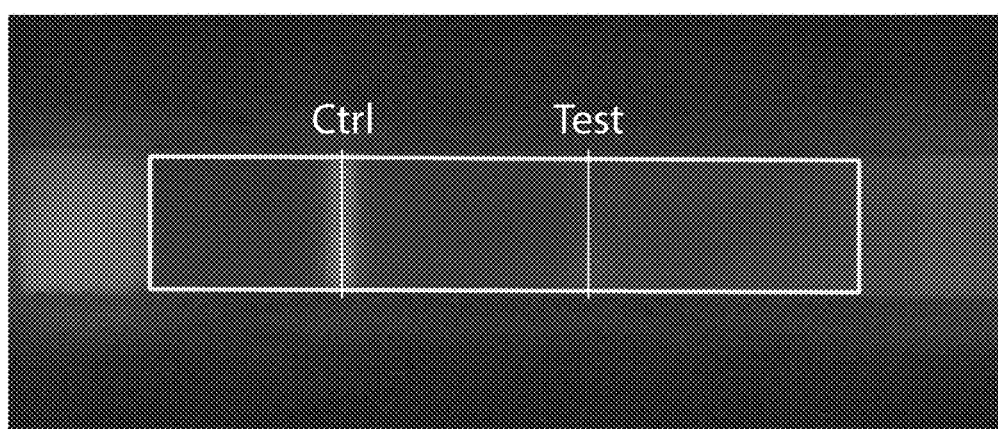
FIG. 15A shows an image wherein an exemplary system has identified the area of the key boundaries of an assay and the locations of the control and test signal, according to one set of embodiments.
Figure 15B:
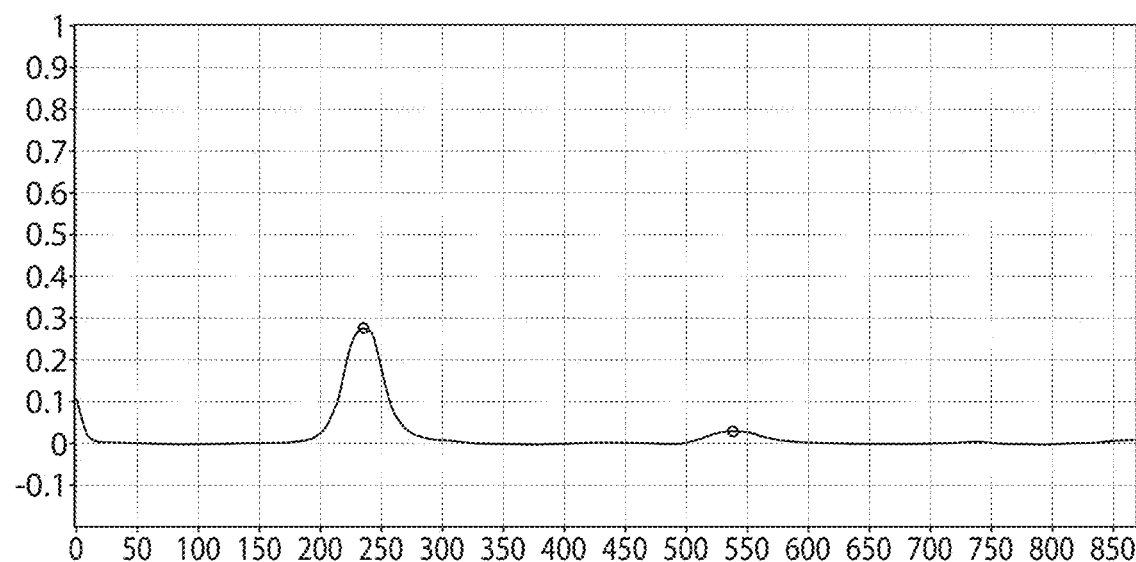
FIG. 15B shows integrated line data corresponding to the image in FIG. 15, according to one set of embodiments.

An exemplary computational procedure for detecting test strip binding on a given assay is as follows: (1) Machine vision methods such as object detection, edge detection and shape estimation are employed to locate workpiece datums and establish a reference coordinate frame. (2) Emission intensity is measured within the localized binding region of the assay. (3) Methods of curve/surface fitting and smoothing are applied to disambiguate the measured signal. (4) Peaks are detected in the enhanced signal and correlated with nominal test strip locations to report presence/absence of significant test strip binding events. FIG. 15A shows an image wherein machine vision has identified the area of the key boundaries of an assay and the locations of the control and test signal. FIG. 15B shows integrated line data obtained from the image in FIG. 15A showing the in circles at the top of the peaks, which corresponds to the locations of the vertical lines projected on the image.

Example 7—Simultaneously Imaging Multiple LFAs

Figure 16:
FIG. 16 shows representative photographs of Europium-based assays, according to one set of embodiments.
Figure 17A:
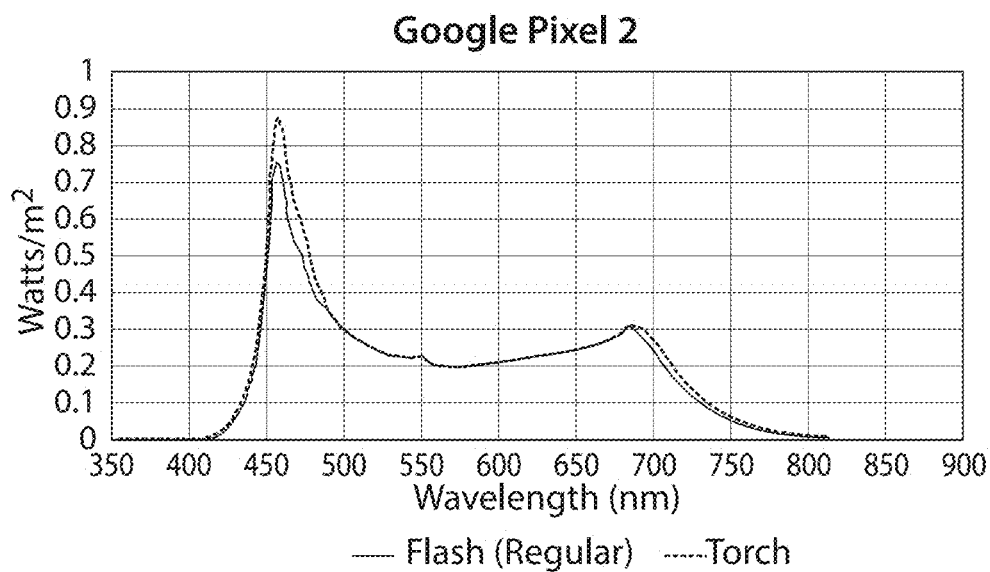
FIGS. 17A-17I demonstrate spectral outputs from exemplary sources of electromagnetic radiation associated with various consumer electronic devices, according to some embodiments.
Figure 17B:
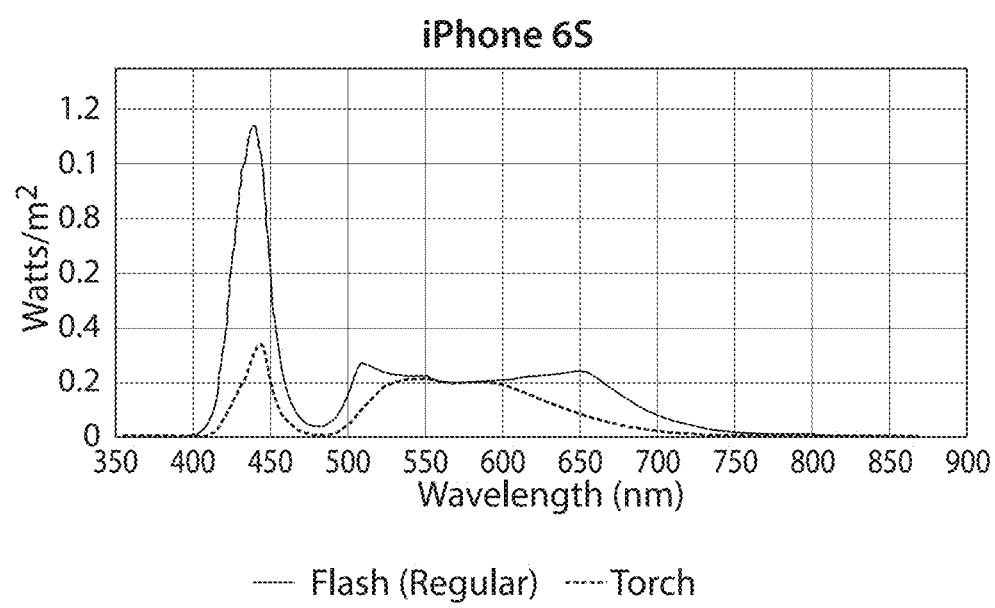
Figure 17C:
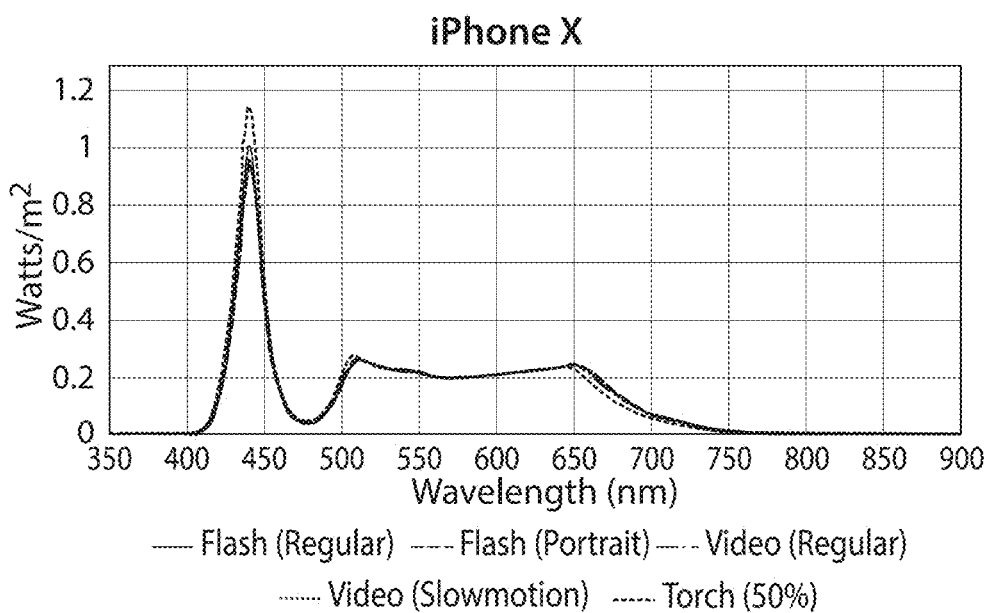
Figure 17D:
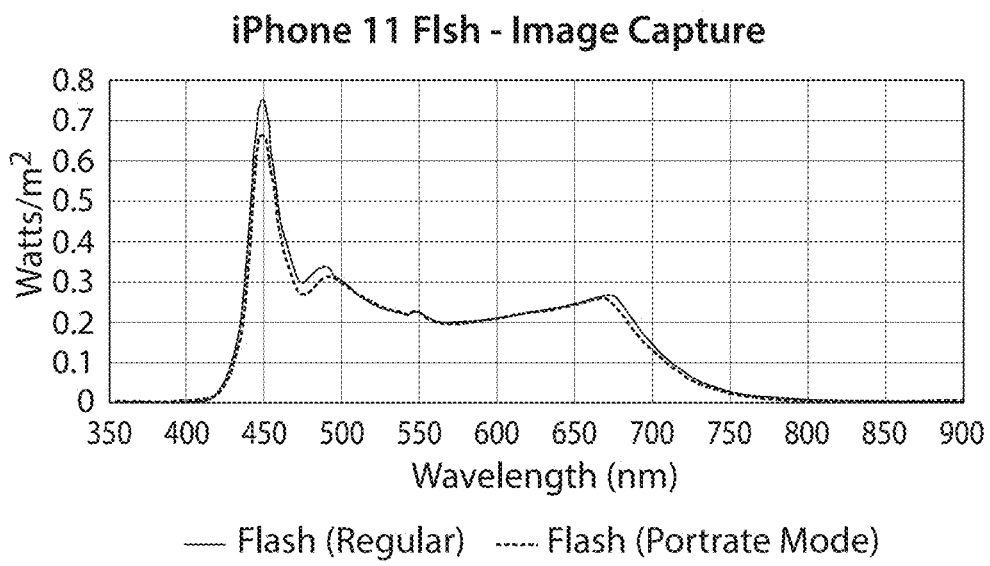
Figure 17E:
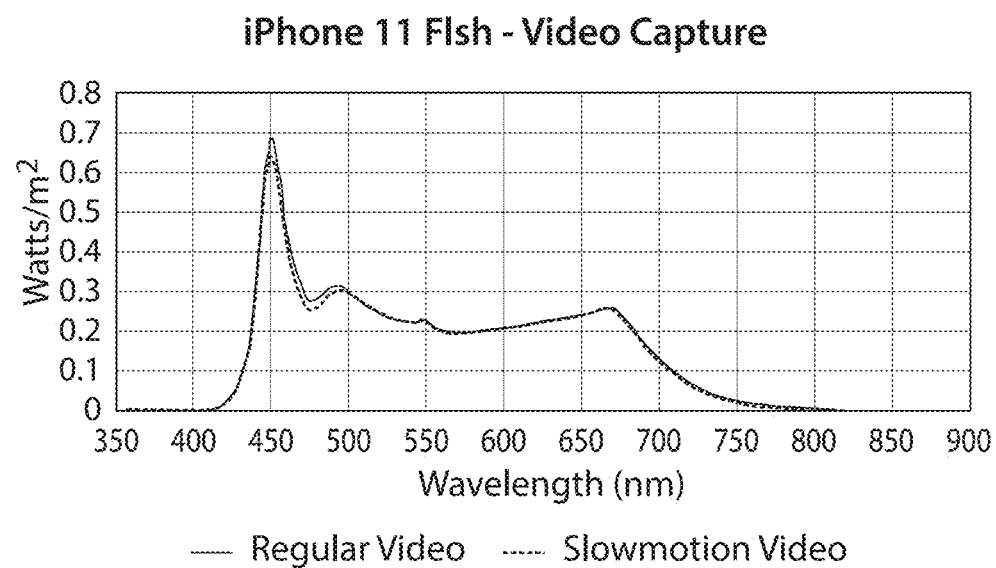
Figure 17F:
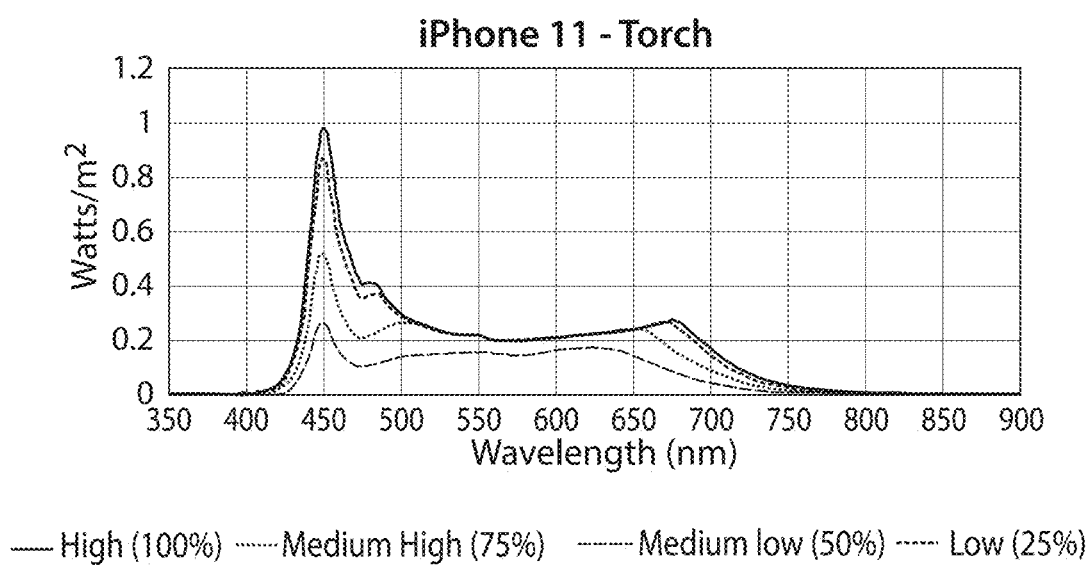
Figure 17G:
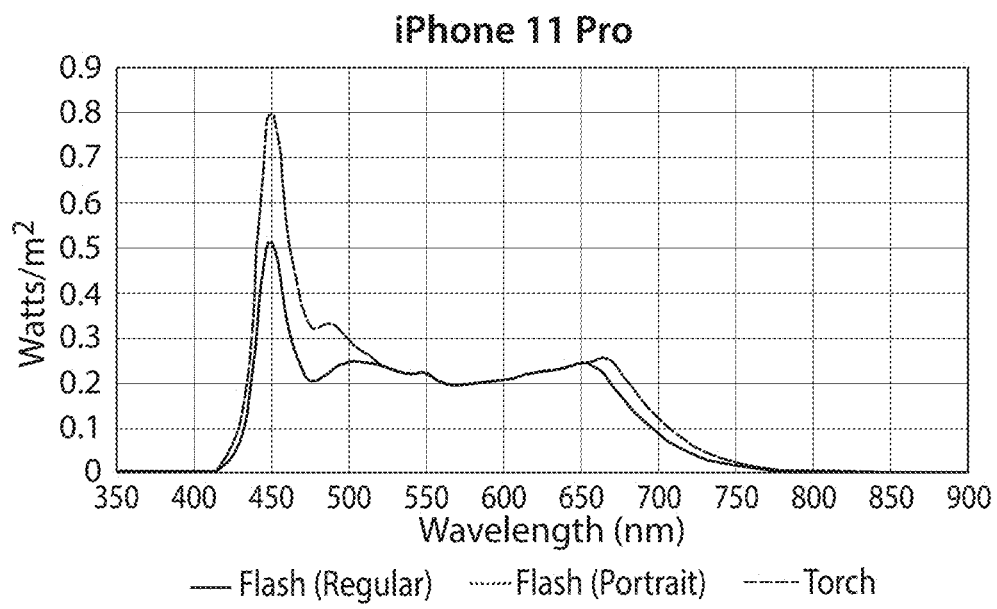
Figure 17H:
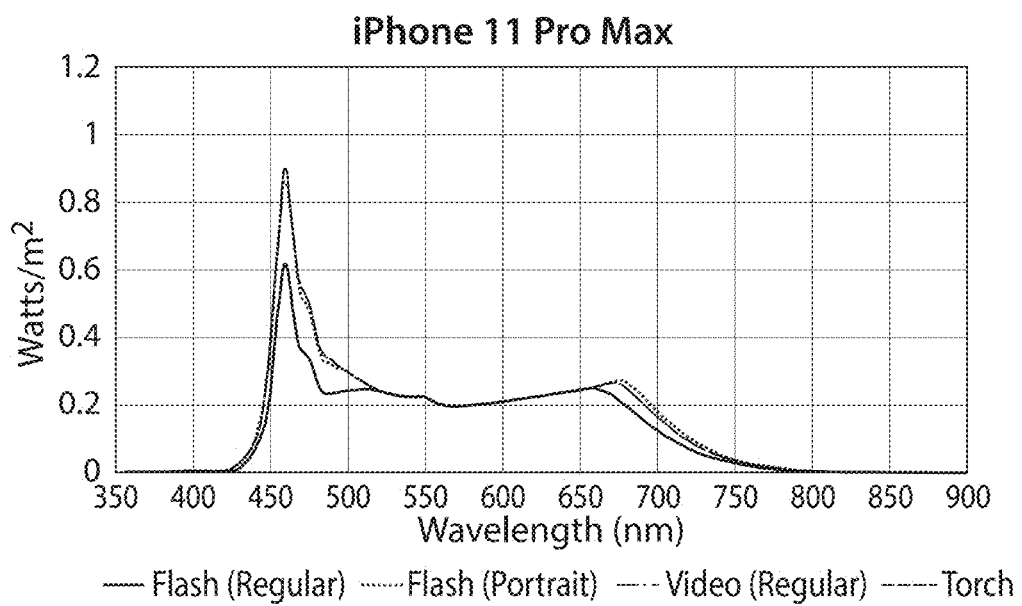
Figure 17I:
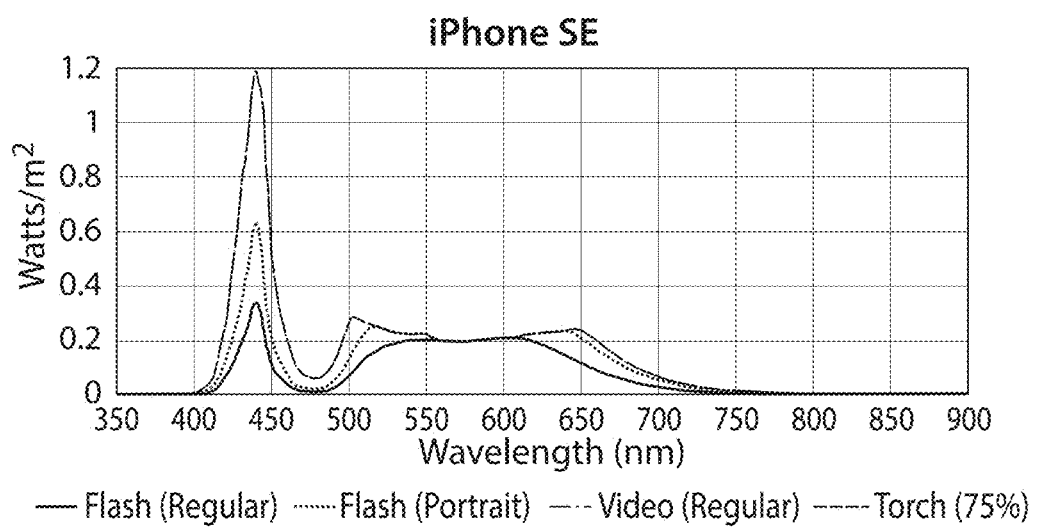
Figure 18A:
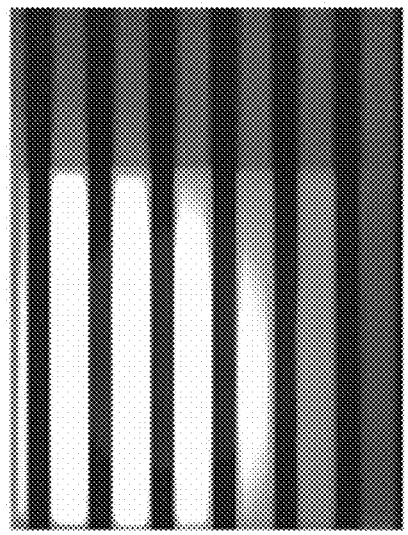
Figure 18B:
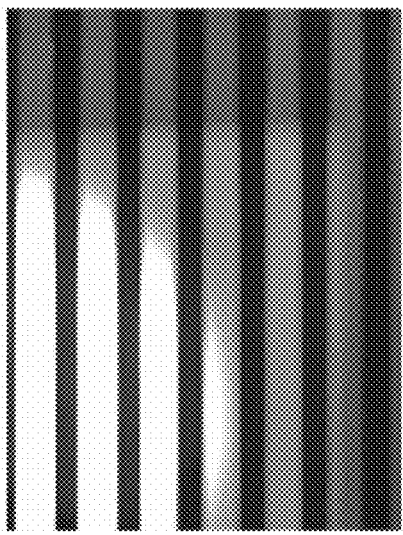
Figure 18C:
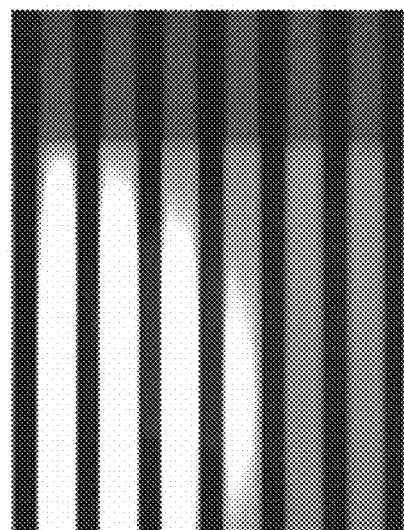
Figure 18D:
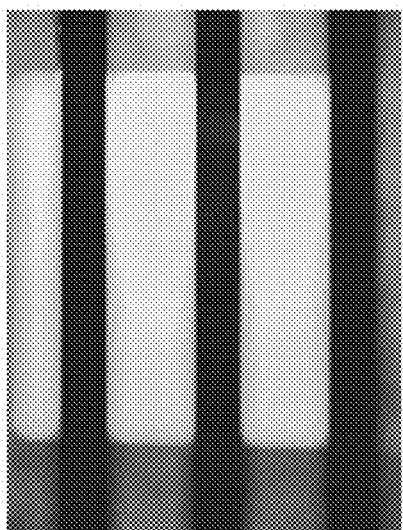

FIG. 16 shows representative photographs of 5 Europium-based ladder assays simultaneously imaged using a customized smartphone device, holder, and algorithm/app under different camera settings. The rolling shutter effect may be clearly observed at faster shutter speeds (shorter exposures). Higher throughputs are also feasible.

Example 8—Synthesis of Europium-tris(6,6,7,7,8,8, 8-heptafluoro-2,2-dimethyloctane-3,5-dione) [Eu (fod)$_3$] and Michler's Ketone (MK) Complex, Eu(fod)$_3$-MK

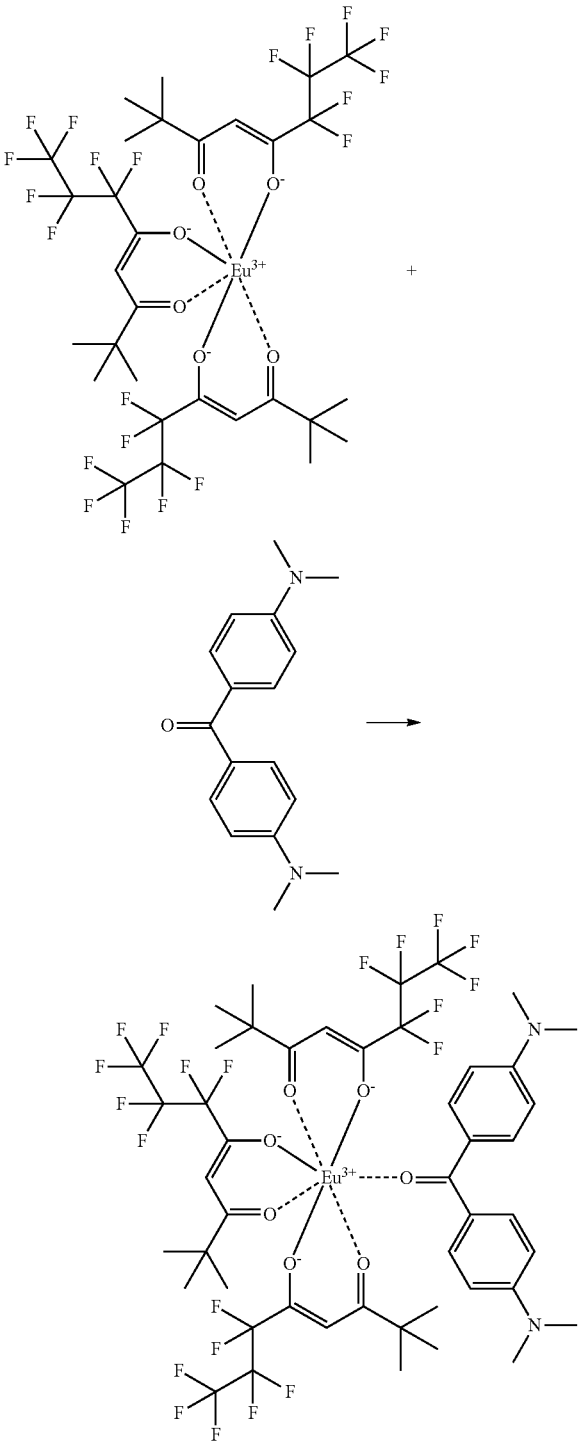

Europium-tris(6,6,7,7,8,8,8-heptafluoro-2,2-dimethyloctane-3,5-dione) [Eu(fod)$_3$] (0.050 g) and Michler's ketone (0.013 g) was placed in an oven-dried. Shlenck flask. The reaction vessel was placed under vacuum for 30 min, and then back filled with argon. Toluene (10 mL) was added via a syringe. The reaction was stirred for 5 min at room temperature until all of the starting materials dissolved. A light-yellow solution of Eu(fod)$_3$-MK was obtained. Intense red emission was observed when the sample was irradiated with a blue LED.

Example 9—Preparation of 2-acetyl-9-ethylcarbazole

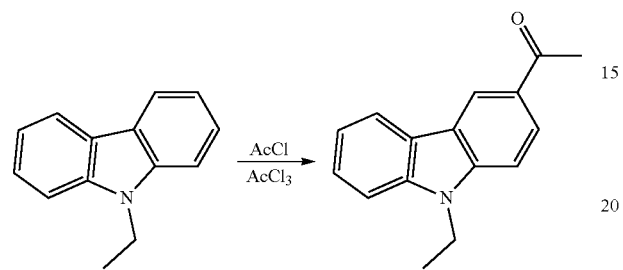

9-Ethylcarbazole (2.0 g, 0.010 mol) and acetyl chloride (0.884 g) was dissolved in dry dichloromethane (100 mL), and the solution cooled to 0° C. under argon. To this solution, aluminum chloride (1.5 g) was added in small aliquots over 30 min. The reaction was then allowed to warm to room temperature and stirred for 5 hours. Concentrated hydrochloric acid (5 mL) was slowly added to the reaction mixture, followed by 1 M hydrochloric acid (30 mL). The organic layer was separated and dried over MgSO$_4$. The solvent was removed and the residue purified by flash chromatography (2:1 dichloromethane/hexanes) to afford the 2-acetyl-9-ethylcarbazole (1.43 g).

Example 10—Preparation of 1-(9-ethyl-9H-carbazol-3-yl)-4,4,4-trifluorobutane-1,3-dione

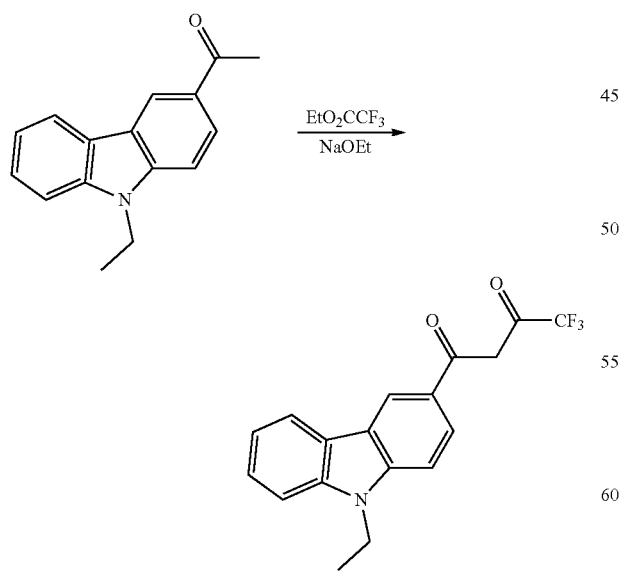

To a 100 mL flask purged with argon was added a solution of potassium tort-butoxide in THE (1M, 10.1 mL) and the reaction vessel cooled to 0° C. A solution of 2-acetyl-9-ethylcarbazole (1.2 g) and ethyl trifluoroacetate (0.72 g) in dry THF (10 mL) was slowly added. The reaction was then allowed to warm to RT and stirred for 8 hours. The solvent was removed under vacuum and 1M hydrochloric acid (12 mL) was slowly added, followed by water (30 mL) and dichloromethane (50 mL). The organic layer was separated, washed with water, and dried over sodium sulfate. The solvent was removed to afford the β-diketo ligand (1.25 g).

Example 11—Preparation of an Europium(III) Complex with 4,4,4-Trifluoro-1-(ethylcarbazole)-1,3-butanedione as Ionic Ligands

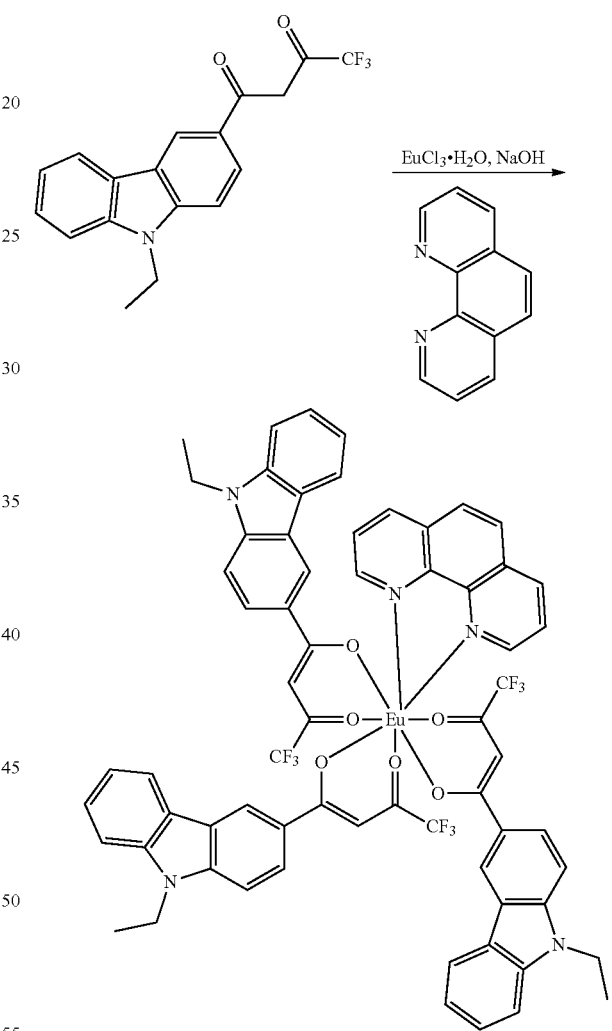

4,4,4-Trifluoro-1-(ethylcarbazole)-1,3-butanedione (200 mg) and 1,10-Phenanthroline monohydrate (39.6 mg) was dissolved in ethanol (30 mL) under argon. Sodium hydroxide (24 mg) was then added. The reaction was stirred for 30 min at 60° C. and then a solution of Europium(III) chloride hexahydrate (73.3 mg) in ethanol (10 mL) was slowly added. The reaction was stirred at 60° C. for 8 hours under argon. The reaction was cooled to T and the solids collected by filtration and washed with ethanol. The crude complex was then dissolved in a small amount of dichloromethane (~5 mL) and any insolubles removed. Ethanol was then added to the dichloromethane solution to cause the europium complex to precipitate. The solids were again collected by filtration and dried under vacuum to afford the complex in pure form. Yield: 188 rag.

Example 12—Preparation of 2-acetyl-9-phenylcarbazole

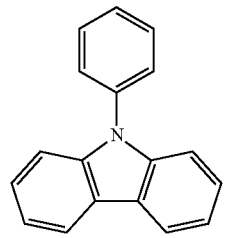

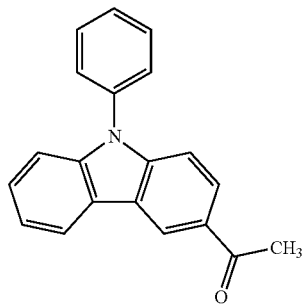

9-Phenylcarbazole (1.0 g, 0.00373 mol) and acetyl chloride (0.322 g. 0.00410 mol) was dissolved in dry dichloromethane (100 mL) and the solution cooled to 0° C. under argon. To this solution, aluminum chloride (0.547 g) was added in small portions. The reaction was then allowed to warm to room temperature and stirred for 5 hours. Concentrated hydrochloric acid (5 mL) was then slowly added to the reaction mixture, followed by 1 M hydrochloric acid (30 mL). The organic layer was separated and dried over $MgSO_4$, the solvent removed, and the residue purified by flash chromatography (2:1 dichloromethane/hexanes) to afford the ketone (0.562 g, 62% yield).

Example 13—Preparation of 4,4,4-Trifluoro-1-(phenylcarbazole)-1,3-butanedione

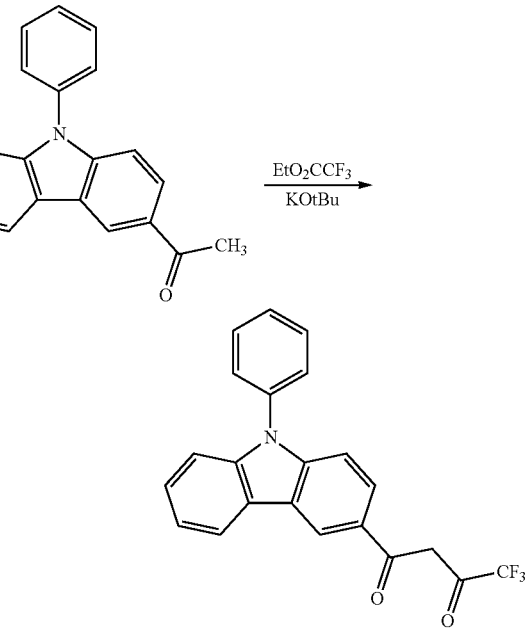

To a 100 mL flask purged with argon was added a solution of potassium tert-butoxide in THF (1M, 7.0 mL). The solution was then cooled to 0° C. A solution of 2-acetyl-9-ethylcarbazole (1.0 g) and ethyl trifluoroacetate (0.50 g) in dry THF (10 mL) was slowly added. The reaction was allowed to warm to RT and stirred for 8 hours. The solvent was removed under vacuum and 1M hydrochloric acid (7 mL) was slowly added followed by water (30 mL) and dichloromethane (50 mL). The organic layer was separated, washed with water, and dried over sodium sulfate. The solvent was removed and the residue purified by silica gel flash chromatography eluted with dichloromethane/hexanes (1:1) to afford the ß-diketo ligand (0.92 g, 69% yield).

Example 14—Preparation of an Europium(III) Complex with 4,4,4-Trifluoro-1-(phenylcarbazole)-1,3-butanedione as Ionic Ligands

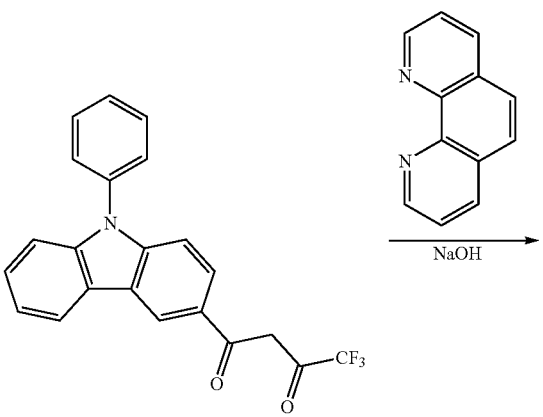

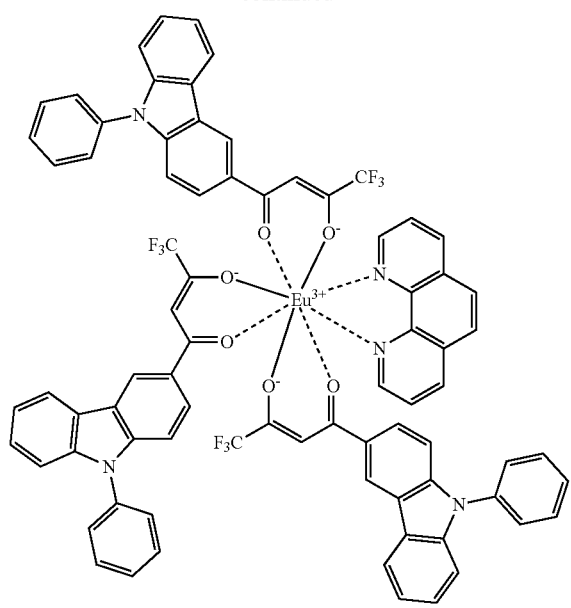

4,4,4-Trifluoro-1-(9-phenyl-9H-carbazol-3-yl)butane-1,3-dione (200 mg, 0.524 mmol) and 1,10-Phenanthroline monohydrate (34.7 mg, 0.175 mmol) was dissolved in ethanol (30 mL) under argon. Sodium hydroxide (21 mg) was then added. The reaction was stirred for 30 min at 60° C. and then a solution of Europium(III) chloride hexahydrate (64.1 mg, 0.175 mmol) in ethanol (10 mL) was slowly added. The reaction was stirred at 60° C. for 8 hours under argon. The reaction was cooled to RT and the solids collected by filtration and washed with ethanol. The crude complex was then dissolved in a small amount of dichloromethane (~5 mL) and the insolubles removed. Hexanes was then added to the dichloromethane solution to cause the europium complex to precipitate. The solids were again collected by filtration and dried under vacuum to afford the complex in pure form (188 mg, 73% yield).

Example 15—Preparation 4-(4,6-dichloro-1,3,5-triazin-2-yl)-N,N-diethylaniline

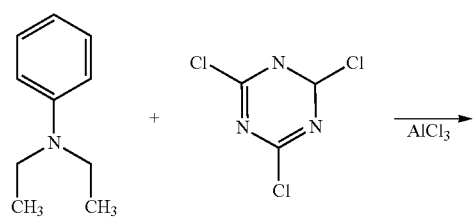

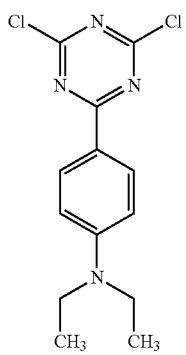

N,N-Diethylaniline (10.0 g, 0.067 mol) and cyanuric chloride (12.4 g, 0.067 mol) was dissolved in dry dichloromethane (200 mL) under argon. Aluminum chloride (8.93 g, 0.067 mol) was added in small portions over 30 min. The reaction was stirred for 4 hours at 0° C. and then allowed to warm to morn temperature and stirred for 16 hours. Concentrate hydrochloric acid (50 mL) was slowly added, followed by water (150 mL). The organic layer was separated, washed with water, and dried over anhydrous MgSO$_4$. The solvent was removed and the residue purified by silica gel flash chromatography with dichloromethane/hexanes (1:1) as eluent. The pure product was crystalized from dichloromethane and hexanes (8.16 g, 41% yield).

Example 16—Preparation of 2-(N,N-Diethylanilin-4-yl)-4,6-bis(3,5-dimethyl-pyrazol-1-yl)-1,3,5-triazine (dpbt)

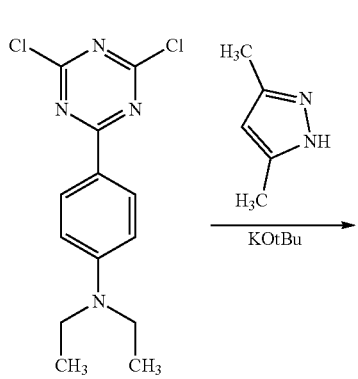

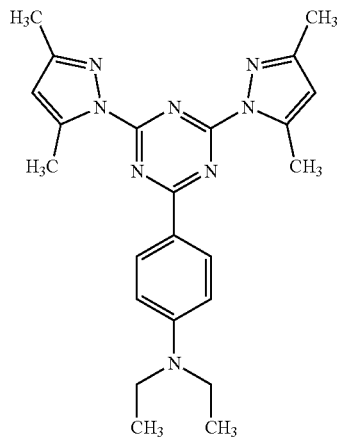

3,5-Dimethylpyrazole (1.0 g, 0.0104 mol) was dissolved in dry THF (20 mL) under argon. A solution of Potassium tert-Butoxide (12% in Tetrahydrofuran, ca. 1 M, 10.4 ML) was added. The reaction was stirred for 30 min at room temperature and cooled to 0° C. A solution of 4-(4,6-dichloro-1,3,5-triazin-2-yl)-N,N-diethylaniline (1.47 g, 0.00495 mol) in dry THF (15 mL) was slowly added and the reaction allowed to warm to room temperature and stirred for 8 hours, and then heated to 80° C. under argon for 16 hours. The reaction was then cooled to room temperature and the solvent removed under vacuum. The residue was purified by silica gel flash chromatography with dichloromethane/ethyl acetate (3:2) as eluent. The pure product was crystalized from dichloromethane and hexanes (1.17 g, % yield).

Example 17—Preparation 2-(N,N-di-ethylanilin-4-yl)-4,6-bis(pyrazol-1-yl)-1,3,5-triazine (bpt)

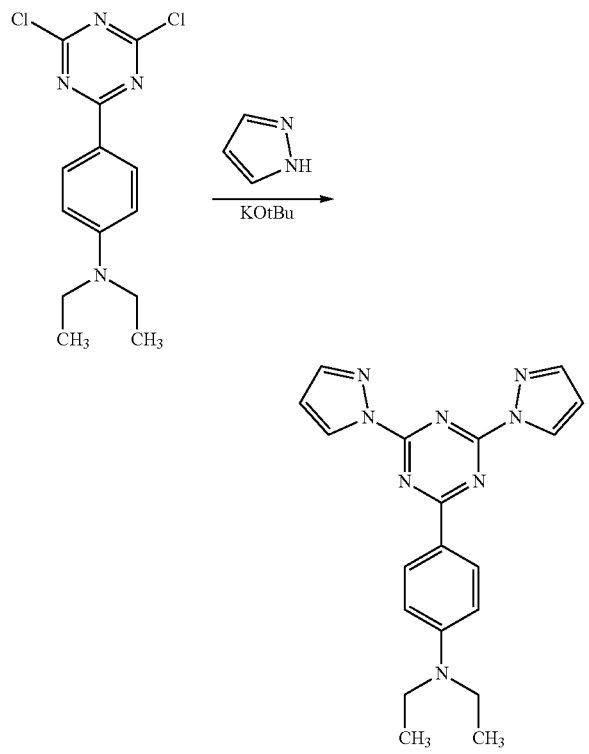

Pyrazol (0.434 g, 0.00639 mol) was dissolved in dry THF (30 mL) under argon. A solution of potassium cert-butoxide (12% in tetrahydrofuran, ca. 1 M, 6.10 mL) was added. The reaction was stirred for 30 min at room temperature and cooled to 0° C. A solution of 4-(4,6-dichloro-1,3,5-triazin-2-yl)-N,N-diethylaniline (1.00 g, 0.00304 mol) in dry THF (15 mL) was slowly added and the reaction allowed to warm to room temperature and stirred for 8 hours, and then heated to 80° C. under argon for 16 hours. The reaction was then cooled to room temperature and the solvent removed under vacuum. The residue was purified by silica gel flash chromatography with dichloromethane/ethyl acetate (1:1) as eluent. The pure product was crystalized from dichloromethane and hexanes (0.23 g, 21% yield).

Example 18—Preparation of Europium tris-thenoyl-trifluoroacetonato-2-(N,N-diethylanilin-4-yl)-4,6-bis(3,5-dimethyl-pyrazol-1-yl)-1,3,5-triazine Complex [Eu(tta)$_3$(dpbt)]

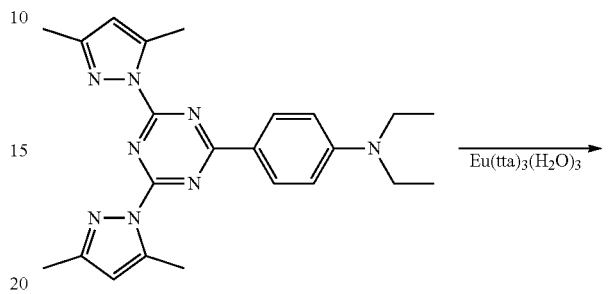

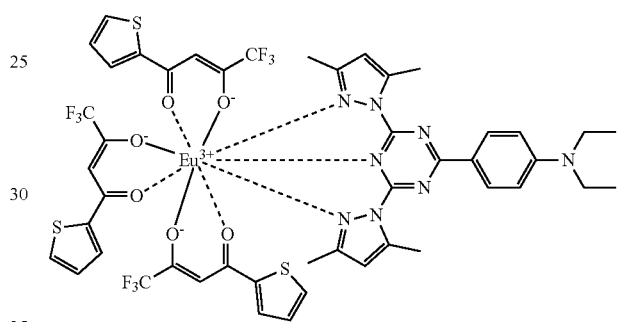

A solution of Eu(tta)$_3$.3H$_2$O (100 mg, 0.115 mmol) in THF (10 mL) was added to a solution of bpt (49.3 mg, 0.115 mmol) in THF (10 mL) and the mixture stirred for 30 min at room temperature. The solvent was removed under vacuum and the residue dissolved in a small amount of dichloromethane. Hexanes was added and the yellow precipitate collected by filtration to afford the Eu(tta)$_3$(dpbt) (126 mg, 88%).

Example 19—Preparation of Europium tris-thenoyl-trifluoroacetonato-2-(N,N-di-ethylanilin-4-yl)-4,6-bis(pyrazol-1-yl)-1,3,5-triazine Complex [Eu(tta)$_3$(bpt)]

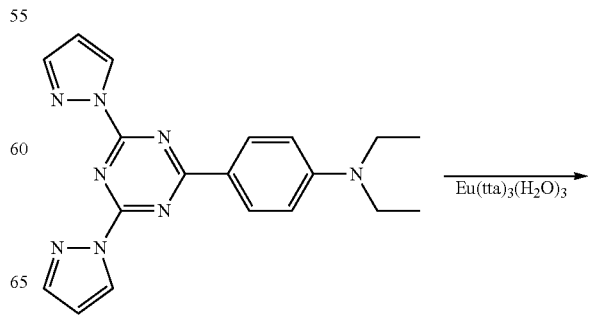

-continued

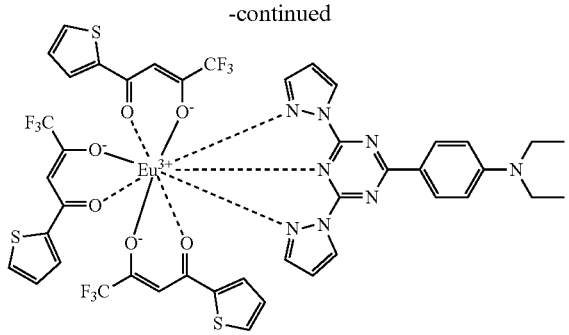

A solution of Eu(tta)$_3$·3H$_2$O (100 mg, 0.115 mmol) in THF (10 mL) was added to a solution of bpt (41.5 mg, 0.115 mmol) in THF (10 mL) and the mixture was stirred for 30 min at room temperature. The solvent was removed under vacuum and the residue was dissolved in small amount of dichloromethane. Hexanes was added and the yellow precipitates were collected by filtration to afford the Eu(tta)$_3$(bpt) (108 mg, 80%).

Example 20

The following example demonstrates the use of exemplary emissive species.

FIGS. 18A-18D show images collected using an iPhone 11 and external (pulsed) white light LED of drop-cast samples of: a) Eu(fod)$_3$-MK; b) Eu(tta)$_3$(dpbt); c) Eu(tta)$_3$(bpt); and d) Eu(pfppd)$_3$(tpy), as prepared as described above.

Figure 19:
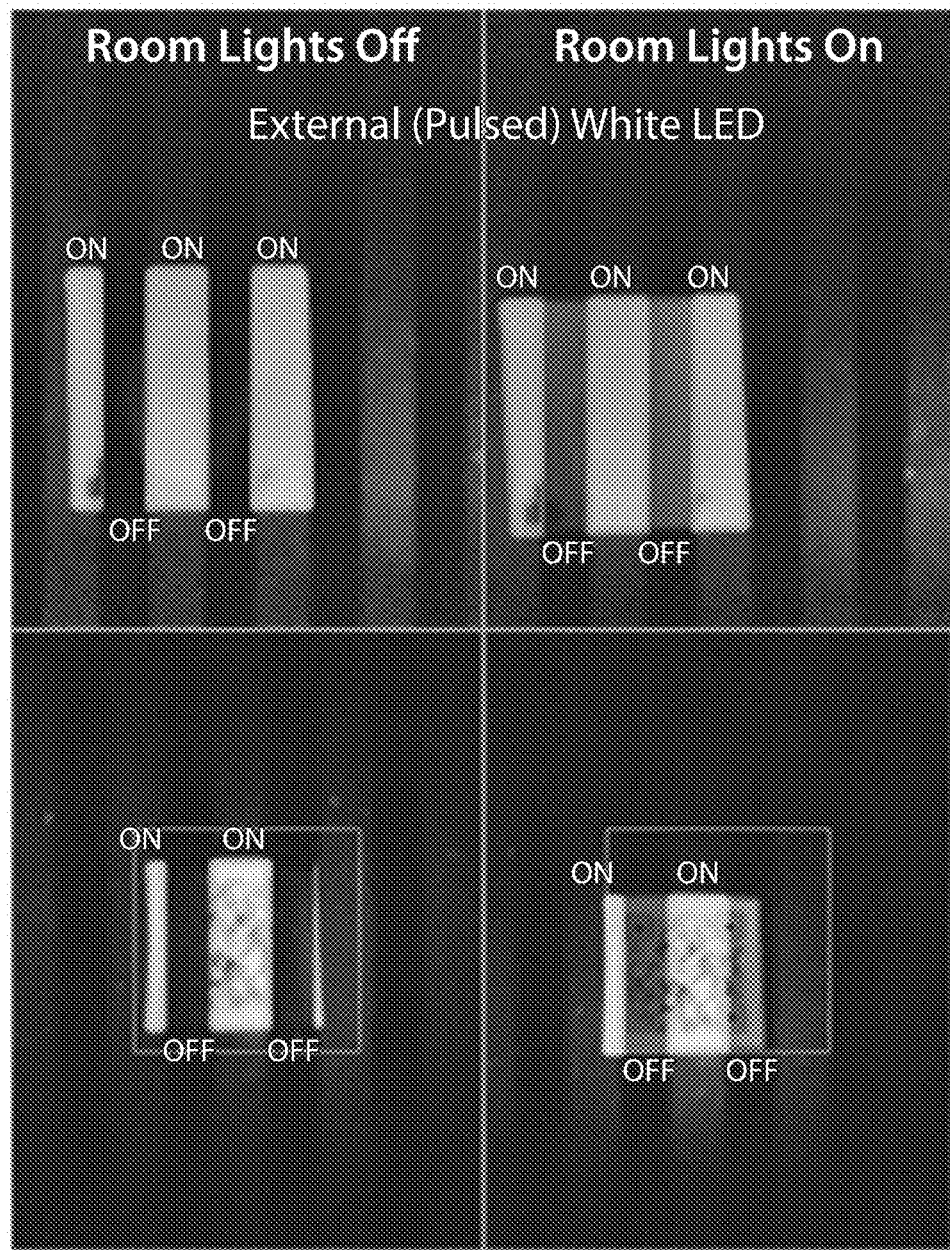
FIG. 19 shows samples of Eu(fod)$_3$-MK, with or without PMMA, drop-cast or spin-coated onto plain labels or labels pre-printed with a matrix (2D) barcode, according to some embodiments, with images collected using an iPhone 11 and external (pulsed) white light LED, with or without the presence of room lighting.

FIG. 19 shows samples of Eu(fod)$_3$-MK, with or without PMMA, drop-cast or spin-coated onto plain labels or labels pre-printed with a matrix (2D) barcode. Images collected using an iPhone 11 and external (pulsed) white light LED, with or without the presence of room lighting.

Figure 20A:
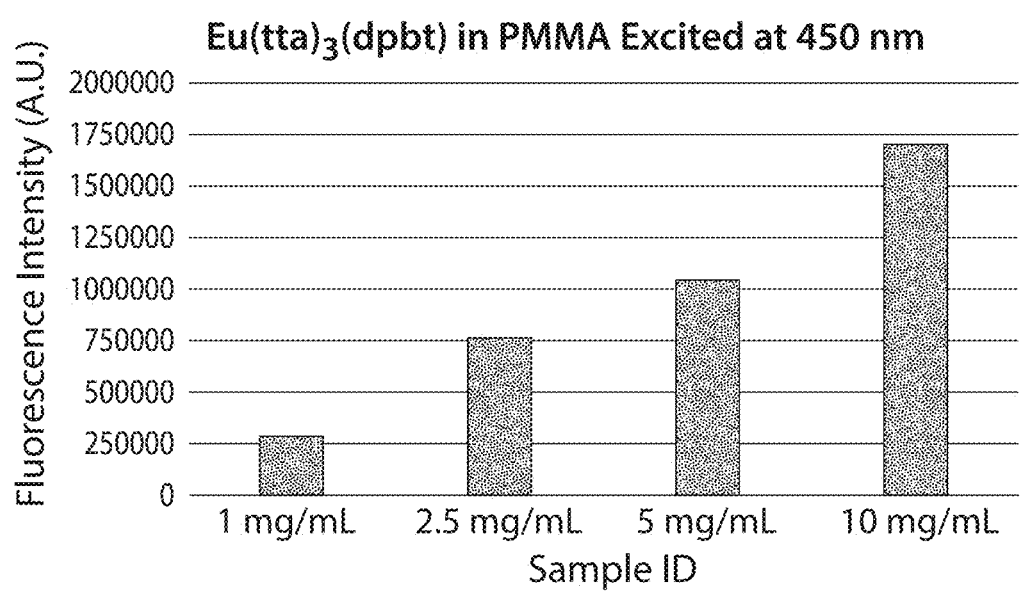
Figure 20B:
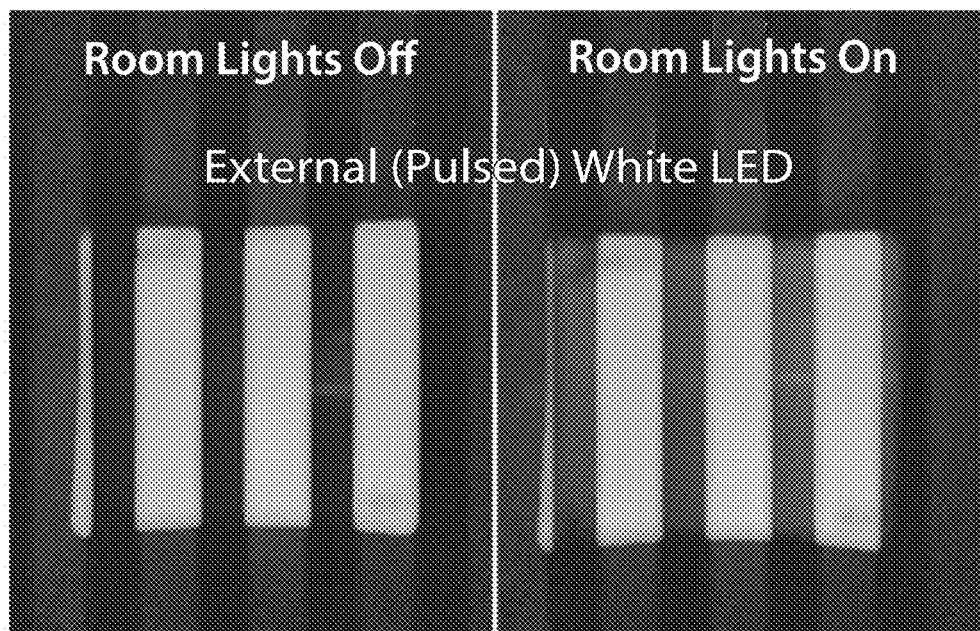

FIG. 20 shows samples of Eu(tta)$_3$(dpbt) in PMMA analyzed using a: a) fluorimeter; or b) an iPhone 11 with external (pulsed) white light LED, with or without the presence of room lighting.

Figure 21:
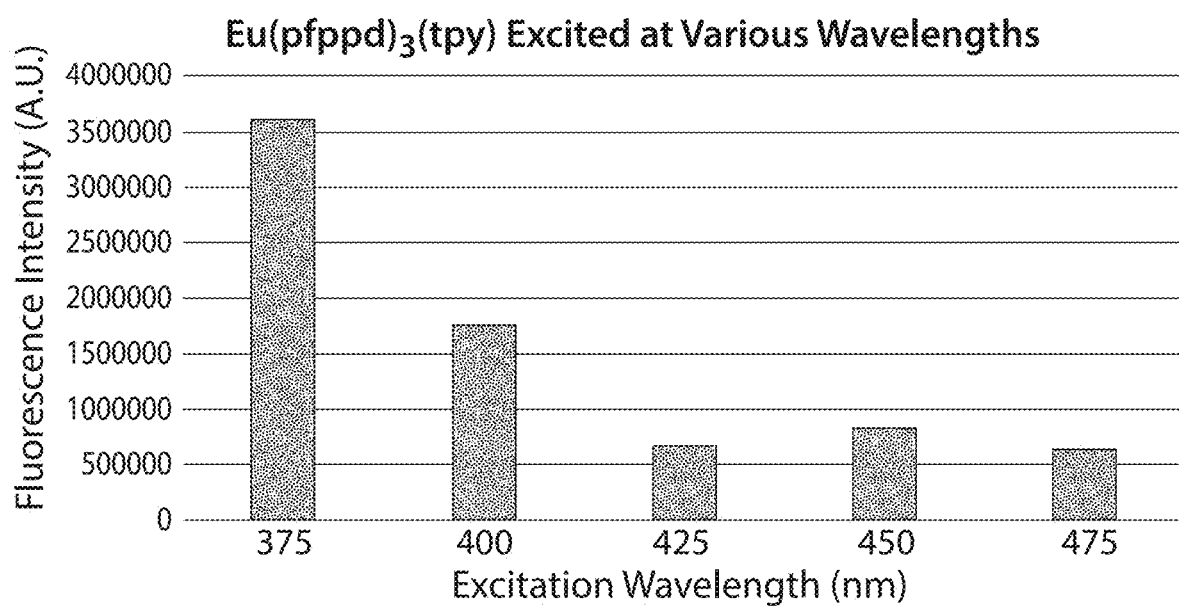
FIG. 21 is a plot of fluorescence intensity versus excitation wavelength for a drop-cast sample of Eu(pfppd)$_3$(tpy) excited at various excitation wavelengths in a fluorimeter, according to one set of embodiments.

FIG. 21 is a plot of fluorescence intensity versus excitation wavelength for a drop-cast sample of Eu(pfppd)$_3$(tpy) excited at various excitation wavelengths in a fluorimeter.

Figure 22A:
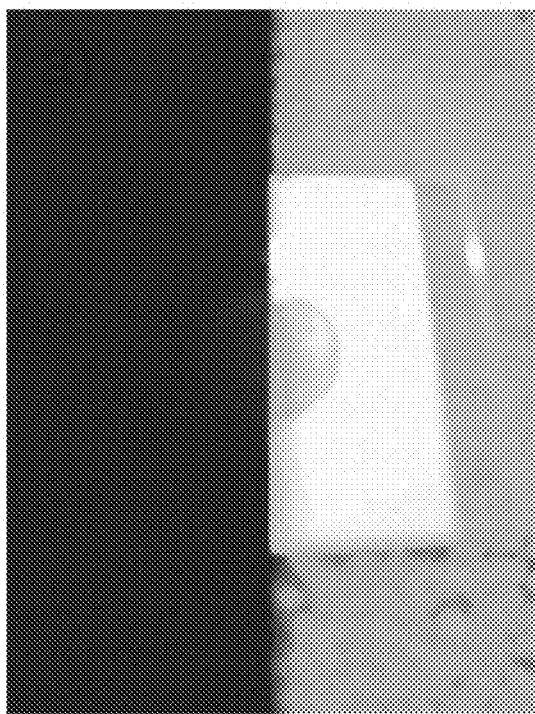
Figure 22B:
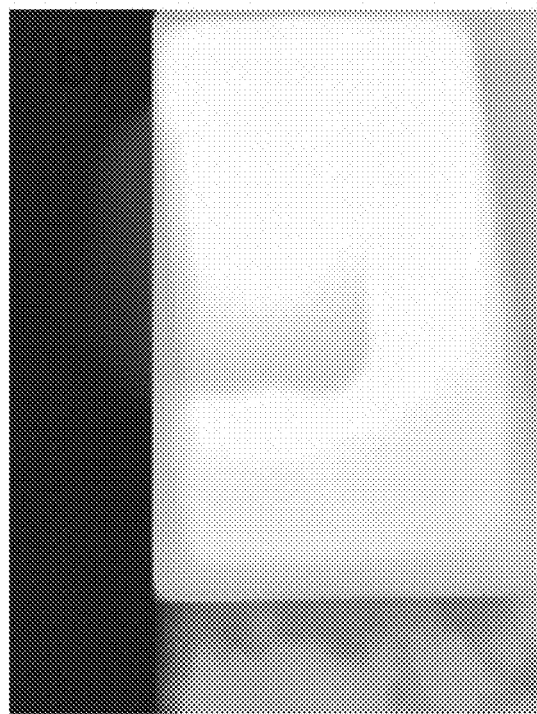

FIGS. 22A-22B show images of drop-cast samples of Eu(tta)$_3$(bpt) in a F8BT/PMMA mixture at: FIG. 22A) 0.6 mg/mL; and FIG. 22B) 1 mg/mL. Images were obtained using a commercially available flashlight app to strobe the white light LED of an iPhone 11.

Figure 23A:
FIGS. 23A-23B show images of airbrushed samples of Eu(tta)$_3$(bpt) in a F8BT/PMMA analyzed with (FIG. 23A) or without (FIG. 23B) the presence of room lighting, according to one set of embodiments, with images obtained using a commercially available flashlight app to strobe the white light LED of an iPhone 11.
Figure 23B:

FIGS. 23A-23B show images of airbrushed samples of Eu(tta)$_3$(bpt) in a F8BT/PMMA analyzed with (FIG. 23A) or without (FIG. 23B) the presence of room lighting, with images obtained using a commercially available flashlight app to strobe the white light LED of an iPhone 11.

FIGS. 24A-24B show images of a sample of Erythrosin B, a commercially available food coloring, incorporated into a Poly Vinyl Alcohol (PVA) matrix. The sample was imaged using an iPhone 11 under ambient (room) lighting (FIG. 24A) and in the dark using an external (pulsed) white light LED (FIG. 24B).

Example 21

The following example demonstrates the use of a smartphone (or other consumer electronic device) in accordance with the embodiments described herein e.g., for authentication of a sample.

Figure 25A:
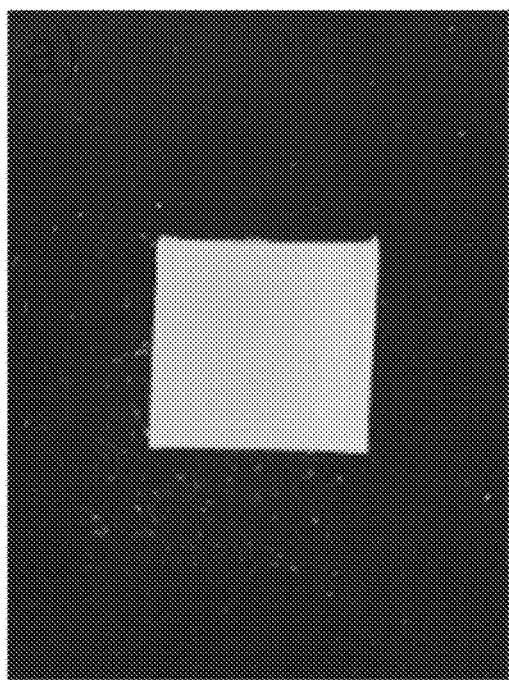
FIGS. 25A-25B show images of a sample of tan colored leather, with authentication tag airbrushed on top. The sample was imaged with an iPhone 11 using a custom application (app) and pulsed UV LED excitation source, with pulsed UV light source off (FIG. 25A) and on (FIG. 25B) in a lit room, according to some embodiments.
Figure 25B:
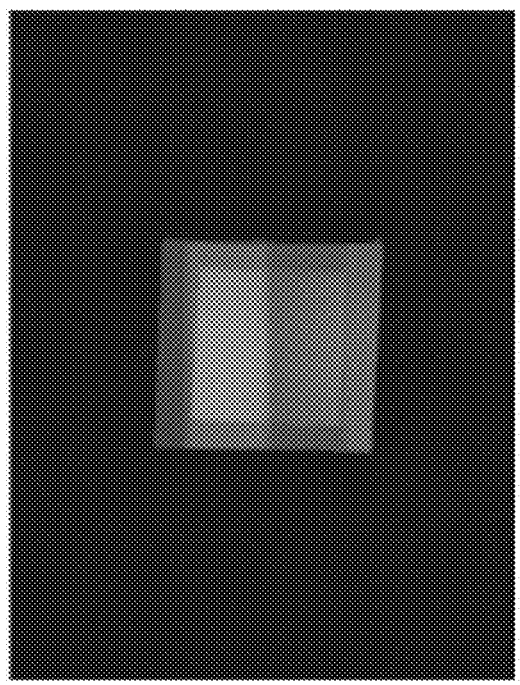

FIGS. 25A-25B show images of a sample of tan colored leather, with authentication tag airbrushed on top. The sample was imaged with an iPhone 11 using a custom application (app) and pulsed UV LED excitation source, with pulsed UV light source off (FIG. 25A) and on (FIG. 25B) in a lit room.

Figure 26A:
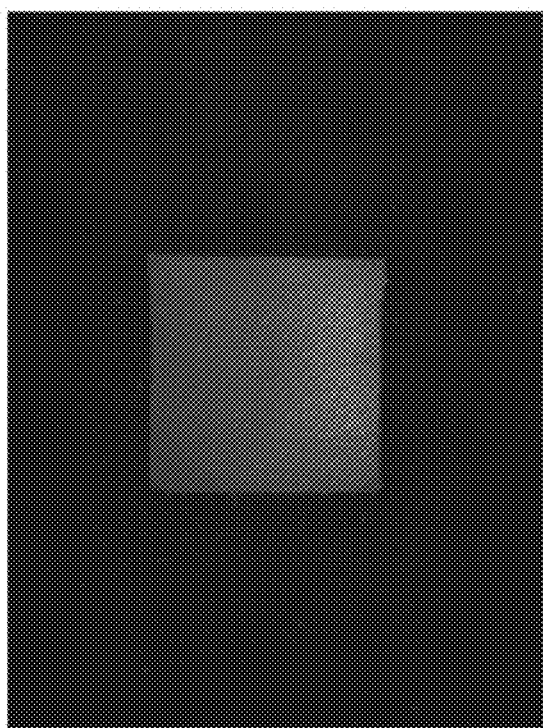
FIGS. 26A-26B show images of a sample of blue colored leather, with authentication tag airbrushed on top. The sample was imaged with an iPhone 11 using a custom application (app) and pulsed UV LED excitation source with the pulsed UV light source off (FIG. 26A) and on (FIG. 26B) in a lit room, according to some embodiments.
Figure 26B:
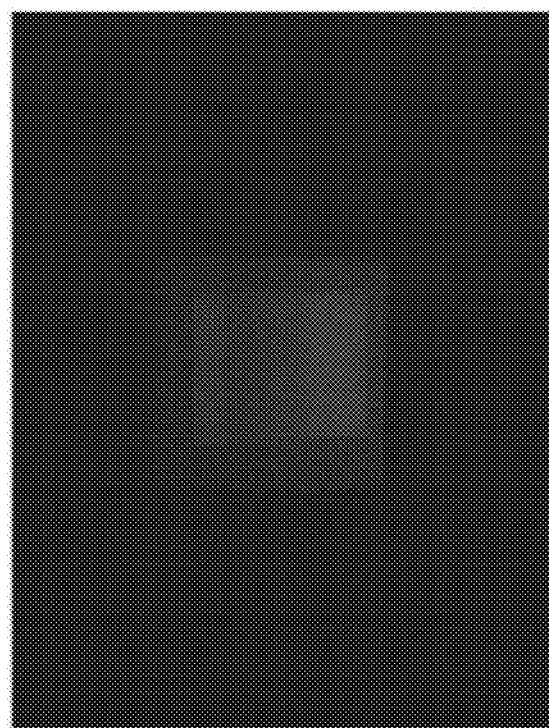

FIGS. 26A-26B show images of a sample of blue colored leather, with authentication tag airbrushed on top. The sample was imaged with an iPhone 11 using a custom application (app) and pulsed UV LED excitation source with the pulsed UV light source off (FIG. 26A) and on (FIG. 26B) in a lit room.

Figure 27A:
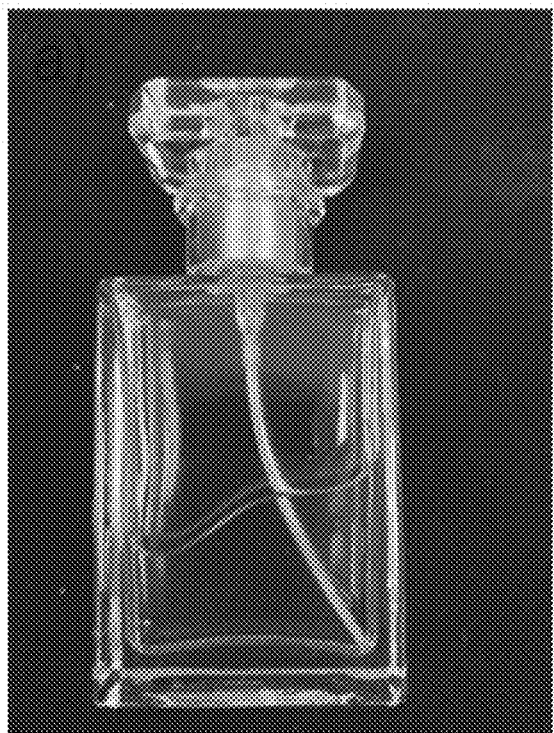
FIGS. 27A-27B show images of a clear glass, alcohol filled perfume bottle, with authentication tag airbrushed on one side. The sample was imaged with an iPhone 11 using a custom application (app) and pulsed UV LED excitation source with the pulsed UV light source off (FIG. 27A) and on (FIG. 27B) in a lit room, according to some embodiments.
Figure 27B:
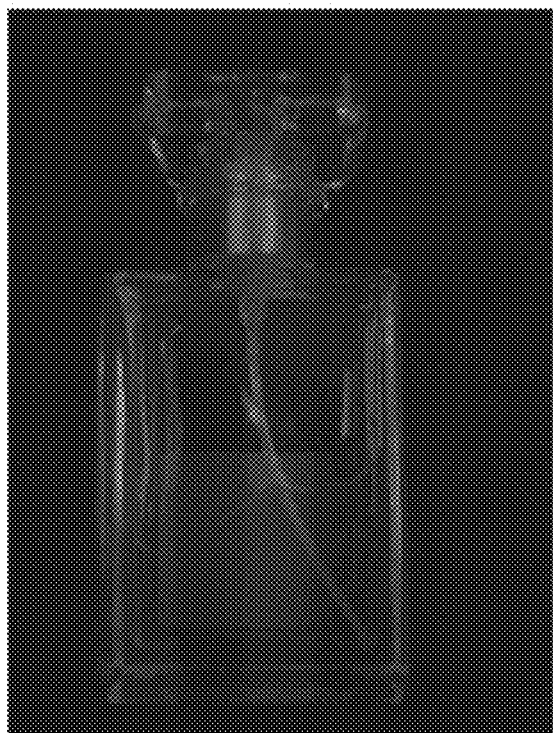

FIGS. 27A-27B show images of a clear glass, alcohol filled perfume bottle, with authentication tag airbrushed on one side. The sample was imaged with an iPhone 11 using a custom application (app) and pulsed UV LED excitation source with the pulsed UV light source off (FIG. 27A) and on (FIG. 27B) in a lit room.

Figure 28A:
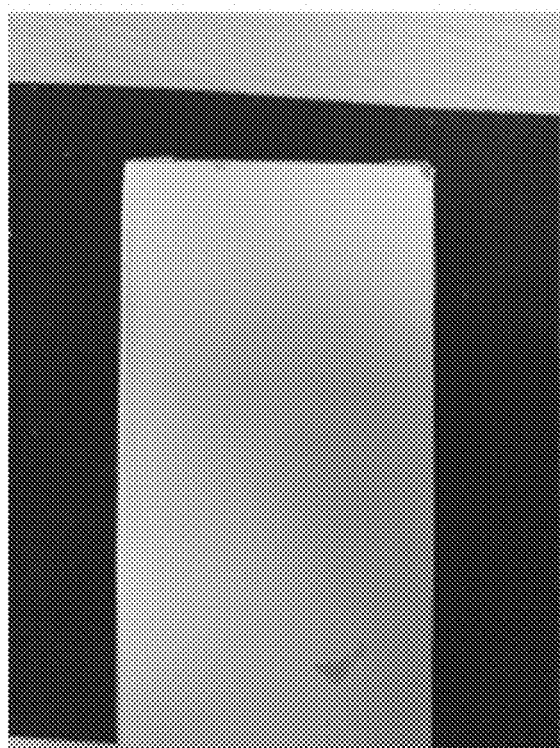
FIGS. 28A-28B show images of a white cardboard box, with authentication tag (smart logo) airbrushed on one side. The sample was imaged with an iPhone 11 using a custom application (app) and pulsed UV LED excitation source, with the pulsed UV light source off (FIG. 28A) and on (FIG. 28B) in a lit room, according to some embodiments.
Figure 28B:
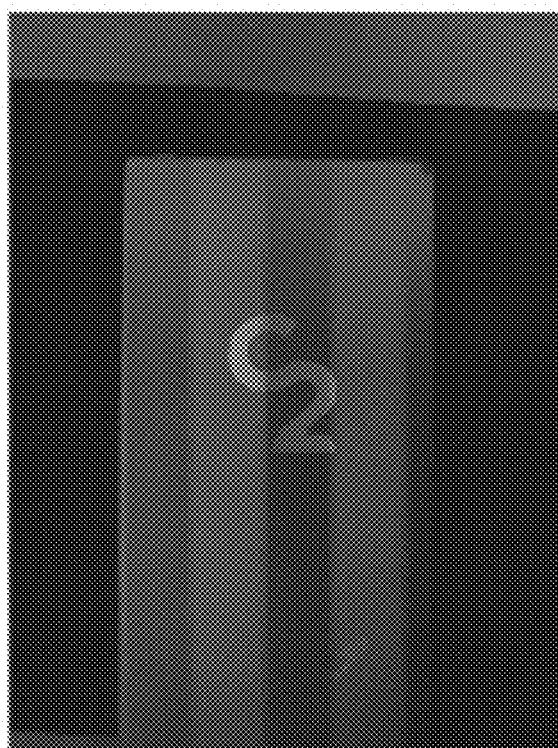

FIGS. 28A-28B show images of a white cardboard box, with authentication tag (smart logo) airbrushed on one side. The sample was imaged with an iPhone 11 using a custom application (app) and pulsed UV LED excitation source, with the pulsed UV light source off (FIG. 28A) and on (FIG. 28B) in a lit room.

Figure 29A:
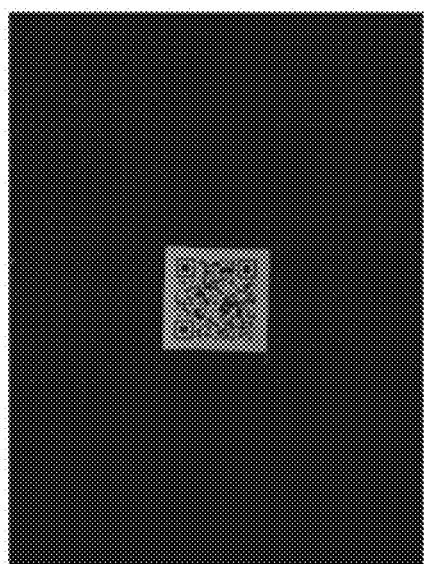
FIGS. 29A-29B show images of a printed 2D (matrix) barcode on a white label, with authentication tag airbrushed on top. The sample was imaged with an iPhone 11 using a custom application (app) and pulsed UV LED excitation source, with the pulsed UV light source off (FIG. 29A) and on (FIG. 29B) in a lit room, according to some embodiments.
Figure 29B:
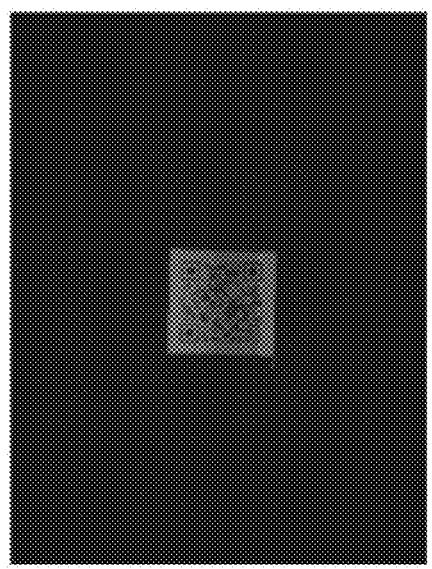

FIGS. 29A-29B show images of a printed 2D (matrix) barcode on a white label, with authentication tag airbrushed on top. The sample was imaged with an iPhone 11 using a custom application (app) and pulsed UV LED excitation source, with the pulsed UV light source off (FIG. 29A) and on (FIG. 29B) in a lit room.

Figure 30A:
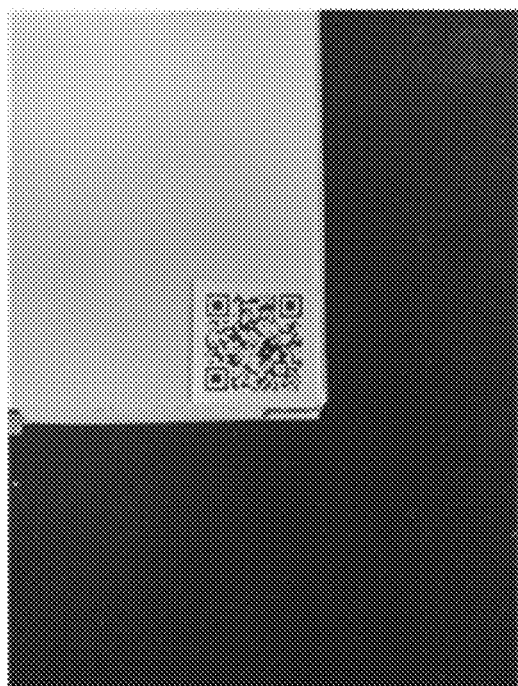
FIGS. 30A-30B show images of a printed 2D (matrix) barcode on a white box, with authentication tag airbrushed on top. The sample was imaged with an iPhone 11 using a custom application (app) and pulsed UV LED excitation source, with the pulsed UV light source off (FIG. 30A) and on (FIG. 30B) in a lit room, according to some embodiments.
Figure 30B:
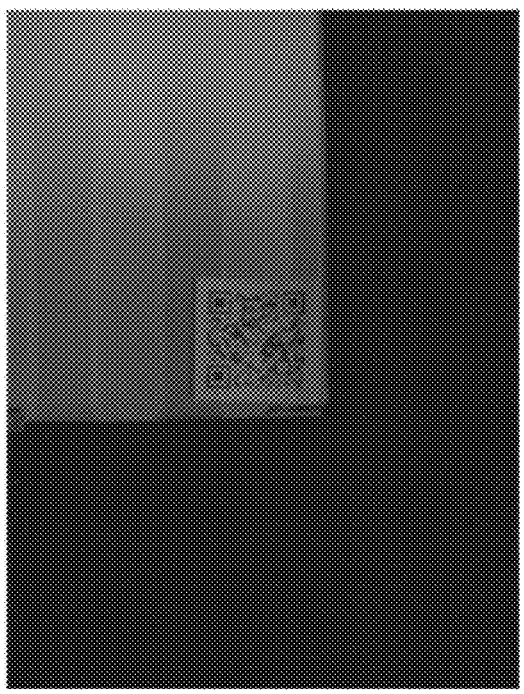

FIGS. 30A-30B show images of a printed 2D (matrix) barcode on a white box, with authentication tag airbrushed on top. The sample was imaged with an iPhone 11 using a custom application (app) and pulsed UV LED excitation source, with the pulsed UV light source off (FIG. 30A) and on (FIG. 30B) in a lit room.

Figure 31A:
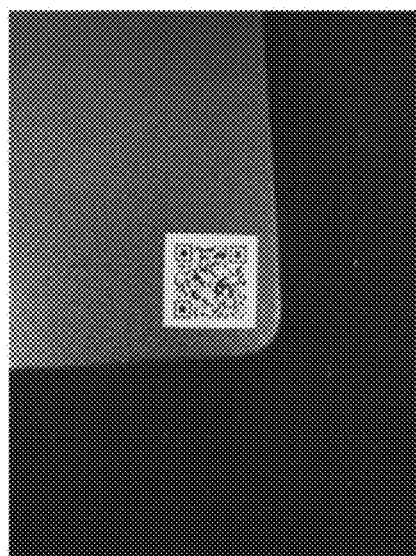
FIGS. 31A-31B shows images of a printed 2D (matrix) barcode on a black notebook, with authentication tag airbrushed on top. The sample was imaged with an iPhone 11 using a custom application (app) and pulsed UV LED excitation source, with the pulsed UV light source off (FIG. 31A) and on (FIG. 31B) in a lit room, according to some embodiments.
Figure 31B:
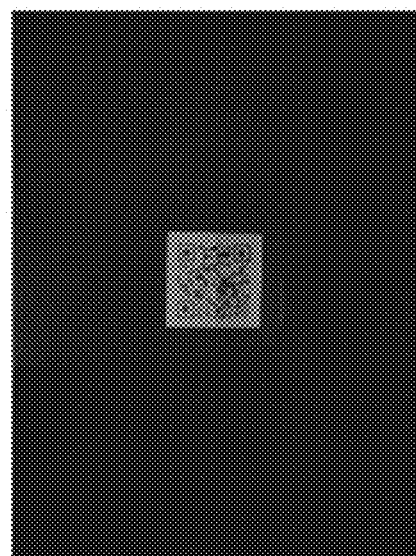

FIGS. 31A-31B shows images of a printed 2D (matrix) barcode on a black notebook, with authentication tag airbrushed on top. The sample was imaged with an iPhone 11 using a custom application (app) and pulsed UV LED excitation source, with the pulsed UV light source off (FIG. 31A) and on (FIG. 31B) in a lit room.

Figure 32A:
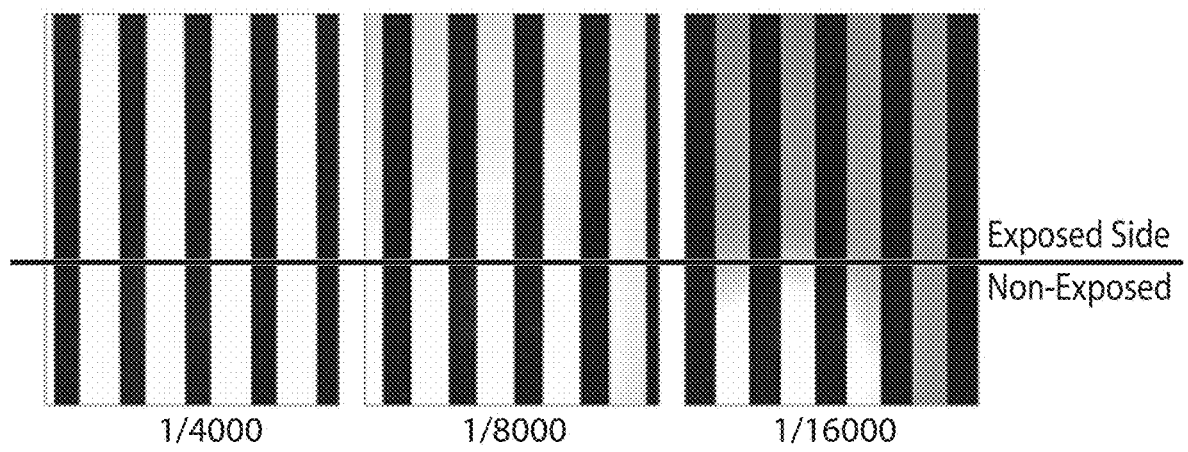
FIG. 32A shows an image of a drop-cast sample of $Eu(fod)_3$-MK on a glass coverslip, imaged with an iPhone 11 using a custom application (app) and pulsed excitation source. The images were collected using the same ISO setting but different shutter speeds. The top half of the coverslip had been exposed to diethylamine for 2 minutes, the bottom half had not been exposed, according to some embodiments.

FIG. 32A shows an image of a drop-cast sample of Eu(fod)$_3$-MK on a glass coverslip, imaged with an iPhone 11 using a custom application (app) and pulsed excitation source. The images were collected using the same ISO setting but different shutter speeds. The top half of the coverslip had been exposed to diethylamine for 2 minutes, the bottom half had not been exposed.

Figure 32B:
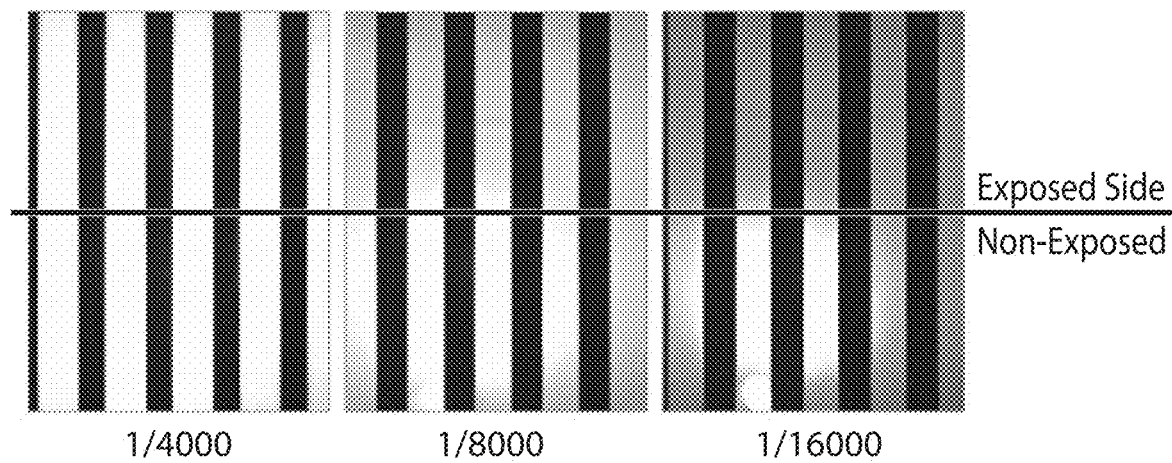
FIG. 32B shows an image of a drop-cast sample of $Eu(fod)_3$-MK on a glass coverslip, imaged with an iPhone 11 using a custom application (app) and pulsed excitation source. The images collected using the same ISO setting but different shutter speeds. The top half of the coverslip had been exposed to water for 15 minutes, the bottom half had not been exposed, according to some embodiments.

FIG. 32B shows an image of a drop-cast sample of Eu(fod)$_3$-MK on a glass coverslip, imaged with an iPhone 11 using a custom application (app) and pulsed excitation source. The images collected using the same ISO setting but different shutter speeds. The top half of the coverslip had been exposed to water for 15 minutes, the bottom half had not been exposed.

Figure 33A:
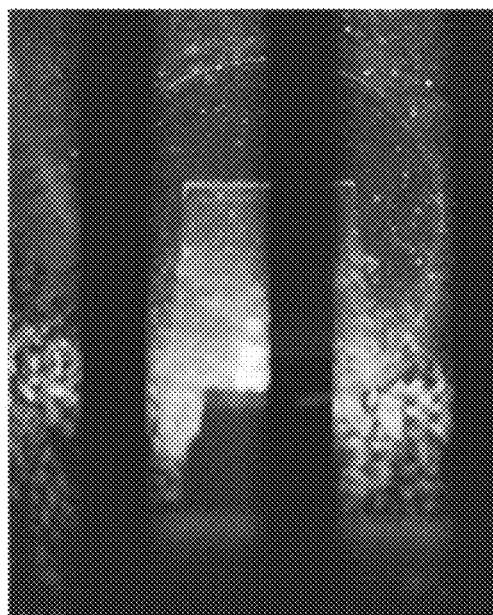
FIGS. 33A-33B show images of a drop-cast sample of PdOEP on a glass coverslip in an air-free environment inside a vacuum chamber, imaged with an iPhone 11 and pulsed white light LED excitation source, before (FIG. 33A) and after (FIG. 33B) exposure to air/oxygen, according to some embodiments.
Figure 33B:
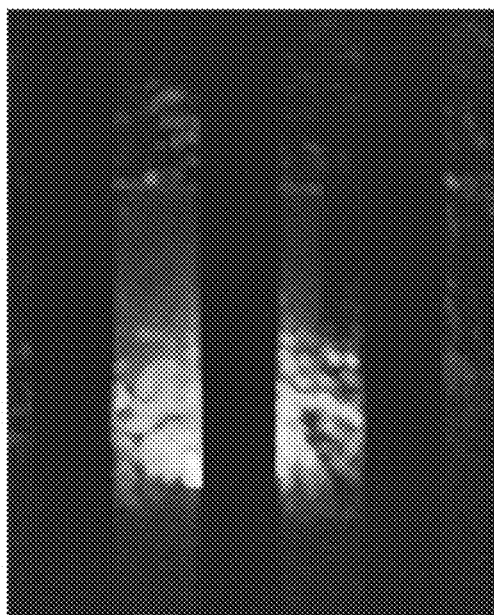

FIGS. 33A-33B show images of a drop-cast sample of PdOEP on a glass coverslip in an air-free environment inside a vacuum chamber, imaged with an iPhone 11 and pulsed white light LED excitation source, before (FIG. 33A) and after (FIG. 33B) exposure to air/oxygen.

Figure 34A:
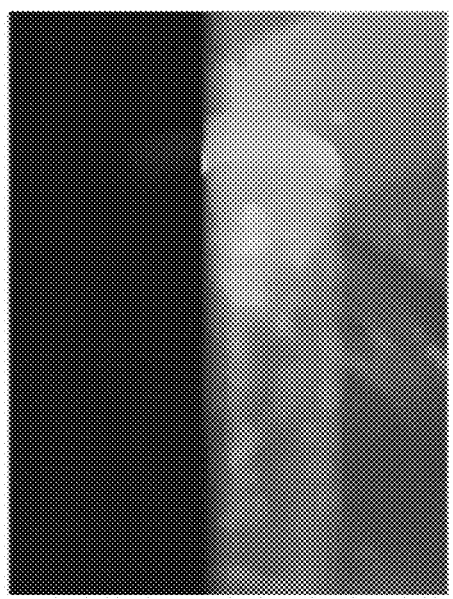
FIGS. 34A-34B show images of a cast film of PdOEP inside a glass vial, imaged with an iPhone 11 using a custom application (app) and pulsed white light LED excitation source, before (FIG. 34A) and after (FIG. 34B) exposure to air/oxygen, according to some embodiments.
Figure 34B:
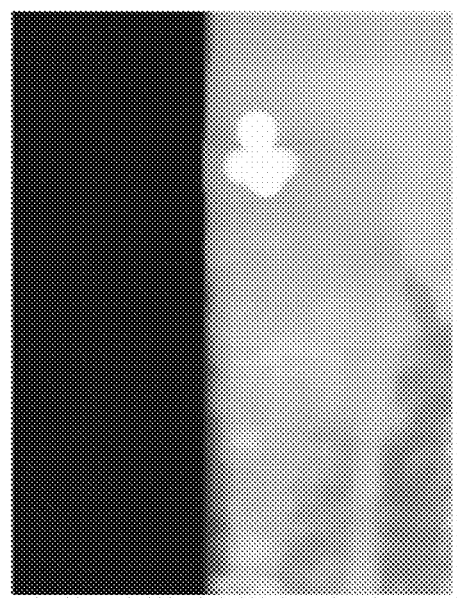

FIGS. 34A-34B show images of a cast film of PdOEP inside a glass vial, imaged with an iPhone 11 using a custom application (app) and pulsed white light LED excitation source, before (FIG. 34A) and after (FIG. 34B) exposure to air/oxygen.

FIG. 35A shows chemical structures of exemplary oligomeric/polymeric white light excitable Eu-based delayed emitters $(PCBH)_6Eu_2(Phen)_2$, $(PCBH)(PCH)Eu(bpt)$, and $(PCBH)(PCH)Eu(Phen)$.

Figure 35B:
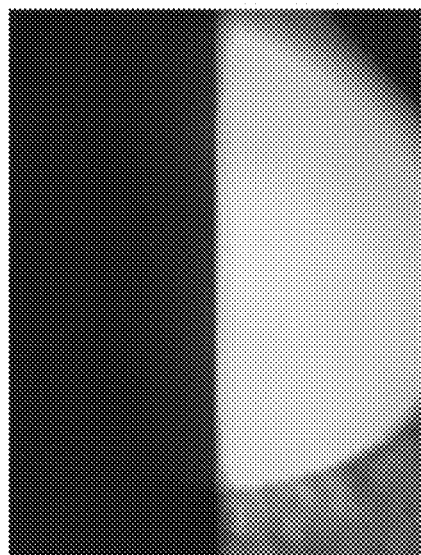
FIG. 35B-35C show images of a solid sample of (PCBH)(PCH)Eu(bpt) in a glass vial (FIG. 35B) and drop-cast on white paper (FIG. 35C), imaged with an iPhone 11 using a custom application (app) and the iPhone's flash LED.
Figure 35C:
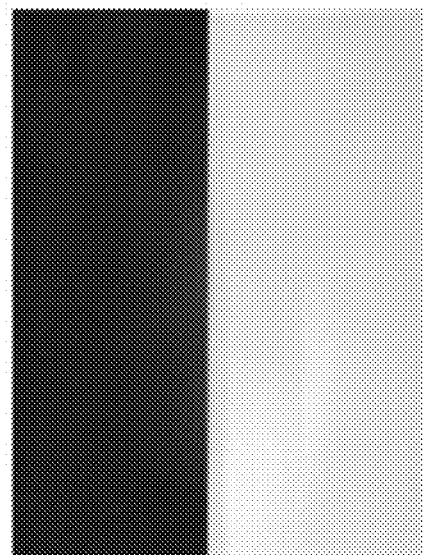

FIG. 35B-35C show images of a solid sample of (PCBH)(PCH)Eu(bpt) in a glass vial (FIG. 35B) and drop-cast on white paper (FIG. 35C), imaged with an iPhone 11 using a custom application (app) and the iPhone's flash LED.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. The alkyl groups may be optionally substituted, as described more fully below. Examples of alkyl groups include, but are not limited to, methyl, ethyl, propyl, isopropyl, butyl, isobutyl, tert-butyl, 2-ethylhexyl, cyclopropyl, cyclobutyl, cyclopentyl, cyclohexyl, and the like. "Heteroalkyl" groups are alkyl groups wherein at least one atom is a heteroatom (e.g., oxygen, sulfur, nitrogen, phosphorus, etc.), with the remainder of the atoms being carbon atoms. Examples of heteroalkyl groups include, but are not limited to, alkoxy, poly(ethylene glycol)-, alkyl-substituted amino, tetrahydrofuranyl, piperidinyl, morpholinyl, etc.

The terms "alkenyl" and "alkynyl" refer to unsaturated aliphatic groups analogous to the alkyl groups described above, but containing at least one double or triple bond respectively. The "heteroalkenyl" and "heteroalkynyl" refer to alkenyl and alkynyl groups as described herein in which one or more atoms is a heteroatom (e.g., oxygen, nitrogen, sulfur, and the like).

The term "aryl" refers to an aromatic carbocyclic group having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl), all optionally substituted. "Heteroaryl" groups are aryl groups wherein at least one ring atom in the aromatic ring is a heteroatom, with the remainder of the ring atoms being carbon atoms. Examples of heteroaryl groups include furanyl, thienyl, pyridyl, pyrrolyl, N lower alkyl pyrrolyl, pyridyl N oxide, pyrimidyl, pyrazinyl, imidazolyl, indolyl and the like, all optionally substituted.

The terms "amine" and "amino" refer to both unsubstituted and substituted amines, e.g., a moiety that can be represented by the general formula: N(R')(R'')(R''') wherein R', R'', and R''' each independently represent a group permitted by the rules of valence.

The terms "acyl," "carboxyl group," or "carbonyl group" are recognized in the art and can include such moieties as can be represented by the general formula:

wherein W is H, OH, O-alkyl, O-alkenyl, or a salt thereof. Where W is O-alkyl, the formula represents an "ester." Where W is OH, the formula represents a "carboxylic acid." In general, where the oxygen atom of the above formula is replaced by sulfur, the formula represents a "thiolcarbonyl" group. Where W is a S-alkyl, the formula represents a "thiolester." Where W is SH, the formula represents a "thiolcarboxylic acid." On the other hand, where W is alkyl, the above formula represents a "ketone" group. Where W is hydrogen, the above formula represents an "aldehyde" group.

As used herein, the term "heteroaromatic" or "heteroaryl" means a monocyclic or polycyclic heteroaromatic ring (or radical thereof) comprising carbon atom ring members and one or more heteroatom ring members (such as, for example, oxygen, sulfur or nitrogen). Typically, the heteroaromatic ring has from 5 to about 14 ring members in which at least 1 ring member is a heteroatom selected from oxygen, sulfur, and nitrogen. In another embodiment, the heteroaromatic ring is a 5 or 6 membered ring and may contain from 1 to about 4 heteroatoms. In another embodiment, the heteroaromatic ring system has a 7 to 14 ring members and may contain from 1 to about 7 heteroatoms. Representative heteroaryls include pyridyl, furyl, thienyl, pyrrolyl, oxazolyl, imidazolyl, indolizinyl, thiazolyl, isoxazolyl, pyrazolyl, isothiazolyl, pyridazinyl, pyrimidinyl, pyrazinyl, triazinyl, triazolyl, pyridinyl, thiadiazolyl, pyrazinyl, quinolyl, isoquinolyl, indazolyl, benzoxazolyl, benzofuryl, benzothiazolyl, indolizinyl, imidazopyridinyl, isothiazolyl, tetrazolyl, benzimidazolyl, benzoxazolyl, benzothiazolyl, benzothiadiazolyl, benzoxadiazolyl, carbazolyl, indolyl, tetrahydroindolyl, azaindolyl, imidazopyridyl, qunizaolinyl, purinyl, pyrrolo[2,3]pyrimidyl, pyrazolo[3,4]pyrimidyl, benzo(b)thienyl, and the like. These heteroaryl groups may be optionally substituted with one or more substituents.

The term "substituted" is contemplated to include all permissible substituents of organic compounds, "permissible" being in the context of the chemical rules of valence known to those of ordinary skill in the art. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl" must still comprise the phenyl moiety and cannot be modified by substitution, in this definition, to become, e.g., a heteroaryl group such as pyridine. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valencies of the heteroatoms. This disclosure is not intended to be limited in any manner by the permissible substituents of organic compounds.

Examples of substituents include, but are not limited to, alkyl, aryl, aralkyl, cyclic alkyl, heterocycloalkyl, hydroxy, alkoxy, aryloxy, perhaloalkoxy, aralkoxy, heteroaryl, heteroaryloxy, heteroarylalkyl, heteroaralkoxy, azido, amino, halogen, alkylthio, oxo, acyl, acylalkyl, carboxy esters, carboxyl, carboxamido, nitro, acyloxy, aminoalkyl, alkylaminoaryl, alkylaryl, alkylaminoalkyl, alkoxyaryl, arylamino, aralkylamino, alkylsulfonyl, carboxamidoalkylaryl, carboxamidoaryl, hydroxyalkyl, haloalkyl, alkylaminoalkylcarboxy, aminocarboxamidoalkyl, alkoxyalkyl, perhaloalkyl, arylalkyloxyalkyl, and the like.

What is claimed is:

1. A system, comprising:
a radiation source configured to generate electromagnetic radiation for exciting an emissive species such that the emissive species produces a detectable non-steady-state emission during an emission time period of the emissive species;
an electromagnetic radiation sensor including a plurality of photodetectors configured to detect the non-steady state emission during the emission time period;
a controller configured to control a timing of generation of the electromagnetic radiation by the radiation source such that pulsed or frequency modulated intensity electromagnetic radiation is generated during the capture of the one or more images; and
processing circuitry configured to:
a) generate, based on output of the plurality of photodetectors, one or more images, the emission time period being less than a time to capture a single image of the one or more images and for each of the one or more images, determine a first property of a first portion of the image and a second property of a second portion of the image, and identify a characteristic of the emissive species based, at least in part, on the first property and the second property; or
b) globally expose and/or read data from the electromagnetic radiation sensor to provide a plurality of time-encoded signals and identify a characteristic of the emissive species based on a comparison of two or more of the plurality of time-encoded signals.

2. A system as in claim 1, wherein the source of electromagnetic radiation is configured to emit radiation to excite a steady-state emission in a second emissive species.

3. A system as in claim 1, wherein a second source of electromagnetic radiation is configured to emit radiation to excite a steady-state emission in a second emissive species.

4. A system as in claim 1, wherein the second emissive species is the same as the emissive species.

5. A system as in claim 1, wherein the second portion of the image corresponds to the steady-state emission of the emissive species.

6. A system as in claim 1, wherein the radiation source is configured to generate electromagnetic radiation for exciting a second emissive species such that the second emissive species produces a second detectable non-steady-state emission during a second emission time period, the second emission time period being at least 10 nanoseconds.

7. A system as in claim 1, wherein the sensor is configured to detect, during a first portion of the second emission time period, a first emission from the second emissive species, and to detect, during a second portion of the second emission time period, a second emission from the second emissive species.

8. A system as in claim 1, wherein each emissive species comprises the same emitter.

9. A system as in claim 1, wherein each emissive species comprises a plurality of emitters.

10. The system of claim 1, wherein the electromagnetic radiation sensor is configured to capture a plurality of images, and wherein the processing circuitry is further configured to:
   determine an average of the first property over the plurality of images;
   determine an average of the second property over the plurality of images; and
   identify a characteristic of the emissive species based, at least in part, on the average of the first property and the average of the second property.

11. A system as in 10 wherein a delayed emission can be detected in the same image with normal reflected/scattered light.

12. A system as in 10, wherein excitation is performed by pulsed light and/or frequency modulated light intensity.

13. The system of claim 1, wherein the electromagnetic radiation sensor is configured to capture a plurality of images, and wherein the controller is further configured to control the radiation source to generate a pulse or intensity modulated at different frequencies of electromagnetic radiation prior to capture of each of the plurality of images.

14. The system of claim 1, wherein the plurality of photodetectors are arranged in an array of rows and columns, and wherein the processing circuitry is further configured to:
   sequentially read out rows or columns of the array to provide a plurality of time-encoded signals; and
   generate the one or more images based on the plurality of time-encoded signals.

15. A system as in claim 1, wherein the plurality of photodetectors are contained within a single integrated electronic chip.

16. A system as in claim 1, wherein the plurality of photodetectors are contained in multiple integrated electronic chips.

17. A system as in claim 1, further comprising a source of colorimetric signals.

18. A system as in claim 17, wherein the colorimetric signal is associated with including images of the assay cartridge, markers that may be used for alignment, text, numbers, pictures, logos, bar codes, and/or QR codes.

19. A system as in claim 1, further comprising an article.

20. A system as in claim 19, wherein the article is associated with a chemical tag.

21. A system as in claim 20, wherein the chemical tag further comprises the emissive species.

22. A system as in claim 19, wherein a difference between the first property of the first portion of the image and the second property of the second portion of the image is associated with a characteristic of the article.

23. A system as in claim 1, wherein the emission time period is at least 10 nanoseconds.

24. A system, comprising:
   an excitation component configured to excite an emissive species such that the emissive species produces a detectable non-steady-state emission during an emission time period of the emissive species;
   an image sensor including a plurality of photodetectors configured to detect at least a portion of the detectable non-steady-state emission; and
   an electronic hardware component comprising processing circuitry configured to:
   a) generate, based on output of the plurality of photodetectors, one or more images, the emission time period being less than a time to capture a single image of the one or more images and for each of the one or more images, determine a first property of a first portion of the image and a second property of a second portion of the image, and identify a characteristic of the emissive species based, at least in part, on the first property and the second property; or
   b) globally expose and/or read data from the image sensor to provide a plurality of time-encoded signals and identify a characteristic of the emissive species based on a comparison of two or more of the plurality of time-encoded signals.

25. A system as in claim 24, wherein the emission time period is at least 10 nanoseconds.

26. A system as in claim 24, wherein the excitation component is configured to emit radiation to excite a steady-state emission in a second emissive species.

27. A system as in claim 24, wherein a second excitation component is configured to emit radiation to excite a steady-state emission in a second emissive species.

28. A system as in claim 24, wherein the second emissive species is the same as the emissive species.

29. A system as in claim 24, wherein the one or more images further comprises a third portion corresponding to a third portion of the emission time period.

30. A system as in claim 24, wherein the one or more images further comprises subsequent portions corresponding to multiple other portions of the emission time period.

31. A system as in claim 24, wherein the first portion of the emission time period is different from the second portion of the emission time period.

32. A system as in claim 24, wherein the first portion of the emission time period at least partially overlaps with the second portion of the emission time period.

33. A system as in claim 24, wherein the electronic hardware component is configured to:
   a. produce the one or more images comprising more than two image portions corresponding to emission of electromagnetic radiation by the emissive species at more than two respective points in time, and/or
   b. produce multiple images each comprising at least a first image portion corresponding to emission of electromagnetic radiation by the emissive species at least at a first point in time, and second image portion corresponding to emission of electromagnetic radiation by the emissive species at least at a second point in time.

34. A system as in claim 24, further comprising an article.

35. A system as in claim 34, wherein the article is associated with a chemical tag.

36. A system as in claim 35, wherein the chemical tag further comprises the emissive species.

37. A system as in claim 34, wherein a difference between the first property of the first portion of the image and the second property of the second portion of the image is associated with a characteristic of the article.

\* \* \* \* \*